(12) United States Patent
Selwood et al.

(10) Patent No.: US 10,087,144 B2
(45) Date of Patent: Oct. 2, 2018

(54) AGENTS FOR USE IN THE TREATMENT OF CARDIOVASCULAR AND INFLAMMATORY DISEASES STRUCTURALLY BASED ON 4(1 H)-QUINOLONE

(71) Applicant: UCL Business PLC, London (GB)

(72) Inventors: David Selwood, Welwyn Garden (GB); Adrian Hobbs, London (GB)

(73) Assignee: UCL Business PLC, London, Great London (GB)

( * ) Notice: Subject to any disclaimer, the term of this patent is extended or adjusted under 35 U.S.C. 154(b) by 0 days.

(21) Appl. No.: 15/356,311

(22) Filed: Nov. 18, 2016

(65) Prior Publication Data

US 2017/0066722 A1 Mar. 9, 2017

Related U.S. Application Data

(63) Continuation of application No. PCT/GB2015/051500, filed on May 21, 2015.

(51) Int. Cl.
*C07D 215/56* (2006.01)
*C07D 401/04* (2006.01)
(Continued)

(52) U.S. Cl.
CPC ............ *C07D 215/56* (2013.01); *A61K 31/47* (2013.01); *A61K 31/4709* (2013.01);
(Continued)

(58) Field of Classification Search
CPC .... A61K 31/47; A61K 31/4709; A61K 45/06; C07D 215/56; C07D 401/04; C07D 406/04
See application file for complete search history.

(56) References Cited

U.S. PATENT DOCUMENTS

| 4,014,877 A | 3/1977 | Gerster |
| 4,621,088 A | 11/1986 | Laruelle et al. |
| 4,959,363 A | 9/1990 | Wentland |

FOREIGN PATENT DOCUMENTS

| EP | 0811613 | 12/1997 |
| GB | 1568962 | 6/1980 |

(Continued)

OTHER PUBLICATIONS

Lager, et al, 4-Quinoline derivatives: High-affinity Ligands at the Benzodiazepine Site of Brain GABAA Receptors. Synthesis, Pharmacology, and Pharmacophore Modeling, J. of Med. Chem., Am. Chem. Soc., vol. 49, No. 8, 2526-2533 (2006).*

(Continued)

Primary Examiner — Erich A Leeser
(74) Attorney, Agent, or Firm — Klarquist Sparkman LLP

(57) ABSTRACT

The present invention provides a compound of formula I, a tautomer thereof, or a pharmaceutically acceptable salt or N-oxide thereof for use in the treatment or prevention of cardiovascular disease or of an inflammatory disease or condition:

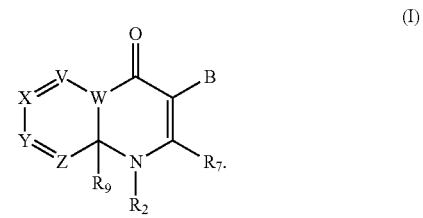

(I)

wherein:
V is N or $CR_3$;
X is N or $CR_4$;
Y is N or $CR_5$;
Z is N or $CR_6$;
B is —(C=O)$R_1$, a 5- to 10-membered heteroaryl group, or a group
L'''-NRR', wherein R and R' are the same or different and each represents a hydrogen atom, a $C_1$-$C_6$ alkyl group or a $C_1$-$C_6$ haloalkyl group;
$R_1$ is a 5- to 10-membered heterocyclyl group, or —OR', wherein R' is a hydrogen atom, a $C_1$-$C_6$ alkyl group or a $C_1$-$C_6$ haloalkyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group, or $R_1$ is —NR"R'", —NR$^{IV}$-L'''-CONR"R'", or —NR$^{IV}$-L'''-COOR, wherein R, R", R''' and R$^{IV}$ are the same or different and each represents a hydrogen atom, a $C_1$-$C_6$ alkyl group or a $C_1$-$C_6$ haloalkyl group;
either (a) W is N and $R_9$ and $R_2$ together form a bond, or (b) W is $CR_8$, $R_8$ and $R_9$ together form a bond and $R_2$ is a hydrogen atom, or a $C_1$-$C_6$ alkyl, $C_1$-$C_6$ haloalkyl, $C_6$-$C_{10}$ aryl, 5- to 10-membered heteroaryl, 5- to 10-membered heterocyclyl, -L'-$A_2$, $C_3$-$C_{10}$ cycloalkyl, or —COOR' group, wherein R' is a hydrogen atom or $C_1$-$C_6$ alkyl group, or, when Z is a moiety $CR_6$, $R_2$ may form, together with $R_6$ and the carbon and nitrogen atoms which connect $R_2$ and $R_6$ in the formula (I), a 5- to 6-membered heterocyclic ring;
$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;
$R_4$ and $R_5$ are the same or different and each represent a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —$CO_2$R''', $C_6$-$C_{10}$ aryl, 5- to 10-membered heteroaryl, 5 to 10-membered heterocyclyl, or (Continued)

—CO—($C_1$-$C_6$ alkyl) group, wherein R', R" and R'" are the same or different and each represent a hydrogen atom or $C_1$-$C_6$ alkyl group, or $R_4$ and $R_5$ and the carbon atoms bonded to $R_4$ and $R_5$ together form a 5- to 6-membered heterocyclic ring;

$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —$CO_2$R' group, wherein R' is hydrogen or $C_1$-$C_6$ alkyl, or, when W is a moiety $CR_8$, $R_6$ may form, together with $R_2$ and the carbon and nitrogen atoms which connect $R_6$ and $R_2$ in the formula (I), a 5- to 6-membered heterocyclic ring;

$R_7$ is a hydrogen atom, a halogen atom, or a $C_1$-$C_6$ alkyl, or $C_1$-$C_6$ haloalkyl group, $A_2$ represents a $C_6$-$C_{10}$ aryl or 5- to 10-membered heteroaryl group;

L', and L'" are the same or different and each represent a $C_1$-$C_6$ alkylene, $C_2$-$C_6$ alkenylene, or $C_2$-$C_6$ alkynylene group;

said aryl, heteroaryl, cycloalkyl and heterocyclyl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —$SO_2$R, —NR'R", —NR'(C=O)R", —COOR, nitro and cyano substituents, wherein R, R' and R" are the same or different and each represents a hydrogen atom or $C_1$-$C_4$ alkyl group.

16 Claims, 9 Drawing Sheets
(5 of 9 Drawing Sheet(s) Filed in Color)

(51) Int. Cl.
  C07D 409/04   (2006.01)
  A61K 45/06    (2006.01)
  A61K 31/47    (2006.01)
  A61K 31/4709  (2006.01)

(52) U.S. Cl.
  CPC ............ *A61K 45/06* (2013.01); *C07D 401/04* (2013.01); *C07D 409/04* (2013.01)

(56) References Cited

FOREIGN PATENT DOCUMENTS

| WO | WO 1997/04779  | 2/1997  |
|----|----------------|---------|
| WO | WO 2001/34570  | 5/2001  |
| WO | WO 2006/117660 | 11/2006 |
| WO | WO 2007/059108 | 5/2007  |
| WO | WO 2015/131259 | 9/2015  |

OTHER PUBLICATIONS

Wentland, et al, 3-Quinolinecarboxamides. A Series of Novel Orally-active Antiherpetic Agents, J. of Med. Chem., Am. Chem. Soc., vol. 36, No. 11, 1580-1596 (1993).*
RN: 1153437-25-2 with a publication date of Mar. 10, 2010.*
Ahluwalia et al., "Endothelium-derived C-type natriuretic peptide: more than just a hyperpolarizing factor," *Trends in Pharmacological Sciences* 26(3): 162-167, Mar. 31, 2005.
Belicova et al., "Biological activity of new aza analogues of quinolones." *Folia Microbiologica* 42(3): 193-198, Jun. 1, 1997.
Chauhan et al., "Release of C-type natriuretic peptide accounts for the biological activity of endothelium-derived hyperpolarizing factor." *Proceedings of the National Academy of Sciences* 100(3): 1426-1431 Feb. 4, 2003.
CHEMCATS Accession No. 0017369117, Mar. 10, 2010, Compound Registry No. 1153437-25-2.
CHEMCATS Accession No. 0018410795, Mar. 10, 2010, Compound Registry No. 1098367-70-4.
Clemenzia, et al., "Behavior of certain forms of enzymuria in subjects treated with pipemidic acid," *Minerva Medica* 77(16): 621-626, Apr. 1986 (English abstract provided).
Erkens et al., "Use of fluorquinolones is associated with a reduced risk of coronary heart disease in *Diabetes mellitus* type 2 patients," *European Heart Journal* 23(20): 1575-1579, Oct. 1, 2002.
Golub et al., "Evaluation of 3-Carboxy-4 (1 H)-quinolones as Inhibitors of Human Protein Kinase CK2," *Journal of Medicinal Chemistry* 49(22): 6443-6450, Nov. 2, 2006.
He et al., "Design, synthesis, and biological evaluation of novel 4-hydro-quinoline-3-carboxamide derivatives as an immunomodulatory," *Bioorganic & Medicinal Chemistry Letters* 15(12): 2980-2985, Jun. 15, 2005.
Hobbs et al., "Natriuretic peptide receptor-C regulates coronary blood flow and prevents myocardial ischemia/reperfusion injury," *Circulation* 110(10): 1231-1235, Aug. 30, 2004.
International Search Report and Written Opinion from International Application No. PCT/GB2015/051500 dated Oct. 7, 2015.
Koga et al., "Structure-activity relationships of antibacterial 6, 7-and 7, 8-disubstituted 1-alkyl-1, 4-dihydro-4-oxoquinoline-3-carboxylic acids," *Journal of Medicinal Chemistry* 23(12): 1358-1363, Dec. 1, 1980.
Lager et al., "4-Quinolone derivatives: high-affinity ligands at the benzodiazepine site of brain GABAA receptors. Synthesis, pharmacology, and pharmacophore modeling," *Journal of Medicinal Chemistry* 49(8): 2526-2533, Apr. 20, 2006.
Loew et al., "Piromidic acid and beta-hydroxypiromidic acid: therapeutic effectiveness on experimental *E. coli* pyelonephritis in the rat," *International Journal of Clinical Pharmacology, Therapy and Toxicology* 7(2): 234-237, Apr. 7, 1973.
Macinga et al., "Unique biological properties and molecular mechanism of 5, 6-bridged quinolones.," *Antimicrobial Agents and Chemotherapy* 47(8): 2526-2537, Aug. 1, 2003.
Moyes et al., "Endothelial C-type natriuretic peptide maintains vascular homeostasis," *The Journal of Clinical Investigation* 124(9): 4039-4051, Sep. 2, 2014.
Ogino et al., "In vivo and in vitro effects of fluoroquinolones on lipopolysaccharide-induced pro-inflammatory cytokine production," *Journal of Infection and Chemotherapy* 15(3): 168-173, Jan. 1, 2009.
Quinteiro et al., "Design and development of novel non-peptide agonists at NPR-C," *BMC Pharmacology* 11(S1): P54, Jun. 24, 2011.
Rimola et al., "Partially-absorbable quinolones in the prophylaxis of spontaneous bacterial peritonitis recurrence in cirrhosis," *J Hepatol* 7(1): S72, 1988 (abstract only).
Scotland et al., "C-type natriuretic peptide inhibits leukocyte recruitment and platelet-leukocyte interactions via suppression of P-selectin expression," *Proceedings of the National Academy of Sciences of the United States of America* 102(40): 14452-14457, Oct. 4, 2005.
Search Report issued by UK IPO on related British patent application (GB 1012899.9) dated Nov. 17, 2000.
Search Report issued by UK IPO on British priority application (GB 1409044.3) dated Jan. 13, 2015.
Taniguchi et al., "Clinical studies with antimicrobic agent 'Dolcol' for chronic prostatitis," *Hinyokika Kiyo. Acta Urologica Japonica* 31(9): 1661-1665, Sep. 31, 1985 (English abstract provided).
Tao et al., "The inhibitory Effects of Quinolones on Hepatitis B Virus in Vitro [J],"*Virologica Sinica* 9(2): 113-118, 1994 (English abstract provided).
Villar et al., "Definitive role for natriuretic peptide receptor-C in mediating the vasorelaxant activity of C-type natriuretic peptide and endothelium-derived hyperpolarising factor," *Cardiovascular Research* 74(3): 515-525, Jun. 1, 2007.
Wang et al., "CoMFA and DISCOtech studies of 4-quinolone derivative agonists for GABAA/BZ receptor," *Jisuanji Yu Yingyong Huaxue Bianjibu* (Computers and Applied Chemistry), 25(10): 1197-1201, CAS Abstract Accession No. 2009:173425, 2008 (English abstract only).

(56) References Cited

OTHER PUBLICATIONS

Wentland et al., "3-Quinolinecarboxamides. A series of novel orally-active antiherpetic agents," *Journal of Medicinal Chemistry* 36(11): 1580-1596, May 1, 1993.
Yang et al., "Parallel synthesis of N-biaryl quinolone carboxylic acids as selective $M_1$ positive allosteric modulators," *Bioorganic & Medicinal Chemistry Letters* 20(2): 531-536, Nov. 24, 2009.
Zhang et al., "Besitioxacin, a novel fluoroquinolone antimicrobial agent, exhibits potent inhibition of pro-inflammatory cytokines in human THP-1 monocytes," *Journal of Antimicrobial Chemotherapy* 61(1): 111-116, Oct. 25, 2007.

\* cited by examiner

AGENTS FOR USE IN THE TREATMENT OF CARDIOVASCULAR AND INFLAMMATORY DISEASES STRUCTURALLY BASED ON 4(1 H)-QUINOLONE

CROSS REFERENCE TO RELATED APPLICATION

This application is a continuation of International Application No. PCT/GB2015/051500, filed on May 21, 2015, which in turn claims the benefit of Great Britain Application No. 1409044.3, filed on May 21, 2014. These prior applications are incorporated herein in their entirety.

FIELD

The present invention relates to a series of quinolone derivatives which act as C-type natriuretic peptide receptor (NPRC) agonists.

BACKGROUND

C-type natriuretic peptide (CNP) is a vasoactive peptide that has vasodilatory and diuretic properties. CNP is a potent relaxant of vascular smooth muscle, particularly in the coronary circulation. CNP also inhibits smooth muscle cell proliferation and aldosterone production. CNP is also an atherogenic agent, i.e. has antiaggregatory and anticoagulant properties, and is an anti-inflammatory. The biological actions of CNP are mediated via activation of specific natriuretic peptide receptors (NPR$_5$), particularly the NPR-B and -C subtypes. NPR-C is the predominant subtype involved in the vasorelaxant response to CNP (Chauhan, S. D. et al, (2003) *Proceedings of the National Academy of Sciences,* 100, 3, 1426-1431).

CNP has been found to be useful in the prevention and treatment of ischemic vascular disease, e.g. myocardial infarction or stroke, and other cardiovascular disorders, e.g. hypertension, atherosclerosis, restenosis, and myocardial ischaemia/reperfusion injury (Hobbs, A., et al, (2004), *Circulation,* 110, 1231-1235). CNP has also been found to exert a strong anti-atherogenic influence on blood vessel walls (Ahluwali, A., et al, (2005) *Trends in Pharmacological Sciences,* 26, 3, 162-167).

CNP is therefore potentially useful in treating a wide range of vascular disorders. There are, of course, disadvantages associated with using a protein-based drug in a therapeutic context. In particular, oral administration results in the rapid hydrolysis of amide bonds in the protein, leading to the destruction of the protein and loss of therapeutic efficacy in vivo. There is therefore a need to provide small molecules that mimic CNP and which do not degrade easily when administered in a therapeutic context.

SUMMARY

It has now been found that the quinolone derivatives of formula I mimic CNP in binding to NPRC receptors. They will therefore be therapeutically useful, but are unlikely to suffer from the disadvantages outlined above.

Quinolone antibacterial agents are disclosed in Koga, et al, J. Med. Chem. 1980, 23, 1358-1363.

The present invention therefore provides compounds of formula I, tautomers thereof, or pharmaceutically acceptable salts or N-oxides thereof for use in the treatment or prevention of cardiovascular disease:

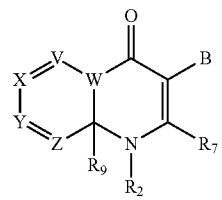

(I)

wherein:
V is N or $CR_3$;
X is N or $CR_4$;
Y is N or $CR_5$;
Z is N or $CR_6$;
B is —(C=O)$R_1$, a 5- to 10-membered heteroaryl group, or a group -L'''-NRR', wherein R and R' are the same or different and each represents a hydrogen atom, a $C_1$-$C_6$ alkyl group or a $C_1$-$C_6$ haloalkyl group;
$R_1$ is a 5- to 10-membered heterocyclyl group, or —OR', wherein R' is a hydrogen atom, a $C_1$-$C_6$ alkyl group or a $C_1$-$C_6$ haloalkyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group, or $R_1$ is —NR"R''', —NR$^{IV}$-L'''-CONR"R''', or —NR$^{IV}$-L'''-COOR, wherein R, R", R''' and R$^{IV}$ are the same or different and each represents a hydrogen atom, a $C_1$-$C_6$ alkyl group or a $C_1$-$C_6$ haloalkyl group;
either (a) W is N and $R_9$ and $R_2$ together form a bond, or (b) W is $CR_8$, $R_8$ and $R_9$ together form a bond and $R_2$ is a hydrogen atom, or a $C_1$-$C_6$ alkyl, $C_1$-$C_6$ haloalkyl, $C_6$-$C_{10}$ aryl, 5- to 10-membered heteroaryl, 5- to 10-membered heterocyclyl, $C_3$-$C_{10}$ cycloalkyl, or —COOR' group, wherein R' is a hydrogen atom or $C_1$-$C_6$ alkyl group, or, when Z is a moiety $CR_6$, $R_2$ may form, together with $R_6$ and the carbon and nitrogen atoms which connect $R_2$ and $R_6$ in the formula (I), a 5- to 6-membered heterocyclic ring;
$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;
$R_4$ and $R_5$ are the same or different and each represent a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —CO$_2$R''', $C_6$-$C_{10}$ aryl, 5- to 10-membered heteroaryl, 5 to 10-membered heterocyclyl, or —CO—($C_1$-$C_6$ alkyl) group, wherein R', R" and R''' are the same or different and each represent a hydrogen atom or $C_1$-$C_6$ alkyl group, or $R_4$ and $R_5$ and the carbon atoms bonded to $R_4$ and $R_5$ together form a 5- to 6-membered heterocyclic ring;
$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —CO$_2$R' group, wherein R' is hydrogen or $C_1$-$C_6$ alkyl, or, when W is a moiety $CR_8$, $R_6$ may form, together with $R_2$ and the carbon and nitrogen atoms which connect $R_6$ and $R_2$ in the formula (I), a 5- to 6-membered heterocyclic ring;

3

R$_7$ is a hydrogen atom, a halogen atom, or a C$_1$-C$_6$ alkyl, or C$_1$-C$_6$ haloalkyl group, A$_2$ represents a C$_6$-C$_{10}$ aryl or 5- to 10-membered heteroaryl group;

L', and L''' are the same or different and each represent a C$_1$-C$_6$ alkylene, C$_2$-C$_6$ alkenylene, or C$_2$-C$_6$ alkynylene group;

said aryl, heteroaryl, cycloalkyl and heterocyclyl groups being unsubstituted or substituted with one or more substituents selected from halogen, hydroxy, C$_1$-C$_4$ alkyl, C$_1$-C$_4$ hydroxyalkyl, C$_1$-C$_4$ alkoxy, C$_1$-C$_4$ haloalkyl, C$_1$-C$_4$ haloalkoxy, —SOR, —SO$_2$R, —NR'R'', —NR'(C=O)R'', —COOR, nitro and cyano substituents, wherein R, R' and R'' are the same or different and each represents a hydrogen atom or C$_1$-C$_4$ alkyl group.

Some of the compounds of formula I are new, and accordingly, the present invention also provides compounds of formula (1), tautomers thereof, or pharmaceutically acceptable salts or N-oxides thereof:

$$\text{(I)}$$

wherein (a)—V is N or CR$_3$;
X is N or CR$_4$;
Y is N or CR$_5$;
Z is N or CR$_6$;
B is —(C=O)R$_1$, a 5- to 10-membered heteroaryl group, or a group -L'''-NRR', wherein R and R' are the same or different and each represents a hydrogen atom, a C$_1$-C$_6$ alkyl group or a C$_1$-C$_6$ haloalkyl group and L''' is as defined in any one of the preceding claims;

R$_1$ is a 5- to 10-membered heterocyclyl group, or R$_1$ is a proteinogenic α amino acid, which is linked to the carbonyl moiety in the compound of formula (I) via the α amino group, which amino acid is optionally esterified at the α carboxylic acid group with a C$_1$-C$_6$ alkyl group or a C$_6$-C$_{10}$ aryl group, or R$_1$ is —NR''R''', —NR$^{IV}$-L'''-CONR''R''', or —NR$^{IV}$-L'''-COOR, wherein R, R'', R''' and R$^{IV}$ are the same or different and each represents a hydrogen atom, a C$_1$-C$_6$ alkyl group or a C$_1$-C$_6$ haloalkyl group, either (a) W is N and R$_9$ and R$_2$ together form a bond, or (b) W is CR$_8$, R$_8$ and R$_9$ together form a bond and R$_2$ is a hydrogen atom, or a C$_1$-C$_6$ alkyl, C$_1$-C$_6$ haloalkyl, C$_6$-C$_{10}$ aryl, 5- to 10-membered heteroaryl, 5- to 10-membered heterocyclyl, C$_3$-C$_{10}$ cycloalkyl, or —COOR' group, wherein R' is a hydrogen atom or C$_1$-C$_6$ alkyl group, or, when Z is a moiety CR$_6$, R$_2$ may form, together with R$_6$ and the carbon and nitrogen atoms which connect R$_2$ and R$_6$ in the formula (I), a 5- to 6-membered heterocyclic ring;

R$_3$ is a hydrogen atom, a halogen atom, or a hydroxy, C$_1$-C$_6$ alkyl, C$_1$-C$_6$ alkoxy, C$_1$-C$_6$ haloalkyl, C$_1$-C$_6$ haloalkoxy, nitro, or —NR'R'' group, wherein R' and R'' are the same or different and each represent a hydrogen atom or C$_1$-C$_6$ alkyl group;

4

R$_4$ and R$_5$ are the same or different and each represent a hydrogen atom, a halogen atom, or a hydroxyl, C$_1$-C$_8$ alkyl, C$_1$-C$_8$ haloalkyl, C$_1$-C$_6$ alkoxy, C$_1$-C$_6$ haloalkoxy, nitro, —NR'R'', —CO$_2$R''', C$_6$-C$_{10}$ aryl, 5- to 10-membered heteroaryl, 5 to 10-membered heterocyclyl, or —CO—(C$_1$-C$_6$ alkyl) group, wherein R', R'' and R''' are the same or different and each represent a hydrogen atom or C$_1$-C$_6$ alkyl group, or R$_4$ and R$_5$ and the carbon atoms bonded to R$_4$ and R$_5$ together form a 5- to 6-membered heterocyclic ring;

R$_6$ is a hydrogen atom, a halogen atom, or a C$_1$-C$_6$ alkyl, C$_1$-C$_6$ haloalkyl, C$_1$-C$_6$ alkoxy, C$_1$-C$_6$ haloalkoxy or —CO$_2$R' group, wherein R' is hydrogen or C$_1$-C$_6$ alkyl, or, when W is a moiety CR$_8$, R$_6$ may form, together with R$_2$ and the carbon and nitrogen atoms which connect R$_6$ and R$_2$ in the formula (I), a 5- to 6-membered heterocyclic ring;

R$_7$ is a hydrogen atom, a halogen atom, or a C$_1$-C$_6$ alkyl, or C$_1$-C$_6$ haloalkyl group, A$_2$ represents a C$_6$-C$_{10}$ aryl or 5- to 10-membered heteroaryl group;

L', and L''' are the same or different and each represent a C$_1$-C$_6$ alkylene, C$_2$-C$_6$ alkenylene, or C$_2$-C$_6$ alkynylene group;

said aryl, heteroaryl, cycloalkyl and heterocyclyl groups being unsubstituted or substituted with one or more substituents selected from halogen, hydroxy, C$_1$-C$_4$ alkyl, C$_1$-C$_4$ hydroxyalkyl, C$_1$-C$_4$ alkoxy, C$_1$-C$_4$ haloalkyl, C$_1$-C$_4$ haloalkoxy, —SOR, —SO$_2$R, —NR'R'', —NR'(C=O)R'', —COOR, nitro and cyano substituents, wherein R, R' and R'' are the same or different and each represents a hydrogen atom or C$_1$-C$_4$ alkyl group, provided that the compound is other than and and/or (b)—V is N or CR$_3$;
X is N or CR$_4$;
Y is N or CR$_5$;
Z is N or CR$_6$;
B is —(C=O)R$_1$, a 5- to 10-membered heteroaryl group, or a group -L'''-NRR', wherein R and R' are the same or different and each represents a hydrogen atom, a C$_1$-C$_6$ alkyl group or a C$_1$-C$_6$ haloalkyl group;

R$_1$ is a 5- to 10-membered heterocyclyl group, or —OR', wherein R' is a hydrogen atom, a C$_1$-C$_6$ alkyl group or a C$_1$-C$_6$ haloalkyl group, or R$_1$ is a proteinogenic α amino acid, which is linked to the carbonyl moiety in the compound of formula (I) via the α amino group, which amino acid is optionally esterified at the α carboxylic acid group with a C$_1$-C$_6$ alkyl group or a C$_6$-C$_{10}$ aryl group, or R$_1$ is —NR''R''', —NR$^{IV}$-L'''-CONR''R''', or —NR$^{IV}$-L'''-COOR, wherein R, R'', R''' and $R^{IV}$ are the same or different and each represents a hydrogen atom, a $C_1$-$C_6$ alkyl group or a $C_1$-$C_6$ haloalkyl group;

either (a) W is N and $R_9$ and $R_2$ together form a bond, or
(b) W is $CR_8$, $R_8$ and $R_9$ together form a bond and $R_2$ is a hydrogen atom, or a $C_1$-$C_6$ alkyl, $C_1$-$C_6$ haloalkyl, $C_6$-$C_{10}$ aryl, 5- to 10-membered heteroaryl, 5- to 10-membered heterocyclyl, $C_3$-$C_{10}$ cycloalkyl, or —COOR' group, wherein R' is a hydrogen atom or $C_1$-$C_6$ alkyl group, or, when Z is a moiety $CR_6$, $R_2$ may form, together with $R_6$ and the carbon and nitrogen atoms which connect $R_2$ and $R_6$ in the formula (I), a 5- to 6-membered heterocyclic ring;

$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;

$R_4$ is a bromine atom, nitro group, or a $C_6$-$C_{10}$ aryl or 5- to 10-membered heteroaryl group, said aryl and heteroaryl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'R", —NR'(C=O)R", —COOR, nitro and cyano substituents, wherein R, R' and R" are the same or different and each represents a hydrogen atom or $C_1$-$C_4$ alkyl group, $R_5$ is a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —CO$_2$R''', $C_6$-$C_{10}$ aryl, 5- to 10-membered heteroaryl, 5 to 10-membered heterocyclyl, or —CO—($C_1$-$C_6$ alkyl) group, wherein R', R" and R''' are the same or different and each represent a hydrogen atom or $C_1$-$C_6$ alkyl group;

$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —CO$_2$R' group, wherein R' is hydrogen or $C_1$-$C_6$ alkyl, or, when W is a moiety $CR_8$, $R_6$ may form, together with $R_2$ and the carbon and nitrogen atoms which connect $R_6$ and $R_2$ in the formula (I), a 5- to 6-membered heterocyclic ring;

$R_7$ is a hydrogen atom, a halogen atom, or a $C_1$-$C_6$ alkyl, or $C_1$-$C_6$ haloalkyl group, $A_2$ represents a $C_6$-$C_{10}$ aryl or 5- to 10-membered heteroaryl group;

L', and L''' are the same or different and each represent a $C_1$-$C_6$ alkylene, $C_2$-$C_6$ alkenylene, or $C_2$-$C_6$ alkynylene group;

said aryl, heteroaryl, cycloalkyl and heterocyclyl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'R", —NR'(C=O)R", —COOR, nitro and cyano substituents, wherein R, R' and R" are the same or different and each represents a hydrogen atom or $C_1$-$C_4$ alkyl group, provided that the compound is other than

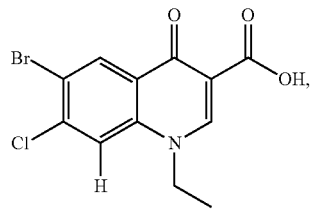

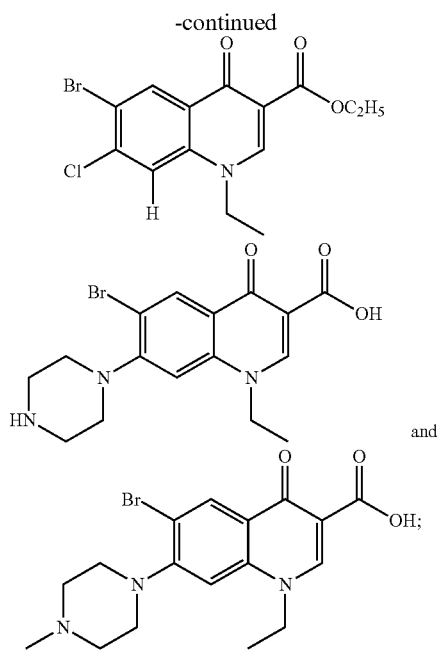

and/or
(c) the compound is of formula (Ik')

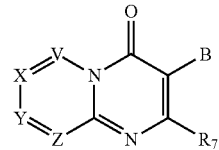

wherein:
V is N or $CR_3$;
X is N or $CR_4$;
Y is N or $CR_5$;
Z is N or $CR_6$;
B is —(C=O)$R_1$, a 5- to 10-membered heteroaryl group, or a group -L'''-NRR', wherein R and R' are the same or different and each represents a hydrogen atom, a $C_1$-$C_6$ alkyl group or a $C_1$-$C_6$ haloalkyl group;

$R_1$ is a 5- to 10-membered heterocyclyl group, or —OR', wherein R' is a hydrogen atom, a $C_1$-$C_6$ alkyl group or a $C_1$-$C_6$ haloalkyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group, or $R_1$ is —NR"R''', —NR$^{IV}$-L'''-CONR"R''', or —NR$^{IV}$-L'''-COOR, wherein R, R", R''' and $R^{IV}$ are the same or different and each represents a hydrogen atom, a $C_1$-$C_6$ alkyl group or a $C_1$-$C_6$ haloalkyl group;

$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;

$R_4$ and $R_5$ are the same or different and each represent a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —$CO_2$R'", $C_6$-$C_{10}$ aryl, 5- to 10-membered heteroaryl, 5 to 10-membered heterocyclyl, or —CO—($C_1$-$C_6$ alkyl) group, wherein R', R" and R'" are the same or different and each represent a hydrogen atom or $C_1$-$C_6$ alkyl group, or $R_4$ and $R_5$ and the carbon atoms bonded to $R_4$ and $R_5$ together form a 5- to 6-membered heterocyclic ring;

$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —$CO_2$R' group, wherein R' is hydrogen or $C_1$-$C_6$ alkyl, or, when W is a moiety $CR_8$, $R_6$ may form, together with $R_2$ and the carbon and nitrogen atoms which connect $R_6$ and $R_2$ in the formula (I), a 5- to 6-membered heterocyclic ring;

$R_7$ is a hydrogen atom, a halogen atom, or a $C_1$-$C_6$ alkyl, or $C_1$-$C_6$ haloalkyl group, L'" is a $C_1$-$C_6$ alkylene, $C_2$-$C_6$ alkenylene, or $C_2$-$C_6$ alkynylene group;

said aryl, heteroaryl, cycloalkyl and heterocyclyl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —$SO_2$R, —NR'R", —NR'(C=O)R", —COOR, nitro and cyano substituents, wherein R, R' and R" are the same or different and each represents a hydrogen atom or $C_1$-$C_4$ alkyl group, provided that the compound is other than

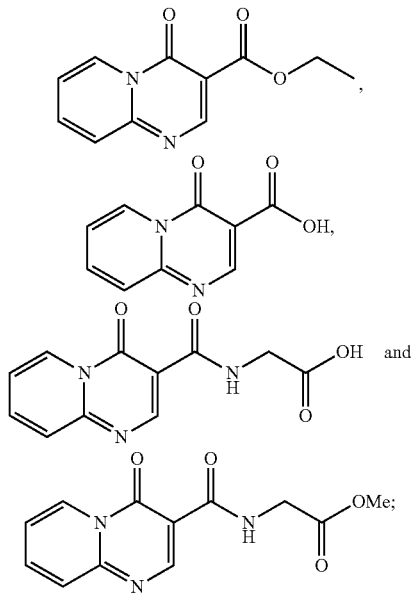

and/or (d)—V is N or $CR_3$;
X is N or $CR_4$;
Y is N or $CR_5$;
Z is N or $CR_6$;
B is —(C=O)$R_1$, a 5- to 10-membered heteroaryl group, or a group -L'"-NRR', wherein R and R' are the same or different and each represents a hydrogen atom, a $C_1$-$C_6$ alkyl group or a $C_1$-$C_6$ haloalkyl group;

$R_1$ is a 5- to 10-membered heterocyclyl group, or —OR', wherein R' is a hydrogen atom, a $C_1$-$C_6$ alkyl group or a $C_1$-$C_6$ haloalkyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group, or $R_1$ is —NR"R'", —$NR^{IV}$-L'"-CONR"R'", or —$NR^{IV}$-L'"-COOR, wherein R, R", R'" and $R^{IV}$ are the same or different and each represents a hydrogen atom, a $C_1$-$C_6$ alkyl group or a $C_1$-$C_6$ haloalkyl group;

W is $CR_8$, $R_8$ and $R_9$ together form a bond, and $R_2$ is -L'-$A_2$ or —COOR', wherein R' is a hydrogen atom or $C_1$-$C_6$ alkyl group, and wherein L' is as defined in any one of the preceding claims, and $A_2$ represents a $C_6$-$C_{10}$ aryl or 5- to 10-membered heteroaryl group, which group is substituted with two substituents selected from $C_1$-$C_4$ alkyl substituents;

$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;

$R_4$ and $R_5$ are the same or different and each represent a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —$CO_2$R'", $C_6$-$C_{10}$ aryl, 5- to 10-membered heteroaryl, 5 to 10-membered heterocyclyl, or —CO—($C_1$-$C_6$ alkyl) group, wherein R', R" and R'" are the same or different and each represent a hydrogen atom or $C_1$-$C_6$ alkyl group, or $R_4$ and $R_5$ and the carbon atoms bonded to $R_4$ and $R_5$ together form a 5- to 6-membered heterocyclic ring;

$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —$CO_2$R' group, wherein R' is hydrogen or $C_1$-$C_6$ alkyl;

$R_7$ is a hydrogen atom, a halogen atom, or a $C_1$-$C_6$ alkyl, or $C_1$-$C_6$ haloalkyl group, $A_2$ represents a $C_6$-$C_{10}$ aryl or 5- to 10-membered heteroaryl group;

L', and L'" are the same or different and each represent a $C_1$-$C_6$ alkylene, $C_2$-$C_6$ alkenylene, or $C_2$-$C_6$ alkynylene group;

said aryl, heteroaryl, cycloalkyl and heterocyclyl groups unless otherwise specified being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —$SO_2$R, —NR'R", —NR'(C=O)R", —COOR, nitro and cyano substituents, wherein R, R' and R" are the same or different and each represents a hydrogen atom or $C_1$-$C_4$ alkyl group.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
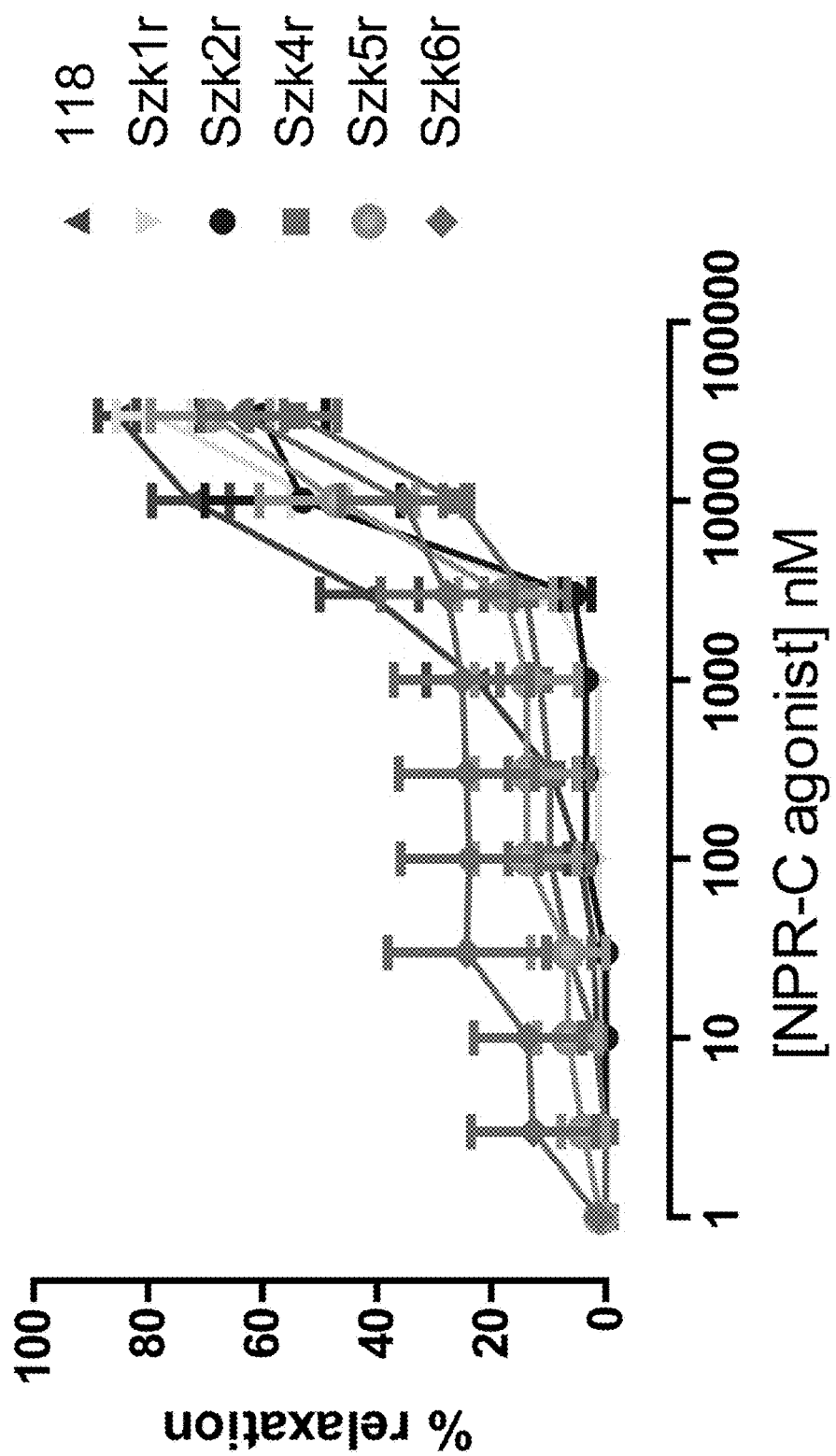
FIG. 1 shows concentration-response curves for relaxation of mouse mesenteric resistance arteries induced by compounds of the present invention.

Compounds of formula I containing one or more chiral centres may be used in enantiomerically or diastereoisomerically pure form, or in the form of a mixture of isomers. For the avoidance of doubt, the compounds of formula I can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

A compound of formula I can be salified by known methods, by contacting the compound with an appropriate acid or base.

As used herein, a said $C_1$-$C_6$ alkylene group or moiety is a linear or branched alkylene group or moiety. Typically, a $C_1$-$C_6$ alkylene group or moiety is a $C_1$-$C_4$ alkylene group or moiety, preferably a $C_1$-$C_2$ alkylene group or moiety. Examples of a $C_1$-$C_6$ alkylene group or moiety include methylene, ethylene, n-propylene and n-butylene groups and moieties. Methylene and ethylene are preferred.

As used herein, a $C_2$-$C_6$ alkenylene group or moiety is a linear or branched alkenylene group or moiety. Typically, a $C_2$-$C_6$ alkenylene group or moiety is a $C_2$-$C_4$ alkenylene group or moiety. Examples include —CH=CH—, —CH$_2$—CH=CH—, —CH=CH—CH$_2$—, —CH=CH—CH$_2$—CH$_2$—, —CH$_2$—CH=CH—CH$_2$—, —CH$_2$—CH$_2$—CH=CH—, and —CH=CH—CH=CH—. —CH=CH— is preferred.

As used herein, a $C_2$-$C_6$ alkynylene group or moiety is a linear or branched alkynylene group or moiety. Typically, a $C_2$-$C_6$ alkynylene group or moiety is a $C_2$-$C_4$ alkynylene group or moiety. Examples include —C≡C—, —CH$_2$—C≡C—, —C≡C—CH$_2$—, —C≡C—CH$_2$—CH$_2$—, CH$_2$—C≡C—CH$_2$—, —CH$_2$—CH$_2$—C≡C—, and —C≡C—C≡C—. —C≡C— is preferred.

As used herein, a halogen is typically chlorine, fluorine, bromine or iodine and is preferably chlorine, bromine or fluorine, more preferably chlorine or bromine, most preferably bromine. A halogen atom may be chosen from chlorine, bromine and iodine.

As used herein, a $C_1$-$C_8$ alkyl group or moiety is a linear or branched alkyl group or moiety containing from 1 to 8 carbon atoms. Typically, a $C_1$-$C_8$ alkyl group or moiety is a $C_1$-$C_6$ alkyl group or moiety. Examples of $C_1$-$C_6$ alkyl groups and moieties include methyl, ethyl, n-propyl, i-propyl, n-butyl, i-butyl, t-butyl and hexyl. More typically, a $C_1$-$C_8$ alkyl group or moiety is a $C_1$-$C_4$ alkyl group or moiety. Examples of $C_1$-$C_4$ alkyl groups and moieties include methyl, ethyl, n-propyl, i-propyl, n-butyl, i-butyl and t-butyl. For the avoidance of doubt, where two alkyl moieties are present in a group or compound of formula (I), the alkyl moieties may be the same or different.

As used herein, a $C_1$-$C_6$ alkoxy group is typically a said $C_1$-$C_6$ alkyl group attached to an oxygen atom. Typically, a $C_1$-$C_6$ alkoxy group or moiety is a $C_1$-$C_4$ alkoxy group or moiety, preferably a $C_1$-$C_2$ alkoxy group. Methoxy is preferred.

A haloalkyl or haloalkoxy group is typically a said alkyl or alkoxy group substituted by one or more said halogen atoms. Typically, it is substituted by 1, 2 or 3 said halogen atoms. Preferred haloalkyl and haloalkoxy groups include perhaloalkyl and perhaloalkoxy groups such as —CX$_3$ and —OCX$_3$ wherein X is a said halogen atom, for example chlorine and fluorine. Particularly preferred haloalkyl groups are —CF$_3$ and —CCl$_3$, —CF$_3$ is especially preferred. Particularly preferred haloalkoxy groups are —OCF$_3$ and —OCCl$_3$. —OCF$_3$ is especially preferred.

A $C_1$-$C_4$ hydroxyalkyl group is typically a said alkyl group substituted by one or more hydroxyl (—OH) groups. Typically, it is substituted by 1, 2 or 3 hydroxyl groups, preferably 1 or 2, more preferably one hydroxyl group. Preferred hydroxyalkyl groups are —CH$_2$OH, —CH$_2$CH$_2$OH and —CH(OH)CH$_3$ groups. —CH$_2$OH is especially preferred.

As used herein, a $C_6$-$C_{10}$ aryl group or moiety is a monocyclic or polycyclic, aromatic ring containing from 6 to 10 carbon atoms. Examples of such aryl groups include phenyl, naphthalene and azulene. Phenyl and naphthylene are preferred.

As used herein, a 5- to 10-membered heteroaryl group or moiety is typically a monocyclic 5- to 10-membered aromatic group or moiety, such as a 5- or 6-membered ring containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl, pyridazolyl, and pyrazolyl, groups. Preferred examples include furanyl, pyridyl, and thienyl groups. Thienyl and pyridyl groups are particularly preferred.

As used herein, a $C_3$-$C_{10}$ cycloalkyl group or moiety is typically a monocyclic or bicyclic, preferably monocyclic, non-aromatic, saturated or unsaturated $C_5$-$C_{10}$ carbocyclic ring. Saturated rings are preferred. Typically, a $C_3$-$C_{10}$ cycloalkyl group or moiety is a $C_3$-$C_6$ cycloalkyl group or moiety, preferably a $C_3$-$C_4$ cycloalkyl group or moiety.

Examples of $C_3$-$C_{10}$ cycloalkyl groups and moieties include cyclopropyl and cyclobutyl groups. Cyclopropyl groups are preferred.

As used herein, a 5- to 10-membered heterocyclyl group or moiety or heterocyclic ring is typically a monocyclic or bicyclic, non-aromatic, saturated or unsaturated $C_5$-$C_{10}$ carbocyclic ring in which one or more, for example 1, 2 or 3, of the carbon atoms are replaced with a moiety selected from N, O, S, S(O) and S(O)$_2$, preferably N or O. One or more, for example 1, 2 or 3, of the carbon atoms may be replaced with a moiety selected from C=O and C=NR, where R is hydrogen or $C_1$-$C_4$ alkyl, preferably hydrogen. Typically, it is a 5- to 9-membered ring. Suitable heterocyclyl groups, moieties and rings include pyrazolidinyl, piperidyl, piperazinyl, morpholinyl, pyrrolidinyl, pyrrolinyl, imidazolidinyl, imidazolinyl, 1,3-dioxolanyl, 1,4-dioxolyl, pyrazolinyl and octahydro-1H-pyrrolo[3,4-b]pyridine groups and moieties and the group

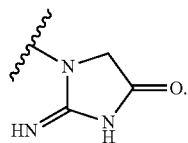

Piperidyl, piperazinyl, morpholinyl, 1,3-dioxolanyl, 1H-pyrrolo[3,4-b]pyridine and

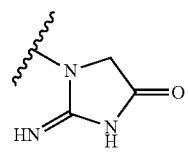 [SMILES: *N1CC(=O)NC1=N]

groups, moieties and rings are preferred.

The aryl, heteroaryl, cycloalkyl and heterocyclyl groups in the compounds of formula (I) are unsubstituted or substituted with one or more substituents, for example 1, 2 or 3 substituents, selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'R", —NR'(C=O)R", —COOR, nitro and cyano substituents, wherein R, R' and R" are the same or different and each represents a hydrogen atom or $C_1$-$C_4$ alkyl group.

Typically, said aryl, heteroaryl, cycloalkyl and heterocyclyl groups in the compounds of formula (I) are unsubstituted or substituted with one or more, for example 1, 2 or 3, substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'R", —NR'(C=O)R", and —COOR substituents, wherein R, R' and R" are the same or different and each represents a hydrogen atom or $C_1$-$C_4$ alkyl group. For the avoidance of doubt, the substituents on said aryl, heteroaryl, cycloalkyl and heterocyclyl groups in the compound of formula (I) are themselves unsubstituted.

Typically, the present invention provides a compound of formula I as defined herein, or a pharmaceutically acceptable salt or N-oxide thereof for use in the treatment or prevention of cardiovascular disease. Preferably, the present invention provides a compound of formula I as defined herein, or a pharmaceutically acceptable salt thereof for use in the treatment or prevention of cardiovascular disease.

Typically, the compound of formula (I) is other than 4-hydroxyquinoline-3-carboxylic acid, 5-phenylethyl-4-hydroxyquinoline-3-carboxylic acid, 7-benzyloxy-4-hydroxyquinoline-3-carboxylic acid, 7-phenethyloxy-4-hydroxyquinoline-3-carboxylic acid, 7-phenoxyethoxy-4-hydroxyquinoline-3-carboxylic acid, or tautomers thereof, for example

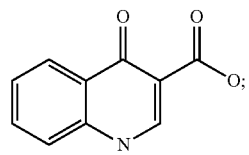

57 and/or when R is —OH, then $R_2$, $R_3$, $R_4$, $R_5$, $R_6$ and $R_7$ are not all hydrogen atoms; and/or when R is —OR' wherein R' is a hydrogen atom, a $C_1$-$C_6$ alkyl group or a $C_1$-$C_6$ haloalkyl group, then $R_2$, $R_3$, $R_4$, $R_5$, $R_6$ and $R_7$ are not all hydrogen atoms; and/or when R is —OR' wherein R' is a hydrogen atom, a $C_1$-$C_6$ alkyl group or a $C_1$-$C_6$ haloalkyl group, then $R_4$ and $R_5$ are not both isobutoxy groups; and/or when R is —OR' wherein R' is a hydrogen atom, a $C_1$-$C_6$ alkyl group or a $C_1$-$C_6$ haloalkyl group, then $R_6$ is hydrogen.

More typically, when R is —OH, then $R_2$, $R_3$, $R_4$, $R_5$, and $R_7$ are not all hydrogen atoms; and/or when R is —OR' wherein R' is a hydrogen atom, a $C_1$-$C_6$ alkyl group or a $C_1$-$C_6$ haloalkyl group, then $R_2$, $R_3$, $R_4$, $R_5$, and $R_7$ are not all hydrogen atoms.

Generally, when R is —OR' wherein R' is a hydrogen atom, a $C_1$-$C_6$ alkyl group or a $C_1$-$C_6$ haloalkyl group, then $R_2$, $R_3$, $R_4$, $R_5$, and $R_7$ are not all hydrogen atoms; when R is —OR' wherein R' is a hydrogen atom, a $C_1$-$C_6$ alkyl group or a $C_1$-$C_6$ haloalkyl group, then $R_4$ and $R_5$ are not both isobutoxy groups; when R is —OR' wherein R' is a hydrogen atom, a $C_1$-$C_6$ alkyl group or a $C_1$-$C_6$ haloalkyl group, then $R_6$ is hydrogen; and the compound of formula (I) is other than 5-phenylethyl-4-hydroxyquinoline-3-carboxylic acid, 7-benzyloxy-4-hydroxyquinoline-3-carboxylic acid, 7-phenethyloxy-4-hydroxyquinoline-3-carboxylic acid, 7-phenoxyethoxy-4-hydroxyquinoline-3-carboxylic acid, or tautomers thereof.

Typically, the compound of formula (I) is other than flumequine, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, danofloxacin, difloxacin, enrofloxacin, ibafloxacin, marbofloxacin, orbifloxacin, and sarafloxacin. Preferably, the compound of formula (I) is other than a compound of formula (If) or (Ig), as defined herein, where $R_4$ and/or $R_5$ is a fluorine atom. More preferably in the compound of formula (I), $R_4$ and/or $R_5$ is other than a fluorine atom. Thus, in certain embodiments, the compound of formula (I) is other than a fluoroquinolone. Fluoroquinolones are a well-known class of antiobiotic compound which would be familiar to the skilled person.

Typically, V is CR$_3$.

Typically, B is —(C=O)R$_1$.

Typically, the 5- to 10-membered heteroaryl groups which may be present at the B position are 5- to 6-membered, preferably 5-membered. Preferred groups include oxadiazole and thiazole groups. Those groups are typically unsubstituted or substituted with 1, 2 or 3, preferably 1 or 2, more preferably 1 substituent chosen from halogen, hydroxy, $C_1$-$C_4$ alkyl and $C_1$-$C_4$ haloalkyl substituents.

Typically, in the group -L'''-NRR', which may be present at the B position, R is a hydrogen atom. Typically, R' is a hydrogen atom or a $C_1$-$C_4$ alkyl or C haloalkyl group. The group L''' in the group -L'''-NRR', which may be present at the B position, is typically a $C_1$-$C_6$ alkylene group, preferably a C alkylene group, more preferably a C alkylene group, most preferably a methylene group.

Typically, the 5- to 10-membered heterocyclyl groups which may be present at the $R_1$ position are 5- to 6-membered, preferably 5-membered. Typically, the heterocyclyl group is a monocyclic carbocyclic ring in which 1, 2 or 3, preferably 2 of the carbon atoms are replaced with a moiety selected from N, O, or S, preferably N. One or more, for example 1, 2 or 3, preferably 2 of the carbon atoms may be replaced with a moiety selected from C=O and C=NR, where R is hydrogen or $C_1$-$C_4$ alkyl, preferably hydrogen. Suitable groups include the group

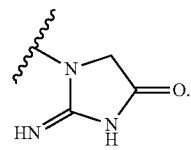 [SMILES: *N1CC(=O)NC1=N]

Those groups are typically unsubstituted or substituted with 1, 2 or 3, preferably 1 or 2, more preferably 1 substituent chosen from halogen, hydroxy, $C_1$-$C_4$ alkyl and $C_1$-$C_4$ haloalkyl substituents. Those groups are preferably unsubstituted.

Typically, $R_1$ is —OR', wherein R' is a hydrogen atom, a $C_1$-$C_6$ alkyl group or a $C_1$-$C_6$ haloalkyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group.

Typically, in the group —NR"R'", which may be present at the $R_1$ position, R" is a hydrogen atom. R'" is typically a hydrogen atom, a $C_1$-$C_4$ alkyl or $C_1$-$C_4$ haloalkyl group.

Typically, in the group —$NR^{IV}$-L'''-(C=O)NR"R'" which may be present at the $R_1$ position, $R^{IV}$ is a hydrogen atom. L''' is typically a a $C_1$-$C_6$ alkylene group, preferably a $C_1$-$C_4$ alkylene group, more preferably a $C_1$-$C_2$ alkylene group, most preferably a methylene group. R" is typically a hydrogen atom. R'" is typically a hydrogen atom, a $C_1$-$C_4$ alkyl or $C_1$-$C_4$ haloalkyl group. The group —$NR^{IV}$-L'''-(C=O)NR"R'" is preferably —NH—$CH_2$—(C=O)NHR'".

Typically, in the group —$NR^{IV}$-L'''-(C=O)OR which may be present at the $R_1$ position, $R^{IV}$ is a hydrogen atom. L''' is typically a a $C_1$-$C_6$ alkylene group, preferably a $C_1$-$C_4$ alkylene group, more preferably a $C_1$-$C_2$ alkylene group, most preferably an ethylene group. R is typically a hydrogen atom or $C_1$-$C_4$ alkyl group, preferably a hydrogen atom or methyl group. The group —$NR^{IV}$-L'''-(C=O)OR is preferably —NH—$(CH_2)_2$—(C=O)OR, more preferably —NH—$(CH_2)_2$—(C=O)OH or —NH—$(CH_2)_2$—(C=O)OCH$_3$.

Typically, the compound of formula I is of formula I':

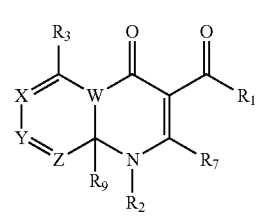

(I')

wherein W, X, Y, Z, $R_1$, $R_2$, $R_3$, $R_7$ and $R_9$ are as defined above.

As mentioned above, either (a) W is N and $R_9$ and $R_2$ together form a bond, or (b) W is $CR_8$, and $R_8$ and $R_9$ together form a bond. Thus, the compound of formula (I) is either a compound of formula (Ia) or (Ib):

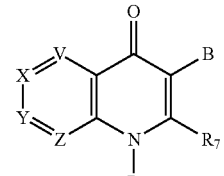

(Ia)

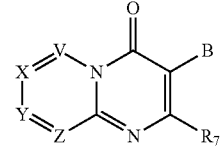

(Ib)

wherein $R_2$, $R_7$, B, V, X, Y and Z are as defined herein.

Typically, $A_2$, represents a $C_6$-$C_{10}$ aryl group or a 5-6-membered heteroaryl group, preferably a phenyl, naphthyl or 5- to 6-membered heteroaryl group, more preferably a phenyl group.

$R_1$ may be a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group. Proteinogenic α amino acids are well known to the person skilled in the art. For the avoidance of doubt, however, the proteinogenic α amino acids are those amino acids that are found in proteins. These are alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan and tyrosine.

When $R_1$ is a proteinogenic α amino acid, then $R_1$ is typically a group of formula —NH—CHR—$CO_2$R', wherein R' is a hydrogen atom, $C_1$-$C_6$ alkyl group or $C_6$-$C_{10}$ aryl group and R is a hydrogen atom, or a methyl, —$(CH_2)_3$—NH—(C=NH)—$NH_2$, —$CH_2CONH_2$, —$CH_2CO_2H$, —$CH_2SH$, —$(CH_2)_2CO_2H$, —$(CH_2)_2CONH_2$, —CH($CH_3$)$CH_2CH_3$, $CH_2CH(CH_3)_2$, —$(CH_2)_4NH_2$, —$(CH_2)_2SCH_3$, —$CH_2Ph$, —$CH_2OH$, —CH($CH_3$)OH, —$CH_2$-p-hydroxy-Ph, —CH($CH_3$)$_2$, —$CH_2SeH$ group, or a

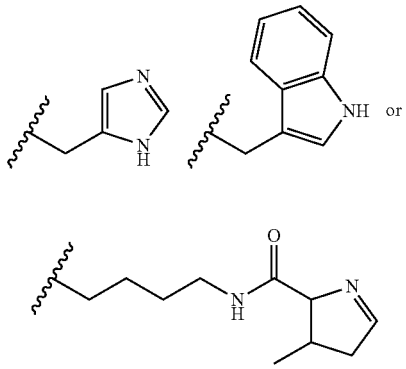

group.

R' in the moiety —NH—CHR—CO$_2$R' is typically a hydrogen atom or C$_1$-C$_6$ alkyl group, preferably a hydrogen atom or C$_1$-C$_4$ alkyl group, more preferably a hydrogen atom, or a methyl or t-butyl group.

R in the moiety —NH—CHR—CO$_2$R' is preferably a hydrogen atom, or a methyl, —CH$_2$CH(CH$_3$)$_2$, —CH$_2$-Ph or —CH(CH$_3$)$_2$ group.

Thus, the proteinogenic α amino acid is preferably glycine, alanine, leucine, phenylalanine or valine. Alanine is typically L-alanine. Leucine is typically L-leucine. Phenylalanine is typically L-phenylalanine. Valine is typically L-valine.

The amino acid is typically optionally esterified at the α carboxylic acid group with a C$_1$-C$_6$ alkyl group, preferably a C$_1$-C$_4$ alkyl group, more preferably a methyl or t-butyl group.

Typically, when R is a moiety OR', it is a hydroxyl group or C$_1$-C$_6$ alkoxy group, preferably a hydroxyl group or C$_1$-C$_4$ alkoxy group, more preferably a hydroxyl group or C$_1$-C$_2$ alkoxy group.

When R$_1$ is a group —NR$^{IV}$-L'''-COOR, L''' is typically a C$_2$-C$_6$ alkylene group. Typically, the group —NR$^{IV}$-L'''-COOR is other than a proteinogenic α amino acid which is linked to the carbonyl moiety in the compound of formula (I) via the α amino group as defined herein.

Typically, R$_1$ is a 5- to 10-membered heterocyclyl group, or R$_1$ is a proteinogenic α amino acid, which is linked to the carbonyl moiety in the compound of formula (I) via the α amino group, which amino acid is optionally esterified at the a carboxylic acid group with a C$_1$-C$_6$ alkyl group or a C$_6$-C$_{10}$ aryl group, or R$_1$ is —NR"R''', —NR$^{IV}$-L'''-CONR"R''', or —NR$^{IV}$-L'''-COOR, wherein L''', R, R", R''' and R$^{IV}$ are the same or different and each represents a hydrogen atom, a C$_1$-C$_6$ alkyl group or a C$_1$-C$_6$ haloalkyl group;

More typically, R$_1$ is a 5- to 10-membered heterocyclyl group, or —OR', wherein R' represents a hydrogen atom or C$_1$-C$_4$ alkyl group, or R$_1$ is a group of formula —NH—CHR$^{IV}$—CO$_2$R$^V$, wherein R$^V$ is a hydrogen atom or C$_1$-C$_6$ alkyl group, and R$^{IV}$ is a hydrogen atom, or a methyl, —(CH$_2$)$_3$—NH—(C=NH)—NH$_2$, —CH$_2$CONH$_2$, —CH$_2$CO$_2$H, —CH$_2$SH, —(CH$_2$)$_2$CO$_2$H, —(CH$_2$)$_2$CONH$_2$, —CH(CH$_3$)CH$_2$CH$_3$, CH$_2$CH(CH$_3$)$_2$, —(CH$_2$)$_4$NH$_2$, —(CH$_2$)$_2$SCH$_3$, —CH$_2$Ph, —CH$_2$OH, —CH(CH$_3$)OH, —CH$_2$-p-hydroxy-Ph, —CH(CH$_3$)$_2$, —CH$_2$SeH group, or a

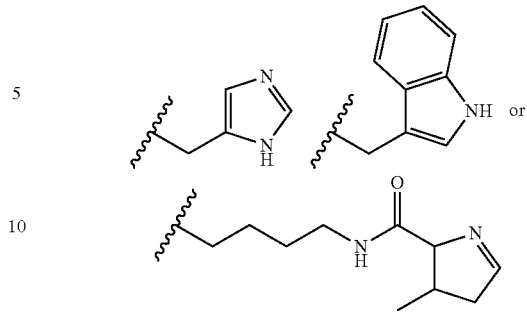

group; or R$_1$ is a group of formula —NR$^{IV}$-L'''-COOR wherein R$^{IV}$ is a hydrogen atom, L''' is a C$_2$-C$_4$ alkylene group, and R is a hydrogen atom or C$_1$-C$_4$ alkyl group.

Even more typically, R$_1$ is a 5- to 10-membered heterocyclyl group, or R$_1$ is a group of formula —NH—CHR$^{IV}$—CO$_2$R$^V$, wherein R$^V$ is a hydrogen atom or C$_1$-C$_6$ alkyl group, and R$^{IV}$ is a hydrogen atom, or a methyl, —(CH$_2$)$_3$—NH—(C=NH)—NH$_2$, —CH$_2$CONH$_2$, —CH$_2$CO$_2$H, —CH$_2$SH, —(CH$_2$)$_2$CO$_2$H, —(CH$_2$)$_2$CONH$_2$, —CH(CH$_3$)CH$_2$CH$_3$, CH$_2$CH(CH$_3$)$_2$, —(CH$_2$)$_4$NH$_2$, —(CH$_2$)$_2$SCH$_3$, —CH$_2$Ph, —CH$_2$OH, —CH(CH$_3$)OH, —CH$_2$-p-hydroxy-Ph, —CH(CH$_3$)$_2$, —CH$_2$SeH group, or a

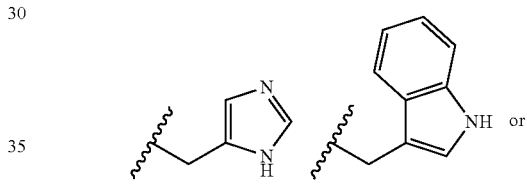

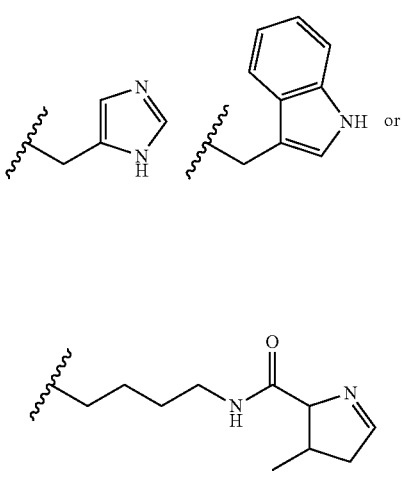

group; or R$_1$ is a group of formula —NR$^{IV}$-L'''-COOR wherein R$^{IV}$ is a hydrogen atom, L''' is a C$_2$-C$_4$ alkylene group, and R is a hydrogen atom or C$_1$-C$_4$ alkyl group.

Preferably, R$_1$ is a 5-membered heterocyclyl group, or —OR', wherein R' is a hydrogen atom or C$_1$-C$_4$ alkyl group, or R$_1$ is a group of formula —NH—CHR$^{IV}$—CO$_2$R$^V$, wherein R$^V$ is a hydrogen atom or C$_1$-C$_6$ alkyl group, and R$^{IV}$ is a hydrogen atom, or a methyl, —CH$_2$CH(CH$_3$)$_2$, —CH$_2$-Ph or —CH(CH$_3$)$_2$ group; or R$_1$ is a group —NH—(CH$_2$)$_2$—COOR, where R is hydrogen or C$_1$-C$_4$ alkyl.

More preferably, R$_1$ is a 5-membered heterocyclyl group, or R$_1$ is a group of formula —NH—CHR$^{IV}$—CO$_2$R$^V$, wherein R$^V$ is a hydrogen atom or C$_1$-C$_6$ alkyl group, and R$^{IV}$ is a hydrogen atom, or a methyl, —CH$_2$CH(CH$_3$)$_2$, —CH$_2$-Ph or —CH(CH$_3$)$_2$ group; or R$_1$ is a group of —NH—(CH$_2$)$_2$—COOR, where R is hydrogen or C$_1$-C$_4$ alkyl.

Even more preferably, $R_1$ is

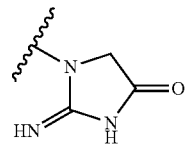 [SMILES: *N1CC(=O)NC1=N]

or $R_1$ is —OR' wherein R' is a hydrogen atom or $C_1$-$C_2$ alkyl group,
or $R_1$ is a group of formula —NH—CHR$^{IV}$—CO$_2$R$^V$, wherein R$^V$ is a hydrogen atom or $C_1$-$C_4$ alkyl group, and R$^{IV}$ is a hydrogen atom, or a methyl, —CH$_2$CH(CH$_3$)$_2$, —CH$_2$-Ph or —CH(CH$_3$)$_2$ group; or $R_1$ is —NH—(CH$_2$)$_2$—COOH or —NH—(CH$_2$)$_2$—COOCH$_3$.

Most preferably, $R_1$ is

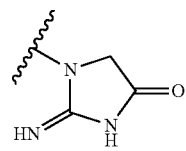 [SMILES: *N1CC(=O)NC1=N]

or $R_1$ is a group of formula —NH—CHR$^{IV}$—CO$_2$R$^V$, wherein R$^V$ is a hydrogen atom or $C_1$-$C_4$ alkyl group, and R$^{IV}$ is a hydrogen atom, or a methyl, —CH$_2$CH(CH$_3$)$_2$, —CH$_2$-Ph or —CH(CH$_3$)$_2$ group; or $R_1$ is —NH—(CH$_2$)$_2$—COOH or —NH—(CH$_2$)$_2$—COOCH$_3$.

Typically, L' is a $C_1$-$C_6$ alkylene group, preferably a $C_1$-$C_4$ alkylene group, more preferably a $C_1$-$C_2$ alkylene group, most preferably a —CH$_2$— group.

Typically, $A_2$ is a $C_6$-$C_{10}$ aryl group, preferably a phenyl group.

Typically, the moiety $A_2$ is unsubstituted or substituted with one, two or three, preferably one or two, substituents selected from halogen, $C_1$-$C_4$ alkyl, $C_1$-$C_4$ alkoxy, $C_1$-$C_4$ haloalkyl, $C_1$-$C_4$ haloalkoxy, —SO$_2$R, and —NR'(C=O)R" substituents, wherein R, R' and R" are the same or different and each represents a hydrogen atom or $C_1$-$C_4$ alkyl group. Preferably, these substituents are selected from halogen, $C_1$-$C_2$ alkyl, $C_1$-$C_2$ alkoxy, $C_1$-$C_2$ haloalkyl, $C_1$-$C_2$ haloalkoxy —SO$_2$R, and —NH(C=O)R" substituents wherein R and R" are the same or different and each represents a $C_1$-$C_2$ alkyl group.

More preferably, $A_2$ is a phenyl group which is unsubstituted or substituted by one or two substituents selected from chlorine, fluorine, $C_1$-$C_2$ alkyl, $C_1$-$C_2$ alkoxy, CF$_3$O—, —SO$_2$Me, and —NHAc substituents. Most preferably, $A_2$ is unsubstituted phenyl, chlorophenyl, fluorophenyl, methoxyphenyl, trifluoromethoxyphenyl, dimethylphenyl, methylsulphonylphenyl and acetaminophenyl.

As mentioned above, when W is CR$_8$ and Z is CR$_6$, $R_2$ may form, together with $R_6$ and the carbon and nitrogen atoms which connect $R_2$ and $R_6$ in the formula (I), a 5- to 6-membered heterocyclic ring. In this embodiment, the compound of formula (I) is of formula (Ic):

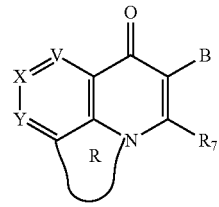

(Ic)

wherein B, V, X, Y, $R_1$, and $R_7$ are as defined herein and the ring R represents a 5- to 6-membered heterocyclic ring.

In addition to the nitrogen atom to which $R_2$ is bonded, said heterocyclic ring typically contains zero, one or two, preferably one, further heteroatoms selected from N and O, preferably O. Said heterocyclic ring is typically a 6-membered ring. Said heterocyclic ring is more preferably a piperidine or morpholine ring. Said heterocyclic ring is typically unsubstituted or substituted substituted with one or two substituents selected from halogen, $C_1$-$C_4$ alkyl and $C_1$-$C_4$ alkoxy substituents. Said heterocyclic ring is preferably substituted with one $C_1$-$C_4$ alkyl substituent, more preferably one $C_1$-$C_2$ alkyl substituent, most preferably a methyl substituent.

In a preferred embodiment, $R_2$ forms, together with $R_6$ and the carbon and nitrogen atoms which connect $R_2$ and $R_6$ in the formula (I), a morpholine or piperidine group, said morpholine and piperidine groups being unsubstituted or substituted with a $C_1$-$C_2$ alkyl group.

In one particularly preferred embodiment, said heterocyclic ring is a piperidine ring substituted with a methyl group. In this embodiment, said compound of formula (I) is preferably a compound of formula (Ic'):

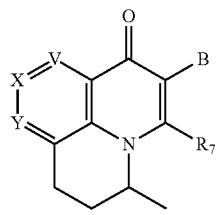

(Ic')

wherein B, V, X, Y, $R_1$, and $R_7$ are as defined herein.

In another particularly preferred embodiment, said heterocyclic ring is a morpholine ring substituted with a methyl group. In this embodiment, said compound of formula (I) is preferably a compound of formula (Id):

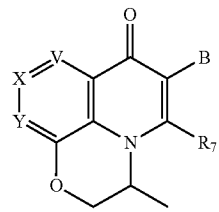

(Id)

wherein B, V, X, Y, $R_1$, and $R_7$ are as defined herein.

Typically, when W is CR$_8$, $R_2$ is a hydrogen atom, or a $C_1$-$C_6$ alkyl, phenyl, -L'-$A_2$, $C_3$-$C_6$ cycloalkyl, or —COOR' group, wherein R' is a hydrogen atom or $C_1$-$C_4$ alkyl group, or when Z is a moiety $CR_6$, $R_2$ may form, together with $R_6$ and the carbon and nitrogen atoms which connect $R_2$ and $R_6$ in the formula (I), a 5- to 6-membered heterocyclic ring, said cycloalkyl, phenyl and heterocyclic groups being typically unsubstituted or substituted with one or two substituents selected from halogen, $C_1$-$C_4$ alkyl and $C_1$-$C_4$ alkoxy substituents, L' is a $C_1$-$C_6$ alkylene group, and $A_2$ is a phenyl group, which is unsubstituted or substituted with one, two or three substituents selected from halogen, $C_1$-$C_4$ alkyl, $C_1$-$C_4$ alkoxy, $C_1$-$C_4$ haloalkyl, $C_1$-$C_4$ haloalkoxy, —$SO_2R$, and —NR'(C=O)R" substituents, wherein R, R' and R" are the same or different and each represents a hydrogen atom or $C_1$-$C_4$ alkyl group.

Preferably, when W is $CR_8$, $R_2$ is a hydrogen atom, or a $C_1$-$C_4$ alkyl, phenyl, $A_2$, $C_3$-$C_4$ cycloalkyl, or —COOR' group, wherein R' is a $C_1$-$C_4$ alkyl group, or when Z is a moiety $CR_6$, $R_2$ may form, together with $R_6$ and the carbon and nitrogen atoms which connect $R_2$ and $R_6$ in the formula (I), a 6-membered heterocyclic ring, said cycloalkyl group typically being unsubstituted, said heterocyclic ring typically being unsubstituted or substituted with one $C_1$-$C_4$ alkyl group, said phenyl group typically being substituted with one halogen substituent, L' is a $C_1$-$C_4$ alkylene group, and $A_2$ is a phenyl group, which is unsubstituted or substituted with one or two substituents selected from halogen, $C_1$-$C_2$ alkyl, $C_1$-$C_2$ alkoxy, $C_1$-$C_2$ haloalkyl, $C_1$-$C_2$ haloalkoxy —$SO_2R$, and —NH(C=O)R" substituents wherein R and R" are the same or different and each represents a $C_1$-$C_2$ alkyl group.

More preferably, when W is $CR_8$, $R_2$ is a hydrogen atom, or a $C_1$-$C_3$ alkyl, -L'-$A_2$, cyclopropyl, —COO$^t$Bu group, or a phenyl group which is unsubstituted or substituted with a fluorine atom, or when Z is a moiety $CR_6$, $R_2$ may form, together with $R_6$ and the carbon and nitrogen atoms which connect $R_2$ and $R_6$ in the formula (I), a morpholine or piperidine group, said morpholine and piperidine groups being unsubstituted or substituted with a $C_1$-$C_2$ alkyl group, L' is a —$CH_2$— group, and $A_2$ is a phenyl group which is unsubstituted or substituted by one or two substituents selected from chlorine, fluorine, $C_1$-$C_2$ alkyl, $C_1$-$C_2$ alkoxy, $CF_3O$—, —$SO_2Me$, and —NHAc substituents.

Typically, $R_3$ is a hydrogen atom, or —NR'R" group, wherein R' and R" are the same or different and each represent a hydrogen atom or $C_1$-$C_4$ alkyl group.

Preferably, $R_3$ is hydrogen or —$NH_2$.

$R_4$ and $R_5$ may form, together with the carbon atoms bonded to $R_4$ and $R_5$, a 5- to 6-membered heterocyclic ring. Said heterocyclic ring typically contains one, two or three, preferably two, heteroatoms selected from N and O, preferably O. Said heterocyclic ring is typically a 5-membered ring. Said heterocyclic ring is preferably a dioxolane ring, more preferably a 1,3-dioxolane ring. Said heterocyclic ring is preferably unsubstituted. In one particularly preferred embodiment, said heterocyclic ring is an unsubstituted 1,3-dioxolane ring. In this embodiment, said compound of formula (I) is preferably a compound of formula (Ie):

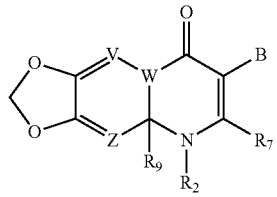

(Ie)

wherein W, Z, $R_1$, $R_2$, $R_3$, $R_7$ and $R_9$ are as defined herein.

Typically, when $R_4$ and $R_5$ form, together with the carbon atoms bonded to $R_4$ and $R_5$, a 5- to 6-membered heterocyclic ring, then $R_2$ does not form, together with $R_6$ and the carbon and nitrogen atoms which connect $R_2$ and $R_6$ in the formula (I), a 5- to 6-membered heterocyclic ring.

Typically, $R_4$ is a hydrogen atom, a halogen atom, or a hydroxy, $C_1$-$C_8$ alkyl, $C_1$-$C_8$ haloalkyl, $C_1$-$C_6$ alkoxy, $C_1$-$C_6$ haloalkoxy, nitro, —NR'R", —$CO_2$R'", 5- to 10-membered heteroaryl, $C_6$-$C_{10}$ aryl or —CO—($C_1$-$C_6$ alkyl) group, wherein R', R" and R'" are the same or different and each represent a hydrogen atom or $C_1$-$C_6$ alkyl group, or when Y is a moiety $CR_5$, $R_4$ may form, together with $R_5$ and the carbon atoms bonded to $R_4$ and $R_5$, a 5- to 6-membered heterocyclic ring.

Preferably, $R_4$ is a hydrogen atom, a halogen atom, or a $C_1$-$C_8$ alkyl, $C_1$-$C_4$ alkoxy, $C_1$-$C_4$ haloalkoxy, nitro, —NR'R", —$CO_2$R'", 5- to 6-membered heteroaryl, $C_6$-$C_{10}$ aryl or —CO—($C_1$-$C_4$ alkyl) group, wherein R', R" and R'" are the same or different and each represent a hydrogen atom or $C_1$-$C_4$ alkyl group, or when Y is a moiety $CR_5$, $R_4$ may form, together with $R_5$ and the carbon atoms bonded to $R_4$ and $R_5$, a 5- to 6-membered heterocyclic ring, said heterocyclic and heteroaryl groups being unsubstituted or substituted with one or two substituents selected from halogen, $C_1$-$C_4$ alkyl and $C_1$-$C_4$ alkoxy substituents, said aryl groups being unsubstituted or substituted with one or two substitutents selected from halogen, $C_1$-$C_4$ alkyl, $C_1$-$C_4$ hydroxyalkyl, $C_1$-$C_4$ alkoxy, —NR'(C=O)R", or —COOR substituents, wherein R, R' and R" are the same or different and each represents a hydrogen atom or $C_1$-$C_4$ alkyl group.

More preferably, $R_4$ is a hydrogen atom, a halogen atom, or a $C_1$-$C_6$ alkyl, $C_1$-$C_2$ alkoxy, $C_1$-$C_2$ haloalkoxy, nitro, —NR'R", —$CO_2$R'", 5- or 6-membered heteroaryl, phenyl or —CO—($C_1$-$C_2$ alkyl) group, wherein R' and R" are the same or different and each represent a $C_1$-$C_4$ alkyl group, and R'" is a hydrogen atom, or when Y is a moiety $CR_5$, $R_4$ may form, together with $R_5$ and the carbon atoms bonded to $R_4$ and $R_5$, a 5-membered heterocyclic ring, wherein the 5-membered heterocyclic and 5- or 6-membered heteroaryl groups are unsubstituted and the phenyl group is unsubstituted or substituted with a $C_1$-$C_2$ hydroxyalkyl, —NH(C=O)R", or —COOR substituent, wherein R and R" are the same or different and each represents a $C_1$-$C_2$ alkyl group.

Most preferably, $R_4$ is a hydrogen, bromine or fluorine atom, or a $C_1$-$C_6$ alkyl, methoxy, trifluoromethoxy, nitro, —$NMe_2$, —$CO_2H$, unsubstituted thiophene, unsubstituted pyridine, phenyl or —COMe group, or when Y is a moiety $CR_5$, $R_4$ may form, together with $R_5$ and the carbon atoms bonded to $R_4$ and $R_5$, an unsubstituted 1,3-dioxolane group, said phenyl group being substituted with one —COOH, —$CH_2OH$ or —NH(C=O)Me substituent.

Typically, $R_4$ is a bromine atom, or a $C_6$-$C_{10}$ aryl or 5- to 10-membered heteroaryl group, said aryl and heteroaryl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —$SO_2R$, —NR'(C=O)R", —COOR, nitro and cyano substituents, wherein R, R' and R" are the same or different and each represents a hydrogen atom or $C_1$-$C_4$ alkyl group.

Preferably, $R_4$ is a bromine atom, or a 5- to 10-membered heteroaryl or $C_6$-$C_{10}$ aryl group, said heteroaryl groups being unsubstituted or substituted with one or two substituents selected from halogen, $C_1$-$C_4$ alkyl and $C_1$-$C_4$ alkoxy substituents, and said aryl groups being unsubstituted or substituted with one or two substitutents selected from halogen, $C_1$-$C_4$ alkyl, $C_1$-$C_4$ hydroxyalkyl, $C_1$-$C_4$ alkoxy, —NR'(C=O)R", or —COOR substituents, wherein R, R' and R" are the same or different and each represents a hydrogen atom or $C_1$-$C_4$ alkyl group.

More preferably, $R_4$ is a bromine atom, or a 5- or 6-membered heteroaryl or phenyl group, wherein the 5- or 6-membered heteroaryl groups are unsubstituted and the phenyl group is unsubstituted or substituted with a $C_1$-$C_2$ hydroxyalkyl, —NH(C=O)R", or —COOR substituent, wherein R and R" are the same or different and each represents a hydrogen atom or $C_1$-$C_2$ alkyl group.

Most preferably, $R_4$ is a bromine atom, or an unsubstituted thiophene group, an unsubstituted pyridine group or a phenyl group which is substituted with one —COOH, —$CH_2OH$ or —NH(C=O)Me substituent.

$R_4$ and/or $R_5$ may be a 5 to 10-membered heterocyclyl group. Said group is typically a monocyclic or bicyclic, saturated $C_5$-$C_{10}$ carbocyclic ring in which one or more, for example 1 or 2 of the carbon atoms are replaced with a moiety selected from N, O, and S, preferably N and O. Examples of such groups include piperidine, piperazine and octahydro-1H-pyrrolo[3,4-b]pyridine. Said heterocyclyl group is typically 6 to 9-membered. Said heterocyclyl group is typically unsubstituted or substituted with one, two or three substituents selected from halogen atoms, $C_1$-$C_4$ alkyl and hydroxy groups, preferably one or two substituents selected from $C_1$-$C_2$ alkyl and hydroxy groups. Particularly preferred examples are unsubstituted octahydro-1H-pyrrolo[3,4-b]pyridine, unsubstituted piperazine, N-methyl-piperazine, dimethylpiperazine, and hydroxypiperidine.

Typically, when $R_5$ is a 5 to 10-membered heterocyclyl group, $R_4$ is other than a 5 to 10-membered heterocyclyl group.

Typically, $R_5$ is a hydrogen atom, a halogen atom, or a $C_1$-$C_6$ alkyl, $C_1$-$C_6$ haloalkyl, 5 to 10-membered heterocyclyl, or —$CO_2R'$ group, wherein R' is a hydrogen atom or $C_1$-$C_6$ alkyl group, or when X is a moiety $CR_4$, $R_5$ may form, together with $R_4$ and the carbon atoms bonded to $R_4$ and $R_5$, a 5- to 6-membered heterocyclic ring.

Preferably, $R_5$ is a hydrogen atom, or a $C_1$-$C_4$ alkyl, $C_1$-$C_4$ haloalkyl, 5 to 10-membered heterocyclyl, or —$CO_2R'$ group, wherein R' is a hydrogen atom or a $C_1$-$C_4$ alkyl group, or when X is a moiety $CR_4$, $R_5$ may form, together with $R_4$ and the carbon atoms bonded to $R_4$ and $R_5$, a 5- to 6-membered heterocyclic ring, said heterocyclicgroups typically being unsubstituted or substituted with one or two substituents selected from halogen, hydroxyl, $C_1$-$C_4$ alkyl and $C_1$-$C_4$ alkoxy substituents.

More preferably, $R_5$ is a hydrogen atom, or a $C_1$-$C_2$ alkyl, $C_1$-$C_2$ haloalkyl, 6 to 9-membered heterocyclyl, or —$CO_2H$ group, said 6 to 9-membered heterocyclyl group typically being unsubstituted or substituted with one or two substituents selected from hydroxyl and $C_1$-$C_2$ alkyl groups, or when X is a moiety $CR_4$, $R_5$ may form, together with $R_5$ and the carbon atoms bonded to $R_4$ and $R_5$, a 5-membered heterocyclic ring which is typically unsubstituted.

Most preferably, $R_5$ is a hydrogen atom, or a methyl, trifluoromethyl, unsubstituted octahydro-1H-pyrrolo[3,4-b]pyridine, unsubstituted piperazine, N-methyl-piperazine, dimethylpiperazine, hydroxypiperidine, or —$CO_2H$ group, or when X is a moiety $CR_4$, $R_5$ may form, together with $R_5$ and the carbon atoms bonded to $R_4$ and $R_5$, an unsubstituted 1,3-dioxolane group.

Typically, $R_6$ is a hydrogen atom, a halogen atom, or a $C_1$-$C_6$ alkyl, $C_1$-$C_6$ alkoxy, or —$CO_2R'$ group, wherein R' is a hydrogen atom or $C_1$-$C_4$ alkyl group, or when W is a moiety $CR_8$, $R_6$ may form, together with $R_2$ and the carbon and nitrogen atoms which connect $R_6$ and $R_2$ in the formula (I), a 5- to 6-membered heterocyclic ring, said heterocyclic ring being typically unsubstituted or substituted with one or two substituents selected from halogen, $C_1$-$C_4$ alkyl and $C_1$-$C_4$ alkoxy substituents.

Preferably, $R_6$ is a hydrogen atom, a halogen atom, or a $C_1$-$C_4$ alkyl, $C_1$-$C_2$ alkoxy, or —$CO_2H$ group, or when W is a moiety $CR_8$, $R_6$ may form, together with $R_2$ and the carbon and nitrogen atoms which connect $R_6$ and $R_2$ in the formula (I), a 6-membered heterocyclic ring, said heterocyclic ring being unsubstituted or substituted with one $C_1$-$C_4$ alkyl substituent.

More preferably, $R_6$ is a hydrogen atom, or a $C_1$-$C_3$ alkyl, methoxy, or —$CO_2H$ group, or when W is a moiety $CR_8$, $R_6$ may form, together with $R_2$ and the carbon and nitrogen atoms which connect $R_6$ and $R_2$ in the formula (I), a morpholine or piperidine group, said morpholine and piperidine groups being unsubstituted or substituted with a methyl group.

Typically, $R_7$ is hydrogen.

Typically, not more than three of V, W, X, Y and Z are N.

Preferably, not more than two of V, W, X, Y and Z are N.

In a preferred embodiment, the compounds of formula (I) are of formula (If):

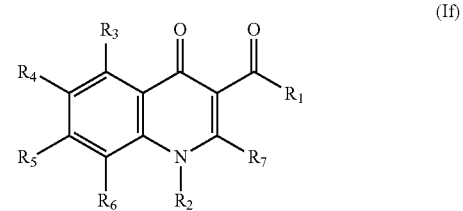

(If)

wherein $R_1$-$R_7$ are as defined herein.

In a further preferred embodiment, the compounds of formula (I) are of formula (Ig):

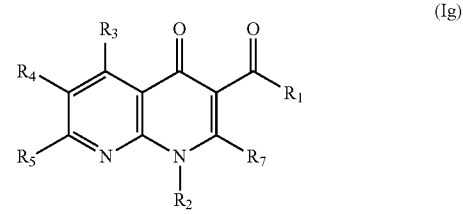

(Ig)

wherein $R_1$-$R_5$ and $R_7$ are as defined herein.

In a further preferred embodiment, the compounds of formula (I) are of formula (Ih):

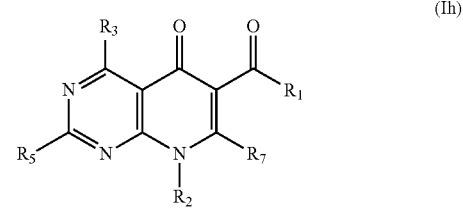

(Ih)

wherein $R_1$-$R_3$, $R_5$ and $R_7$ are as defined herein.

In a further preferred embodiment, the compounds of formula (I) are of formula (Ij):

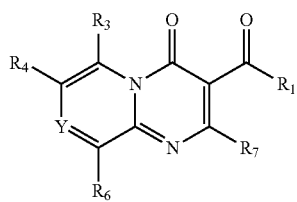

(Ij)

wherein Y, $R_1$, $R_3$, $R_4$, $R_6$ and $R_7$ are as defined herein.

Preferred compounds of the invention are compounds in which:
V is N or $CR_3$;
X is N or $CR_4$;
Y is N or $CR_5$;
Z is N or $CR_6$;
B is —(C=O)$R_1$, a 5- to 6-membered heteroaryl group, or -L'''-NHR', wherein R' is a hydrogen atom, a $C_1$-$C_4$ alkyl or $C_1$-$C_4$ haloalkyl group, said heteroaryl groups being unsubstituted or substituted with one or two substituents selected from halogen, $C_1$-$C_4$ alkyl and $C_1$-$C_4$ alkoxy substituents;
$R_1$ is a 5- to 10-membered heterocyclyl group, or —OR', wherein R', represents a hydrogen atom or $C_1$-$C_4$ alkyl group, or $R_1$ is a group of formula —NH—CHR$^{IV}$—CO$_2$R$^V$, wherein R$^V$ is a hydrogen atom or $C_1$-$C_6$ alkyl group, and R$^{IV}$ is a hydrogen atom, or a methyl, —(CH$_2$)$_3$—NH—(C=NH)—NH$_2$, —CH$_2$CONH$_2$, —CH$_2$CO$_2$H, —CH$_2$SH, —(CH$_2$)$_2$CO$_2$H, —(CH$_2$)$_2$CONH$_2$, —CH(CH$_3$)CH$_2$CH$_3$, CH$_2$CH(CH$_3$)$_2$, —(CH$_2$)$_4$NH$_2$, —(CH$_2$)$_2$SCH$_3$, —CH$_2$Ph, —CH$_2$OH, —CH(CH$_3$)OH, —CH$_2$-p-hydroxy-Ph, —CH(CH$_3$)$_2$, —CH$_2$SeH group, or a

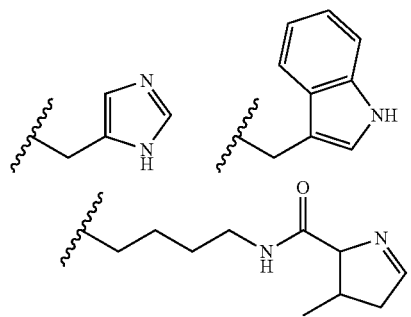

group, or $R_1$ is a group of formula NR$^{IV}$-L'''-COOR wherein R$^{IV}$ is a hydrogen atom and R is a hydrogen atom or a $C_1$-$C_4$ alkyl group, said heterocyclyl groups being unsubstituted or substituted with one or two substituents selected from halogen, $C_1$-$C_4$ alkyl and $C_1$-$C_4$ alkoxy substituents;
either (a) W is N and $R_9$ and $R_2$ together form a bond, or (b) W is $CR_8$, $R_8$ and $R_9$ together form a bond and $R_2$ is a hydrogen atom, or a $C_1$-$C_6$ alkyl, phenyl, -L'-$A_2$, $C_3$-$C_6$ cycloalkyl, or —COOR' group, wherein R' is a hydrogen atom or $C_1$-$C_4$ alkyl group, or when Z is a moiety $CR_6$, $R_2$ may form, together with $R_6$ and the carbon and nitrogen atoms which connect $R_2$ and $R_6$ in the formula (I), a 5- to 6-membered heterocyclic ring, said cycloalkyl, phenyl and heterocyclic groups being typically unsubstituted or substituted with one or two substituents selected from halogen, $C_1$-$C_4$ alkyl and $C_1$-$C_4$ alkoxy substituents;
$R_3$ is a hydrogen atom, or —NR'R'' group, wherein R' and R'' are the same or different and each represent a hydrogen atom or $C_1$-$C_4$ alkyl group;
$R_4$ is a hydrogen atom, a halogen atom, or a $C_1$-$C_8$ alkyl, $C_1$-$C_4$ alkoxy, $C_1$-$C_4$ haloalkoxy, nitro, —NR'R'', —CO$_2$R''', 5- to 6-membered heteroaryl, $C_6$-$C_{10}$ aryl or —CO—($C_1$-$C_4$ alkyl) group, wherein R', R'' and R''' are the same or different and each represent a hydrogen atom or $C_1$-$C_4$ alkyl group, or when Y is a moiety $CR_5$, $R_4$ may form, together with $R_5$ and the carbon atoms bonded to $R_4$ and $R_5$, a 5- to 6-membered heterocyclic ring, said heterocyclic and heteroaryl groups being unsubstituted or substituted with one or two substituents chosen from halogen, $C_1$-$C_4$ alkyl and $C_1$-$C_4$ alkoxy substituents, and said aryl groups being unsubstituted or substituted with one or two substituents selected from halogen, $C_1$-$C_4$ alkyl, $C_1$-$C_4$ hydroxyalkyl, $C_1$-$C_4$ alkoxy, —NR'(C=O)R'', or —COOR substituents, wherein R, R' and R'' are the same or different and each represents a hydrogen atom or $C_1$-$C_4$ alkyl group;
$R_5$ is a hydrogen atom, or a $C_1$-$C_4$ alkyl, $C_1$-$C_4$ haloalkyl, 5 to 10-membered heterocyclyl, or —CO$_2$R' group, wherein R' is a hydrogen atom or a $C_1$-$C_4$ alkyl group, or when X is a moiety $CR_4$, $R_5$ may form, together with $R_4$ and the carbon atoms bonded to $R_4$ and $R_5$, a 5- to 6-membered heterocyclic ring, said heterocyclic ring being typically unsubstituted or substituted with one or two substituents chosen from halogen, $C_1$-$C_4$ alkyl and $C_1$-$C_4$ alkoxy substituents;
$R_6$ is a hydrogen atom, a halogen atom, or a $C_1$-$C_6$ alkyl, $C_1$-$C_6$ alkoxy, or —CO$_2$R' group, wherein R' is a hydrogen atom or $C_1$-$C_4$ alkyl group, or when W is a moiety $CR_8$, $R_6$ may form, together with $R_2$ and the carbon and nitrogen atoms which connect $R_6$ and $R_2$ in the formula (I), a 5- to 6-membered heterocyclic ring, said heterocyclic ring being typically unsubstituted or substituted with one or two substituents selected from halogen, $C_1$-$C_4$ alkyl and $C_1$-$C_4$ alkoxy substituents;
$R_7$ is a hydrogen atom;
L' is a $C_1$-$C_6$ alkylene group;
L''' is a $C_2$-$C_6$ alkylene group;
$A_2$ is a phenyl group, said phenyl group being unsubstituted or substituted with one, two or three substituents selected from halogen, $C_1$-$C_4$ alkyl, $C_1$-$C_4$ alkoxy, $C_1$-$C_4$ haloalkyl, $C_1$-$C_4$ haloalkoxy, —SO$_2$R and —NR' (C=O)R'' substituents, wherein R, R' and R'' are the same or different and each represents a hydrogen atom or $C_1$-$C_4$ alkyl group; and
Further preferred compounds of the invention are compounds in which:
V is $CR_3$,
X is N or $CR_4$;
Y is N or $CR_5$;
Z is N or $CR_6$;
B is —(C=O)$R_1$, an oxadiazole or thiazole group, or -L'''-NHR', wherein R' is a hydrogen atom, a $C_1$-$C_4$ alkyl or $C_1$-$C_4$ haloalkyl group, said oxadiazole and thiazole groups being unsubstituted or substituted with one or two substituents selected from halogen, $C_1$-$C_2$ alkyl and $C_1$-$C_2$ alkoxy substituents;

$R_1$ is an unsubstituted 5-membered heterocyclyl group, or —OR', wherein R' is a hydrogen atom or $C_1$-$C_4$ alkyl group, or $R_1$ is a group of formula —NH—$CHR^{IV}$—$CO_2R^V$, wherein $R^V$ is a hydrogen atom or $C_1$-$C_6$ alkyl group, and $R^{IV}$ is a hydrogen atom, or a methyl, —$CH_2CH(CH_3)_2$, —$CH_2$-Ph or —$CH(CH_3)_2$ group, or $R_1$ is a group —NH—$(CH_2)_2$—COOR, where R is hydrogen or $C_1$-$C_4$ alkyl;

either (a) W is N and $R_9$ and $R_2$ together form a bond, or (b) W is $CR_8$, $R_8$ and $R_9$ together form a bond and $R_2$ is a hydrogen atom, or a $C_1$-$C_4$ alkyl, phenyl, -L'-$A_2$, $C_3$-$C_4$ cycloalkyl, or —COOR' group, wherein R' is a $C_1$-$C_4$ alkyl group, or when Z is a moiety $CR_6$, $R_2$ may form, together with $R_6$ and the carbon and nitrogen atoms which connect $R_2$ and $R_6$ in the formula (I), a 6-membered heterocyclic ring, said cycloalkyl group typically being unsubstituted, said heterocyclic ring typically being unsubstituted or substituted with one $C_1$-$C_4$ alkyl group, and said phenyl group typically being substituted with one halogen substituent;

$R_3$ is hydrogen or —$NH_2$;

$R_4$ is a hydrogen atom, a halogen atom, or a $C_1$-$C_6$ alkyl, $C_1$-$C_2$ alkoxy, $C_1$-$C_2$ haloalkoxy, nitro, —NR'R'', —$CO_2R'''$, 5- or 6-membered heteroaryl, phenyl or —CO—($C_1$-$C_2$ alkyl) group, wherein R' and R'' are the same or different and each represent a $C_1$-$C_4$ alkyl group, and R''' is a hydrogen atom, or when Y is a moiety $CR_5$, $R_4$ may form, together with $R_5$ and the carbon atoms bonded to $R_4$ and $R_5$, a 5-membered heterocyclic ring, wherein the 5-membered heterocyclic and 5- or 6-membered heteroaryl groups are unsubstituted and the phenyl group is unsubstituted or substituted with a $C_1$-$C_2$ hydroxyalkyl, —NH(C=O)R'' or —COOR substituent, wherein R and R'' are the same or different and each independently represents a hydrogen atom or $C_1$-$C_2$ alkyl group;

$R_5$ is a hydrogen atom, or a $C_1$-$C_2$ alkyl, $C_1$-$C_2$ haloalkyl, 6 to 9-membered heterocyclyl, or —$CO_2H$ group, said 6 to 9-membered heterocyclyl group being unsubstituted or substituted with one or two substituents selected from hydroxyl and $C_1$-$C_2$ alkyl groups, or when X is a moiety $CR_4$, $R_5$ may form, together with $R_5$ and the carbon atoms bonded to $R_4$ and $R_5$, a 5-membered heterocyclic ring, wherein the 5-membered heterocyclic group is typically unsubstituted;

$R_6$ is a hydrogen atom, a halogen atom, or a $C_1$-$C_4$ alkyl, $C_1$-$C_2$ alkoxy, or —$CO_2H$ group, or when W is a moiety $CR_8$, $R_6$ may form, together with $R_2$ and the carbon and nitrogen atoms which connect $R_6$ and $R_2$ in the formula (I), a 6-membered heterocyclic ring, said heterocyclic group being unsubstituted or substituted with one $C_1$-$C_4$ alkyl substituent;

$R_7$ is a hydrogen atom;

L' is a $C_1$-$C_4$ alkylene group;

$A_2$ is a phenyl group, which group is unsubstituted or substituted with one or two substituents selected from halogen, $C_1$-$C_2$ alkyl, $C_1$-$C_2$ haloalkyl, $C_1$-$C_2$ alkoxy, $C_1$-$C_2$ haloalkoxy, —$SO_2R$ and —NH(C=O)R'' substituents wherein R and R'' are the same or different and each independently represents a $C_1$-$C_2$ alkyl group;

Most preferably, compounds of the invention are compounds in which:

V is $CR_3$;

X, Y and Z are as defined herein;

B is —(C=O)$R_1$;

$R_1$ is

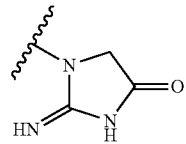 [SMILES: *N1CC(=O)NC1=N]

or —OR' wherein R' is a hydrogen atom or $C_1$-$C_2$ alkyl group, or $R_1$ is a group of formula —NH—CHR—$CO_2R''$, wherein R'' is a hydrogen atom or $C_1$-$C_4$ alkyl group, and R is a hydrogen atom, or a methyl, —$CH_2CH(CH_3)_2$, —$CH_2$-Ph or —$CH(CH_3)_2$ group, or $R_1$ is —NH—$(CH_2)_2$COOH or —NH—$(CH_2)_2$$COOCH_3$;

either (a) W is N and $R_9$ and $R_2$ together form a bond, or (b) W is $CR_8$, $R_8$ and $R_9$ together form a bond and $R_2$ is a hydrogen atom, or a $C_1$-$C_3$ alkyl, -L'-$A_2$, cyclopropyl, —COO'Bu group, or a phenyl group which is unsubstituted or substituted with a fluorine atom, or when Z is a moiety $CR_6$, $R_2$ may form, together with $R_6$ and the carbon and nitrogen atoms which connect $R_2$ and $R_6$ in the formula (I), a morpholine or piperidine group, said morpholine and piperidine groups being unsubstituted or substituted with a $C_1$-$C_2$ alkyl group, L' is a —$CH_2$— group, and $A_2$ is a phenyl group which is unsubstituted or substituted by one or two substituents selected from chlorine, fluorine, $C_1$-$C_2$ alkyl, $C_1$-$C_2$ alkoxy, $CF_3O$—, —NHAc or —$SO_2Me$ substituents;

V is $CR_3$;

$R_3$ is hydrogen or —$NH_2$;

$R_4$ is a hydrogen, bromine or fluorine atom, or a $C_1$-$C_6$ alkyl, methoxy, trifluoromethoxy, nitro, —$NMe_2$, —$CO_2H$, —COMe, unsubstituted thiophene, unsubstituted pyridine, or phenyl group, which phenyl group is unsubstituted or substituted by a substituent selected from —COOH, —$CH_2OH$ and —NHAc; or when Y is a moiety $CR_5$, $R_4$ may form, together with $R_5$ and the carbon atoms bonded to $R_4$ and $R_5$, an unsubstituted 1,3-dioxolane group;

$R_5$ is a hydrogen atom, or a methyl, trifluoromethyl, unsubstituted octahydro-1H-pyrrolo[3,4-b]pyridine, unsubstituted piperazine, N-methyl-piperazine, dimethylpiperazine, hydroxypiperidine, or —$CO_2H$ group, or when X is a moiety $CR_4$, $R_5$ may form, together with $R_5$ and the carbon atoms bonded to $R_4$ and $R_5$, an unsubstituted 1,3-dioxolane group;

$R_6$ is a hydrogen atom, or a $C_1$-$C_3$ alkyl, methoxy, or —$CO_2H$ group, or when W is a moiety $CR_8$, $R_6$ may form, together with $R_2$ and the carbon and nitrogen atoms which connect $R_6$ and $R_2$ in the formula (I), a morpholine or piperidine group, said morpholine and piperidine groups being unsubstituted or substituted with a methyl group; and $R_7$ is a hydrogen atom.

Typically, in compounds of formula (If),

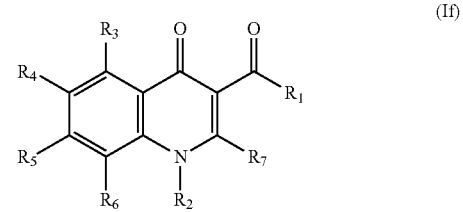

(If)

$R_1$ is —OR', wherein R' is a hydrogen atom or $C_1$-$C_4$ alkyl group, or $R_1$ is a group of formula —NH—$CHR^{IV}$—$CO_2R^V$, wherein $R^V$ is a hydrogen atom or $C_1$-$C_4$ alkyl group, and $R^{IV}$ is a hydrogen atom, —$CH(CH_3)CH_2CH_3$, —$CH_2Ph$, or —$CH(CH_3)_2$ group;

$R_2$ is a hydrogen atom, or a -L'-$A_2$, group, L' is a $C_1$-$C_4$ alkylene group and $A_2$ is a phenyl group, said phenyl group being unsubstituted or substituted with one, two or three substituents selected from halogen, $C_1$-$C_4$ alkyl, $C_1$-$C_4$ alkoxy, $C_1$-$C_4$ haloalkyl, and $C_1$-$C_4$ haloalkoxy substituents;

$R_3$ is a hydrogen atom;
$R_4$ is a hydrogen atom, or a halogen atom;
$R_5$ is a hydrogen atom;
$R_6$ is a hydrogen atom; and
$R_7$ is a hydrogen atom.

Preferably, in compounds of formula (If):

$R_1$ is —OH, or $R_1$ is a group of formula —NH—$CHR^{IV}$—$CO_2R^V$, wherein $R^V$ is a hydrogen atom or $^tButyl$ group, and $R^{IV}$ is a hydrogen atom, —$CH(CH_3)CH_2CH_3$, —$CH_2Ph$, or —$CH(CH_3)_2$ group;

$R_2$ is a hydrogen atom, or a -L'-$A_2$, group, L' is an ethylene group and $A_2$ is an unsubstituted phenyl group;

$R_3$ is a hydrogen atom;
$R_4$ is a hydrogen atom, or a bromine atom;
$R_5$ is a hydrogen atom;
$R_6$ is a hydrogen atom; and
$R_7$ is a hydrogen atom.

Preferably, in compounds of formula (If):

(a) $R_1$ is a group of formula —NH—$CHR^{IV}$—$CO_2R^V$, wherein $R^V$ is a hydrogen atom or $^tButyl$ group, and $R^{IV}$ is a hydrogen atom, —$CH(CH_3)CH_2CH_3$, —$CH_2Ph$, or —$CH(CH_3)_2$ group;

(b) $R_2$ is a -L'-$A_2$, group, L' is an ethylene group and $A_2$ is an unsubstituted phenyl group; or (c) $R_4$ is a bromine atom.

More preferably, in compounds of formula (If):

(a) $R_1$ is a group of formula —NH—$CHR^{IV}$—$CO_2R^V$, wherein $R^V$ is a hydrogen atom or $^tButyl$ group, and $R^{IV}$ is a hydrogen atom, —$CH(CH_3)CH_2CH_3$, —$CH_2Ph$, or —$CH(CH_3)_2$ group;

(b) $R_2$ is a -L'-$A_2$, group, L' is an ethylene group and $A_2$ is an unsubstituted phenyl group; and (c) $R_4$ is a bromine atom.

Preferred compounds of the invention are

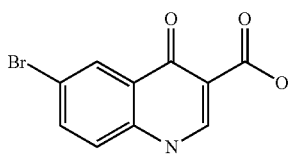

6

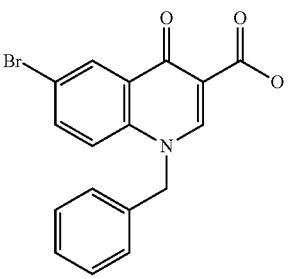

27

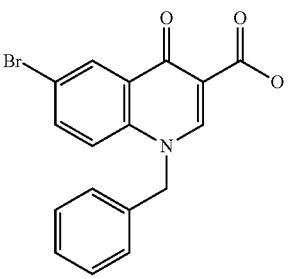

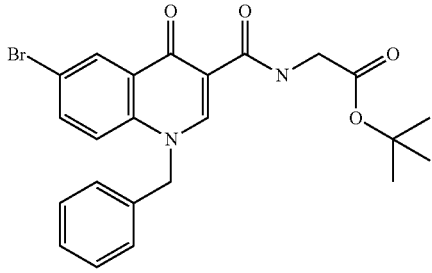

28

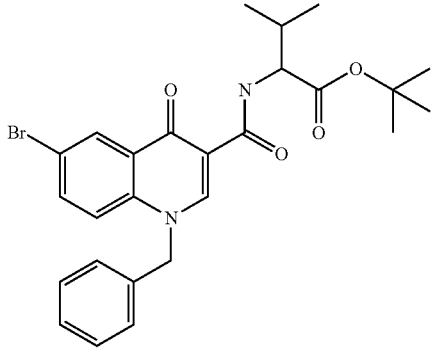

63

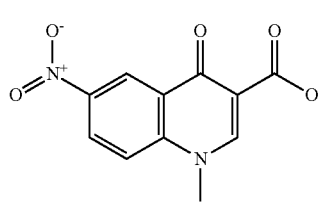

29

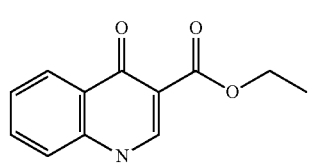

84

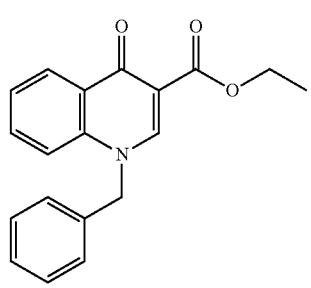

85

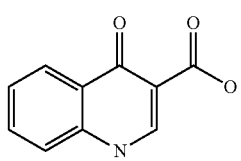

57

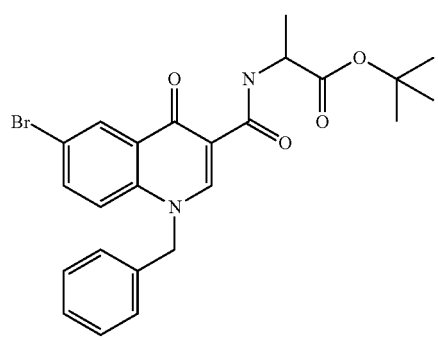
59
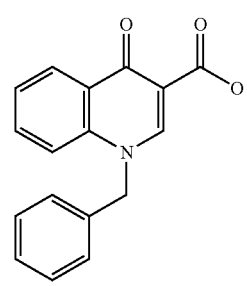
86
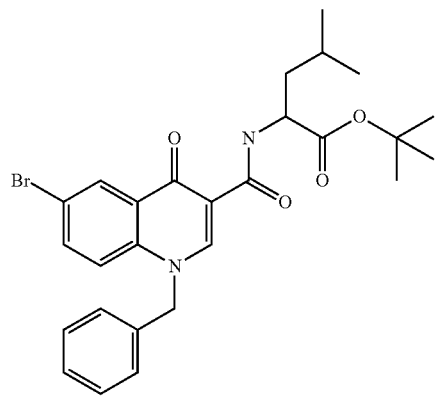
60
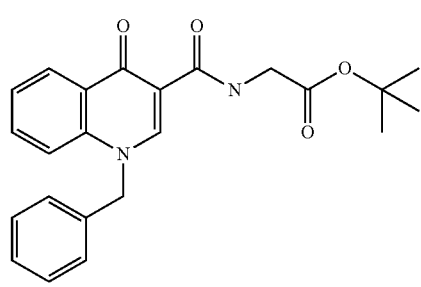
87
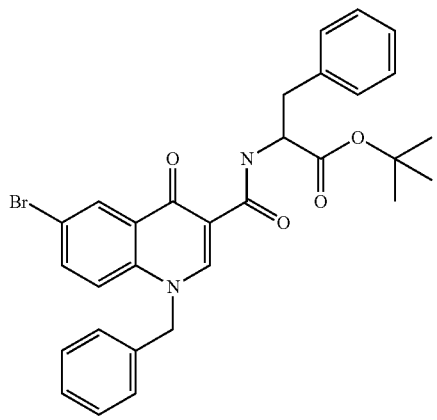
61
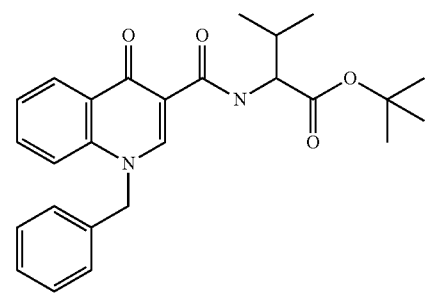
88
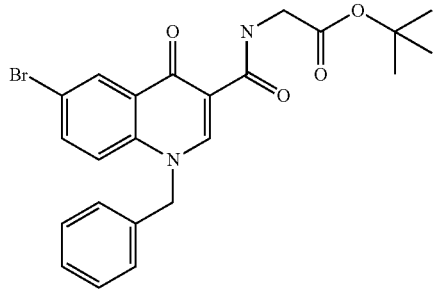
62
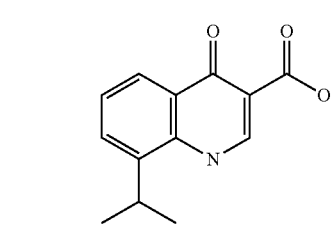
103
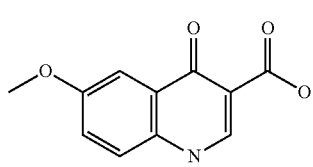
104

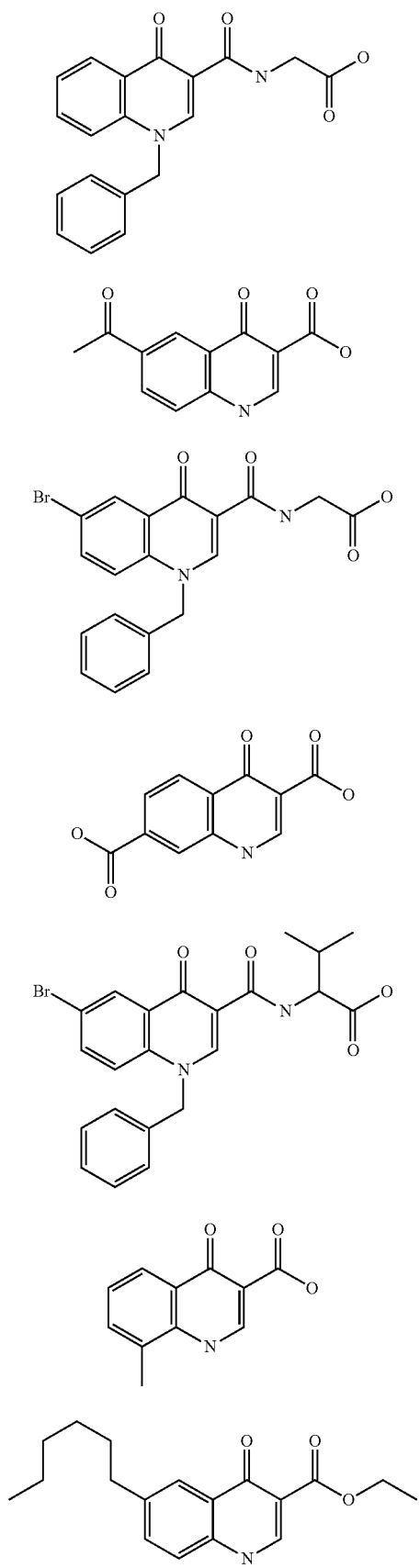

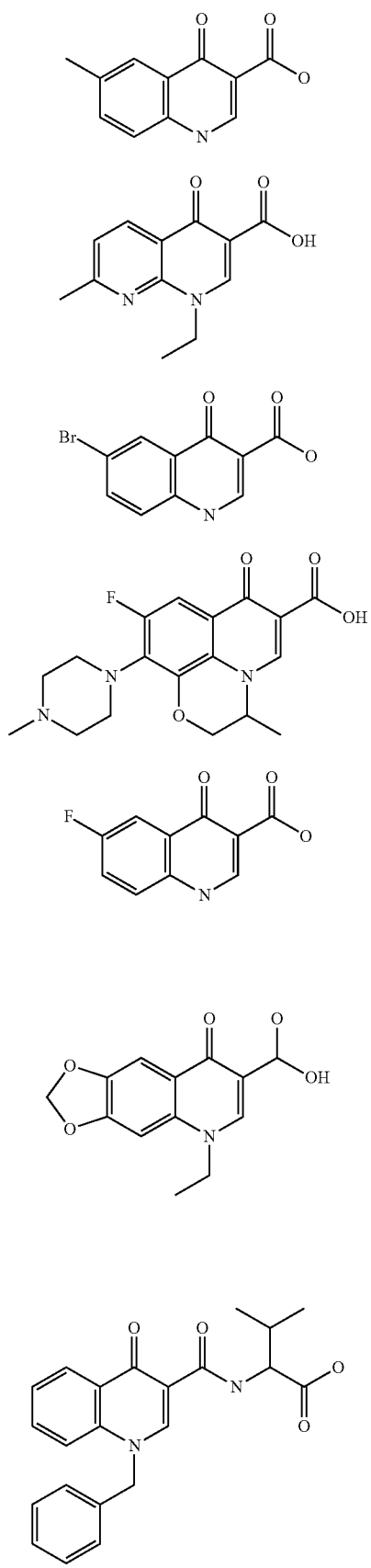

-continued
154
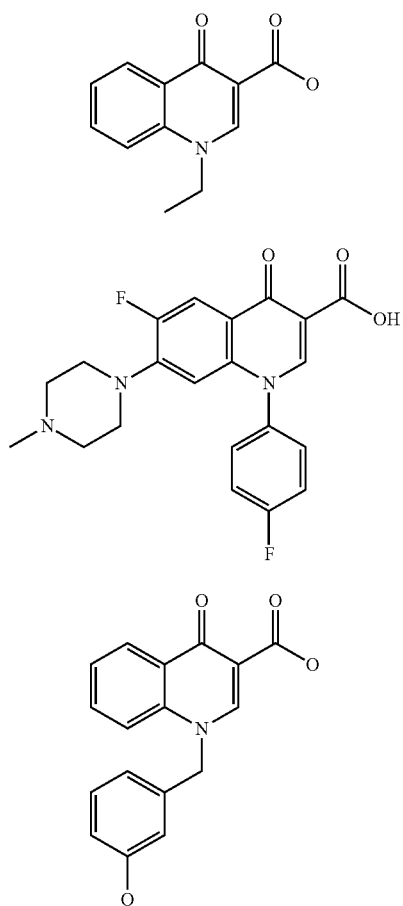
144
155
147
156
-continued
148
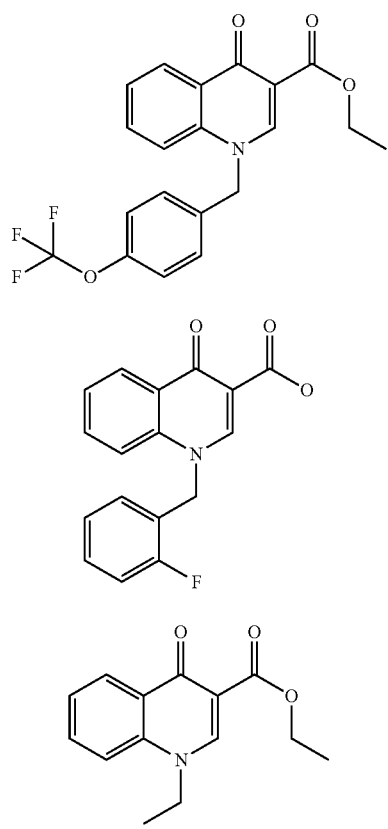
157
149
158
150

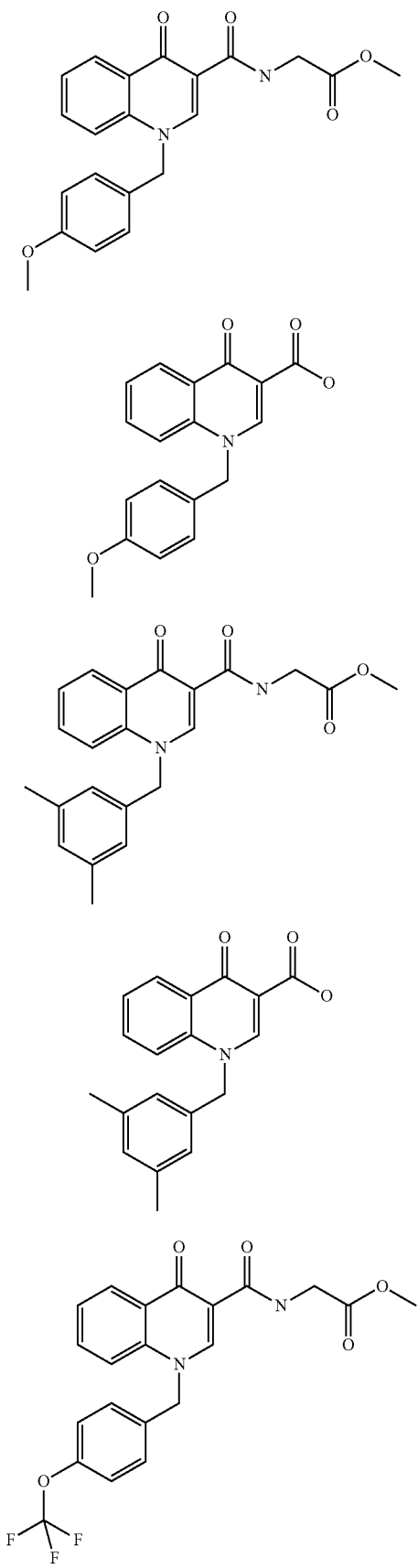
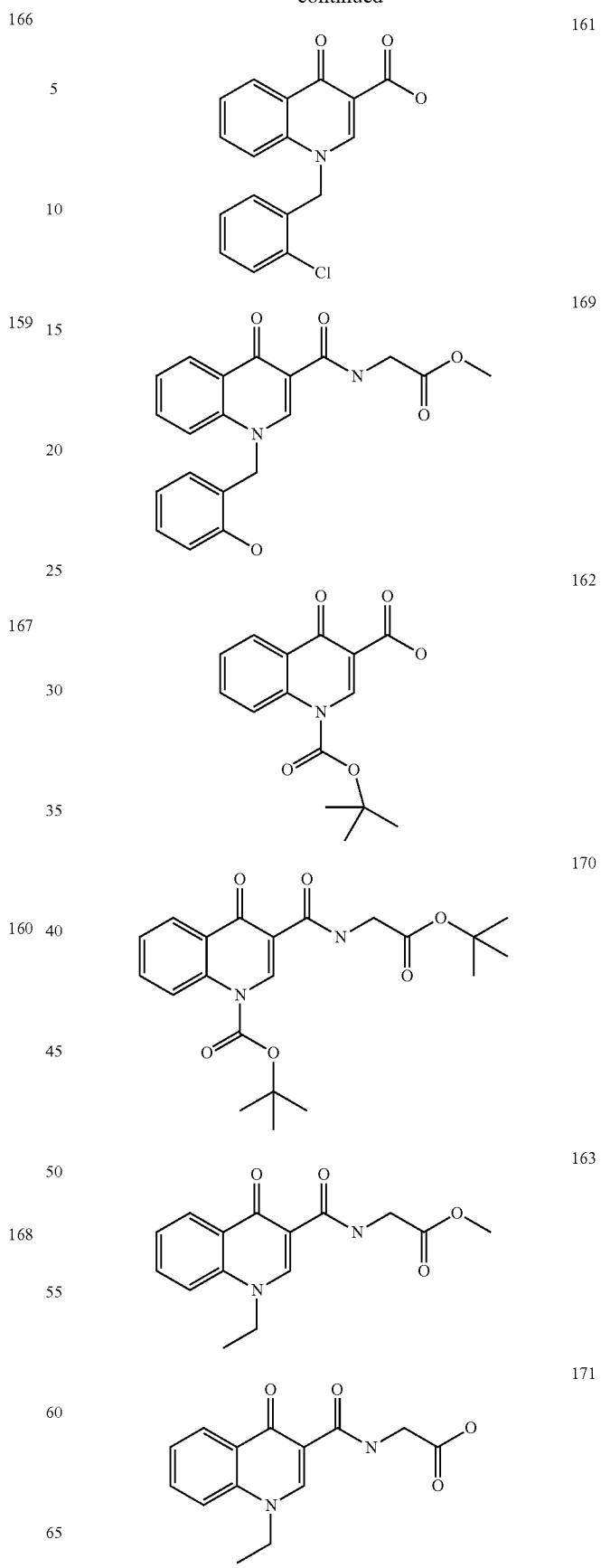

164
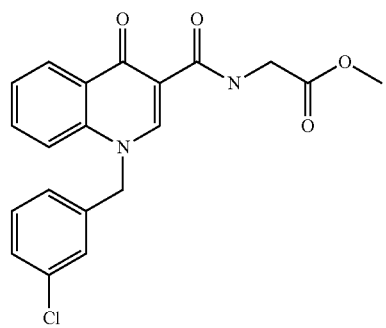
172
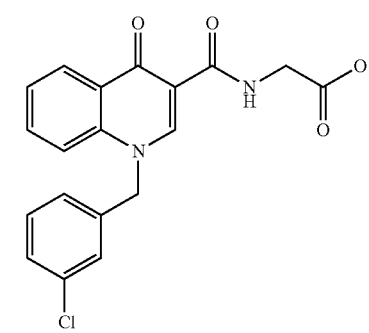
165
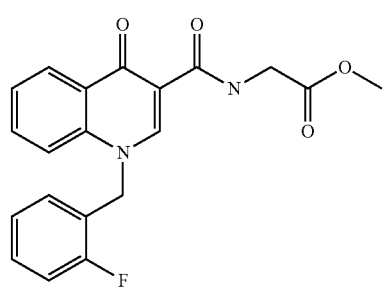
173
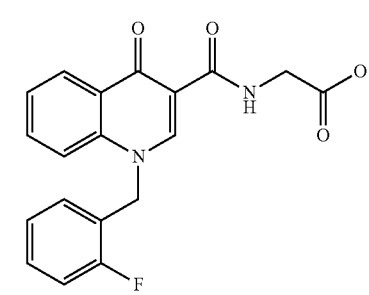
174
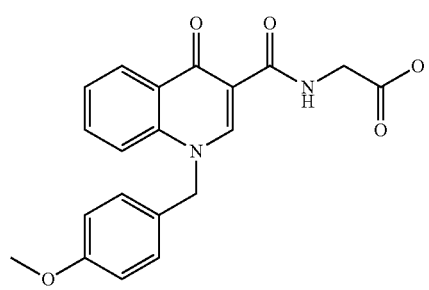
184
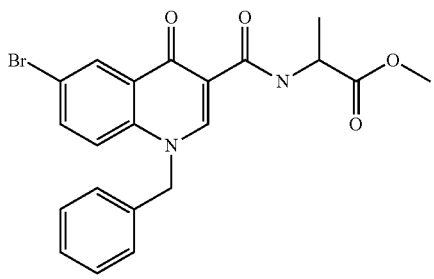
175
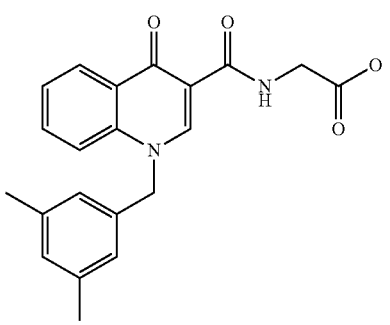
185
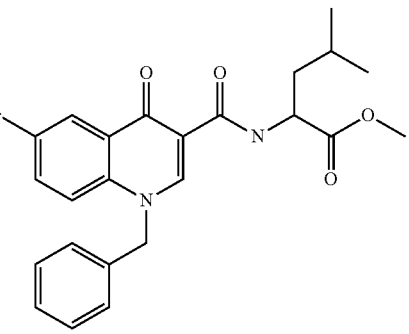
176
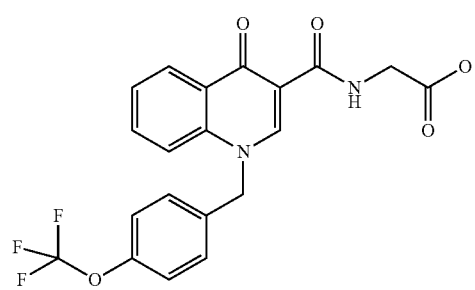
186
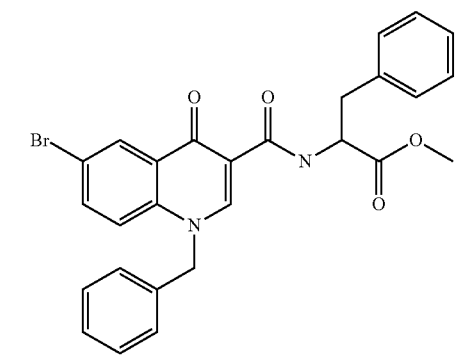

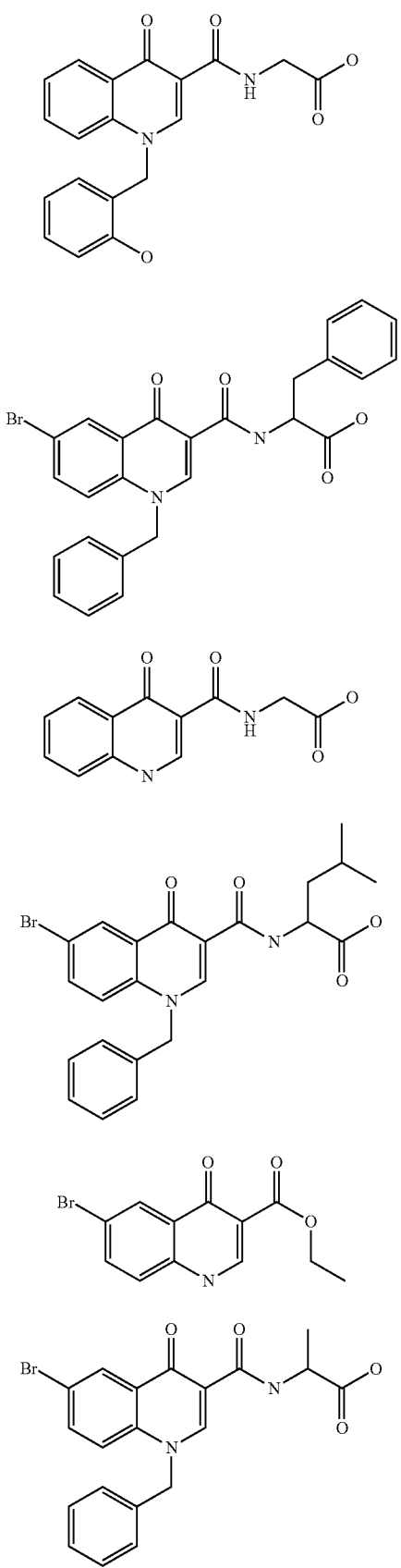
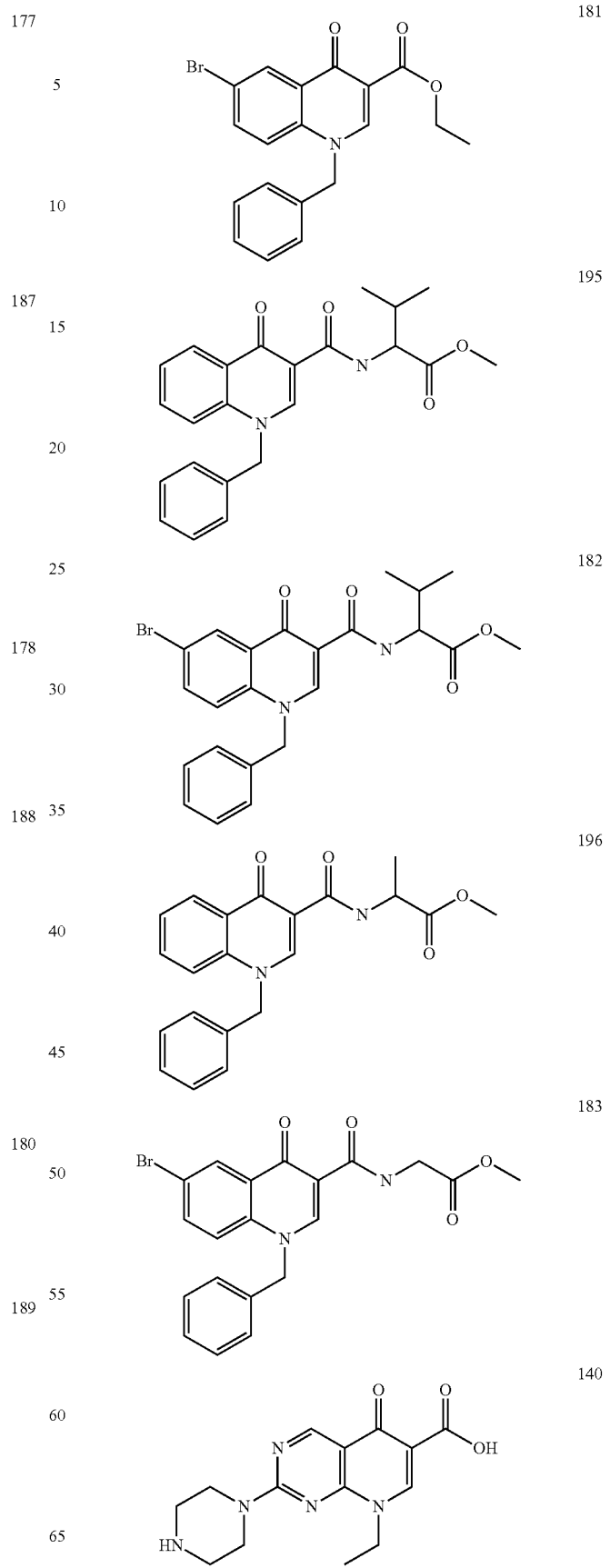

-continued
197
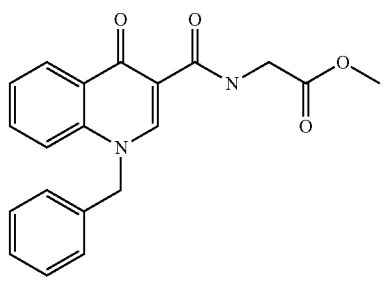
198
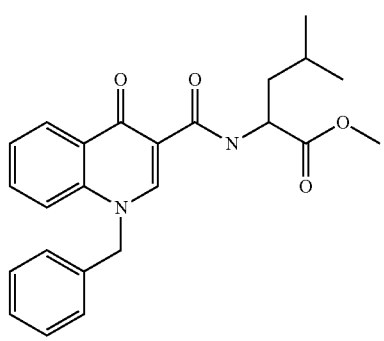
199
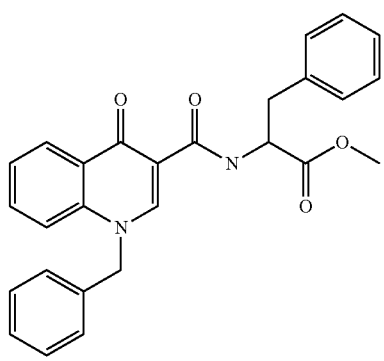
64
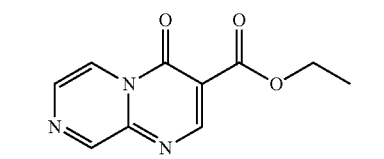
200
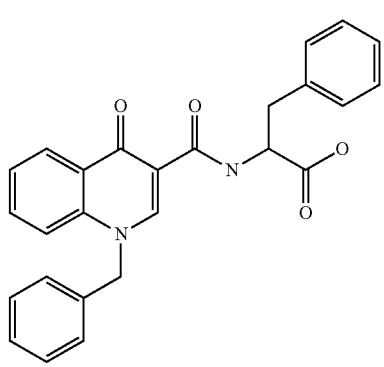
65
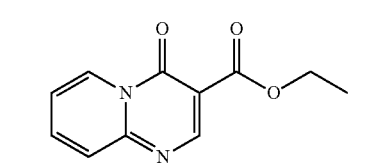
-continued
201
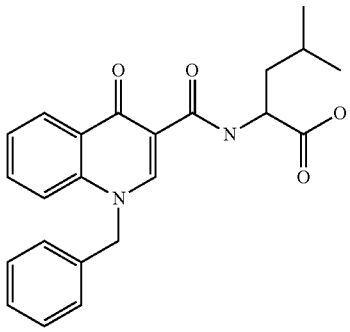
81
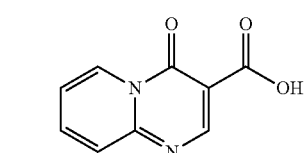
202
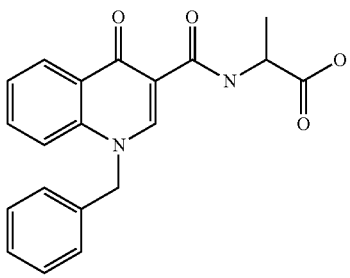
120
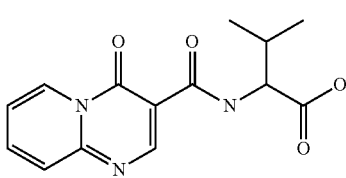
82
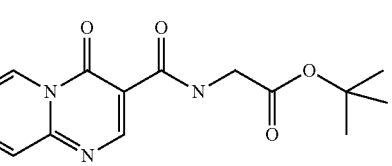
194
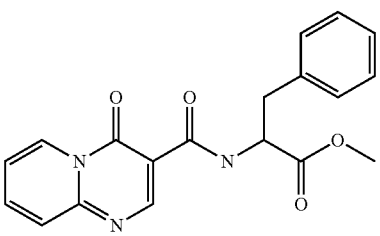
83
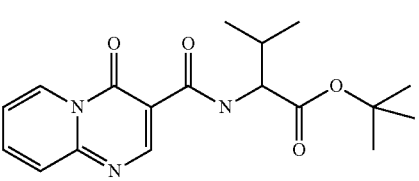

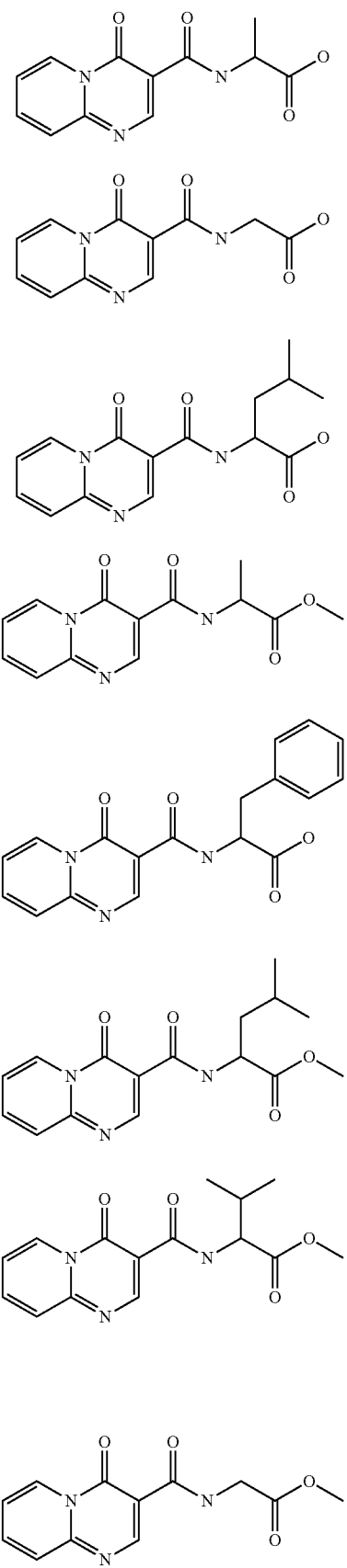
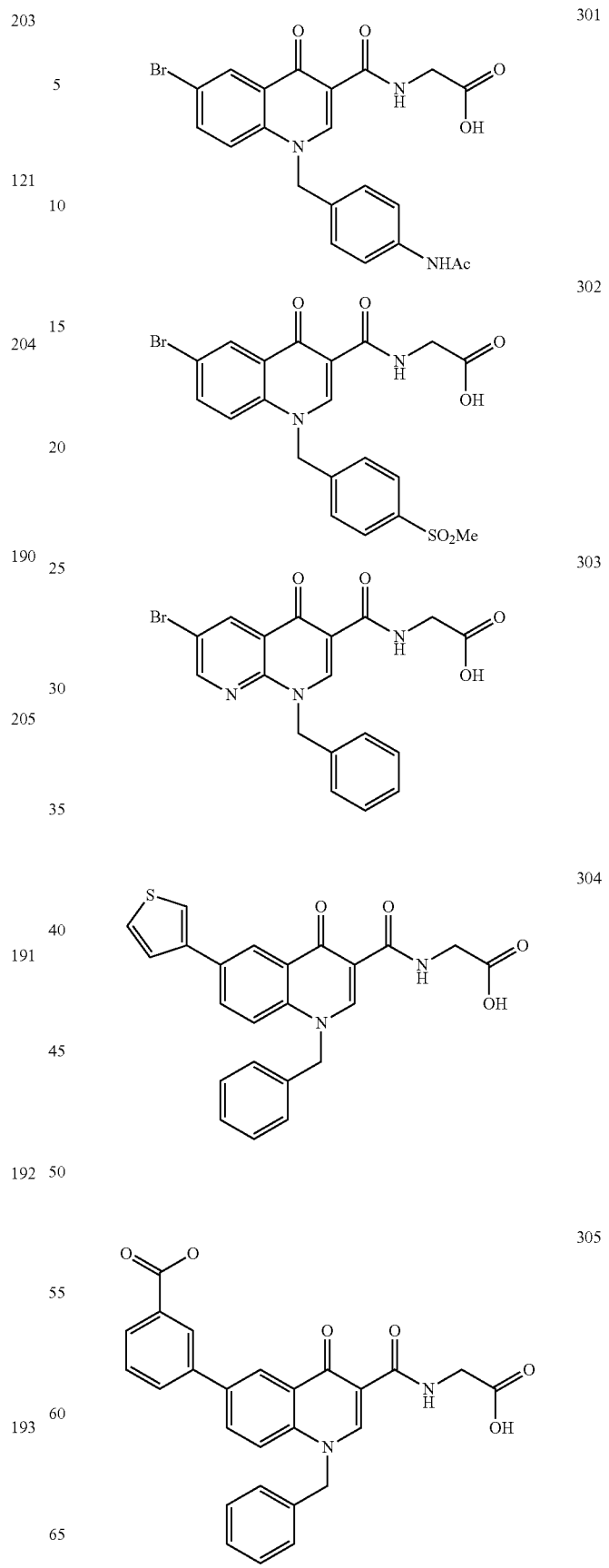

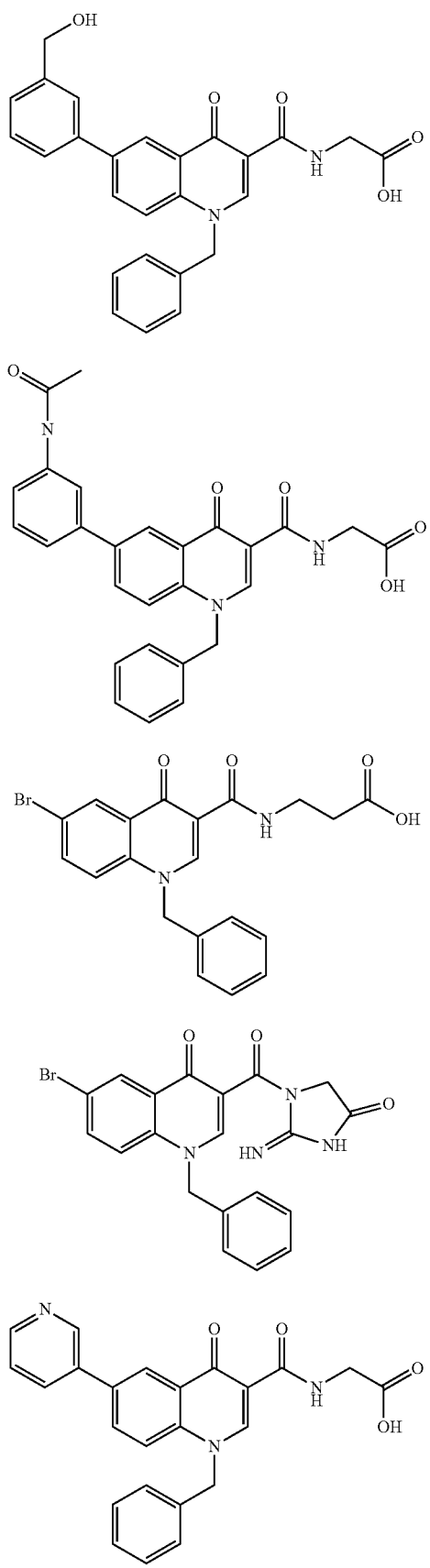

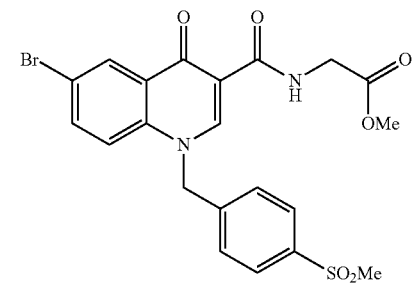

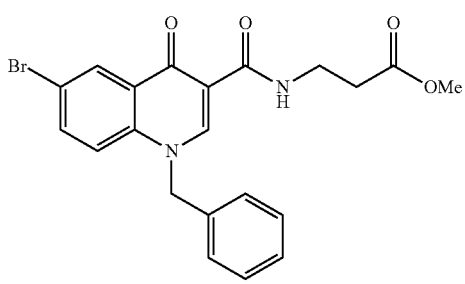

tautomers thereof, pharmaceutically acceptable salts thereof, and/or N-oxides thereof.

Particularly preferred compounds are compounds 28, 57, 59, 60, 61, 62, 63, 85, 87, 88, 103, 104, 105, 106, 107, 108, 109, 110, 111, 112, 113, 114, 116, 117, 118, 119, 134, 139, 142, 178, 187, 202, 200, 189, 301, 302, 303, 304, 305, 306, 307, 308, 309, 310, 311 and 312, tautomers thereof, pharmaceutically acceptable salts thereof, and/or N-oxides thereof.

Compounds 28, 61, 63, 88, 111, 112, 114, 116, 117, 118, 119, 134 and 187, tautomers thereof, pharmaceutically acceptable salts thereof, and/or N-oxides thereof are more preferred.

Compounds 28, 118 and 187, tautomers thereof, pharmaceutically acceptable salts thereof, and/or N-oxides thereof are even more preferred.

Compounds 28, 118, tautomers thereof, pharmaceutically acceptable salts thereof, and/or N-oxides thereof are particularly preferred.

Compounds of the invention can be made in accordance with known methods.

When W is $CR_8$, and $R_8$ and $R_9$ together form a bond, compounds of formula I'' can be prepared following the reaction scheme below.

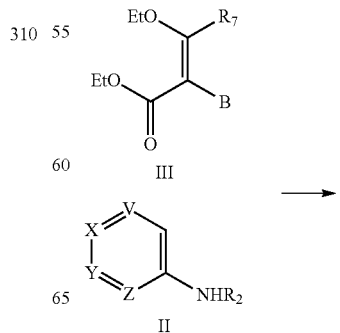

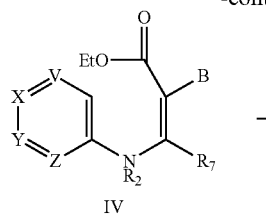 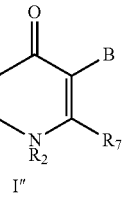

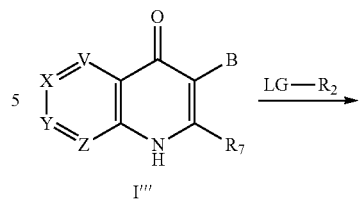 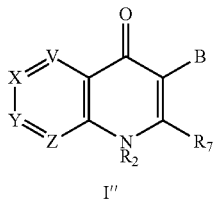

wherein B, V, X, Y, Z, $R_2$ and $R_7$ are as defined herein, provided that $R_2$ together with $R_6$ and the carbon and nitrogen atoms which connect $R_2$ and $R_6$ so not form a 5- to 6-membered heterocyclic ring. The first step of the reaction is typically carried out at 120-130 degrees C. for between 2 and 3 hours. The second step of the reaction is typically carried out by refluxing in diphenyl ether for 8 hours. Compounds of formula II and III are typically commercially available or can be prepared by analogy with known methods.

When W is N, and $R_2$ and $R_9$ are linked to form a bond, compounds of formula Ia" can be prepared following the reaction scheme below.

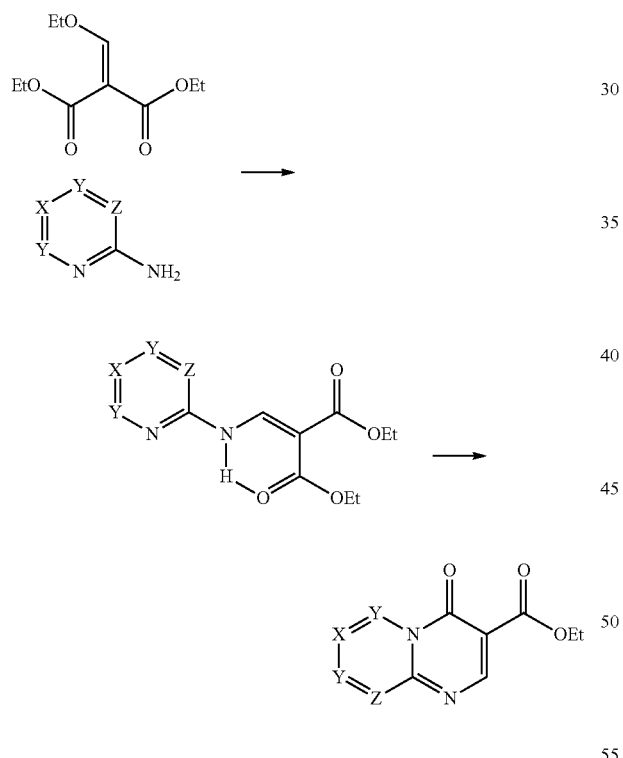

wherein B, V, X, Y, Z, and $R_7$ are as defined herein. The first step of the reaction is typically carried out at 120-130 degrees C. for between 2 and 3 hours. The second step of the reaction is typically carried out by refluxing in diphenyl ether for 8 hours. Compounds of formula IIa and III are typically commercially available or can be prepared by analogy with known methods.

When $R_2$ is a $C_1$-$C_6$ alkyl, $C_1$-$C_6$ haloalkyl, $C_6$-$C_{10}$ aryl, 5- to 10-membered heteroaryl, 5- to 10-membered heterocyclyl, $C_3$-$C_{10}$ cycloalkyl, or —COOR' group, wherein R' is a hydrogen atom or $C_1$-$C_6$ alkyl group, compounds of formula I" can be prepared following the reaction scheme below.

wherein LG is a good leaving group, typically a halogen atom, triflate or mesylate group, preferably a halogen atom, more preferably a bromine atom. Compounds of formula I'" by analogy with the method described above.

When B is —(C=O)$R_1$, and $R_1$ is a proteinogenic α amino acid, which is optionally esterified at the α carboxylic acid group with a $C_1$-$C_6$ alkyl group or a $C_6$-$C_{10}$ aryl group, compounds of formula I" can be prepared by reacting a compound of $I^{IV}$ with N,N-dimethylacetamide, and N-ethyldiisopropylamine followed by O-(7-Azabenzotriazol-1-yl)-N,N,N'N'-tetramethylutonium hexafluorophosphate and the hydrochloride salt of the proteinogenic α amino acid, which is optionally esterified at the α carboxylic acid group with a $C_1$-$C_6$ alkyl group or a $C_6$-$C_{10}$ aryl group.

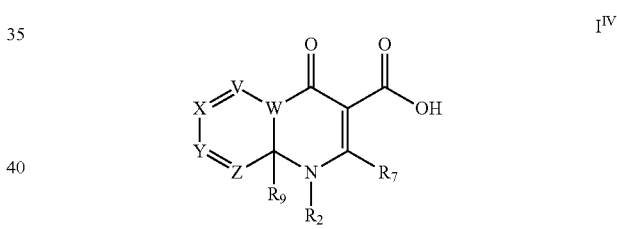

wherein W, V, X, Y, Z, $R_2$, $R_7$ and $R_9$ are as defined herein.
Compounds of formula $I^{IV}$ can be prepared by saponifying a compound of formula $I^V$

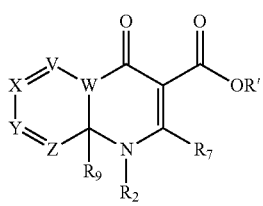

wherein W, V, X, Y, Z, $R_2$, $R_7$ and $R_9$ are as defined herein, and R' is a $C_1$-$C_6$ alkyl group or a $C_1$-$C_6$ haloalkyl group. Compounds of formula $I^V$ can be prepared by analogy with the method for producing compounds of formula I from compounds of formula II and III above.

The present invention also provides a pharmaceutical composition comprising a compound of the invention and one or more pharmaceutically acceptable diluents or carriers.

The compounds of the invention may be administered in a variety of dosage forms.

Thus, they can be administered orally, for example as tablets, troches, lozenges, aqueous or oily suspensions, dispersible powders or granules. The compounds of the invention may also be administered parenterally, either subcutaneously, intravenously, intramuscularly, intrasternally, transdermally or by infusion techniques. The compounds may also be administered as suppositories.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusions may contain as carrier, for example, sterile water or preferably they may be in the form of sterile, aqueous, isotonic saline solutions.

A therapeutically effective amount of a compound of the invention is administered to a patient. A typical daily dose is from about 0.1 to 50 mg per kg of body weight, according to the activity of the specific compound, the age, weight and conditions of the subject to be treated, the type and severity of the disease and the frequency and route of administration. Preferably, daily dosage levels are from 5 mg to 2 g.

The present invention also provides a product containing (i) a compound of the invention and (ii) a further therapeutic agent. The further therapeutic agent is typically a therapeutic agent that is used in the treatment of cardiovascular disease. Examples of such therapeutic agents include statins, anti-platelet agents and anti-hypertensives. Thus, the compounds of the present invention may be administered as a monotherapy or in combination with one or more further therapeutic agents as defined herein. The potent therapeutic effect of the compounds of the present invention is such that they are particularly suitable for administration as a monotherapy.

Statins are a well known class of drug that lowers blood cholesterol levels. A person skilled in the art would have no difficulty in choosing a statin for combination with compounds of the present invention. Examples of statins suitable for use in combination with compounds of the present invention include atorvastatin, cerivastatin, fluvastatin, lovastatin, mevastatin, pitavastatin, pravastatin, rosuvastatin, and simvastatin.

Anti-platelet agents are a well known class of drug that decreases blood platelet aggregation and inhibits thrombus formation. A person skilled in the art would have no difficulty in choosing an anti-platelet agent for combination with compounds of the present invention. Examples of anti-platelet agents suitable for use in combination with compounds of the present invention include aspirin, clopidogrel, ticlopidine, cilostazol, abciximab, eptifibatide, tirofiban, defibrotide and dipyridamole. Preferred anti-platelet agents are aspirin and clopidogrel.

Anti-hypertensives are a well known class of drug that decrease blood pressure. A person skilled in the art would have no difficulty in choosing an anti-hypertensive agent for combination with compounds of the present invention. Examples of anti-hypertensive agents include diuretics, adrenergic receptor antagonists, calcium channel blockers, renin inhibitors, ACE inhibitors, angiotensin II receptor antagonists, aldosterone antagonists, vasodilators, alpha-2 agonists, and endothelin receptor blockers. Specific examples of anti-hypertensive agents suitable for use in combination with compounds of the present invention include bumetanide, ethacrynic acid, furosemide, torsemide, epitizide, hydrochlorothiazide, chlorothiazide, bendroflumethiazide, indapamide, chlorthalidone, metolazone, amiloride, triamterene, spironolactone, atenolol, metoprolol, nadolol, nebivolol, oxprenolol, pindolol, propranolol, timolol, doxazosin, phentolamine, indoramin, phenoxybenzamine, prazosin, terazosin, tolazoline, bucindolol, carvedilol, labetalol, amlodipine, Cilnidipine, felodipine, isradipine, lercanidipine, nicardipine, nifedipine, nimodipine, nitrendipine, diltiazem, verapamil, aliskiren, captopril, enalapril, fosinopril, lisinopril, perindopril, quinapril, ramipril, trandolapril, benazepril, candesartan, eprosartan, irbesartan, losartan, olmesartan, telmisartan, valsartan, eplerenone, spironolactone, sodium nitroprusside, hydralazine, Clonidine, Guanabenz, Methyldopa, Moxonidine, Guanethidine, Reserpine and bosentan, and combinations thereof.

The compounds of the present invention are capable of agonising C-type natriuretic peptide receptors. They can therefore be used to treat or prevent any disease or condition that responds to agonism of the C-type natriuretic peptide receptors. The present invention therefore also provides a compound, composition or product of the invention for use in the treatment of a disease or condition alleviated by agonism of the natriuretic peptide receptors, in particular the natriuretic peptide receptor C.

Diseases and conditions alleviated by agonism of the natriuretic peptide receptors include cardiovascular and/or heart disease, peripheral vascular disease, and sepsis.

Examples of cardiovascular diseases which can be treated or prevented with the compounds of the invention include arteriosclerosis, atherosclerosis, myocardial ischemia, angina, congestive heart failure, ischemic vascular disease, stroke, myocardial infarction, aneurism, hypertension, restenosis, hypercholesterolaemia, hypertensive heart disease, ischemia/reperfusion injury and pulmonary hypertension.

In certain embodiments, the cardiovascular disease is heart disease.

In certain embodiments, the disease which can be treated or prevented is hypertension.

In other embodiments, the disease which can be treated or prevented is myocardial infarction.

The compounds of the present invention have been found to be vasodilators. Thus, the present invention also provides a compound of formula I, a tautomer thereof, or a pharmaceutically acceptable salt or N-oxide thereof as defined herein for use in the treatment or prevention of cardiovascular disease as defined herein by vasodilation. Also provided is a compound of formula I, a tautomer thereof, or a pharmaceutically acceptable salt or N-oxide thereof as defined herein for use in a method of vasodilation in a patient suffering from cardiovascular disease as defined herein.

The present invention also provides use of a compound of the invention in the manufacture of a medicament, for use in the treatment or prevention of a disease or condition that responds to agonism of the natriuretic peptide receptors, as defined herein.

The present invention also provides a method of treating or preventing a condition that responds to agonism of the natriuretic peptide receptors, as defined herein, in a patient, which method comprises administering to said patient an effective amount of a compound of the present invention.

The present invention also provides a compound of formula I, a tautomer thereof, or a pharmaceutically acceptable salt or N-oxide thereof as defined herein for use in the treatment or prevention of an inflammatory disease. Also provided is a compound of formula I, a tautomer thereof, or a pharmaceutically acceptable salt or N-oxide thereof as defined herein for use as an anti-inflammatory in a patient suffering from cardiovascular disease as defined herein.

The present invention also provides use of a compound of the invention in the manufacture of a medicament, for use in the treatment or prevention of an inflammatory disease or condition.

The present invention also provides a method of treating or preventing of an inflammatory disease or condition in a patient, which method comprises administering to said patient an effective amount of a compound of the present invention.

Examples of inflammation and inflammatory diseases or conditions which can be treated or prevented with the compounds of the invention include acne vulgaris, Alzheimer's, ankylosing spondylitis, arthritis (including e.g. osteoarthritis, rheumatoid arthritis (RA), psoriatic arthritis), asthma, atherosclerosis, autoimmune diseases, celiac disease, chronic prostatitis, colitis, crohn's disease, dermatitis, diverticulitis, fibromyalgia, glomerulonephritis, hepatitis, hypersensitivities, inflammatory bowel diseases, interstitial cystitis, irritable bowel syndrome (IBS), lupus erythematosus, nephritis, Parkinson's disease, pelvic inflammatory disease, peritonitis, reperfusion injury, rheumatoid arthritis, sarcoidosis, systemic lupus erythematous (SLE), systemic sclerosis, transplant rejection, ulcerative colitis and vasculitis.

Typically, the patient treated in accordance with the present invention is a human.

Generally, the patient treated in accordance with the present invention does not have type 2 diabetes; and/or has not been diagnosed as having type 2 diabetes; and/or is not being treated with antidiabetic treatment; and/or has not been treated with antidiabetic treatment.

In compounds of formula (1), typically one of criteria (a) to (d) applies. Alternatively, more than one of (a) to (d) applies.

Thus, in certain embodiments (a) and (b) both apply, in which case the present invention provides compounds of formula (1) wherein:

V is N or $CR_3$;
X is N or $CR_4$;
Y is N or $CR_5$;
Z is N or $CR_6$;

B is —(C=O)$R_1$, a 5- to 10-membered heteroaryl group, or a group -L'''-NRR', wherein R and R' are the same or different and each represents a hydrogen atom, a $C_1$-$C_6$ alkyl group or a $C_1$-$C_6$ haloalkyl group and L''' is as defined in any one of the preceding claims;

$R_1$ is a 5- to 10-membered heterocyclyl group, or $R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group, or $R_1$ is —NR"R''', —NR$^{IV}$-L'''-CONR"R''', or —NR$^{IV}$-L'''-COOR, wherein R, R", R''' and R$^{IV}$ are the same or different and each represents a hydrogen atom, a $C_1$-$C_6$ alkyl group or a $C_1$-$C_6$ haloalkyl group, either (a) W is N and $R_9$ and $R_2$ together form a bond, or (b) W is $CR_8$, $R_8$ and $R_9$ together form a bond and $R_2$ is a hydrogen atom, or a $C_1$-$C_6$ alkyl, $C_1$-$C_6$ haloalkyl, $C_6$-$C_{10}$ aryl, 5- to 10-membered heteroaryl, 5- to 10-membered heterocyclyl, $C_3$-$C_{10}$ cycloalkyl, or —COOR' group, wherein R' is a hydrogen atom or $C_1$-$C_6$ alkyl group, or, when Z is a moiety $CR_6$, $R_2$ may form, together with $R_6$ and the carbon and nitrogen atoms which connect $R_2$ and $R_6$ in the formula (I), a 5- to 6-membered heterocyclic ring;

$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;

$R_4$ is a bromine atom, nitro group, or a $C_6$-$C_{10}$ aryl or 5- to 10-membered heteroaryl group, said aryl and heteroaryl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'(C=O)R", —COOR, nitro and cyano substituents, wherein R, R' and R" are the same or different and each represents a hydrogen atom or $C_1$-$C_4$ alkyl group, $R_5$ is a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —CO$_2$R''', $C_6$-$C_{10}$ aryl, 5- to 10-membered heteroaryl, 5 to 10-membered heterocyclyl, or —CO—($C_1$-$C_6$ alkyl) group, wherein R', R" and R''' are the same or different and each represent a hydrogen atom or $C_1$-$C_6$ alkyl group;

$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —CO$_2$R' group, wherein R' is hydrogen or $C_1$-$C_6$ alkyl, or, when W is a moiety $CR_8$, $R_6$ may form, together with $R_2$ and the carbon and nitrogen atoms which connect $R_6$ and $R_2$ in the formula (I), a 5- to 6-membered heterocyclic ring;

$R_7$ is a hydrogen atom, a halogen atom, or a $C_1$-$C_6$ alkyl, or $C_1$-$C_6$ haloalkyl group;

$A_2$ represents a $C_6$-$C_{10}$ aryl or 5- to 10-membered heteroaryl group;

L', and L''' are the same or different and each represent a $C_1$-$C_6$ alkylene, $C_2$-$C_6$ alkenylene, or $C_2$-$C_6$ alkynylene group;

said aryl, heteroaryl, cycloalkyl and heterocyclyl groups being unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —SO$_2$R, —NR'R", —NR'(C=O)R", —COOR, nitro and cyano substituents, wherein R, R' and R" are the same or different and each represents a hydrogen atom or $C_1$-$C_4$ alkyl group.

Typically, preferred substituent definitions for compounds of formula (1) are the same as those for compounds of formula (I).

Typically, in (a), B is —(C═O)$R_1$, and $R_1$ is a 5- to 10-membered heterocyclyl group, or $R_1$ is a group of formula —NH—CHR$^{IV}$—CO$_2$R$^{V}$, wherein R$^{V}$ is a hydrogen atom or $C_1$-$C_6$ alkyl group, and R$^{IV}$ is a hydrogen atom, or a methyl, —(CH$_2$)$_3$—NH—(C═NH)—NH$_2$, —CH$_2$CONH$_2$, —CH$_2$CO$_2$H, —CH$_2$SH, —(CH$_2$)$_2$CO$_2$H, —(CH$_2$)$_2$CONH$_2$, —CH(CH$_3$)CH$_2$CH$_3$, CH$_2$CH(CH$_3$)$_2$, —(CH$_2$)$_4$NH$_2$, —(CH$_2$)$_2$SCH$_3$, —CH$_2$Ph, —CH$_2$OH, —CH(CH$_3$)OH, —CH$_2$-p-hydroxy-Ph, —CH(CH$_3$)$_2$, —CH$_2$SeH group, or a

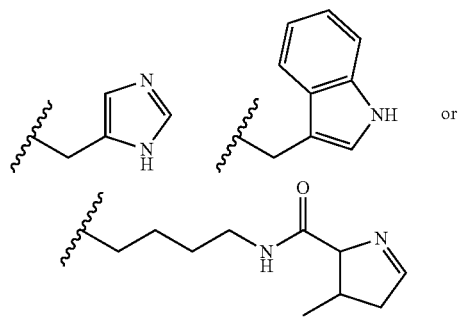

group; or $R_1$ is a group of formula —NR$^{IV}$-L'''-COOR wherein R$^{IV}$ is a hydrogen atom, L''' is a $C_2$-$C_4$ alkylene group, and R is a hydrogen atom or $C_1$-$C_4$ alkyl group, provided that the compound is other than

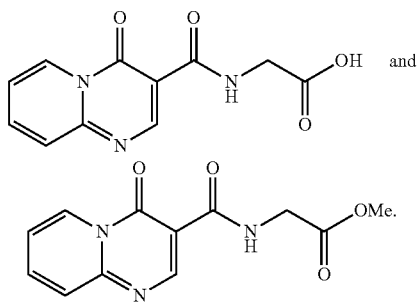

More typically in (a), $R_1$ is a 5-membered heterocyclyl group, or $R_1$ is a group of formula —NH—CHR$^{IV}$—CO$_2$R$^{V}$, wherein R$^{V}$ is a hydrogen atom or $C_1$-$C_6$ alkyl group, and R$^{IV}$ is a hydrogen atom, or a methyl, —CH$_2$CH(CH$_3$)$_2$, —CH$_2$-Ph or —CH(CH$_3$)$_2$ group; or $R_1$ is a group of —NH—(CH$_2$)$_2$—COOR, where R is hydrogen or $C_1$-$C_4$ alkyl provided that the compound is other than

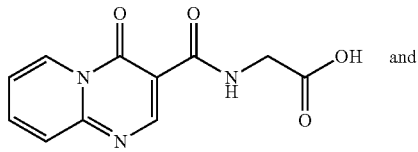

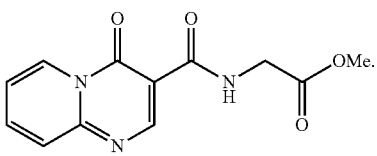

Generally in (a), $R_1$ is

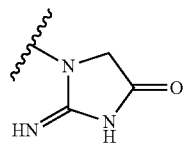 [SMILES: *N1CC(=O)NC1=N]

or $R_1$ is a group of formula —NH—CHR$^{IV}$—CO$_2$R$^{V}$, wherein R$^{V}$ is a hydrogen atom or $C_1$-$C_4$ alkyl group, and R$^{IV}$ is a hydrogen atom, or a methyl, —CH$_2$CH(CH$_3$)$_2$, —CH$_2$-Ph or —CH(CH$_3$)$_2$ group; or $R_1$ is —NH—(CH$_2$)$_2$—COOH or —NH—(CH$_2$)$_2$—COOCH$_3$, provided that the compound is other than

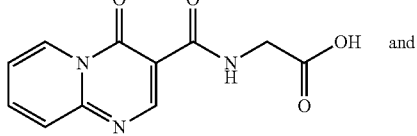

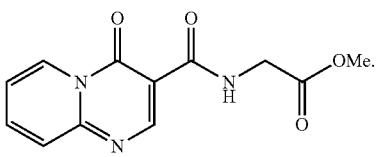

Typically in (b), $R_4$ is a bromine atom, nitro group, or a $C_6$-$C_{10}$ aryl or 5- to 6-membered heteroaryl group, said heteroaryl groups being unsubstituted or substituted with one or two substituents selected from halogen, $C_1$-$C_4$ alkyl and $C_1$-$C_4$ alkoxy substituents, and said aryl groups being unsubstituted or substituted with one or two substitutents selected from halogen, $C_1$-$C_4$ alkyl, $C_1$-$C_4$ hydroxyalkyl, $C_1$-$C_4$ alkoxy, —NR'(C═O)R", or —COOR substituents, wherein R, R' and R" are the same or different and each represents a hydrogen atom or $C_1$-$C_4$ alkyl group, providing that the compound is other than

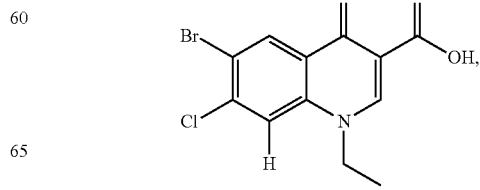

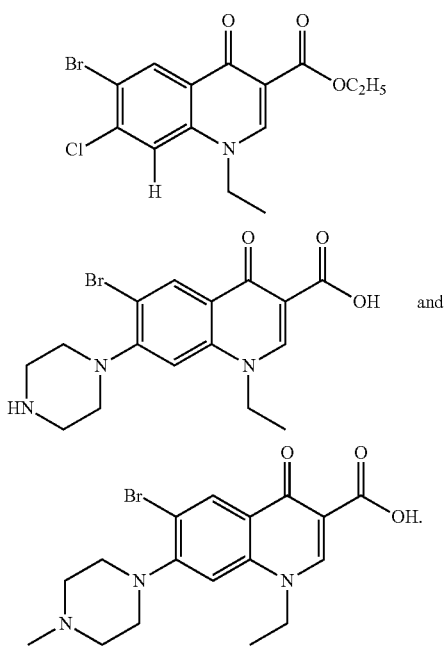

More typically in (b), R₄ is a bromine atom, nitro group, or a phenyl or 5- or 6-membered heteroaryl group wherein the heteroaryl groups are unsubstituted and the phenyl group is unsubstituted or substituted with a $C_1$-$C_2$ hydroxyalkyl, —NH(C=O)R″, or —COOR substituent, wherein R and R″ are the same or different and each represents a $C_1$-$C_2$ alkyl group, providing that the compound is other than

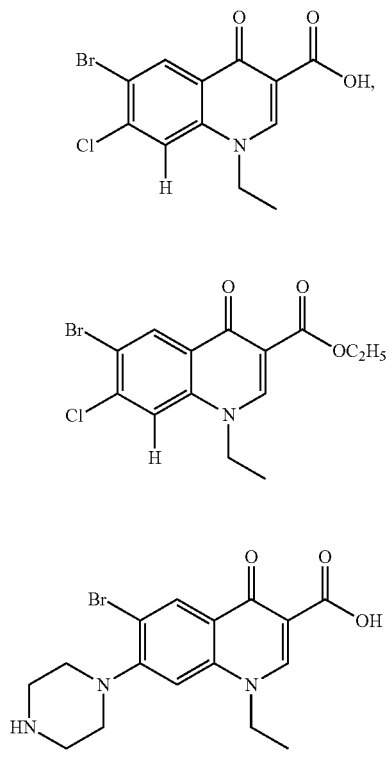

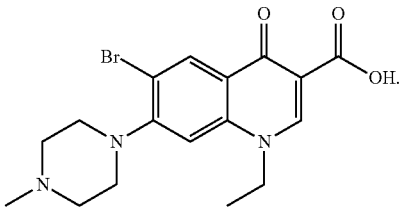

Generally in (b), R₄ is a bromine atom, nitro group, or a phenyl or unsusbstituted thiophene or pyridine group, said phenyl group being substituted with one —COOH, —CH₂OH or —NH(C=O)Me substituent, providing that the compound is other than

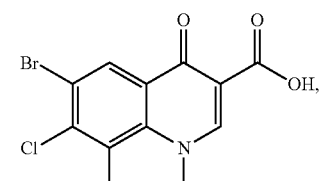

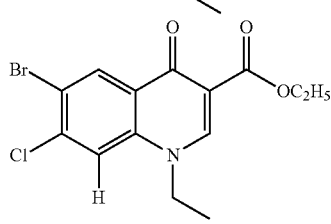

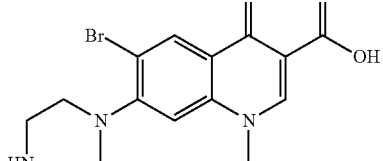

and

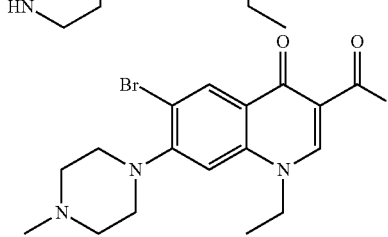

Typically in (c), the compound is of formula (Ij) as defined herein, providing that the compound is other than

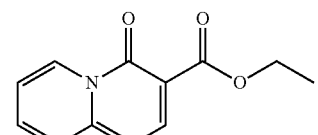

,

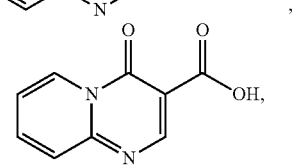

,

Typically in (d), $R_2$ is -L'-$A_2$ or —COOR', wherein R' is a hydrogen atom or $C_1$-$C_4$ alkyl group, and wherein L' is a $C_1$-$C_6$ alkylene group, and $A_2$ is a phenyl group, which is substituted with two substituents selected from $C_1$-$C_4$ alkyl substituents.

More typically in (d), $R_2$ is -L'-$A_2$ or —COOR', wherein R' is a $C_1$-$C_4$ alkyl group, and wherein L' is a $C_1$-$C_4$ alkylene group, and $A_2$ is a phenyl group, which is substituted with two substituents selected from $C_1$-$C_4$ alkyl substituents.

Generally in (d), $R_2$ is -L'-$A_2$ or —COO'Bu, wherein L' is a —$CH_2$— group, and $A_2$ is a phenyl group which is substituted by two $C_1$-$C_2$ alkyl substituents.

The present invention also provides a compound, a tautomer thereof, or a pharmaceutically acceptable salt and//or N-oxide thereof, the compound being selected from compounds 6, 27, 28, 29, 59, 60, 61, 62, 63, 64, 82, 83, 87, 88, 116, 117, 118, 119, 120, 127, 128, 152, 160, 162, 163, 164, 165, 166, 167, 168, 169, 170, 171, 172, 173, 174, 175, 176, 177, 178, 180, 181, 182, 183, 184, 185, 186, 187, 188, 189, 190, 191, 192, 194, 195, 196, 197, 198, 199, 200, 201, 202, 203, 204, 205 301, 302, 303, 304, 305, 306, 307, 308 and 309, whose structures are given above.

Compounds 28, 59, 60, 61, 62, 63, 87, 88, 116, 117, 118, 119, 178, 187, 189, 200, 202, 301, 302, 303, 304, 305, 306, 307, 308 and 309, tautomers thereof, pharmaceutically acceptable salts and//or N-oxides thereof are preferred.

Compounds 28, 61, 63, 88, 116, 117, 118, 119 and 187, tautomers thereof, pharmaceutically acceptable salts and//or N-oxides thereof are more preferred.

Compounds 28, 118, and 187, tautomers thereof, pharmaceutically acceptable salts and//or N-oxides thereof are even more preferred.

Compounds 28, and 118, tautomers thereof, pharmaceutically acceptable salts and//or N-oxides thereof are still more preferred. The structures of these compounds are shown below.

The present invention also provides a compound as defined herein or product as defined herein, for use in a method of treatment of the human or animal body.

The present invention also provides use of a compound as defined herein or product as defined herein, in the manufacture of a medicament for the treatment of the human or animal body.

The following Examples illustrate the invention.

1. General Experimental

Solvents

N,N-Dimethylformamide, tetrahydrofuran, 1,4-dioxane were purchased dry from the Aldrich Chemical Company in sure-Seal™ bottles. Water was distilled. All other solvents were used as supplied without further purification (Analytical or HPLC grade).

Reagents

Reactions performed under an atmosphere of nitrogen or hydrogen gas were maintained by an inflated balloon.

Chromatography

Thin layer chromatography (TLC) was performed on Whatman glass plates coated with MK6F Silica Gel 60 Å, visualized using UV light and/or iodine gas. Purification via flash column chromatography was performed on Biotage Isolute® pre-packed columns (Flash Si II type) unless otherwise stated.

Melting Points

Melting points were recorded on a Gallenkamp Melting Point Apparatus.

Nuclear Magnetic Resonance Spectroscopy

Nuclear Magnetic Resonance (NMR) Spectra were recorded on Bruker DRX 500, AMX 300 spectrometers in the deuterated solvent stated. Chemical shifts (δ) are quoted in ppm and coupling constants (J) in Hz. Coupling constants are quoted twice. Residual signals from the solvents were used as an internal reference.

Infra-Red Spectroscopy

Infra-red (IR) spectra were recorded on a Perkin-Elmer Spectrum One IR Fourier Transform spectrophotometer and using thin films on KBr or Ge plates as stated. Only the characteristic peaks are quoted and in units of $cm^{-1}$.

Mass Spectrometry

High resolution mass spectra (HRMS) were measured on a VG70 SE mass spec or a Thermo Finnigan MAT900xp mass spec Electrospray-Thermo Finnigan MAT900xp.

Elemental Microanalysis

Elemental analyses were performed by the microanalysis service of the Department of Chemistry, University College London, London.

Polarimetry

Optical rotations, $[\alpha]_D$, were measured on a Perkin-Elmer Model 343 polarimeter with a path length of 1.0 dm. Concentrations are quoted in g 100 ml$^{-1}$. The Na lamp was set at 589 nm.

Example 1

Ethyl 6-bromo-4-oxo-1,4-dihydroquinoline-3-carboxylate 2

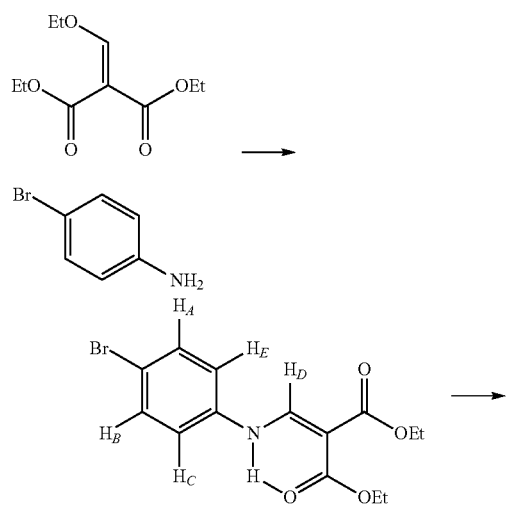

Reference paper: H. Koga, Itoh, S. Murayama, S. Suzue, T. Irikura, *J. Med. Chem.*, 1980, 23, 1358. 4-Bromoaniline (3.440 g, 20.00 mMol) was stirred in diethyl ethoxymethylenemalonate (4.04 mL, 20.00 mMol) at 120-130° C. for 2 hours and 20 minutes. T.l.c. analysis (ethyl acetate:cyclohexane, 1:2) showed the presence of one UV-active product ($R_f$ 0.56) and complete consumption of both starting materials ($R_f$ 0.42 and 0.45). Upon cooling down of the reaction solution to room temperature, intermediate 1 solidified (a white crystalline solid). The solid was then re-heated (86° C.) and concentrated in vacuo in order to remove any ethanol formed during the reaction. M.p. 94.5-97° C. (dichloromethane); HRMS (EI): found 341.02539 [M]$^+$ $C_{14}H_{16}NO_4{}^{79}Br$ requires 341.02572; found 343.02298 [M]$^+$ $C_{14}H_{16}NO_4{}^{81}Br$ requires 343.02338; peak ratio: 49.7%: 50.3%; $\nu_{max}$ (thin film): 3258, 3199, 3164 (w, NH, hydrogen-bonding), 3105, 3069 (w, ArC—H), 2981, 2938, 2902 (m, alkyl C—H), 1686 (s, 2×intramolecularly hydrogen-bonded C═O conjugated with C═C), 1641, 1614 (s, C═C conjugated with C═O) cm$^{-1}$; $\delta_H$ (CDCl$_3$, 300 MHz): 1.32 (3H, t, $J_{CH3,CH2}$ 7.2 Hz, CH$_3$), 1.37 (3H, t, $J_{CH3,CH2}$ 7.2 Hz, CH$_3$), 4.24 (2H, q, $J_{CH2,CH3}$ 7.2 Hz, CH$_2$), 4.30 (2H, q, $J_{CH2,CH3}$ 7.1 Hz, CH$_2$), 7.01 (2H, d, J 9.1 Hz, 2×ArCH—C—Br), 7.48 (2H, d, J 8.8 Hz, 2×ArCH—C—N), 8.45 (1H, d, $J_{CH,NH}$ 13.3 Hz, CH—NH), 11.00 (1H, d, $J_{NH,CH}$ 13.4 Hz, CH—NH); $\delta_C$ (CDCl$_3$, 75 MHz): 14.3, 14.4 (2×CH$_3$), 60.2, 60.5 (2×CH$_2$), 94.4 (O═C—C—C═O), 117.6 (ArCquat-Br), 118.7 (2×ArCH—Cquat-NH), 132.8 (2×ArCH—Cquat-Br), 138.4 (ArCquat-NH), 151.4 (NH—CH), 165.6 (C═O), 169.0 (hydrogen bonded C═O). Diphenyl ether (100 g) was then added to the crude solid and the mixture was refluxed at 260° C. for 8 hours. After 1.5 hours a white solid started crushing out of solution in the reaction flask. T.l.c. analysis (ethyl acetate:cyclohexane, 1:4) showed the presence of one UV-active product ($R_f$ 0.75) and complete consumption of the intermediate starting material 1 ($R_f$ 0.49). Upon cooling of the reaction solution to room temperature, more ethyl 6-bromo-4-oxo-1,4-dihydroquinoline-3-carboxylate 2 crushed out of solution as a white powder (at 230° C.). The white solid was filtered, washed with toluene and dried in vacuo to afford ethyl 6-bromo-4-oxo-1,4-dihydroquinoline-3-carboxylate 2 (2.587 g, 43.4%) as a pale yellow/white powder. M.p. 285-290° C. (decomposition: gas evolved); HRMS (EI): found 294.98314 [M]$^+$ $C_{12}H_{10}NO_3{}^{79}Br$ requires 294.98386; found 296.98073 [M]$^+$ $C_{12}H_{10}NO_3{}^{81}Br$ requires 296.98152; peak ratio: 49.5%:50.5%; $\nu_{max}$ (Ge): 3421 (br s, NH), 3149, 3088 (w, ArC—H), 2981 (m, alkyl C—H), 1694 (s, 2×intramolecularly hydrogen-bonded C═O conjugated with C═C), 1615 (s, C═C conjugated with C═O) cm$^{-1}$; Elemental Analysis: found C, 48.36%, H, 3.34%, N, 4.64%; required C, 48.67%, H, 3.40%, N, 4.73%.

Example 2

Ethyl 1-benzyl-6-bromo-4-oxo-1,4-dihydroquinoline-3-carboxylate 3

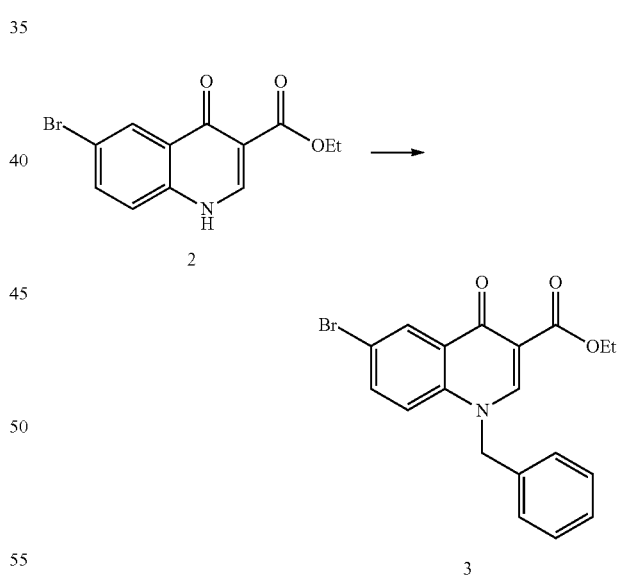

Crude 6-bromo-4-oxo-1,4-dihydroquinoline-3-carboxylate 2 (1.000 g, 3.377 mMol) was stirred in DMF (6.7 mL) with potassium carbonate (1.159 g, 8.386 mMol) at 40° C. After 5 minutes benzyl bromide (1.99 mL, 16.771 mMol) was added dropwise and the temperature raised to 80° C. After 24.5 hours, LCMS analysis showed the presence of one product only (m/z 385-387) and complete consumption of the starting material (m/z 297-299). The reaction mixture was concentrated in vacuo and co-evaporated twice (toluene). The residue was partitioned between water and dichloromethane and the aqueous layer was washed with dichloromethane 3 times. The organic layers were collected, dried (magnesium sulphate), filtered and concentrated in vacuo to give crude ethyl 1-benzyl-6-bromo-4-oxo-1,4-dihydroquinoline-3-carboxylate 3 as a sticky bright pale yellow solid. The solid residue was then dissolved in dichloromethane, pre-absorbed onto silica gel and purified by flash-chromatography (ethyl acetate to ethyl acetate:methanol 5% to ethyl acetate:methanol 10%) to afford ethyl 1-benzyl-6-bromo-4-oxo-1,4-dihydroquinoline-3-carboxylate 3 (1.280 g, 98.1%) as a white crystalline solid. M.p. 166-168° C. (ethyl acetate/methanol); HRMS (EI): found 385.03131 [M]$^+$ C$_{19}$H$_{16}$NO$_3^{79}$Br requires 385.03081; found 387.02894 [M]$^+$ C$_{19}$H$_{16}$NO$_3^{81}$Br requires 387.02847; peak ratio: 51.9%: 48.1%; $\nu_{max}$ (thin film): 3035 (w, ArC—H), 2964, 2928, (m, alkyl C—H), 1725 (s, C=O ketone), 1686 (s, C=O ester, conjugated with C=C), 1623, 1606 (s, C=C conjugated with C=Os) cm$^{-1}$; $\delta_H$ (CDCl$_3$, 300 MHz): 1.32 (3H, t, $J_{CH3,CH2}$ 7.2 Hz, CH$_3$), 4.30 (2H, q, $J_{CH2,CH3}$ 7.2 Hz, CH$_2$), 5.30 (2H, s, CH$_2$, Bn), 7.04-7.09 & 7.22-7.32 (5H, 2×m, 5×ArHs, Bn), 7.10 (1H, d, $J_{H-C,H-B}$ 9.0 Hz, ArH$^C$), 7.50 (1H, dd, $J_{H-B,H-C}$ 9.0 Hz, $J_{H-B,H-A}$ 2.3 Hz, ArH$^B$), 8.47 (1H, s, CH—N-Bn), 8.50 (1H, d, $J_{H-A,H-B}$ 2.3 Hz, ArH$^A$); $\delta_C$ (CDCl$_3$, 75 MHz): 14.4 (CH$_3$), 57.6 (CH$_2$, Bn), 61.0 (OCH$_2$CH$_3$), 111.5 (O=C—C—C=O), 118.6 (ArCquat$^C$), 119.2 (Br-Cq), 126.0, 128.7, 129.4 (5×ArCs, Bn), 130.4 (C$^A$), 130.5 (C$^A$-Cq-C=O), 133.9 (Cq (Bn)), 135.5 (C$^B$), 138.0 (C$^C$-Cq-N-Bn), 149.7 (C$^D$), 165.2 (CO$_2^t$Bu), 173.1 (O=C—C=C). Soluble in DCM and a bit soluble in acetone.

Example 3

Compound 27. 1-benzyl-6-bromo-4-oxo-1,4-dihydroquinoline-3-carboxylic acid 4

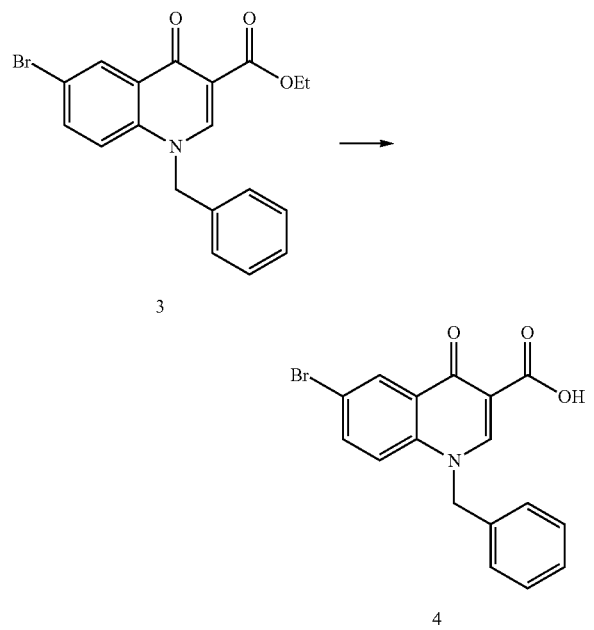

Ethyl 1-benzyl-6-bromo-4-oxo-1,4-dihydroquinoline-3-carboxylate 3 (1.000 g, 2.589 mMol) was refluxed at 150° C. in a 2 M sodium hydroxide aqueous solution (20 mL). After 3 hours the reaction mixture turned into a thick white slurry. LCMS analysis revealed the presence of one product (m/z 359-361) and complete consumption of the starting material (m/z 387-389). The reaction mixture was allowed to cool down to room temperature, distilled water was added (20 mL) to it and was subsequently neutralised with acetic acid (2.3 mL). The resulting precipitate was filtered, washed with water, ground and dried in vacuo to give 1-benzyl-6-bromo-4-oxo-1,4-dihydroquinoline-3-carboxylic acid 4 (786 mg, 84.7%) as a white solid. M.p.>250° C. (water); HRMS (TOF MS ES$^+$): found 358.0096 [M+H$^+$]$^+$ C$_{17}$H$_{13}$NO$_3^{79}$Br requires 358.0079; found 360.0077 [M+H$^+$]$^+$ $\nu_{max}$ (Ge): 3034 (w, ArC—H), 1717 (s, COOH), 1675 (w, intramolecularly hydrogen-bonded C=O conjugated with C=C), 1615 (s, C=C conjugated with C=O) cm$^{-1}$; $\delta_H$ (DMSO, 300 MHz): 14.76 (1H, s, COOH), 9.29 (1H, s, H$^D$), 8.43 (1H, d, $J_{HA,HB}$ 2.3 Hz, H$^A$), 8.01 (1H, dd, $J_{HB,HC}$ 9.2 Hz, $J_{HB,HA}$ 2.4 Hz, H$^B$), 7.80 (1H, d, $J_{HC,HB}$ 9.2 Hz, H$^C$), 7.42-7.14 (5H, m, 5×ArHs (Bn)), 5.86 (2H, s, CH$_2$ (Bn)); $\delta_C$ (DMSO, 75 MHz): 56.5 (CH$_2$(Bn)), 108.7 (O=C—C—C=O), 119.3 (Cq-Br), 121.1 (C$^C$), 126.5, 127.3, 128.9 (5×ArHs (Bn)), 127.9 (C$^A$), 128.0 (C$^A$-Cq-C=O), 135.1 (Cq (Bn)), 136.6 (C$^B$), 138.5 (C$^C$-Cq-N-Bn), 150.5 (C$^D$), 165.5 (COOH), 177.7 (O=C—C=C).

Example 4

Compound 59. Synthesis of (S)-tert-butyl 2-(1-benzyl-6-bromo-4-oxo-1,4-dihydroquinoline-3-carboxamido)propanoate 5

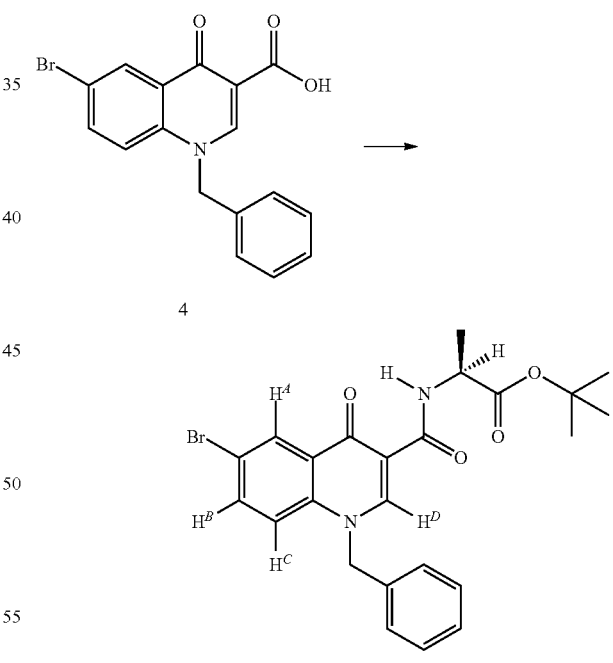

1-Benzyl-6-bromo-4-oxo-1,4-dihydroquinoline-3-carboxylic acid 4 (218 mg, 0.605 mMol) was stirred in N,N-dimethylacetamide (6 mL) and N-ethyldiisopropylamine (0.207 mL, 1.210 mMol). After 5 minutes O-(7-Azabenzotriazol-1-yl)-N,N,N',N'-tetramethyluronium hexafluorophosphate (460 mg, 1.210 mMol) and L-alanine-tert-butyl ester hydrochloride (220 mg, 1210 mMol) were added (a yellow reaction solution) and the temperature was raised to 50° C. After 27 hours L.C.M.S. analysis revealed the presence of various compounds and the starting material (m/z 359-361) in the reaction solution, hence the temperature was raised to 70° C. and let to run for an extra 23 hours. L.C.M.S. and t.l.c. (ethyl acetate:methanol, 5%) analyses showed solely the presence of the product (m/z 486-488, $R_f$ 0.80) and complete consumption of the starting material ($R_f$ 0.00). The reaction solution turned into a deep purple red/red solution and a N,N-dimethylacetamide-soluble white crystalline residue collected on the internal wall of the flask. The reaction solution was co-evaporated in vacuo three times (methanol). The residue was pre-absorbed on silica gel and purified by flash-chromatography (ethyl acetate:cyclohexane, 1:2) to give (S)-tert-butyl 2-(1-benzyl-6-bromo-4-oxo-1,4-dihydroquinoline-3-carboxamido)propanoate 5 (134 mg, 45.6%) as a white crystalline solid). M.p. 144.5-147° C. (ethyl acetate/cyclohexane); HRMS (ESI): found 507.09005 [M+Na]$^+$ $C_{24}H_{25}N_2O_4{}^{79}BrNa$ requires 507.08954; found 509.08684 [M+Na]$^+$ $C_{24}H_{25}N_2O_4{}^{81}BrNa$ requires 509.08749; peak ratio: 49.6%:50.4%; $[\alpha]_D{}^{25}$ +16.176 (c, 0.20 in dichloromethane); $\nu_{max}$ (thin film): 3222, 3192 (w, NH, h-bonded), 3037 (m, ArC—H), 2980, 2933, 2874 (m, alkyl C—H), 1738 (m, C=OO$^t$Bu ester), 1729 (m, C=O ketone conjugated to C=C), 1660 (s, C=ONH, I and C=C conjugated with C=O), 1543 (m, CONH, II), 1601 (m, aromatic ring and C=C conjugated with C=O), 1482 (m, aromatic ring) cm$^{-1}$; $\delta_H$ (Acetone-d$^6$, 500 MHz): 1.44 (3H, d, $J_{CH3,CH}$ 7.2 Hz, Alanine CH$_3$), 1.48 (9H, s, C(CH$_3$)$_3$), 4.55 (1H, a-quint, J 7.2 Hz, Alanine-C$_\alpha$H), 5.84 (2H, s, CH$_2$ (Bn)), 7.25-7.40 (5H, m, 5×ArHs), 7.72 (1H, d, $^3J_{H\text{-}C,H\text{-}B}$ 9.0 Hz, H$^C$), 7.81 (1H, dd, $^3J_{H\text{-}B,H\text{-}C}$ 9.1 Hz, $^4J_{H\text{-}B,H\text{-}A}$ 2.5 Hz, H$^B$), 8.54 (1H, d, $^4J_{H\text{-}A,H\text{-}B}$ 2.5 Hz, H$^A$), 8.98 (1H, s, H$^D$), 10.23 (1H, d, $J_{NH,CH}$ 6.9 Hz, CONH); $\delta_C$ (Acetone-d$^6$, 125 MHz): 18.8 (Alanine-CH$_3$), 28.1 (C(CH$_3$)$_3$), 49.5 (Alanine-C$_\alpha$), 57.6 (CH$_2$ (Bn)), 81.5 (C(CH$_3$)$_3$), 112.9 (O=C—C—C=O), 119.1 (Br-Cq), 121.0 (C$^C$), 127.4, 129.8, 129.9 (5×ArCs (Bn)), 129.0 (C$^A$), 130.4 (C$^A$-Cq-C=O), 136.2 (C$^B$), 136.4 (Cq (Bn)), 139.5 (C$^C$-Cq-N-Bn), 150.0 (C$^D$), 164.2 (C=ONH), 172.7 (C=OO$^t$Bu), 175.7 (O=C—C=C); Elemental Analysis: found C, 59.54%, H, 5.56%, N, 5.60%, required C, 59.39%, H, 5.19%, N, 5.77%.

Example 5

Compound 60. Synthesis of (S)-tert-butyl 2-(1-benzyl-6-bromo-4-oxo-1,4-dihydroquinoline-3-carboxamido)-4-methylpentanoate 6

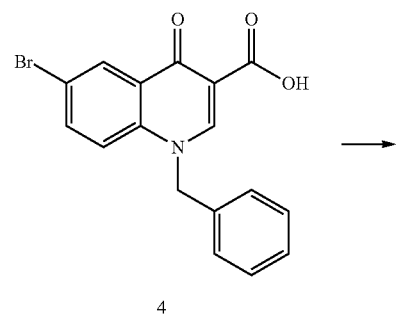

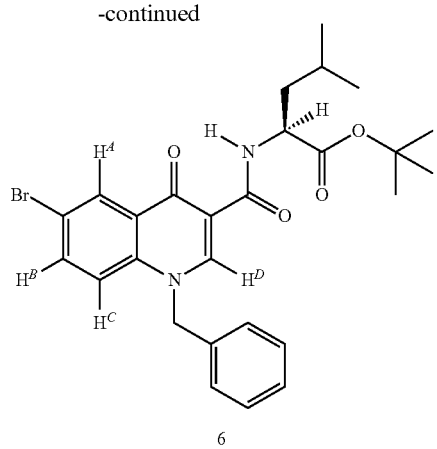

1-Benzyl-6-bromo-4-oxo-1,4-dihydroquinoline-3-carboxylic acid 4 (250 mg, 0.694 mMol) was stirred in N,N-dimethylacetamide (6.9 mL) and N-ethyldiisopropylamine (0.24 mL, 1.388 mMol). After 5 minutes O-(7-Azabenzotriazol-1-yl)-N,N,N',N'-tetramethyluronium hexafluorophosphate (527 mg, 1.388 mMol) and L-leucine-tert-butyl ester hydrochloride (310 mg, 1.388 mMol) were added (a pale yellow reaction mixture) and the temperature was raised to 50° C. After 23 hours the reaction mixture turned pale brown and L.C.M.S. analysis revealed the presence of the starting material (m/z 359-361) and of the product (m/z 528-530), hence the temperature was raised to 70° C. and let to run for an extra 22 hours. L.C.M.S. and t.l.c. (ethyl acetate:methanol, 5%) analysis showed solely the presence of the product ($R_f$ 0.86) and complete consumption of the starting material ($R_f$ 0.00). The reaction mixture was filtered through Celite (acetone), the filtrate was co-evaporated three times (acetone) and the residue was pre-absorbed on silica gel and purified by flash-chromatography (ethyl acetate:cyclohexane, 1:2 to ethyl acetate) to give (S)-tert-butyl 2-(1-benzyl-6-bromo-4-oxo-1,4-dihydroquinoline-3-carboxamido)-4-methylpentanoate 6 (92 mg, 25.1%) as a white crystalline solid. M.p. 185-186° C. (ethyl acetate/cyclohexane); HRMS (FAB$^+$): found 549.13552 [M+Na]$^+$ $C_{27}H_{31}N_2O_4{}^{79}BrNa$ requires 549.13648; found 551.13342 [M+Na]$^+$ $C_{27}H_{31}N_2O_4{}^{81}BrNa$ requires 551.13414; peak ratio: 50.0%:50.0%; $[\alpha]_D{}^{25}$ −7.540 (c, 0.25 in dichloromethane); $\nu_{max}$ (thin film): 3214, 3180 (w, NH, h-bonded), 3034 (m, ArC—H), 2957, 2871 (m, alkyl C—H), 1724 (m with shoulder, C=OO$^t$Bu ester & C=O ketone conjugated to C=C), 1654 (s, C=ONH, I and C=C conjugated with C=O), 1535 (m, CONH, II), 1596 (m, aromatic ring and C=C conjugated with C=O), 1478 (m, aromatic ring) cm$^{-1}$; $\delta_H$ (CDCl$_3$, 300 MHz): 0.91 (6H, d, $J_{CH3,CH}$ 5.8 Hz, (CH$_3$)$_2$CH-leucine), 1.49 (9H, s, C(CH$_3$)$_3$), 1.55-1.70 (2H, m, CH$_2$ (Leucine)), 1.77-1.87 (1H, m, CH (Leucine)), 4.68 (1H, m, J 7.2 Hz, C$_\alpha$H (Leucine)), 5.42 (2H, s, CH$_2$ (Bn)), 7.10-7.15 (2H, m, 2×ArHs (Bn)), 7.22-7.38 (4H, m, 3×ArHs (Bn) & H$^C$), 7.64 (1H, d, J 8.8 Hz, H$^B$), 8.65 (1H, s, H$^A$), 8.90 (1H, s, H$^D$), 10.26 (1H, d, $J_{NH,C\alpha H}$ 7.0 Hz, NH); $\delta_C$ (CDCl$_3$, 125 MHz): 22.0, 23.1 (Leucine (CH$_3$)$_2$), 25.2 (Leucine CH), 28.1 (C(CH$_3$)$_3$), 41.6 (Leucine CH$_2$), 51.9 (Leucine C$_\alpha$), 57.9 (CH$_2$ (Bn)), 81.5 (C(CH$_3$)$_3$), 112.4 (O=C—C—C=O), 118.7 (C$^C$), 119.3 (Br-Cq), 126.1, 128.8, 129.5 (5×ArCs (Bn)), 129.6 (C$^A$-Cq-C=O), 130.2 (C$^A$), 133.9 (Cq (Bn)), 135.9 (C$^B$), 138.2 (C$^C$-Cq-N-Bn), 148.8 (C$^D$), 164.4 (C=ONH), 172.6 (C=OO$^t$Bu), 175.6 (O=C—C=C).

Example 6

Compound 61. Synthesis of (S)-tert-butyl 2-(1-benzyl-6-bromo-4-oxo-1,4-dihydroquinoline-3-carboxamido)-3-phenylpropanoate 7

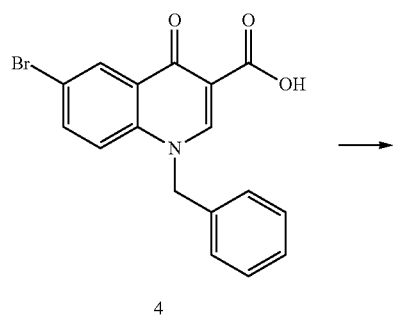

4

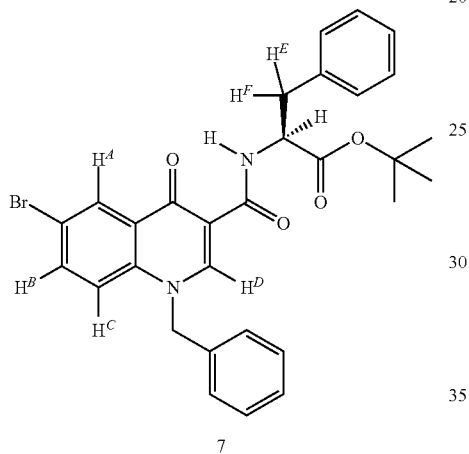

7

1-Benzyl-6-bromo-4-oxo-1,4-dihydroquinoline-3-carboxylic acid 4 (200 mg, 0.558 mMol) was stirred in N,N-dimethylacetamide (5.5 mL). Subsequently N,N-diisopropylethylamine (191 µL, 1.117 mMol), O-(7-Azabenzotriazol-1-yl)-N,N,N',N'-tetramethyluronium hexafluorophosphate (425 mg, 1.117 mMol) and L-phenylalanine tert-butyl ester hydrochloride (288 mg, 1.117 mMol) were added and the yellow reaction solution was allowed to run at 50° C. After 16.5 hours L.C.M.S. analysis of the light brown/red reaction solution showed the presence of one product (m/z 560-562) and the presence of some starting material (m/z 357-359). T.l.c. analysis (ethyl acetate:methanol, 5%) showed the presence of one product ($R_f$ 0.71). The reaction solution was allowed to cool down, the solvent removed by co-evaporation (2 times with toluene, once with acetone). The residue was pre-absorbed on silica gel and purified by flash column chromatography (ethyl acetate: cyclohexane, 1:1 to ethyl acetate) to give (S)-tert-butyl 2-(1-benzyl-6-bromo-4-oxo-1,4-dihydroquinoline-3-carboxamido)-3-phenylpropanoate 7 (313 mg, quantitative) as a white crystalline solid. M.p. 162° C. (DCM) (starts decomposing (turning brown)), 178-182° C. (decomposes and partially melts (turns brown throughout)); HRMS (TOF MS ES$^+$): found 583.1173 [M+Na]$^+$ $C_{30}H_{29}N_2O_4{}^{79}BrNa$ requires 583.1208; found 585.1201 [M+Na]$^+$ $C_{30}H_{29}N_2O_4{}^{81}BrNa$ requires 585.1188; peak ratio: 50.7%: 49.3%; $[\alpha]_D^{25}$ −52.451 (c, 0.20 in dichloromethane); $\nu_{max}$ (thin film): 3221, 3177 (w, NH, h-bonded), 3087, 3033 (m, ArC—H), 2976, 2931 (m, alkyl C—H), 1744 (m, C=OO$^t$Bu ester), 1729 (m, C=O ketone conjugated to C=C), 1661 (s, C=ONH, I and C=C conjugated with C=O), 1542 (m, CONH, II), 1599 (m, aromatic ring and C=C conjugated with C=O), 1481 (m, aromatic ring) cm$^{-1}$; $\delta_H$ (CDCl$_3$, 300 MHz): 1.41 (9H, s, C(CH$_3$)$_3$), 3.18 (1H, d, $J_{H-E,H-F}$ 14.0 Hz, $J_{H-E,CH}$ 6.9 Hz, H$^E$), 3.23 (1H, d, $J_{H-F,H-E}$ 14.0 Hz, $J_{H-F,CH}$ 6.2 Hz, H$^F$), 4.87-4.97 (1H, a-q, $J_{CH,H-E}$ 7.0 Hz, $J_{CH,H-F}$ 6.3 Hz NHCH), 5.93 (2H, s, CH$_2$, Phenylalanine), 7.08-7.38 (11H, m, 10×ArHs & ArH$^C$), 7.61 (1H, dd, $J_{H-B,H-C}$ 9.1 Hz, J 2.6 Hz, ArH$^B$), 8.62 (1H, d, J 2.2 Hz, ArH$^A$), 8.83 (1H, s, H$^D$), 10.41 (1H, d, J 8.0 Hz, NH); $\delta_C$ (CDCl$_3$, 125 MHz): 28.1 (C(CH$_3$)$_3$), 38.7 (CH$_2$, Phenylalanine), 54.6 (Phenylalanine-C$_\alpha$), 57.9 (CH$_2$, Bn), 81.9 (C(CH$_3$)$_3$), 112.3 (O=C—C—C=O), 118.7 (C$^C$), 119.3 (Br-Cq), 126.2 126.9 127.1, 128.4, 128.8, 128.9, 129.4, 129.6, 129.7, (10×ArCs), 129.5 (C$^A$-Cq-C=O), 130.2 (C$^A$), 134.0 (Cq (Bn)), 135.8 (C$^B$), 137.0 (Cq, Phenylalanine), 138.1 (C$^C$-Cq-N-Bn), 148.7 (C$^D$), 164.2 (C=ONH), 170.7 (CO$_2{}^t$Bu), 175.5 (O=C—C=C).

Example 7

Compound 28. Synthesis of tert-butyl 2-(1-benzyl-6-bromo-4-oxo-1,4-dihydroquinoline-3-carboxamido)acetate 8

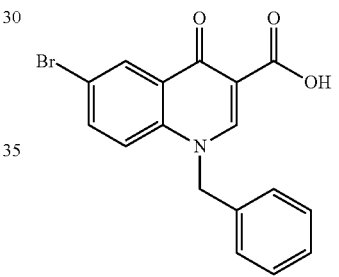

4

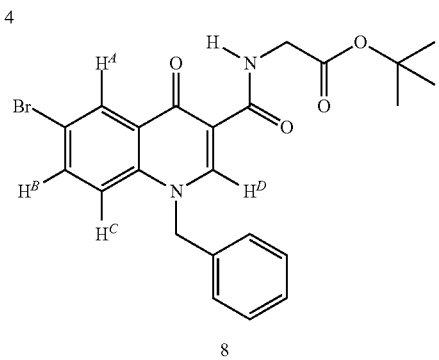

8

1-Benzyl-6-bromo-4-oxo-1,4-dihydroquinoline-3-carboxylic acid 4 (200 mg, 0.558 mMol) was stirred in N,N-dimethylacetamide (5.5 mL). Subsequently N,N-diisopropylethylamine (191 µL, 1.117 mMol), O-(7-Azabenzotriazol-1-yl)-N,N,N',N'-tetramethyluronium hexafluorophosphate (425 mg, 1.117 mMol) and L-glycine tert-butyl ester hydrochloride (187 mg, 1.117 mMol) were added and the yellow reaction solution was allowed to run at 50° C. After 16.5 hours L.C.M.S. analysis of the yellow/white reaction suspension showed the presence of one product (m/z 470-472) and complete consumption of the starting material (m/z 357-359). T.l.c. analysis (ethyl acetate:methanol, 5%) showed the presence of one product ($R_f$ 0.74). The reaction mixture was allowed to cool down, the solvent removed by co-evaporation (3 times with toluene). The residue was pre-absorbed on silica gel and purified by flash column chromatography (ethyl acetate:cyclohexane, 1:2 to 1:1) to give tert-butyl 2-(1-benzyl-6-bromo-4-oxo-1,4-dihydroquinoline-3-carboxamido)acetate 8 (196 mg, 74.5%) as a white crystalline solid. M.p. 150° C. (decomposition only: turned brown); HRMS (TOF MS ES$^+$): found 493.0728 [M+Na]$^+$ $C_{23}H_{23}N_2O_4{}^{79}BrNa$ requires 493.0739; found 495.0677 [M+Na]$^+$ $C_{23}H_{23}N_2O_4{}^{81}BrNa$ requires 495.0718; peak ratio: 52.7%:47.3%; $\nu_{max}$ (thin film): 3186 (w, broad, NH, h-bonded), 3035 (m, ArC—H), 2981, (m, alkyl C—H), 1732 (m with shoulder, C=OO$^t$Bu ester & C=O ketone conjugated to C=C), 1663 (s, C=ONH, I and C=C conjugated with C=O), 1547 (m, CONH, II), 1600 (m, aromatic ring and C=C conjugated with C=O), 1466 (m, Aromatic ring) cm$^{-1}$; $\delta_H$ (CD$_2$Cl$_2$, 300 MHz): 1.49 (9H, s, C(CH$_3$)$_3$), 4.11 (2H, d, $J_{CH2,NH}$ 5.9 Hz, NHCH$_2$C=O), 5.48 (2H, s, CH$_2$ (Bn)), 7.12-7.20 & 7.30-7.40 (6H, 2×m, 5×ArHs (Bn) & ArH$^C$), 7.68 (1H, dd, $J_{H-B,H-C}$ 9.1 Hz, $J_{H-B,H-A}$ 2.4 Hz, ArH$^B$), 8.61 (1H, d, $J_{H-A,H-B}$ 2.4 Hz, ArH$^A$), 8.90 (1H, s, 8.83 (1H, s, H$^D$), 10.21 (1H, a-t, J 5.00 Hz, NH); $\delta_C$ (CD$_2$Cl$_2$, 125 MHz): 28.2 (C(CH$_3$)$_3$), 42.5 (Glycine-C$_\alpha$), 58.2 (CH$_2$ (Bn)), 82.0 (C(CH$_3$)$_3$), 112.3 (O=C—C—C=O), 119.3 (C$^C$), 119.5 (Br-Cq), 126.6 129.0, 129.6 (5×ArCs), 129.9 (C$^A$-Cq-C=O), 130.1 (C$^A$), 134.5 (Cq (Bn)), 136.1 (C$^B$), 138.7 (C$^C$-Cq-N-Bn), 149.2 (C$^D$), 165.0 (C=ONH), 169.4 (CO$_2{}^t$Bu), 175.8 (O=C—C=C).

Example 8

Compound 63. Synthesis of (S)-tert-butyl 2-(1-benzyl-6-bromo-4-oxo-1,4-dihydroquinoline-3-carboxamido)-3-methylbutanoate 9

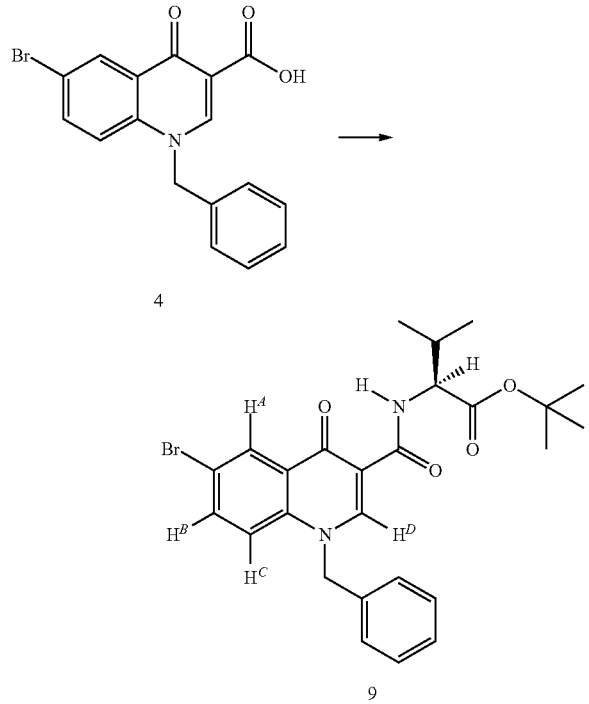

1-Benzyl-6-bromo-4-oxo-1,4-dihydroquinoline-3-carboxylic acid 4 (150 mg, 0.419 mMol) was stirred in N,N-dimethylacetamide (4.1 mL). Subsequently N,N-diisopropylethylamine (143 μL, 0.838 mMol), 2-(7-aza-1H-benzotriazole-1-yl)-1,1,3,3-tetramethyluronium hexafluorophosphate (318 mg, 0.838 mMol) and L-valine tert-butyl ester hydrochloride (176 mg, 0.838 mMol) were added and the light brown reaction solution was allowed to run at 50° C. After 19.5 hours t.l.c. analysis (ethyl acetate:methanol, 5%) of the light brown/white reaction suspension showed the presence of one product of one product ($R_f$ 0.60). The reaction mixture was allowed to cool down, the solvent removed by co-evaporation (3 times with toluene). The residue was pre-absorbed on silica gel (methanol) and purified by flash column chromatography (ethyl acetate:cyclohexane, 2:3) to give (S)-tert-butyl 2-(1-benzyl-6-bromo-4-oxo-1,4-dihydroquinoline-3-carboxamido)-3-methylbutanoate 9 (144 mg, 66.9%) as a white crystalline solid. M.p. 218-219° C. (melting and decomposition); HRMS (TOF MS ES$^+$): found 535.1195 [M+Na]$^+$ $C_{26}H_{29}N_2O_4{}^{79}BrNa$ requires 535.1208; found 537.1179 [M+Na]$^+$ $C_{26}H_{29}N_2O_4{}^{81}BrNa$ requires 537.1188; peak ratio: 50.6%:49.4%; [α]$_D{}^{25}$ +19.000 (c, 0.20 in dichloromethane); $\nu_{max}$ (thin film): 3232, 3179 (w, NH, h-bonded), 3035 (m, ArC—H), 2963, 2930, 2871 (m, alkyl C—H), 1726 (m with shoulder, C=O ketone conjugated to C=C & C=OO$^t$Bu ester), 1663 (s, C=ONH, I and C=C conjugated with C=O), 1543 (m, CONH, II), 1599 (m, aromatic ring and C=C conjugated with C=O), 1482 (m, aromatic ring) cm$^{-1}$; $\delta_H$ (CD$_2$Cl$_2$, 300 MHz): 0.93 (3H, d, $J_{CH3,CH}$ 6.9 Hz, Valine (CH$_3$)$_2$), 0.94 (3H, d, $J_{CH3,CH}$ 6.9 Hz, Valine (CH$_3$)$_2$), 1.40 (9H, s, C(CH$_3$)$_3$), 2.21 (1H, d septet, $J_{CH,CH3}$ 6.8 Hz, $J_{CH,C\alpha H}$ 4.7 Hz, CHCH(CH$_3$)$_2$), 4.46 (1H, dd, $J_{CH,CH}$ 4.7 Hz, $J_{CH,NH}$ 8.5 Hz, Valine C$_\alpha$H), 5.38 (2H, s, CH$_2$, Bn), 7.05-7.12 (2H, m, 2×ArHs (Bn)), 7.20-7.30 (4H, m, 3×ArHs (Bn) & ArH$^C$), 7.59 (1H, dd, $J_{H-B,H-C}$ 9.1 Hz, $J_{H-B,H-A}$ 2.3 Hz, ArH$^B$), 8.56 (1H, d, $J_{H-A,H-B}$ 2.4 Hz, ArH$^A$), 8.79 (1H, s, H$^D$), 10.18 (1H, d, $J_{NH,CH}$ 8.6 Hz, NH); $\delta_C$ (CD$_2$Cl$_2$, 125 MHz): 18.0, 19.5 (Valine CH(CH$_3$)$_2$), 28.2 (C(CH$_3$)$_3$), 31.6 (Valine CH(CH$_3$)$_2$), 58.1 (CH$_2$ (Bn)), 58.4 (Valine-C$_\alpha$), 81.6 (C(CH$_3$)$_3$), 112.8 (O=C—C—C=O), 119.2 (C$^C$), 119.3 (Br-Cq), 126.6 128.9 129.6 (5×ArCs (Bn)), 130.0 (C$^A$-Cq-C=O), 130.2 (C$^A$), 134.6 (Cq (Bn)), 136.0 (C$^B$), 138.7 (C$^C$-Cq-N-Bn), 149.1 (C$^D$), 164.5 (C=ONH), 171.3 (CO$_2{}^t$Bu), 175.9 (O=C—C=C). Elemental Analysis: found C, 60.79%, H, 5.86%, N, 5.19%, required C, 60.82%, H, 5.69%, N, 5.46%.

Example 9

Compound 185. Synthesis of (S)-methyl 2-(1-benzyl-6-bromo-4-oxo-1,4-dihydroquinoline-3-carboxamido)-3-methylbutanoate 27

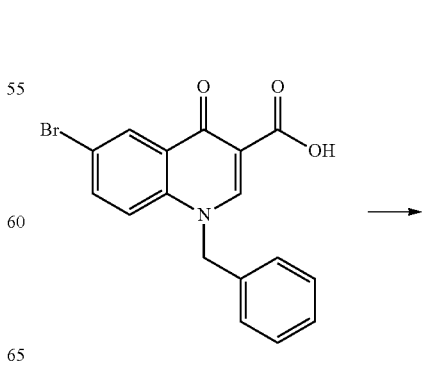

71
-continued

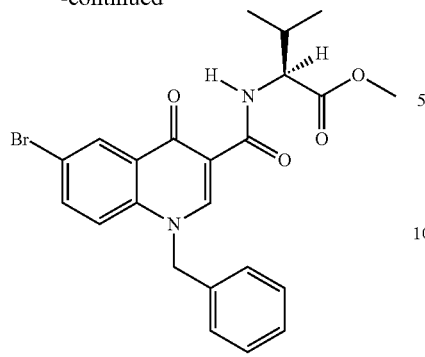

1-Benzyl-6-bromo-4-oxo-1,4-dihydroquinoline-3-carboxylic acid 4 (200 mg, 0.5584 mMol) was stirred in dichloromethane (5 mL) followed by the addition of triethylamine (257 μL, 1.8426 mMol) and DPPA (156 μL, 0.7259 mMol). After 5 minutes L-valine methyl ester hydrochloride (112 mg, 0.6681 mMol) were added to the stirring solution at room temperature and under an atmosphere of nitrogen. After 18 hours t.l.c. analysis (ethyl acetate:cyclohexane, 1:1) showed the presence of one product of one product ($R_f$ 0.31). The reaction mixture was filtered (ethyl acetate), the solvents were removed in vacuo and the residue was pre-absorbed on silica gel and purified by flash column chromatography (ethyl acetate:cyclohexane, 1:1 to 3:1 to ethyl acetate) followed by a recrystallisation of an impurity from dichloromethane/cyclohexane to give (S)-methyl 2-(1-benzyl-6-bromo-4-oxo-1,4-dihydroquinoline-3-carboxamido)-3-methylbutanoate 27 (242 mg, 91.9%) as a white fluffy solid. M.p. 230-232° C.; HRMS (ES$^+$): found 493.0715 [M+Na]$^+$ $C_{23}H_{23}N_2O_4{}^{79}BrNa$ requires 493.0739; found 495.0708 [M+Na]$^+$ $C_{23}H_{23}N_2O_4{}^{81}BrNa$ requires 495.0718; peak ratio: 50.0%:50.0%; $[\alpha]_D^{19.8}$ +83.8 (c, 0.14 in chloroform); $v_{max}$ (thin film): 3194 (w, sharp, 2 bands, sec. NH), 3038 (w, ArC—H), 2962, 2872 (w, alkyl C—H), 1752 (w, C=O ester), 1729 (m, C=O ketone), 1662 (s, C=ONH, I), 1570 (m, C=ONH, II), 1600 (s, C=C conjugated with C=Os) cm$^{-1}$; $\delta_H$ (CDCl$_3$, 500 MHz): 10.44 (1H, d, $J_{NH,C\alpha H}$ 7.5 Hz, NH), 8.93 (1H, s, H$^D$), 8.68 (1H, s, ArH$^4$), 7.68 (1H, d, $J_{H-B,H-C}$ 9.0 Hz, ArH$^B$), 7.53-7.22 (4H, m, 3×ArHs (Bn) & ArH$^C$), 7.16 (2H, m, 2×ArHs (Bn)), 5.48 (2H, s, CH$_2$ (Bn)), 4.72 (1H, dd, $J_{C\alpha H,NH}$ 7.9, $J_{C\alpha H,CH}$ 5.1 Hz, C$_\alpha$H), 3.76 (3H, s, OMe), 2.38 (1H, septet, $J_{CH,CH3}$ 6.6 Hz, CH (Valine)), 1.10 (6H, t, $J_{CH3,CH}$ 6.8 Hz, 2×CH$_3$ (Valine)); $\delta_C$ (CDCl$_3$, 125 MHz): 18.1, 19.5 (2×CH$_3$ (Valine)), 31.0 (CH (Valine)), 52.1 (OCH$_3$), 57.9 (C$_\alpha$ (Valine)), 58.0 (CH$_2$ (Bn)), 112.2 (O=C—C—C=O), 118.8 (C$^C$), 119.4 (Br-Cq), 126.2, 128.9, 129.5 (5×ArCs (Bn)), 129.4 (C$^C$-Cq-N-Bn), 130.1 (C$^A$), 133.9 (Cq(Bn)), 136.0 (C$^B$), 138.2 (C$^A$-Cq-C=O), 148.8 (C$^D$), 164.8 (C=ONH), 172.4 (C=OOMe), 175.7 (O=C—C=C).

72

Example 10

Compound 184. Synthesis of (S)-methyl 2-(1-benzyl-6-bromo-4-oxo-1,4-dihydroquinoline-3-carboxamido)propanoate 14

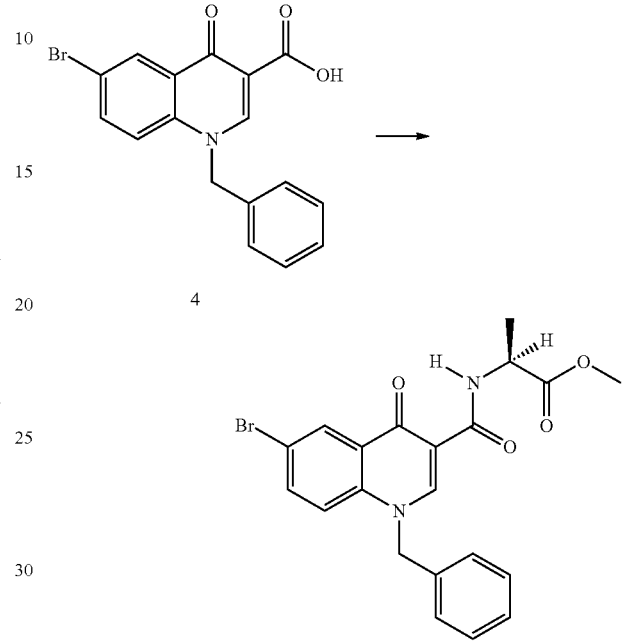

1-Benzyl-6-bromo-4-oxo-1,4-dihydroquinoline-3-carboxylic acid 4 (500 mg, 1.3959 mMol) was stirred in acetonitrile (20 mL) followed by triethylamine (973 μL, 6.9796 mMol) and 2-(7-aza-1H-benzotriazole-1-yl)-1,1,3,3-tetramethyluronium hexafluorophosphate (763 mg, 1.9543 mMol). After 5 minutes L-alanine methyl ester hydrochloride (273 mg, 1.9543 mMol) was added to the stirring solution. After 21 hours t.l.c. analysis (ethyl acetate:methanol, 5%) of the reaction mixture showed the presence of one product ($R_f$ 0.88). The reaction mixture was filtered (ethyl acetate) and the filtrate was concentrated in vacuo. The residue was pre-absorbed on silica gel and purified by flash column chromatography (ethyl acetate:cyclohexane, 1:1, to 3:1, to 1:0) to give (S)-methyl 2-(1-benzyl-6-bromo-4-oxo-1,4-dihydroquinoline-3-carboxamido)propanoate 14 (522 mg, 84%) as a white crystalline solid. M.p. 182-184° C.; HRMS (ES$^+$): found 465.0434 [M+Na]$^+$ $C_{21}H_{19}N_2O_4{}^{79}BrNa$ requires 465.0426; found 467.0415 [M+Na]$^+$ $C_{21}H_{19}N_2O_4{}^{81}BrNa$ requires 467.0405; peak ratio: 51.7%: 49.3%; $[\alpha]_D^{19.8}$ +83.8 (c, 0.14 in chloroform); $v_{max}$ (thin film): 3220, 3189 (w, sharp, sec. NH), 3039 (w, ArC—H), 2997 (w, alkyl C—H), 1755 (m, C=O ester), 1743 (s, C=O ketone), 1662 (s, C=ONH, I), 1574 (m, C=ONH, II), 1602 (s, C=C conjugated with C=Os) cm$^{-1}$; $\delta_H$ (CDCl$_3$, 500 MHz): 1.52 (3H, d, $J_{CH3,C\alpha H}$ 7.2 Hz, CH$_3$ (Ala)), 3.74 (3H, s, OCH$_3$), 4.74 (1H, a-quint, $J_{C\alpha H,CH3}$=$J_{C\alpha H,NH}$ 7.2 Hz, C$_\alpha$H), 5.43 (2H, s, CH$_2$(Bn)), 7.08-7.12 (2H, m, 2×ArHs (Bn)), 7.24-7.32 (4H, m, 3×ArHs (Bn) & ArH$^C$), 7.61 (1H, dd, $J_{H-B,H-C}$ 9.0 Hz, $J_{H-B,H-A}$ 2.3 Hz, ArH$^B$), 8.51 (1H, d, $J_{H-A,H-B}$ 2.2 Hz, ArH$^4$), 8.86 (1H, s, H$^D$), 10.30 (1H, d, $J_{NH,C\alpha H}$ 7.1 Hz, NH); $\delta_C$ (CDCl$_3$, 125 MHz): 18.3 (Alanine-CH$_3$), 48.3 (Alanine-C$_\alpha$), 52.4 (OCH$_3$), 57.9 (CH$_2$ (Bn)), 112.0 (O=C—C—C=O), 118.9 (C$^C$), 119.3

(Br-Cq), 126.2, 128.8, 129.4 (5×ArCs (Bn)), 129.3 ($C^C$-Cq-N-Bn), 129.9 ($C^A$), 134.0 (Cq(Bn)), 135.9 ($C^B$), 138.1 ($C^A$-Cq-C=O), 148.8 ($C^D$), 164.2 (C=ONH), 173.4 (C=OOMe), 175.4 (O=C—C=C).

Example 11

Compound 183. Synthesis of methyl 2-(1-benzyl-6-bromo-4-oxo-1,4-dihydroquinoline-3-carboxamido)acetate 15

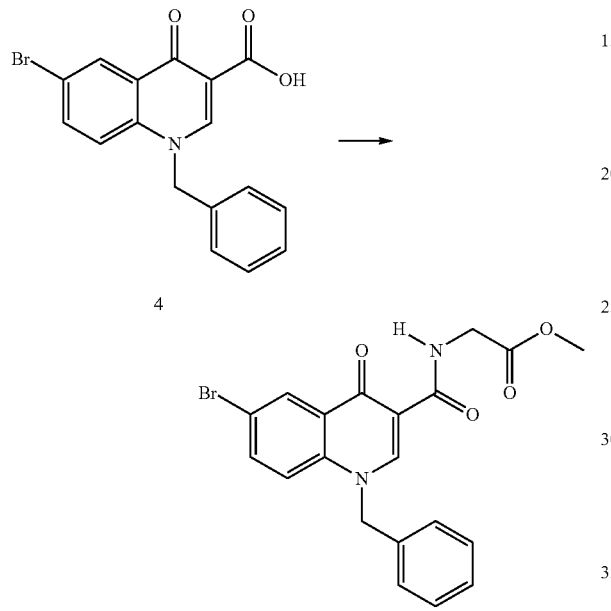

1-Benzyl-6-bromo-4-oxo-1,4-dihydroquinoline-3-carboxylic acid 4 (500 mg, 1.3959 mMol) was stirred in acetonitrile (20 mL) followed by triethylamine (973 μL, 6.9796 mMol) and 2-(7-aza-1H-benzotriazole-1-yl)-1,1,3,3-tetramethyluronium hexafluorophosphate (763 mg, 1.9543 mMol). After 5 minutes glycine methyl ester hydrochloride (245 mg, 1.9543 mMol) was added to the stirring solution. After 21 hours t.l.c. analysis (ethyl acetate:methanol, 5%) of the reaction mixture showed the presence of one product ($R_f$ 0.71). The reaction mixture was filtered (ethyl acetate) and the filtrate was concentrated in vacuo. The residue was pre-absorbed on silica gel and purified by flash column chromatography (ethyl acetate:cyclohexane, 1:1, to 3:1, to 1:0) to give methyl 2-(1-benzyl-6-bromo-4-oxo-1,4-dihydroquinoline-3-carboxamido)acetate 15 (170 mg, 28%) as a white crystalline solid. M.p. 227-228.5° C. melting and decomposition (turned brown); HRMS (ES$^+$): found 451.0268 [M+Na]$^+$ $C_{20}H_{17}N_2O_4{}^{79}$BrNa requires 451.0269; found 453.0245 [M+Na]$^+$ $C_{20}H_{17}N_2O_4{}^{81}$BrNa requires 453.0249; peak ratio: 49.7%:50.3%; $v_{max}$ (thin film): 3473, 3411 (w, sharp, sec. NH), 3050 (w, ArC—H), 2980, 2945 (w, alkyl C—H), 1754 (w, C=O ester), 1742 (s, C=O ketone), 1658 (s, C=ONH, I), 1578 (m, C=ONH, II), 1612 (s, C=C conjugated with C=Os) cm$^{-1}$; $\delta_H$ (CDCl$_3$, 500 MHz): 3.77 (3H, s, OCH$_3$), 4.25 (2H, d, $J_{C\alpha H,NH}$ 5.7 Hz, $C_\alpha H_2$), 5.43 (2H, s, CH$_2$(Bn)), 7.10-7.12 (2H, m, 2×ArHs (Bn)), 7.26-7.36 (4H, m, 3×ArHs (Bn) & ArH$^C$), 7.65 (1H, dd, $J_{H-B,H-C}$ 9.0 Hz, $J_{H-B,H-A}$ 2.4 Hz, ArH$^B$), 8.64 (1H, d, $J_{H-A,H-B}$ 2.2 Hz, ArH$^A$), 8.88 (1H, s, H$^D$), 10.31 (1H, t, $J_{H-B,C\alpha H}$ 5.5 Hz, NH);

$\delta_C$ (CDCl$_3$, 125 MHz): 41.4 ($C_\alpha$), 52.3 (OCH$_3$), 57.9 (CH$_2$ (Bn)), 112.1 (O=C—C—C=O), 118.8 (C$^C$), 119.4 (Br-Cq), 126.1, 128.9, 129.5 (5×ArCs (Bn)), 129.5 ($C^C$-Cq-N-Bn), 130.1 ($C^A$), 133.8 (Cq(Bn)), 136.0 ($C^B$), 138.2 ($C^A$-Cq-C=O), 148.8 ($C^D$), 165.0 (C=ONH), 170.3 (C=OOMe), 175.6 (O=C—C=C).

Example 12

Synthesis of (S)-methyl 2-(1-benzyl-6-bromo-4-oxo-1,4-dihydroquinoline-3-carboxamido)-4-methylpentanoate 16

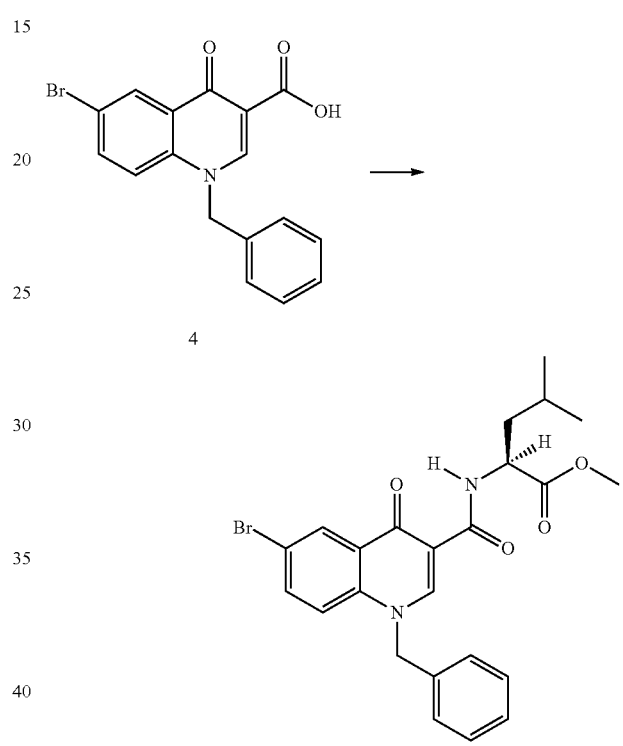

1-Benzyl-6-bromo-4-oxo-1,4-dihydroquinoline-3-carboxylic acid 4 (500 mg, 1.3959 mMol) was stirred in acetonitrile (20 mL). Subsequently triethylamine (973 μL, 6.9796 mMol), 2-(7-aza-1H-benzotriazole-1-yl)-1,1,3,3-tetramethyluronium hexafluorophosphate (763 mg, 1.9543 mMol) and leucine methyl ester hydrochloride (355 mg, 1.9543 mMol) were added. After 27 hours t.l.c. analysis (ethyl acetate:cyclohexane, 1:1) of the reaction mixture showed the presence of one product ($R_f$ 0.40). The reaction mixture was filtered (ethyl acetate) and the filtrate was concentrated in vacuo. The residue was pre-absorbed on silica gel and purified by flash column chromatography (ethyl acetate:cyclohexane, 1:4, to 1:1) to give (S)-methyl 2-(1-benzyl-6-bromo-4-oxo-1,4-dihydroquinoline-3-carboxamido)-4-methylpentanoate 16 (310 mg, 46%) as a pale yellow crystalline solid. M.p. at 120° C. a gas started being released, at 210° C. a pale brown colour started developing, at 250° C. a dark brown colour was produced. Decomposition before melting; HRMS (ES$^+$): found 507.0872 [M+Na]$^+$ $C_{24}H_{25}N_2O_4{}^{79}$BrNa requires 507.0895; found 509.0872 [M+Na]$^+$ $C_{24}H_{25}N_2O_4{}^{81}$BrNa requires 509.0875; peak ratio: 48.1%:51.9%; $v_{max}$ (thin film): 3178 (w, sharp with shoulder, sec. NH), 3038 (w, ArC—H), 2956, 2870 (w, alkyl C—H), 1736 (m, C=O ester), 1662 (s, C=ONH, I), 1545

(m, C=ONH, II), 1600 (s, C=C conjugated with C=Os) cm$^{-1}$; $\delta_H$ (CDCl$_3$, 500 MHz): 10.27 (1H, d, J$_{NH,C\alpha H}$ 7.3 Hz, NH), 8.90 (1H, s, H$^D$), 8.61 (1H, d, J$_{H-A,H-B}$ 2.3, H$^A$), 7.65 (1H, dd, J$_{H-B,H-C}$ 9.0 Hz, J$_{H-B,H-A}$ 2.4, H$^B$), 7.36-7.27 (4H, m, 4×ArHs (Bn)), 7.29 (1H, d, J$_{H-C,H-B}$ 9.0 Hz, H$^C$), 7.14-7.10 (1H, m, ArH), 5.44 (2H, s, CH$_2$ (Bn)), 4.77 (1H, ddd, J 13.0 Hz, J 5.4 Hz, J 3.3 Hz, C$_\alpha$H), 3.74 (3H, s, OMe), 1.92-1.69 (3H, m, CH & CH$_2$ (Leucine)), 0.99 (3H, d, J 6.2 Hz, CH$_3$ (Leucine)), 0.97 (1H, d, J 6.3 Hz, CH$_3$ (Leucine)); $\delta_C$ (CDCl$_3$, 125 MHz): 21.4, 22.7 (2×CH$_3$ (Leucine)), 24.7 (CH (Leucine)), 40.7 (CH$_2$ (Leucine)), 50.8 (C$_\alpha$), 51.9 (OMe), 57.6 (CH$_2$ (Bn)), 112.0 (O=C—C—C=O), 118.5 (C$^C$), 119.5 (Br-Cq), 125.8, 128.4, 129.1 (5×ArCs (Bn)), 129.4 (C$^A$-Cq-C=O), 129.6 (C$^A$), 133.9 (Cq (Bn)), 135.6 (C$^B$), 138.2 (C$^C$-Cq-N-Bn), 148.5 (C$^D$), 164.7 (C=ONH), 173.4 (C=OOMe), 175.6 (O=C—C=C).

Example 13

Compound 186. Synthesis of (S)-methyl 2-(1-benzyl-6-bromo-4-oxo-1,4-dihydroquinoline-3-carboxamido)-3-phenylpropanoate 17

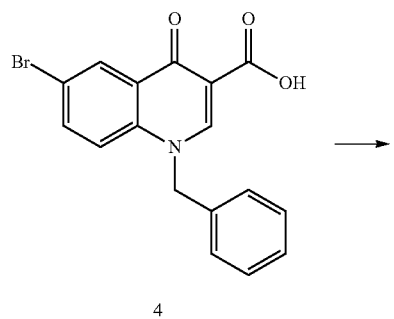

4

1-Benzyl-6-bromo-4-oxo-1,4-dihydroquinoline-3-carboxylic acid 4 (200 mg, 0.5584 mMol) was stirred in dichloromethane (5 mL) followed by triethylamine (257 μL, 1.8426 mMol) and DPPA (156 μL, 0.7259 mMol). After 5 minutes L-phenyl methyl ester hydrochloride (145 mg, 0.6700 mMol) was added. After 17.5 hours t.l.c. analysis (ethyl acetate:cyclohexane, 1:1) of the reaction mixture showed the presence of one product (R$_f$ 0.35). The reaction mixture was pre-absorbed on silica gel and purified by flash column chromatography (ethyl acetate:cyclohexane, 17:83, to 1:3, to 1:1) and recrystallised from dichloromethane/cyclohexane to give (S)-methyl 2-(1-benzyl-6-bromo-4-oxo-1,4-dihydroquinoline-3-carboxamido)-3-phenylpropanoate 17 (201 mg, 69%) as a pale yellow crystalline solid. M.p. 223-224° C. melted and decomposed (turned brown); HRMS (ES$^+$): found 541.0732 [M+Na]$^+$ C$_{27}$H$_{23}$N$_2$O$_4$$^{79}$BrNa requires 541.0739; found 543.0728 [M+Na]$^+$ C$_{27}$H$_{23}$N$_2$O$_4$$^{81}$BrNa requires 543.0718; peak ratio: 49.3%:50.7%; [α]$_D^{20}$ −5.067 (c, 0.25 in chloroform); ν$_{max}$ (thin film): 3216, 3174 (w, sharp, sec. NH), 3033 (w, ArC—H), 2951 (w, alkyl C—H), 1755 (m, C=O ester), 1744 (m, C=O ketone), 1661 (s, C=ONH, I), 1600 (s, C=C conjugated with C=Os), 1572 (m, C=ONH, II), 1542 (m, C=C benzene) cm$^{-1}$; $\delta_H$ (CDCl$_3$, 500 MHz): 3.18 (1H, a-dd, J$_{CHxHy,CHxHy}$ 14.0 Hz, J$_{CHxHy,C\alpha H}$ 8.0 Hz, CH$^X$H$^Y$ (Phenylalanine)), 3.27 (1H, a-dd, J$_{CHxHy,CHxHy}$ 13.9 Hz, J$_{CHxHy,C\alpha H}$ 5.6 Hz, CH$^X$H$^Y$ (Phenylalanine)), 3.72 (3H, s, OMe), 5.01 (1H, ddd, J$_{C\alpha H,NH}$ 7.6 Hz, J$_{C\alpha H,CHxCHy}$ 5.7 Hz, J 13.2 Hz, C$_\alpha$H), 5.39 (2H, s, CH$_2$(Bn)), 7.07-7.13 (2H, m, 2×ArHs (Bn)), 7.20-7.36 (9H, m, 8×ArHs (Bn) & ArH$^C$), 7.62 (1H, dd, 9.1 Hz, J$_{H-B,H-A}$ 2.5 Hz, ArH$^B$), 8.61 (1H, d, J$_{H-A,H-B}$ 2.6 Hz, ArH$^A$), 8.81 (1H, s, H$^D$), 10.38 (1H, d, J$_{NH,C\alpha H}$ 7.6 Hz, NH); $\delta_C$ (CDCl$_3$, 125 MHz): 38.4 (CH$_2$ (Phenylalanine)), 52.3 (OMe), 54.2 (C$_\alpha$), 57.9 (CH$_2$ (Bn)), 112.1 (O=C—C—C=O), 118.7 (C$^C$), 119.3 (Br-Cq), 126.1, 127.0, 128.6, 128.8, 129.4 (10×ArCs (Bn & Phenylalanine), 129.5 (C$^A$-Cq-C=O), 130.1 (C$^A$), 133.8 (Cq (Bn)), 135.9 (C$^B$), 136.6 (Cq, Phenylalanine), 138.2 (C$^C$-Cq-N-Bn), 148.7 (C$^D$), 164.5 (C=ONH), 172.1 (C=OOMe), 175.5 (O=C—C=C); Elemental Analysis: found C, 62.96%, H, 4.75%, N, 5.36%; required C, 62.44%, H, 4.46%, N, 5.39%.

Example 14

Synthesis of (S)-2-(1-benzyl-6-bromo-4-oxo-1,4-dihydroquinoline-3-carboxamido)-3-methylbutanoic acid

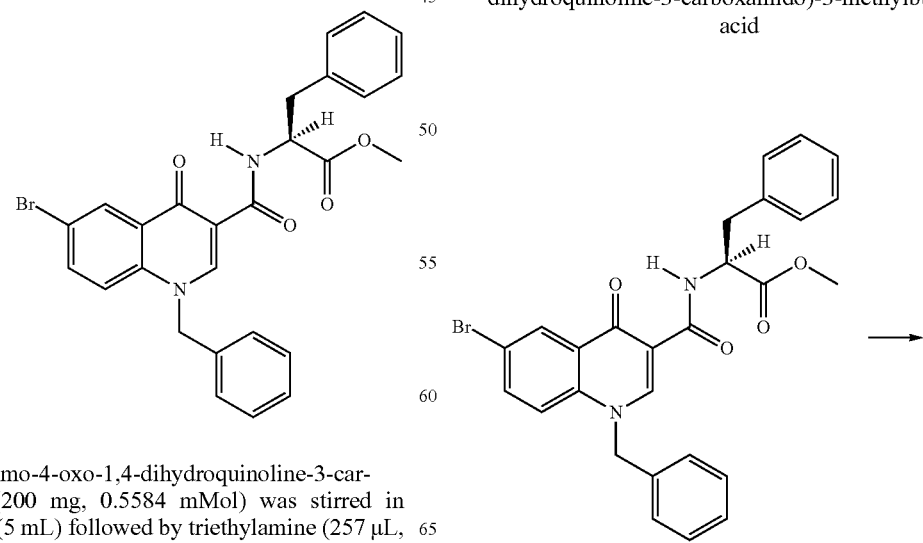

-continued

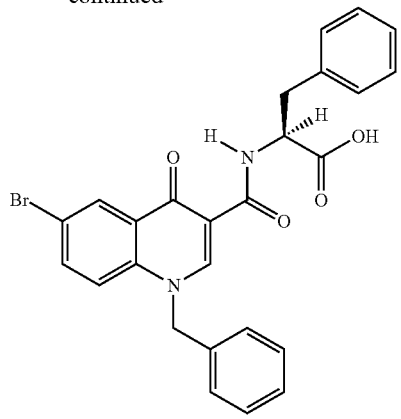

A cloudy mixture of (S)-methyl 2-(1-benzyl-6-bromo-4-oxo-1,4-dihydroquinoline-3-carboxamido)-3-methylbutanoate 27 (75 mg, 0.159 mmol), acetone (2.5 mL) and an aqueous solution of sodium hydroxide (2M, 5 mL) was stirred at room temperature for 24 hours. T.l.c. analysis (ethyl acetate:methanol, 5%) of the solution showed the presence of one UV-active product (Rf 0.00-0.10). The reaction solution was acidified with an aqueous solution of hydrochloric acid (1M), a white solid crushed out of solution and was filtered (water). The solid was dried under reduced pressure to give (S)-2-(1-benzyl-6-bromo-4-oxo-1,4-dihydroquinoline-3-carboxamido)-3-methylbutanoic acid 28 (65 mg, 89%) as a white crystalline solid. M.p. 247-248° C. melting and decomposition (turned brown); HRMS (ES$^+$): found 493.0715 [M+Na]$^+$ C$_{23}$H$_{23}$N$_2$O$_4$$^{79}$BrNa requires 493.0739; found 495.0708 [M+Na]$^+$ C$_{23}$H$_{23}$N$_2$O$_4$$^{81}$BrNa requires 495.0718; peak ratio: 50.0%:50.0%; $\nu_{max}$ (Ge): 3223 (w, sec. CONH), 3067 (w, ArC—H), 2964 (w, alkyl C—H), 3200-2700 (m, h-bonded COOH), 1733 (w, C═O ketone), 1714 (w, C═OOH), 1657 (s, C═ONH, I), 1601 (m, C═C conjugated with C═Os), 1543 (s with shoulder, C═ONH, II & C═C benzene) cm$^{-1}$; $\delta_H$ (Pyridine d$^5$, 500 MHz): 11.15 (1H, d, J$_{NH,C\alpha H}$ 8.4 Hz, NH), 9.52 (1H, s, H$^D$), 8.87 (1H, s, H$^4$), 7.64 (1H, d, J$_{HB,HC}$ 9.0 Hz, H$^B$), 7.60 (1H, d, J$_{HC,HB}$ 8.9 Hz, H$^C$), 7.41-7.20 (5H, m, 5×ArH (Bn)), 5.75 (2H, s, CH$_2$ (Bn)), 5.38 (1H, dd, J$_{C\alpha H,NH}$ 8.3 Hz, J$_{C\alpha H,CH}$ 4.4 Hz, C$_\alpha$H), 2.82-2.64 (1H, m, J 6.5 Hz, CH (Valine)), 1.36 (3H, d, J$_{CH3,CH}$ 6.7 Hz, CH$_3$ (Valine)), 1.30 (3H, d, J$_{CH3,CH}$ 6.7 Hz, CH$_3$ (Valine)); $\delta_C$ (Pyridine d$^5$, 125 MHz): 19.6, 21.2 (6Hs, 2×CH$_3$ (Valine)), 32.9 (CH (Valine)), 58.5 (CH$_2$ (Bn)), 59.8 (C$_\alpha$H), 114.4 (O═C—C—C═O), 120.4 (Br-Cq), 121.4 (C$^C$), 128.1, 129.8, 130.8 (5×ArCs (Bn)), 131.1 (C$^4$-Cq-C═O), 131.2 (C$^A$), 137.0 (Cq (Bn)), 138.8 (C$^B$), 140.0 (Cq-N-Bn), 151.0 (C$^D$), 166.3 (C═ONH), 176.1 (COOH), 177.1 (O═C—C═C).

Example 15

Compound 187. Synthesis of (S)-2-(1-benzyl-6-bromo-4-oxo-1,4-dihydroquinoline-3-carboxamido)-3-phenylpropanoic acid 29

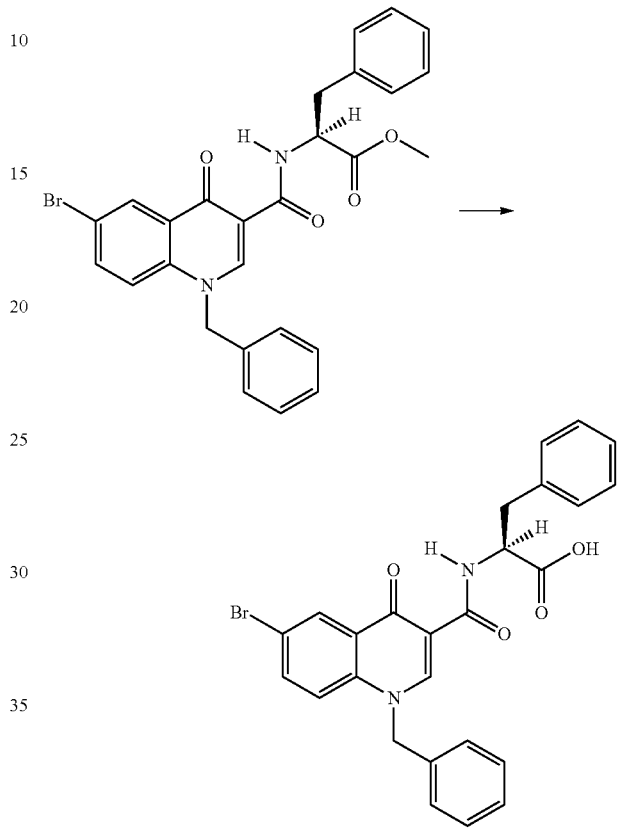

A cloudy mixture of (S)-methyl 2-(1-benzyl-6-bromo-4-oxo-1,4-dihydroquinoline-3-carboxamido)-3-phenylpropanoate 17 (60 mg, 0.116 mmol) in acetone (2 mL) and an aqueous solution of sodium hydroxide (2 M, 4 mL) was stirred at room temperature for 24 hours. T.l.c. analysis (ethyl acetate/methanol, 5%) showed the presence of one UV-active product (R$_f$ 0.00-0.10) and complete consumption of the starting material (R$_f$ 0.88). The reaction solution was acidified with an aqueous solution of hydrochloric acid (1 M) until a white solid crushed out. The reaction mixture was filtered, the solid washed with water and dried under reduced pressure to yield (S)-2-(1-benzyl-6-bromo-4-oxo-1,4-dihydroquinoline-3-carboxamido)-3-phenylpropanoic acid 29 (56 mg, 96%) as a pale yellow crystalline solid. M.p. phase transition occurs at 140-145° C. At higher emperature, decomposition occurs (turns brown); HRMS (ES$^+$): found 527.0582 [M+Na]$^+$ C$_{26}$H$_{21}$N$_2$O$_4$$^{79}$BrNa requires 527.0582; found 529.0552 [M+Na]$^+$ C$_{26}$H$_{21}$N$_2$O$_4$$^{81}$BrNa requires 529.0562; peak ratio: 51.7%:49.3%; $\nu_{max}$ (Ge): 3225 (w, sec. CONH), 3060, 3031 (w, ArC—H), 2922 (w, alkyl C—H), 3200-2700 (w, h-bonded COOH), 1734 (m with shoulder, C═O ketone & C═OOH), 1658 (s, C═ONH, I), 1601 (m, C═C conjugated with C═Os), 1543 (s with shoulder, C═ONH, II & C═C benzene) cm$^{-1}$; $\delta_H$ (pyridine d$^5$, 500 MHz): 11.10 (1H, d, J$_{NH,C\alpha H}$ 7.7 Hz, NH), 9.44 (1H, s, H$^D$), 8.79 (1H, d, J$_{HA,HB}$ 2.1 Hz, H$^A$), 8.69-7.77 (1H, br s, COOH), 7.66 (2H, m, 2×ArHs), 7.60 (1H, dd, $J_{HB,HC}$ 9.0 Hz, $J_{HB,HA}$ 2.3 Hz, $H^B$), 7.55 (1H, d, $J_{HC,HB}$ 9.0 Hz, $H^C$), 7.43-7.10 (8H, m, 8×ArHs), 5.79-5.59 (3H, m, CH$_2$ (Bn) & CαH), 3.73 (1H, dd, $J_{CHxHy,CHxHy}$ 13.8 Hz, $J_{CHxHy,NH}$ 5.1 Hz, $CH^XH^Y$ (Bn)), 3.56 (1H, dd, $J_{CHyHx,CHyHx}$ 13.8 Hz, $J_{CHyHx,NH}$ 7.8 Hz, $CH^XH^Y$ (Bn)); $δ_C$ (Pyridine d$^5$, 125 MHz): 39.32 (CH$_2$ (Phenylalanine)), 55.57 (C$_α$), 55.67 (CH$_2$ (Bn)), 113.38 (O=C—C—C=O), 119.47 (C$^C$), 120.47 (Br-Cq), 127.2, 129.4, 130.0, 130.6 (10×ArCs), 130.3 (C$^A$), 165.2 (C=ONH), 175.1 (C=OOH), 176.1 (C=O).

Example 16

Compound 188. Synthesis of (S)-2-(1-benzyl-6-bromo-4-oxo-1,4-dihydroquinoline-3-carboxamido)-4-methylpentanoic acid 30

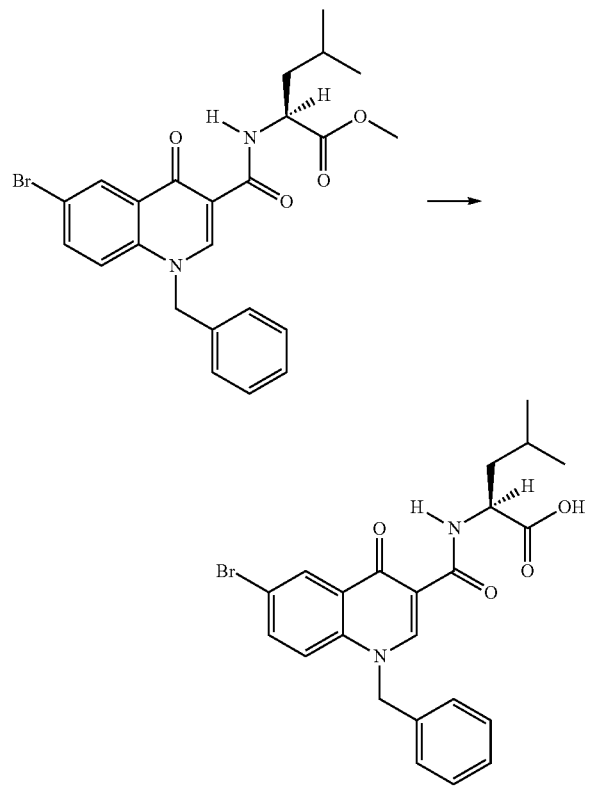

(S)-methyl 2-(1-benzyl-6-bromo-4-oxo-1,4-dihydroquinoline-3-carboxamido)-4-methylpentanoate 16 (20 mg, 4.1206×10$^{-2}$ mMol) was stirred in acetone (2 mL) and an aqueous solution of NaOH (2M, 2 mL) for 21.5 hours at room temperature. T.l.c. (ethyl acetate:cyclohexane, 1:1) revealed the presence of a product (R$_f$ 0.00) and complete consumption of the starting material (R$_f$ 0.40). Amberlite IR 120[H$^+$] was added to the stirring reaction solution and after 15 minutes the reaction mixture was filtered (acetone/water) and the solvents were removed in vacuo to give a residue which was purified by a silica plug (acetone to acetone:methanol, 40%) to give (S)-2-(1-benzyl-6-bromo-4-oxo-1,4-dihydroquinoline-3-carboxamido)-4-methylpentanoic acid 30 (10 mg, 52%) as a white solid. M.p. decomposition occurred above 210° C. (turned brown); HRMS (TOF MS ES$^-$): found 469.0776 [M]$^+$ $C_{23}H_{22}N_2O_4{}^{79}$Br requires 469.0763; found 471.0751 [M]$^+$ $C_{23}H_{22}N_2O_4{}^{81}$Br requires 471.0742; peak ratio: 49.6%:51.4%; $ν_{max}$ (Ge): 3235 (w, sec. CONH), 3067 (w, ArC—H), 2954, 2930 (w, alkyl C—H), 3400-3000 (w, h-bonded COOH), 1734 (w, C=O ketone), 1650 (s, C=ONH, I), 1597 (m, C=C conjugated with C=Os), 1579 (s, COO$^-$), 1542 (s, C=ONH, II) cm$^{-1}$; $δ_H$ (methanol d$^4$, 600 MHz): 9.00 (1H, s, H$^D$), 8.38 (1H, br s, H$^A$), 7.76 (1H, d, J 8.5 Hz, H$^B$), 7.58 (1H, d, J 8.1 Hz, H$^C$), 7.36-7.15 (5Hs, m, 5×ArHs (Bn)), 5.67 (1H, s CH$_2$ (Bn)), 4.63 (1H, m, C$_α$H (Leucine)), 1.87-1.73 (3H, m, CH & CH$_2$ (Leucine)), 1.02 (3H, d, J 5.4 Hz, CH$_3$ (Leucine)), 0.99 (3H, d, J 4.8 Hz, CH$_3$ (Leucine)); $δ_C$ (methanol d$^4$, 150 MHz): 21.0, 22.2 (Leucine 2×CH$_3$), 25.0 (Leucine CH), 41.3 (Leucine CH$_2$), 53.1 (Leucine C$_α$), 57.1 (CH$_2$ (Bn)), 111.1 (O=C—C—C=O), 119.8 (C$^C$), 119.8 (Br-Cq), 126.2, 128.0, 128.8 (5×ArCs (Bn)), 128.7 (C$^A$-Cq-C=O), 128.7 (C$^A$), 134.9 (Cq (Bn)), 135.6 (C$^B$), 138.2 (C$^C$-Cq-N-Bn), 149.2 (C$^D$), 164.9 (C=ONH), 171.6 (C=OOH), 175.2 (O=C—C=C).

Example 17

Compound 189. Synthesis of (S)-2-(1-benzyl-6-bromo-4-oxo-1,4-dihydroquinoline-3-carboxamido)propanoic acid 31

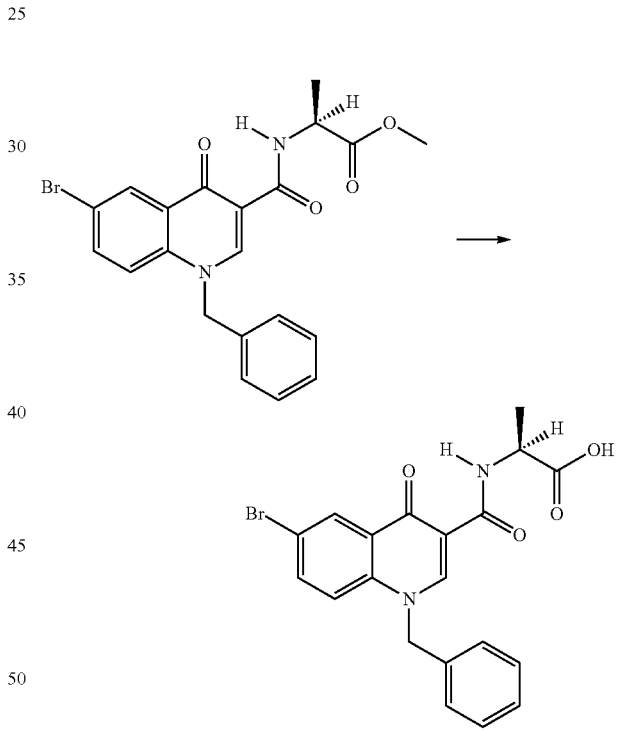

A cloudy mixture of (S)-methyl 2-(1-benzyl-6-bromo-4-oxo-1,4-dihydroquinoline-3-carboxamido)propanoate 14 (100 mg, 0.2256 mMol) was stirred in acetone (3 mL) and an aqueous solution of NaOH (2M, 7 mL) for 2 hours at room temperature. T.l.c. analysis (ethyl acetate:methanol, 5%) of the reaction solution revealed the presence of a product (R$_f$ 0.00-0.20) and complete consumption of the starting material (R$_f$ 0.88). The reaction solution was acidified with an aqueous solution of hydrochloric acid (1M) and a white solid crushed out. The mixture was then filtered (water, then briefly with an acetone:toluene, 1:1 mixture) and the solvents were removed in vacuo to give (S)-2-(1-benzyl-6-bromo-4-oxo-1,4-dihydroquinoline-3-carboxamido)propanoic acid 31 (70 mg, 72%) as a pale yellow crystalline solid. M.p. 234-236° C. melting and decomposition (turned brown); HRMS (ES+): found 451.0264 [M+Na]+ $C_{20}H_{17}N_2O_4{}^{79}BrNa$ requires 451.0269; found 453.0219 [M+Na]+ $C_{20}H_{17}N_2O_4{}^{81}BrNa$ requires 453.0249; peak ratio: 52.8%:47.2%; $\nu_{max}$ (Ge): 3228 (m, sec. CONH), 3063 (m, ArC—H), 2935 (w, alkyl C—H), 3200-2400 (w, h-bonded COOH), 1729 (m, C=O ketone), 1658 (s, C=ONH, I), 1600 (m, C=C conjugated with C=Os), 1580 (s, COO−), 1543 (s, C=ONH, II) cm$^{-1}$; $\delta_H$ (pyridine d$^5$, 500 MHz): 11.09 (1H, d, J 7.2), 11.00-9.70 (1H, br s, COOH), 9.51 (1H, s, H$^D$), 8.85 (1H, d, $J_{HA,HB}$ 2.1 Hz, H$^A$), 7.64 (1H, dt, $J_{HB,HC}$ 9.1 Hz, $J_{HB,HA}$ 2.3 Hz, H$^B$), 7.60 (1H, d, $J_{HC,HB}$ 9.1 Hz, H$^C$), 7.38-7.23 (5H, m, 5×ArHs (Bn)), 5.76 (2H, s, CH$_2$ (Bn)), 5.33 (1H, quintet, $J_{C\alpha H,NH}$=$J_{C\alpha H,CH3}$ 7.2 Hz, C$_\alpha$H (Alanine)), 1.80 (3H, d, $J_{CH3,C\alpha H}$ 7.2 Hz, CH$_3$ (Alanine)); $\delta_C$ (pyridine d$^5$, 125 MHz): 19.6 (Alanine-CH$_3$), 49.8 (Alanine-C$_\alpha$), 57.7 (CH$_2$ (Bn)), 113.5 (O=C—C—C=O), 119.6 (Br-Cq), 120.6 (C$^B$), 127.3, 129.0, 130.0 (5×ArCs (Bn)), 130.3 (C$^A$), 130.5 (C$^C$-Cq-N-Bn), 136.2 (C$^C$ & Cq(Bn)), 139.2 (C$^A$-Cq-C=O), 150.1 (C$^D$), 165.0 (C=ONH), 176.1 (O=C—C=C), 176.4 (C=OOH).

Example 18

Compound 118. Synthesis of 2-(1-benzyl-6-bromo-4-oxo-1,4-dihydroquinoline-3-carboxamido)acetic acid 32

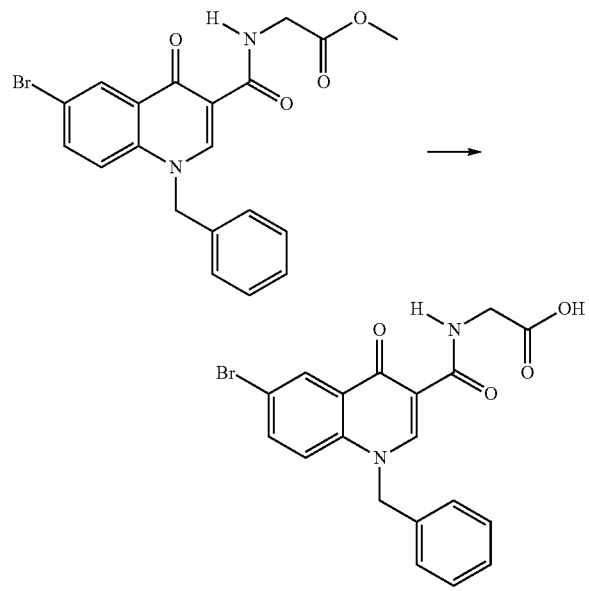

Methyl 2-(1-benzyl-6-bromo-4-oxo-1,4-dihydroquinoline-3-carboxamido)acetate 15 (15 mg, 3.4944×10$^{-2}$ mMol) was stirred in acetone (2 mL) and an aqueous solution of NaOH (2M, 2 mL) for 50 hours at room temperature. T.l.c. analysis (ethyl acetate:cyclohexane, 1:1) of the reaction solution revealed the presence of a product (R$_f$ 0.00) and complete consumption of the starting material (R$_f$ 0.71). The reaction mixture was acidified by stirring Amberlite IR 120[H+] in it for 15 minutes. The mixture was then filtered (water) and the solvents were removed in vacuo to give a residue which was purified by silica plug (acetone, then acetone/methanol 20%) to give 2-(1-benzyl-6-bromo-4-oxo-1,4-dihydroquinoline-3-carboxamido)acetic acid 32 (10 mg, 69%) as a pale yellow solid. M.p. 190° C. decomposition (turned brown); HRMS (ES+): found 437.0106 [M+Na]+ $C_{19}H_{15}N_2O_4{}^{79}BrNa$ requires 437.0113; found 439.0076 [M+Na]+ $C_{19}H_{15}N_2O_4{}^{81}BrNa$ requires 439.0092; peak ratio: 48.5%:51.5%; $\nu_{max}$ (Ge): 3401, 3307 (s broad, sec. CONH), 3600-2800 (m, COOH), 3067 (m, ArC—H), 2917, 2850 (w, alkyl C—H), 1652 (s, C=ONH, I), 1599 (m, C=C conjugated with C=Os), 1540 (s, C=ONH, II) cm$^{-1}$; $\delta_H$ (methanol d$^4$, 500 MHz): 8.98 (1H, s, H$^D$), 8.52 (1H, d, $J_{HA,HB}$ 2.3 Hz, H$^A$), 7.77 (1H, dd, $J_{HB,HC}$ 9.1 Hz, $J_{HB,HA}$ 2.4 Hz, H$^B$), 7.60 (1H, d, $J_{HC,HB}$ 9.1 Hz, H$^C$), 7.38-7.22 (5H, m, 5×ArHs (Bn)), 5.66 (2H, s, CH$_2$ (Bn)), 4.04 (2H, s, C$_\alpha$H$_2$); $\delta_C$ (methanol d$^4$, 150 MHz): 44.6 (Glycine-C$_\alpha$), 58.4 (CH$_2$ (Bn)), 113.1 (O=C—C—C=O), 120.1 (Br-Cq), 121.2 (C$^B$), 127.6, 129.5, 130.3 (5Cs, 5×ArCs (Bn)), 130.2 (C$^A$), 130.3 (C$^C$-Cq-N-Bn), 136.4 (Cq(Bn)), 137.0 (C$^C$), 139.8 (C$^A$-Cq-C=O), 150.5 (C$^D$), 166.2 (C=ONH), 176.2 (O=C—C=C), 176.7 (C=OOH).

Example 19

Compound 84. Synthesis of ethyl 4-oxo-1,4-dihydroquinoline-3-carboxylate 6

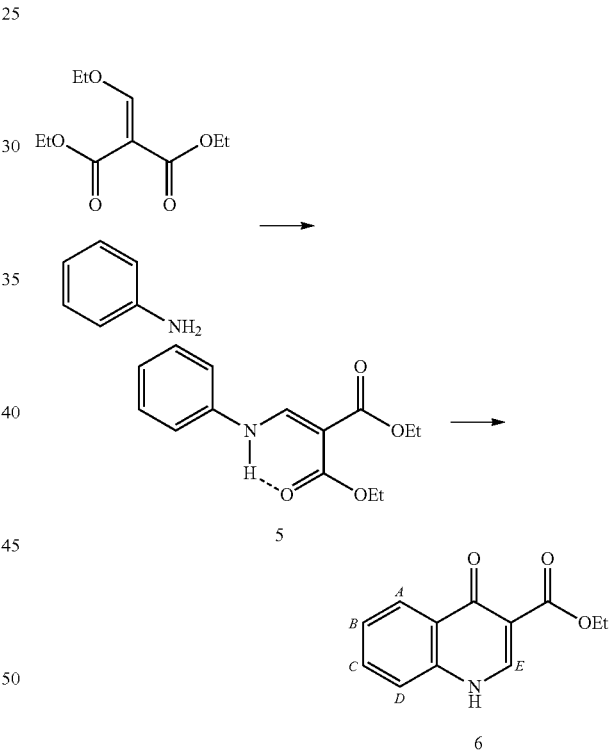

Aniline (2.733 mL, 29.99 mMol) was stirred in diethyl ethoxymethylenemalonate (6.063 mL, 30.00 mMol) at 120-130° C. for 16.5 hours. T.l.c. analysis (ethyl acetate:cyclohexane, 1:1) showed the presence of one UV-active product (R$_f$ 0.84) and complete consumption of both starting materials. Upon cooling down of the reaction solution to room temperature, intermediate diethyl 2-((phenylamino)methylene)malonate 35 solidified (as dark yellow crystalline solid, 7.899 g, quant.). M.p. 36-37° C.; HRMS (EI+): found 263.11531 [M]+ $C_{14}H_{17}NO_4$ requires 263.11521; $\nu_{max}$ (thin film): 3265, 3184 (w, NH), 3050 (w, ArC—H), 2981, 2936, 2904, 2871 (m, alkyl C—H), 1717 (s, 2×intramolecularly hydrogen-bonded C=O conjugated with C=C), 1691 (s, C=C—NH), 1655 (s, C=N—), 1623 (s, aryl conjugated C=C), 1255 (s, C—N stretch) cm$^{-1}$; $\delta_H$ (CD$_3$CN, 500 MHz): 1.31 (3H, t, J$_{CH3,CH2}$ 7.1 Hz, CH$_3$), 1.32 (3H, t, J$_{CH3,CH2}$ 7.2 Hz, CH$_3$), 4.19 (2H, q, J$_{CH2,CH3}$ 7.2 Hz, CH$_2$), 4.25 (2H, q, J$_{CH2,CH3}$ 7.1 Hz, CH$_2$), 7.16 (1H, tt, J$_{paraArH,metaArHs}$ 7.4 Hz, J$_{paraArH,orthoArHs}$ 1.1 Hz, paraArH), 7.20 (2H, dt, J$_{orthoArHs,metaArHs}$ 7.6 Hz, J$_{orthoArHs,paraArH}$ 1.0 Hz, 2×orthoArHs), 7.38 (2H, m, J 7.4 Hz, 2×metaArHs), 8.48 (1H, d, J$_{CH,NH}$ 13.8 Hz, CH—NH), 10.81 (1H, d, J$_{NH,CH}$ 13.6 Hz, CH—NH); $\delta_C$ (CD$_3$CN, 125 MHz): 14.1, 14.2 (2×CH$_3$), 60.3, 60.6 (2×CH$_2$), 93.9 (O=C—C—C=O), 117.6 (2×orthoArCs), 125.1 (paraArC), 130.1 (2×metaArCs), 139.8 (ArCquat-NH), 151.9 (NH—CH), 165.6 (C=O), 168.8 (hydrogen bonded C=O). Diphenyl ether (50 g) was then added to diethyl 2-((phenylamino)methylene)malonate 5 and the mixture (7.4145 g, 28.161 mMol) was refluxed at 250° C. After 6 hours the reaction mixture was allowed to cool down to room temperature and diluted in cyclohexane. A brown solid crushed out of solution. Filtration (eluant cyclohexane) yielded a brown solid which was dried by concentration in vacuo. The solid was then washed with acetone, filtered (eluant acetone) and concentrated in vacuo to yield ethyl 4-oxo-1,4-dihydroquinoline-3-carboxylate 36 (2.431 g, 37.3%) as a white/grey solid. M.p. 235° C. (gas evolved, decomposition); HRMS (EI$^+$): found 217.07455 [M]$^+$ C$_{12}$H$_{11}$NO$_3$ requires 217.07334; $\nu_{max}$ (thin film): 3409 (s broad, NH), 2974, 2899 (m, alkyl C—H), 1682 (s with shoulder, 2×C=O and C=C—NH), 1619, 1610 (s, aryl conjugated C=C) m$^{-1}$; $\delta_H$ (DMSO-d$^6$, 500 MHz): 1.27 (3H, t, J$_{CH3,CH2}$ 7.0 Hz, CH$_3$), 4.20 (2H, q, J$_{CH2,CH3}$ 6.9 Hz, CH$_2$), 7.40 (1H, m, J 7.6 Hz, J 7.0 Hz, H$^B$), 7.60 (1H, d, J$_{HD,HC}$ 7.8 Hz, H$^D$), 7.69 (1H, m, J 7.8 Hz, J 6.9 Hz, H$^C$), 8.14 (1H, d, J$_{HA,HB}$ 7.9 Hz, H$^A$), 8.54 (1H, s, CH—NH), 12.10-12.40 (1H, br s, NH); $\delta_C$ (DMSO-d$^6$, 125 MHz): 14.3 (CH$_3$), 59.6 (CH$_2$), 109.8 (O=C—C—C=O), 118.7 (ArC$^D$), 124.7 (ArC$^B$), 125.6 (ArC$^A$), 127.3 (ArCq-C=O), 132.4 (ArC$^C$), 139.0 (ArCq-NH), 144.9 (NH—CH), 164.8 (C=OOEt), 173.4 (C=O).

Example 20

Compound 85. Synthesis of ethyl 1-benzyl-4-oxo-1,4-dihydroquinoline-3-carboxylate 7

Ethyl 4-oxo-1,4-dihydroquinoline-3-carboxylate 6 (3.00 g, 13.811 mMol) was stirred in DMF (120 mL) with potassium carbonate (4.77 g, 34.527 mMol) at 40° C. under an atmosphere of nitrogen. After 5 minutes benzyl bromide (8.2 mL, 69.054 mMol) was added dropwise and the temperature raised to 80° C. After 4.5 hours, t.l.c. analysis (dichloromethane:acetone, 4:1) showed the presence of one UV-active product (R$_f$ 0.87) and complete consumption of the starting material (R$_f$ 0.10). The reaction mixture was filtered and the filtrate was concentrated in vacuo, pre-absorbed on silica and purified by flash-column chromatography (ethyl acetate:cyclohexane, 3:7, to 1:1, to 7:1, to ethyl acetate) to afford ethyl 1-benzyl-4-oxo-1,4-dihydroquinoline-3-carboxylate 7 (2.70 g, 64%) as a white/pale yellow crystalline solid. M.p. 150-158° C. (ethyl acetate/cyclohexane; melted over the range); HRMS (EI): found 307.12088 [M]$^+$ C$_{19}$H$_{17}$NO$_3$ requires 307.12029; $\nu_{max}$ (thin film): 3109, 3048 (w, ArC—H), 2979, 2935, 2904, 2871 (m, alkyl C—H), 1722 (s, C=O ketone), 1692 (s, C=O ester, conjugated with C=C), 1622, 1610 (s, C=C conjugated with C=Os), 1234 (s, C—N stretch) cm$^{-1}$; $\delta_H$ (CD$_3$CN, 500 MHz): 1.36 (3H, t, J$_{CH3,CH2}$ 7.1 Hz, CH$_3$), 4.31 (2H, q, J$_{CH2,CH3}$ 7.1 Hz, CH$_2$), 5.52 (2H, s, CH$_2$-Bn), 7.25-7.29 (2H, m, 2×ArHs (Bn)), 7.32-7.40 (3H, m, 3×ArHs (Bn)), 7.43 (1H, ddd, J$_{HB,HA}$ 8.0 Hz, J$_{HB,HC}$ 7.1 Hz, J$_{HB,HD}$ 1.0 Hz, H$^B$), 7.51 (1H, d, J$_{HD,HC}$ 8.6 Hz, H$^D$), 7.62 (1H, ddd, J$_{HC,HD}$ 8.6 Hz, J$_{HC,HB}$ 7.0 Hz, J$_{HC,HA}$ 1.6 Hz, H$^C$), 8.38 (1H, dd, J$_{HA,HB}$ 8.5 Hz, J$_{HA,HC}$ 1.6 Hz, H$^A$), 8.74 (1H, s, H$^E$); $\delta_C$ (CD$_3$CN, 125 MHz): 14.1 (CH$_3$), 57.0 (CH$_2$ (Bn)), 60.5 (CH$_2$), 111.1 (O=C—C—C=O), 117.8 (ArC$^D$), 125.3 (ArC$^B$), 127.1 (ArC$^A$), 126.9, 128.5, 129.4 (5×ArCs (Bn) & ArCq-C=O), 132.8 (ArC$^C$), 136.0 (Cq (Bn)), 139.8 (ArCq-NH), 150.5 (ArC$^E$), 165.2 (C=OOEt), 174.2 (C=O).

Example 21

Compound 86. Synthesis of 1-benzyl-4-oxo-1,4-dihydroquinoline-3-carboxylic acid 8

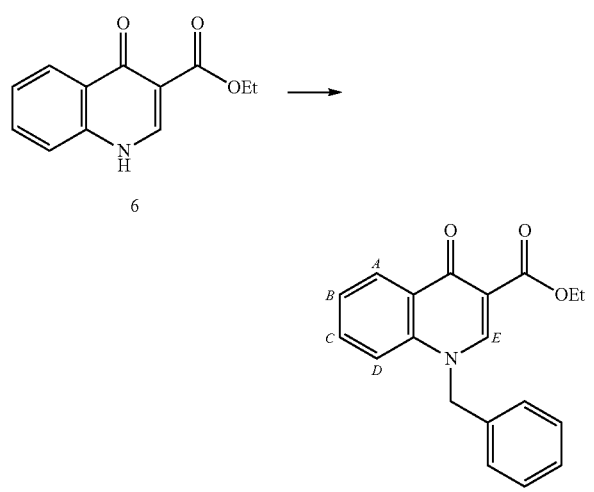

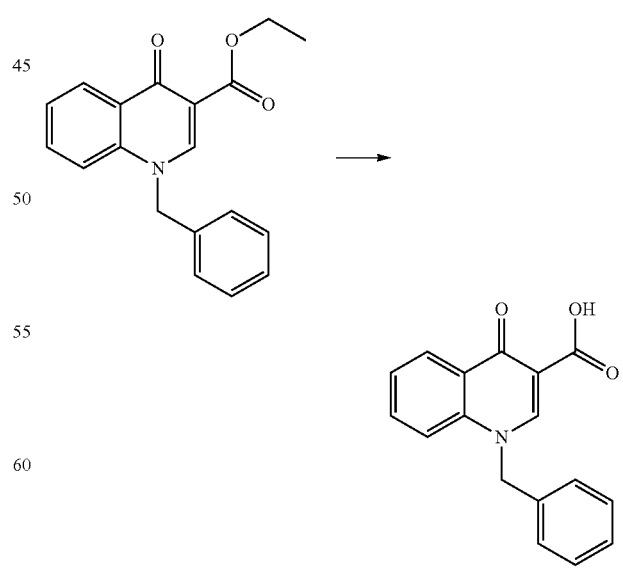

Ethyl 1-benzyl-4-oxo-1,4-dihydroquinoline-3-carboxylate 7 (2.65 g, 8.622 mmol) was srirred in acetone (135 mL)

and an aqueous solution of sodium hydroxide (2 M, 63 mL) for 90 minutes at room temperature and for four hours at 70° C. T.l.c. analysis (dichloromethane:acetone, 4:1) showed the presence of one product ($R_f$ 0.00-0.23) and complete consumption of the starting material ($R_f$ 0.57). the reaction solution was allowed to cool down to room temperature and acidified with an aqueous solution of hydrochloric acid (1 M). A white solid crushed out of solution, was filtered (water) and the solid was dried under reduced pressure to give 1-benzyl-4-oxo-1,4-dihydroquinoline-3-carboxylic acid 8 (2.40 g, quant.) as a white fluffy solid. M.p. 109-110° C.; HRMS (EI$^+$): found 280.09755 [M+H]$^+$ $C_{17}H_{14}NO_3$ requires 280.09737; $v_{max}$ (thin film): 3200-2000 (m, hydrogen-bonded of OH of carboxylic acid), 1708 (m, C=O, carboxylic acid), 1614 (s, C=C conjugated with C=Os) cm$^{-1}$; $\delta_H$ (pyridine d$^5$, 500 MHz): 15.50-15.90 (1H, br s, COOH), 9.55 (1H, s, H$^E$), 8.63 (1H, dd, $J_{HA,HB}$ 8.0 Hz, $J_{HA,HC}$ 1.5 Hz, H$^A$), 7.76 (1H, d, $J_{HD,HC}$ 8.6 Hz, H$^D$), 7.58 (1H, ddd, $J_{HC,HD}$ 11.5 Hz, $J_{HC,HB}$ 6.5 Hz, $J_{HC,HA}$ 3.0 Hz, H$^C$), 7.41 (1H, ddd, $J_{HB,HA}$ 8.0 Hz, $J_{HB,HC}$ 7.1 Hz, $J_{HB,HD}$ 0.9 Hz, H$^B$), 7.36-7.22 (5H, m, 5×ArHs (Bn)), 5.86 (2H, s, CH$_2$ (Bn)); $\delta_C$ (pyridine d$^5$, 125 MHz): 58.9 (CH$_2$ (Bn)), 109.7 (O=C—C=C=O), 118.7 (ArC$^D$), 126.7 (ArC$^A$), 127.3 (ArCq-C=O), 127.4 (ArC$^B$), 127.2, 129.1, 129.9 (5×ArCs (Bn), 134.5 (ArC$^C$), 135.8 (Cq (Bn) mostly masked by the pyridine d$^6$ signal), 140.5 (ArCq-NH), 150.7 (ArC$^E$), 167.2 (COOH), 179.3 (C=O).

Example 22

Compound 87. Synthesis of tert-butyl 2-(1-benzyl-4-oxo-1,4-dihydroquinoline-3-carboxamido)acetate 9

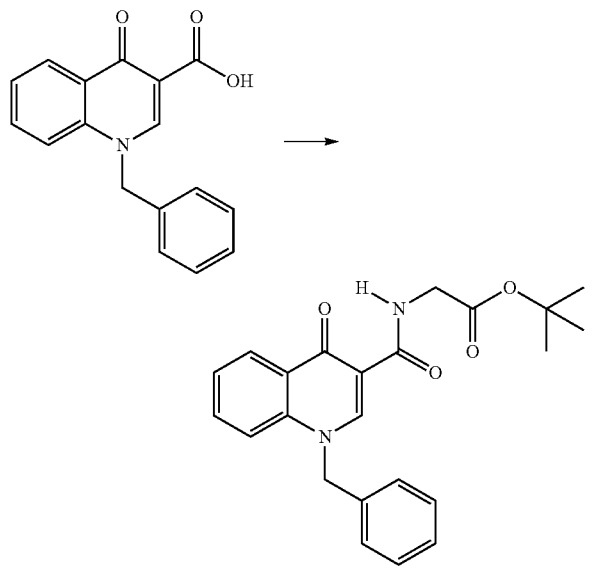

To a stirred mixture of 1-benzyl-4-oxo-1,4-dihydroquinoline-3-carboxylic acid 8 (100 mg, 0.358 mmol), triethylamine (165 μL, 1.182 mmol) and dichloromethane (5 mL), diphenylphosphoryl azide (100 μL, 0.465 mmol) was added dropwise at room temperature under an atmosphere of nitrogen. After 5 minutes L-glycine tert-butyl ester hydrochloride (72 mg, 0.430 mmol) was added and left to stir for 36 hours. T.l.c. analysis (acetone:cyclohexane, 1:1) showed the presence of one UV-active product ($R_f$ 0.62). The reaction mixture was washed with an aqueous solution of hydrochloric acid (1 M, 10 mL), the organic layer was then dried (magnesium sulphate), filtered and purified by flash-column chromatography (acetone:cyclohexane, 1:3, to 1:1) to give tert-butyl 2-(1-benzyl-4-oxo-1,4-dihydroquinoline-3-carboxamido)acetate 10 (110 mg, 78%) as a pale yellow crystalline solid. M.p. 189-190° C.; HRMS (CI$^+$): found 393.18078 [M+H]$^+$ $C_{23}H_{25}N_2O_4$ requires 393.18143; $v_{max}$ (thin film): 3169 (m, 2 peaks, CONH) 3042 (m, ArC—H), 2984, 2929 (m, alkyl C—H), 1732 (s with shoulder, C=O, ester & C=O, ketone), 1660 (s, CONH, I & C=C conjugated with C=O), 1552 (m, CONH, II), 1605 (s, aromatic ring and C=C conjugated with C=O), 1492 (s, aromatic ring) cm$^{-1}$; $\delta_H$ (CDCl$_3$, 500 MHz): 10.44 (1H, t, $J_{NH,CH}$ 5.2 Hz, NH), 8.87 (1H, s, H$^E$), 8.52 (1H, dd, $J_{H-A,H-B}$ 8.1 Hz, $J_{H-A,H-C}$ 1.4 Hz, ArH$^A$), 7.56 (1H, ddd, $J_{HC,HD}$ 8.6 Hz, $J_{HC,HB}$ 7.1 Hz, $J_{HC,HA}$ 1.6 Hz, H$^C$), 7.40 (1H, ddd, $J_{HB,HA}$ 7.9 Hz, $J_{HB,HC}$ 6.9 Hz, $J_{HB,HD}$ 1.0 Hz, H$^B$), 7.37 (1H, d, $J_{HD,HC}$ 8.8 Hz, H$^D$), 7.34-7.25 (3H, m, 3×ArHs (Bn)), 7.16-7.09 (2H, m, 2×ArHs (Bn)), 5.43 (2H, s, CH$_2$ (Bn)), 4.15 (2H, d, $J_{C\alpha H,NH}$ 5.5 Hz, C$_\alpha$H$_2$),), 1.48 (9H, s, C(CH$_3$)$_3$); $\delta_C$ (CDCl$_3$, 125 MHz): 28.1 (C(CH$_3$)$_3$), 42.2 (Glycine-C$_\alpha$), 57.7 (CH$_2$ (Bn)), 81.8 (C(CH$_3$)$_3$), 111.8 (O=C—C—C=O), 116.8 (C$^D$), 125.2 (C$^B$), 126.2 128.6 129.4 (5×ArCs (Bn)), 127.6 (C$^A$), 128.2 (C$^A$-Cq-C=O), 132.9 (C$^C$), 134.3 (Cq (Bn)), 139.4 (C$^C$-Cq-N-Bn), 148.6 (C$^E$), 165.2 (C=ONH), 169.1 (CO$_2^t$Bu), 176.8 (O=C—C=C).

Example 23

Compound 88. Synthesis of (S)-tert-butyl 2-(1-benzyl-4-oxo-1,4-dihydroquinoline-3-carboxamido)-3-methylbutanoate 10

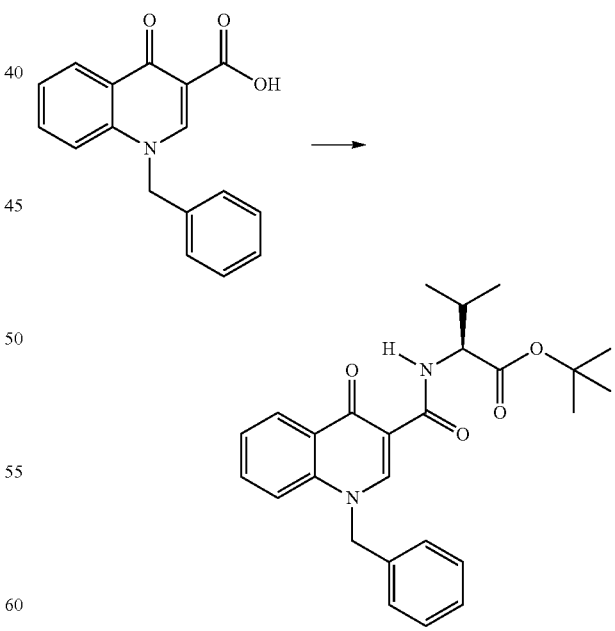

To a stirred mixture of 1-benzyl-4-oxo-1,4-dihydroquinoline-3-carboxylic acid 8 (100 mg, 0.358 mmol), triethylamine (164 μL, 1.182 mmol) and dichloromethane (5 mL) diphenylphosphoryl azide (100 μL, 0.465 mmol) was added dropwise at room temperature under an atmosphere of nitrogen. After 5 minutes L-valine tort-butyl ester hydrochloride (90 mg, 0.430 mmol) was added and left to stir for 72 hours. T.l.c. analysis (acetone:cyclohexane, 1:1) showed the presence of one UV-active product ($R_f$ 0.63). The reaction mixture was washed with an aqueous solution of hydrochloric acid (1 M), dried (magnesium sulphate), filtered and purified by flash-column chromatography (ethyl acetate:cyclohexane, 1:9, to 1:5) to give (S)-tert-butyl 2-(1-benzyl-4-oxo-1,4-dihydroquinoline-3-carboxamido)-3-methylbutanoate 10 (155 mg, quant.) as a white crystalline solid. M.p. 197-198° C.; HRMS (TOF MS ES$^+$): found 457.2099 [M+Na]$^+$ $C_{26}H_{30}N_2O_4Na$ requires 457.2103; $[\alpha]_D^{25}$ +21.032 (c, 0.25 in dichloromethane); $\nu_{max}$ (thin film): 3179 (m, 2 peaks, CONH) 3042, 3008 (m, ArC—H), 2932, 2873 (m, alkyl C—H), 1733 (m, C=O, ester), 1724 (m, C=O, ketone), 1662 (s, CONH, I & C=C conjugated with C=O), 1551 (m, CONH, II), 1605 (m, aromatic ring and C=C conjugated with C=O), 1491 (m, aromatic ring) cm$^{-1}$; $\delta_H$ (CD$_3$CN, 500 MHz): 10.44 (1H, d, $J_{NH,CH}$ 8.4 Hz, NH), 8.91 (1H, s, H$^E$), 8.47 (1H, dd, $J_{H-A,H-B}$ 8.1 Hz, $J_{H-A,H-C}$ 1.6 Hz, ArH$^A$), 7.67 (1H, ddd, $J_{HC,HD}$ 8.6 Hz, $J_{HC,HB}$ 7.0 Hz, $J_{HC,HA}$ 1.6 Hz, H$^C$), 7.59 (1H, d, $J_{HD,HC}$ 8.6 Hz, H$^D$), 7.47 (1H, ddd, $J_{HB,HC}$ 8.0 Hz, $J_{HB,HC}$ 7.0 Hz, $J_{HB,HD}$ 1.0 Hz, H$^B$), 7.39-7.26 (3H, m, 3×ArHs (Bn)), 7.26-7.18 (2H, m, 2×ArHs (Bn)), 5.58 (2H, s, CH$_2$ (Bn)), 4.46 (1H, dd, $J_{C\alpha H,NH}$ 8.4 Hz, $J_{C\alpha H,CH}$ 4.8 Hz, C$_\alpha$H), 2.25 (1H, d septet, $J_{CH,C\alpha H}$ 3.5 Hz, $J_{CH,CH3}$ 6.9 Hz, CH (Valine)), 1.47 (9H, s, C(CH$_3$)$_3$), 1.03 (3H, d, $J_{CH3,CH}$ 6.9 Hz, CH$_3$ (Valine)), 1.02 (3H, d, $J_{CH3,CH}$ 6.9 Hz, CH$_3$ (Valine)); $\delta_C$ (CD$_3$CN, 150 MHz): 16.9, 18.4 (Valine CH(CH$_3$)$_2$), 26.9 (C(CH$_3$)$_3$), 30.5 (Valine CH(CH$_3$)$_2$), 56.6 (CH$_2$ (Bn)), 57.6 (Valine-C$_\alpha$), 80.7 (C(CH$_3$)$_3$), 111.0 (O=C—C—C=O), 117.0 (C$^D$), 124.7 (C$^B$), 126.2, 127.8, 128.7 (5×ArCs (Bn)), 126.3 (C$^A$), 132.5 (C$^C$), 127.7 (C$^A$-Cq-C=O), 135.2 (Cq (Bn)), 139.2 (C$^C$-Cq-N-Bn), 148.5 (C$^E$), 164.2 (C=ONH), 170.8 (CO$_2$$^t$Bu), 176.3 (O=C—C=C).

Example 24

Compound 199. Synthesis of (S)-methyl 2-(1-benzyl-4-oxo-1,4-dihydroquinoline-3-carboxamido)-C3-phenylpropanoate 20

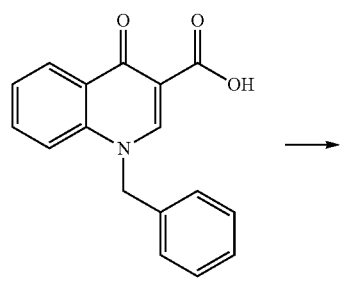

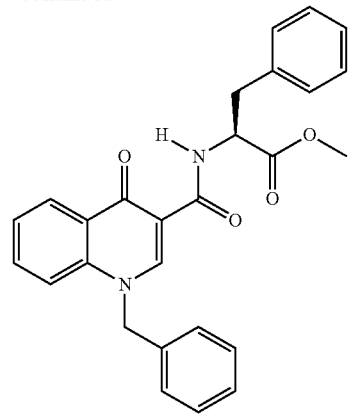

To a stirring solution of 1-benzyl-4-oxo-1,4-dihydroquinoline-3-carboxylic acid 8 (200 mg, 0.716 mmol) and triethylamine (329 μL, 2.363 mmol) in dichloromethane (5 mL), diphenylphosphoryl azide (200 μL, 0.931 mmol) was added dropwise at room temperature under an atmosphere of nitrogen. After 5 minutes L-phenylalanine methyl ester hydrochloride (185 mg, 0.859 mmol) was added to the stirring milky-coloured reaction mixture. After 90 hours, t.l.c. analysis (ethyl acetate/dichloromethane, 1:1) of the pale yellow semi-transparent suspension showed the presence of one new UV-active spot ($R_f$ 0.91). The reaction mixture was pre-absorbed on silica and purified by flash-column chromatography (ethyl acetate:cyclohexane, 1:3, to 1:1, to ethyl acetate) to yield (S)-methyl 2-(1-benzyl-4-oxo-1,4-dihydroquinoline-3-carboxamido)-3-phenylpropanoate 20 (248 mg, 79%) as a pale yellow crystalline solid. M.p. at 165° C. started turning brown. At 174-177° C. melted and decomposed (continued turning brown); $[\alpha]_D^{19.8}$ −10.873 (c, 0.42 in chloroform); $\nu_{max}$ (thin film): 3207, 3171 (w, sharp, sec. NH), 3046 (w, ArC—H), 2950, 2848 (w, alkyl C—H), 1755 (m, C=O ester), 1743 (m, C=O ketone), 1660 (s, C=ONH, I), 1571 (m, C=ONH, II), 1605 (s, C=C conjugated with C=Os) cm$^{-1}$; $\delta_H$ (CDCl$_3$, 500 MHz): 3.16 (1H, dd, $J_{CHxHy,CHxHy}$ 13.7 Hz, $J_{CHxHy,C\alpha H}$ 7.7 Hz, CH$^X$H$^Y$ (Phenylalanine)), 3.26 (1H, dd, $J_{CHxHy,CHxHy}$ 13.9 Hz, $J_{CHxHy,C\alpha H}$ 5.7 Hz, CH$^X$H$^Y$ (Phenylalanine)), 3.69 (3H, s, OMe), 5.01 (1H, (1H, td, $J_{C\alpha H,NH}$=$J_{C\alpha H,CHxHy}$ 7.6 Hz Hz, $J_{C\alpha H,CHxCHy}$ 5.7 Hz, C$_\alpha$H), 5.36 (2H, s, CH$_2$(Bn)), 7.08-7.11 (2H, m, 2×ArHs), 7.18-7.31 (10H, m, 8×ArHs), 7.33 (1H, d, $J_{HD,HC}$ 8.8 Hz, H$^D$), 7.35 (1H, m, J 7.3 Hz, H$^B$), 7.49 (1H, ddd, $J_{HC,HD}$ 8.7 Hz, $J_{HC,HB}$ 7.3 Hz, $J_{HC,HA}$ 1.6 Hz, H$^C$), 8.45 (1H, dd, $J_{HA,HB}$ 7.9 Hz, $J_{HA,HC}$ 1.6 Hz, H$^A$), 8.78 (1H, s, H$^E$), 10.56 (1H, d, $J_{NH,C\alpha H}$ 7.5 Hz, NH); $\delta_C$ (CDCl$_3$, 125 MHz): 38.8 (CH$_2$ (Phenylalanine)), 52.6 (OMe), 54.5 (CH), 57.9 (CH$_2$ (Bn)), 111.4 (O=C—C—C=O), 117.3 (C$^B$), 125.6, 126.6, 127.3, 128.9, 129.6, 129.7 (10×ArCs (Bn) & (Phenylalanine)), 128.4 (C$^A$-Cq-C=O), 128.9 (C$^D$), 133.3 (C$^C$), 134.8 (Cq (Bn)), 137.1 (Cq (Phenylalanine)), 139.6 (Cq-N-Bn), 148.9 (C$^E$), 164.9 (C=ONH), 172.2 (C=OOMe), 176.7 (O=C—C=C).

Example 25

Compound 196. Synthesis of compound (S)-methyl 2-(1-benzyl-4-oxo-1,4-dihydroquinoline-3-carboxamido)propanoate 21

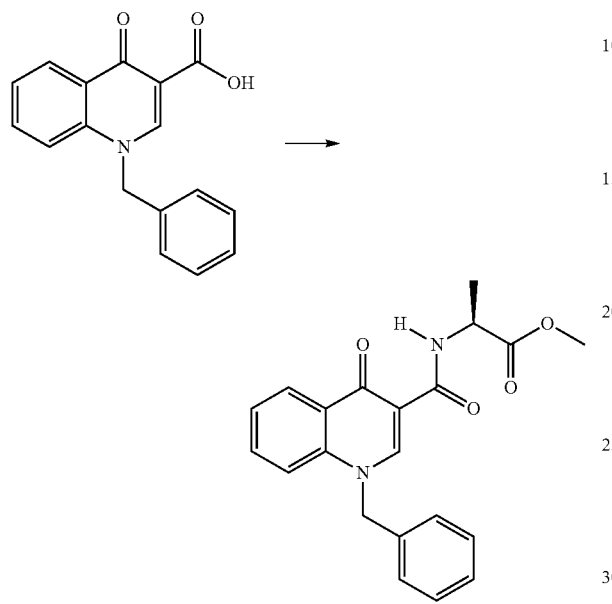

Example 26

Synthesis of compound (S)-methyl 2-(1-benzyl-4-oxo-1,4-dihydroquinoline-3-carboxamido)-3-methylbutanoate 22

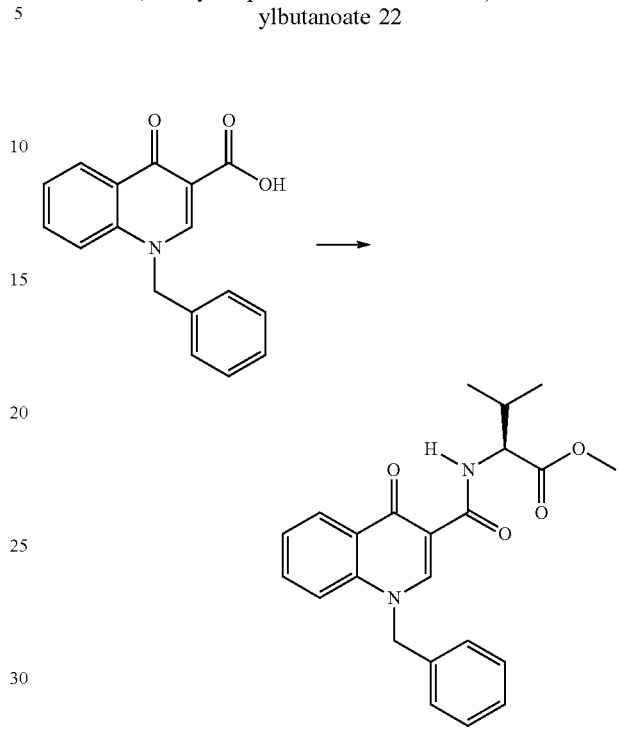

To a stirring solution of 1-benzyl-4-oxo-1,4-dihydroquinoline-3-carboxylic acid 8 (200 mg, 0.716 mmol) and triethylamine (329 μL, 2.363 mmol) in dichloromethane (5 mL), diphenylphosphoryl azide (200 μL, 0.931 mmol) was added dropwise at room temperature under an atmosphere of nitrogen. After 5 minutes L-alanine methyl ester hydrochloride (119 mg, 0.859 mmol) was added to the stirring milky-coloured reaction mixture. After 90 hours, t.l.c. analysis (ethyl acetate) of the pale yellow semi-transparent suspension showed the presence of one new UV-active spot ($R_f$ 0.90). The reaction mixture was pre-absorbed on silica and purified by flash-column chromatography (ethyl acetate:cyclohexane, 1:3, to 1:1, to ethyl acetate) to yield (S)-methyl 2-(1-benzyl-4-oxo-1,4-dihydroquinoline-3-carboxamido)propanoate 21 (188 mg, 72%) as a white solid. M.p. 168-170° C.; HRMS (CI$^+$): found 365.15043 [M+H]$^+$ $C_{21}H_{21}N_2O_4$ requires 365.15012; $[\alpha]_D^{20}$ +49.770 (c, 0.29 in chloroform); $\nu_{max}$ (thin film): 3200 (w, sharp, 2 bands, sec. NH), 3049 (w, ArC—H), 2983, 2952 (w, alkyl C—H), 1738 (s, C=O ester & C=O ketone), 1659 (s, C=ONH, I), 1583 (m, C=ONH, II), 1606 (s, C=C conjugated with C=Os) cm$^{-1}$; $\delta_H$ (CDCl$_3$, 500 MHz): 1.53 (3Hs, d, $J_{CH3,C\alpha H}$ 7.3 Hz, CH$_3$ (Alanine)), 3.74 (3Hs, s, OMe), 4.76 (1H, a-quint, $J_{C\alpha H,CH3}$=$J_{C\alpha H,NH}$ 7.3 Hz, CH), 7.10-7.14 (2Hs, m, 2×ArHs (Bn)), 7.24-7.32 (3Hs, m, 3×ArHs (Bn)), 7.36-7.41 (2Hs, m, H$^B$ & H$^D$), 7.55 (1H, ddd, J 8.9 Hz, J 6.9 Hz, $J_{HC,HA}$ 1.6 Hz, H$^C$), 8.47 (1H, dd, $J_{HA,HB}$ 8.2 Hz, $J_{HA,HC}$ 1.5 Hz, H$^A$), 8.86 (1H, s, H$^E$), 10.45 (1H, d, $J_{NH,C\alpha H}$ 7.4 Hz, NH); $\delta_C$ (CDCl$_3$, 125 MHz): 18.3 (CH$_3$ (Alanine)), 48.2 (C$_\alpha$H), 52.4 (OMe), 57.7 (CH$_2$ (Bn)), 111.6 (O=C—C=C=O), 116.9, 125.3 (C$^B$ & C$^D$), 126.2, 128.6, 129.3 (5×ArCs (Bn)), 127.3 (C$^A$), 128.1 (C$^A$-Cq-C=O), 133.0 (C$^C$), 134.3 (Cq (Bn)), 139.3 (Cq-N-Bn), 148.6 (C$^E$), 164.7 (C=ONH), 173.4 (C=OOMe), 176.8 (O=C—C=C).

To a stirring solution of 1-benzyl-4-oxo-1,4-dihydroquinoline-3-carboxylic acid 8 (200 mg, 0.716 mmol) and triethylamine (329 μL, 2.363 mmol) in dichloromethane (5 mL), diphenylphosphoryl azide (200 μL, 0.931 mmol) was added dropwise at room temperature under an atmosphere of nitrogen. After 5 minutes L-valine methyl ester hydrochloride (144 mg, 0.859 mmol) was added to the stirring milky-coloured reaction mixture. After 90 hours, t.l.c. analysis (ethyl acetate) of the pale yellow semi-transparent suspension showed the presence of one new UV-active spot ($R_f$ 0.90). The reaction mixture was pre-absorbed on silica and purified by flash-column chromatography (ethyl acetate:cyclohexane, 1:3, to 1:1, to ethyl acetate) to yield (S)-methyl 2-(1-benzyl-4-oxo-1,4-dihydroquinoline-3-carboxamido)-3-methylbutanoate 22 (231 mg, 82%) as a white solid. M.p. 194-196° C.; HRMS (CI$^+$): found 393.18079 [M+H]$^+$ $C_{23}H_{25}N_2O_4$ requires 393.18142; $[\alpha]_D^{20}$ +45.591 (c, 0.31 in chloroform); $\nu_{max}$ (thin film): 3173 (w, sharp, 2 bands, sec. NH), 3039 (w, ArC—H), 2961, 2876 (w, alkyl C—H), 1733 (s, C=O ester & C=O ketone), 1661 (s, C=ONH, I), 1574 (m, C=ONH, II), 1604 (s, C=C conjugated with C=Os) cm$^{-1}$; $\delta_H$ (CDCl$_3$, 500 MHz): 1.01 (3Hs, d, $J_{CH3,CH}$ 6.9 Hz, CH$_3$ (Valine)), 1.03 (3Hs, d, $J_{CH3,CH}$ 6.8 Hz, CH$_3$ (Valine)), 2.29 (1H, d septet, $J_{CH,CH3}$ 6.8 Hz, $J_{CH,C\alpha H}$ 5.2 Hz, CH (Valine)), 3.69 (3Hs, s, OMe), 4.64 (1H, dd, $J_{C\alpha H,NH}$ 8.2 Hz, $J_{C\alpha H,CH}$ 5.1 Hz, C$_\alpha$H), 5.63 (2Hs, s, CH$_2$ (Bn)), 7.07-7.11 (2Hs, m, 2×ArHs (Bn)), 7.19-7.28 (3Hs, m, 3×ArHs (Bn)), 7.34 (1H, ddd, $J_{HB,HA}$ 8.0 Hz, $J_{HB,HC}$ 7.1 Hz, $J_{HB,HD}$ 1.0 Hz, H$^B$), 7.37 (1H, d, $J_{HD,HC}$ 8.5 Hz, H$^D$), 7.51 (1H, ddd, $J_{HC,HD}$ 8.7 Hz, $J_{HC,HB}$ 7.1 Hz, $J_{HC,HA}$ 1.6 Hz, H$^C$), 8.43 (1H, dd, $J_{HA,HB}$ 8.1 Hz, $J_{HA,HC}$ 1.6 Hz, H$^A$), 8.86 (1H, s, H$^E$), 10.52 (1H, d, $J_{NH,C\alpha H}$ 8.2 Hz, NH); $\delta_C$ (CDCl$_3$, 125 MHz): 18.2, 19.5 (6Hs, 2×CH$_3$ (Valine)), 31.0 (CH (Valine)), 52.0 (OMe), 57.6 (CH$_2$ (Bn)), 57.8 (C$_\alpha$H), 111.7 (O=C—C—

C=O), 117.0 ($C^D$), 125.2 ($C^B$), 126.2, 128.7, 129.3 (5×ArCs (Bn)), 127.2 ($C^A$), 128.5 ($C^A$-Cq-C=O), 132.9 ($C^C$), 134.4 (Cq (Bn)), 139.3 (Cq-N-Bn), 148.6 ($C^E$), 165.2 (C=ONH), 172.5 (C=OOMe), 176.9 (O=C—C=C).

Example 27

Compound 197. Synthesis of methyl 2-(1-benzyl-4-oxo-1,4-dihydroquinoline-3-carboxamido)acetate 23

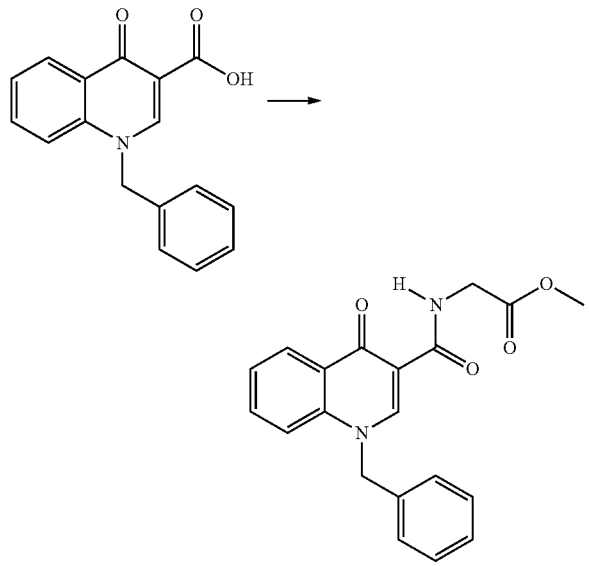

To a stirring solution of 1-benzyl-4-oxo-1,4-dihydroquinoline-3-carboxylic acid 8 (200 mg, 0.716 mmol) and triethylamine (329 μL, 2.363 mmol) in dichloromethane (10 mL), diphenylphosphoryl azide (200 μL, 0.931 mmol) was added dropwise at room temperature under an atmosphere of nitrogen. After 5 minutes L-glycine methyl ester hydrochloride (108 mg, 0.859 mmol) was added to the stirring milky-coloured reaction mixture. After 90 hours, t.l.c. analysis (ethyl acetate) of the pale yellow semi-transparent suspension showed the presence of one new UV-active spot ($R_f$ 0.90). The reaction mixture was pre-absorbed on silica and purified by flash-column chromatography (ethyl acetate: cyclohexane, 1:3, to 1:1, to ethyl acetate) to yield methyl 2-(1-benzyl-4-oxo-1,4-dihydroquinoline-3-carboxamido) acetate 23 (110 mg, 44%) as a white crystalline solid. M.p. 244-245° C. melting and decomposition (turned brown); HRMS (CI$^+$): found 351.13406 [M+H]$^+$ $C_{20}H_{19}N_2O_4$ requires 351.13448; $v_{max}$ (thin film): 3169 (w, sharp, 2 bands, sec. NH), 3044, 3008 (w, ArC—H), 2959, 2909 (w, alkyl C—H), 1743 (s, C=O ester & C=O ketone), 1657 (s, C=ONH, I), 1574 (m, C=ONH, II), 1607 (s, C=C conjugated with C=Os) cm$^{-1}$; $\delta_H$ (CDCl$_3$, 500 MHz): 3.78 (3Hs, s, OMe), 4.27 (1H, d, $J_{C\alpha H2,NH}$ 5.7 Hz, $C_\alpha H_2$), 5.46 (2Hs, s, CH$_2$ (Bn)), 7.13-7.18 (2Hs, m, 2×ArHs (Bn)), 7.28-7.37 (3Hs, m, 3×ArHs (Bn)), 7.40 (1H, d, $J_{HD,HC}$ 8.9 Hz, H$^D$), 7.44 (1H, ddd, $J_{HB,HA}$ 8.2 Hz, $J_{HB,HC}$ 6.9 Hz, $J_{HB,HD}$ 1.1 Hz, H$^B$), 7.60 (1H, ddd, $J_{HC,HD}$ 8.7 Hz, $J_{HC,HB}$ 7.1 Hz, $J_{HC,HA}$ 1.6 Hz, H$^C$), 8.54 (1H, dd, $J_{HA,HB}$ 8.0 Hz, $J_{HA,HC}$ 1.4 Hz, H$^A$), 8.90 (1H, s, H$^E$), 10.48 (1H, t, $J_{NH,C\alpha H2}$ 5.7 Hz, NH); $\delta_C$ (CDCl$_3$, 125 MHz): 41.4 ($C_\alpha H_2$), 52.3 (OMe), 57.8 (CH$_2$ (Bn)), 111.7 (O=C—C—C=O), 116.8 ($C^D$), 125.3 ($C^B$), 126.2, 128.7, 129.4 (5×ArCs (Bn)), 127.5 ($C^A$), 128.2 ($C^A$-Cq-C=O), 133.0 ($C^C$), 134.2 (Cq (Bn)), 139.4 (Cq-N-Bn), 148.7 ($C^E$), 165.5 (C=ONH), 170.4 (C=OOMe), 176.9 (O=C—C=C).

Example 28

Compound 198. Synthesis of (S)-methyl 2-(1-benzyl-4-oxo-1,4-dihydroquinoline-3-carboxamido)-4-methylpentanoate 24

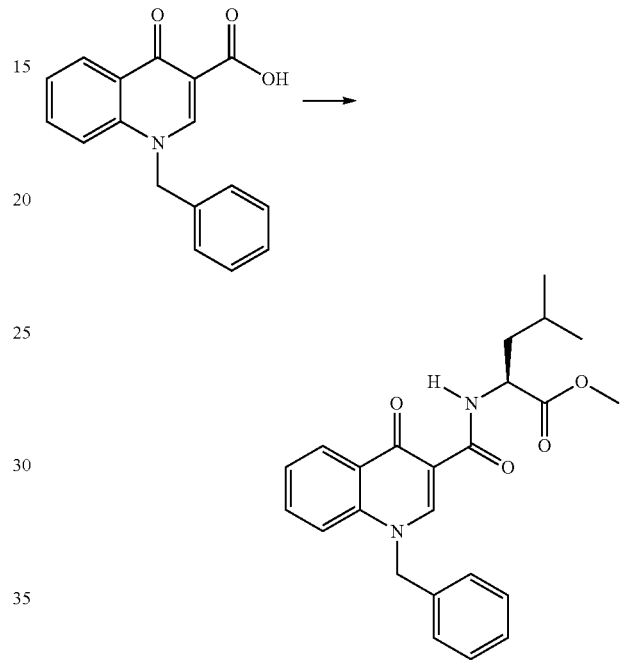

To a stirring solution of 1-benzyl-4-oxo-1,4-dihydroquinoline-3-carboxylic acid 8 (200 mg, 0.716 mmol) and triethylamine (329 μL, 2.363 mmol) in dichloromethane (5 mL), diphenylphosphoryl azide (200 μL, 0.931 mmol) was added dropwise at room temperature under an atmosphere of nitrogen. After 5 minutes L-leucine methyl ester hydrochloride (156 mg, 0.859 mmol) was added to the stirring milky-coloured reaction mixture. After 90 hours, t.l.c. analysis (ethyl acetate) of the pale yellow semi-transparent suspension showed the presence of one new UV-active spot ($R_f$ 0.90). The reaction mixture was pre-absorbed on silica and purified by flash-column chromatography (ethyl acetate: cyclohexane, 1:3, to 1:1, to ethyl acetate) to yield (S)-methyl 2-(1-benzyl-4-oxo-1,4-dihydroquinoline-3-carboxamido)-4-methylpentanoate 24 (229 mg, 79%) as a pale yellow crystalline solid. M.p. 116-117° C. melting and decomposition (turned brown); HRMS (CI$^+$): found 407.19636 [M+H]$^+$ $C_{24}H_{27}N_2O_4$ requires 407.19707; $[\alpha]_D^{20}$ +33.866 (c, 0.25 in chloroform); $v_{max}$ (thin film): 3170 (w, sharp, 2 bands, sec. NH), 3040 (w, ArC—H), 2956, 2929 (w, alkyl C—H), 1748 (m, C=O ester), 1738 (s, C=O ketone), 1661 (s, C=ONH, I), 1571 (m, C=ONH, II), 1605 (s, C=C conjugated with C=Os) cm$^{-1}$; $\delta_H$ (CDCl$_3$, 500 MHz): 0.95 (3Hs, d, $J_{CH3,CH}$ 6.3 Hz, CH$_3$ (Leucine)), 0.97 (3Hs, d, $J_{CH3,CH}$ 6.6 Hz, CH$_3$ (Leucine)), 1.70-1.90 (1H, m, CH (Leucine)), 1.76 (2Hs, dd, $J_{CH2,CH}$ 14.1 Hz, $J_{CH2,C\alpha H}$ 8.6 Hz, CH$_2$ (Leucine)), 3.71 (3Hs, s, OMe), 4.77 (1H, ddd, $J_{C\alpha H,CHH}$ 9.1 Hz, $J_{C\alpha H,NH}$ 7.5 Hz, $J_{C\alpha H,CHH}$ 5.6 Hz, $C_\alpha H$), 5.43 (2Hs, s, CH$_2$ (Bn)), 7.10-7.14 (2Hs, m, 2×ArHs (Bn)), 7.23-7.32 (3Hs, m, 3×ArHs (Bn)), 7.36-7.41 (2Hs, m, H$^B$ & H$^D$), 7.55 (1H, ddd, J$_{HC,HD}$ 8.7 Hz, J$_{HC,HB}$ 6.9 Hz, J$_{HC,HA}$ 1.6 Hz, H$^C$), 8.46 (1H, dd, J$_{HA,HB}$ 8.3 Hz, J$_{HA,HC}$ 1.4 Hz, H$^A$), 8.87 (1H, s, H$^E$), 10.38 (1H, d, J$_{NH,C\alpha H}$ 7.3 Hz, NH); δ$_C$ (CDCl$_3$, 125 MHz): 21.8, 23.1 (6Hs, 2×CH$_3$ (Leucine)), 25.1 (CH (Leucine)), 41.2 (CH$_2$ (Leucine)), 51.1 (C$_\alpha$H), 52.2 (OMe), 57.7 (CH$_2$ (Bn)), 111.6 (O=C—C—C=O), 116.9 (C$^D$), 125.3 (C$^B$), 126.2, 128.6, 129.3 (5×ArCs (Bn)), 127.3 (C$^A$), 128.1 (C$^A$-Cq-C=O), 133.0 (C$^C$), 134.3 (Cq (Bn)), 139.3 (Cq-N-Bn), 148.7 (C$^E$), 165.0 (C=ONH), 173.5 (C=OOMe), 176.9 (O=C—C=C).

Example 29

Compound 201. Synthesis of (S)-2-(1-benzyl-4-oxo-1,4-dihydroquinoline-3-carboxamido)-4-methylpentanoic acid 25

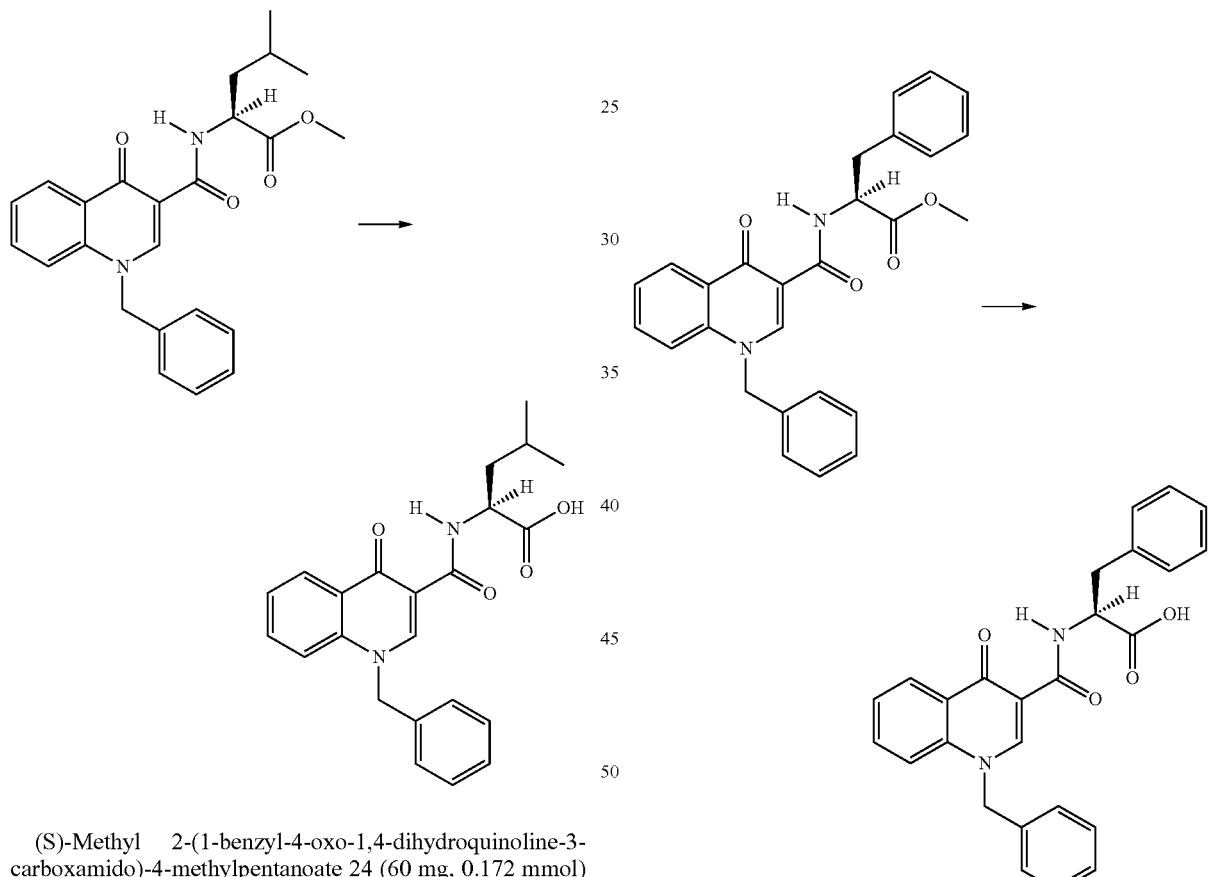

(S)-Methyl 2-(1-benzyl-4-oxo-1,4-dihydroquinoline-3-carboxamido)-4-methylpentanoate 24 (60 mg, 0.172 mmol) was stirred in acetone (2 mL) and an aqueous solution of sodium hydroxide (2 M, 5 mL) at room temperature for 24 hours. T.l.c. analysis (ethyl acetate) showed the presence of one UV-active product and complete consumption of the starting material. The reaction solution was acidified with an aqueous solution of hydrochloric acid (2 M) until a white solid crushed out. The reaction mixture was filtered, the solid washed with water and dried under reduced pressure to yield (S)-2-(1-benzyl-4-oxo-1,4-dihydroquinoline-3-carboxamido)-4-methylpentanoic acid 25 as a white solid. HRMS (TOF MS ES$^+$): found 415.1635 [M+Na]$^+$ C$_{23}$H$_{24}$N$_2$O$_4$Na requires 415.1634; ν$_{max}$ (Ge): 3500-2700 (m, COOH), 3243 (m, broad, sec. NH), 3066 (w, ArC—H), 2955, 2930, 2870 (m, alkyl C—H), 1652 (s broad, C=ONH, I), 1602 (s, C=C conjugated with C=Os), 1548 (m, C=ONH, II) cm$^{-1}$; δ$_H$ (methanol d$^4$, 500 MHz): 0.95-1.00 (6Hs, m, 2×CH$_3$ (Leucine)), 1.70-1.87 (3H, m, CH & CH$_2$ (Leucine)), 4.55-4.63 (1H, m, C$_\alpha$H (Leucine)), 5.69 (2Hs, s, CH$_2$ (Bn)), 7.18-7.34 (5Hs, m, 5×ArHs (Bn)), 7.39-7.46 (1Hs, m, H$^B$), 7.62-7.67 (2Hs, m, H$^C$ & H$^D$), 8.35 (1H, d, J 7.8 Hz, H$^A$), 8.97 (1H, s, H$^E$); δ$_C$ (methanol d$^4$, 150 MHz): 21.6, 23.0 (2Cs, 2×CH$_3$ (Leucine)), 25.6 (CH (Leucine)), 42.4 (CH$_2$ (Leucine)), 54.1 (C$_\alpha$H), 57.6 (CH$_2$ (Bn)), 111.5 (O=C—C—C=O), 117.4 (C$^D$), 125.7 (C$^B$), 126.7, 128.5, 129.4 (5×ArCs (Bn)), 126.9 (C$^A$), 128.1 (C$^A$-Cq-C=O), 133.5 (C$^C$), 135.8 (Cq (Bn)), 139.9 (Cq-N-Bn), 149.5 (C$^E$), 165.7 (C=ONH), 177.3 (COOH), 179.2 (O=C—C=C).

Example 30

Compound 200. Synthesis of (S)-2-(1-benzyl-4-oxo-1,4-dihydroquinoline-3-carboxamido)-3-phenylpropanoic acid 26

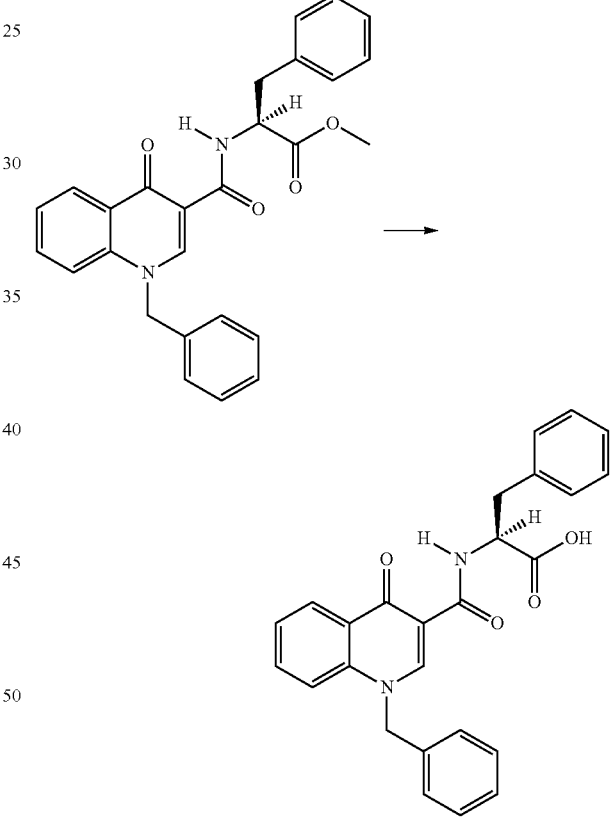

(S)-Methyl 2-(1-benzyl-4-oxo-1,4-dihydroquinoline-3-carboxamido)-3-phenylpropanoate 20 (60 mg, 0.136 mmol) was stirred in acetone (2 mL) and an aqueous solution of sodium hydroxide (2 M, 5 mL) at room temperature for 24 hours. T.l.c. analysis (ethyl acetate) showed the presence of one UV-active product (R$_f$ 0.00-0.10) and complete consumption of the starting material (R$_f$ 0.94). The reaction solution was acidified with an aqueous solution of hydrochloric acid (2 M) until a white solid crushed out. The reaction mixture was filtered, the solid washed with water and dried under reduced pressure to yield (S)-2-(1-benzyl- 4-oxo-1,4-dihydroquinoline-3-carboxamido)-3-phenylpropanoic acid 26 as a white solid. M.p. 227-228° C. melted and decomposed (turned brown); HRMS (TOF MS ES$^+$): found 427.1644 [M+H]$^+$ C$_{26}$H$_{23}$N$_2$O$_4$ requires 427.1658, found 449.1496 [M+Na]$^+$ C$_{26}$H$_{22}$N$_2$O$_4$Na requires 449.1477; $v_{max}$ (Ge): 3132 (m, broad, sec. NH), (masked ArC—H & alkyl C—H), 1713 (m, C=OOH), 1661 (s broad, C=ONH, I), 1598, 1586 (s, C=C conjugated with C=Os), 1552 (s, C=ONH, II) cm$^{-1}$; $\delta_H$ (pyridine d$^5$, 500 MHz): 11.34 (1H, d, J$_{NH,C\alpha H}$ 7.7 Hz, NH), 9.47 (1H, s, H$^E$), 8.78 (1H, d, J$_{HA,HB}$ 8.0 Hz, H$^A$), 7.68 (2H, d, J 7.3 Hz, 2×ArHs), 7.64 (1H, d, J$_{HD,HC}$ 8.5 Hz, H$^D$), 7.51 (1H, ddd, J$_{HC,HD}$ 8.5 Hz, J$_{HC,HB}$ 7.2 Hz, J$_{HC,HA}$ 1.6 Hz, H$^C$), 7.42-7.19 (8H, m, 7×ArHs & H$^B$), 5.73 (1H, m, J 5.2 Hz, C$_\alpha$H), 5.71 (2H, s, CH$_2$ (Bn)), 3.78 (1H, dd, J$_{CHyHx,CHxHy}$ 13.8 Hz, J$_{CHyHx,C\alpha H}$ 5.1 Hz, CH$^Y$H$^X$ (Phenylalanine)), 3.59 (1H, dd, J$_{CHxHy,CHyHx}$ 13.8 Hz, J$_{CHyHx,C\alpha H}$ 7.8 Hz, CH$^Y$H$^X$ (Phenylalanine)); $\delta_C$ (pyridine d$^5$, 125 MHz): 39.3 (CH$_2$ (Phenylalanine)), 55.4 (Phenylalanine C$_\alpha$), 57.4 (CH$_2$ (Bn)), 112.7 (O=C—C=O), 118.1 (C$^D$), 125.5 (C$^B$), 127.0 127.3, 128.7, 129.1 129.7, 130.4 (10×ArCs (Bn & Phenylalanine)), 127.6 (C$^A$), 128.9 (C$^A$-Cq-C=O), 133.2 (C$^C$), 136.2 (Cq (Bn)), 138.7 (Cq Phenylalanine)), 140.1 (C$^C$-Cq-N-Bn), 149.7 (C$^E$), 165.4 (C=ONH), 175.0 (CO$_2$H), 177.3 (O=C—C=C).

Example 31

Compound 202. Synthesis of (S)-2-(1-benzyl-4-oxo-1,4-dihydroquinoline-3-carboxamido)-2-methylethanoic acid 27 ous solution of hydrochloric acid (2 M) until a white solid crushed out. The reaction mixture was filtered, the solid washed with water and dried under reduced pressure to yield (S)-2-(1-benzyl-4-oxo-1,4-dihydroquinoline-3-carboxamido)-2-methylethanoic acid 27 as a white solid. M.p. Decomposition before melting. At 205° C. the compound started turning brown. Kept turning brown until at 230° C. it was dark brown; HRMS (CI$^+$): found 351.13380 [M+H]$^+$ C$_{20}$H$_{19}$N$_2$O$_4$ requires 351.13448; $v_{max}$ (Ge): 3500-2700 (m, COOH), (masked sec. NH & ArC—H), 2945 (w, alkyl C—H), (masked C=OOH), 1654 (s broad, C=ONH, I), 1603 (s, C=C conjugated with C=Os), 1546 (m, C=ONH, II) cm$^{-1}$; $\delta_H$ (methanol d$^4$, 500 MHz) 8.98 (1H, s, H$^E$), 8.30 (1H, d, J$_{HA,HB}$ 7.0 Hz, H$^A$), 7.62 (2H, m, H$^C$ & H$^D$), 7.43-7.37 (1H, m, H$^B$), 7.35-7.11 (5H, m, 5×ArHs (Bn)), 5.64 (2H, s, CH$_2$ (Bn)), 4.54 (1H, dd, J 12.9 Hz, 6.0 Hz, C$_\alpha$H), 1.50 (3H, d, J 7.0 Hz, CH$_3$ (Alanine)). $\delta_C$ (methanol d$^4$, 150 MHz): 19.1 (CH$_3$ (Alanine)), 51.3 (C$_\alpha$H), 58.4 (CH$_2$ (Bn)), 112.1 (O=C—C—C=O), 119.0 (C$^D$), 126.6 (C$^B$), 127.5, 129.4, 130.2 (5×ArCs (Bn)), 127.6 (C$^A$), 128.9 (C$^A$-Cq-C=O), 134.3 (C$^C$), 136.6 (Cq (Bn)), 140.7 (Cq-N-Bn), 150.4 (C$^E$), 166.4 (C=ONH), 177.9 (COOH), 179.2 (O=C—C=C).

Example 32

Synthesis of (S)-2-(1-benzyl-4-oxo-1,4-dihydroquinoline-3-carboxamido)-3-methylbutanoic acid 27

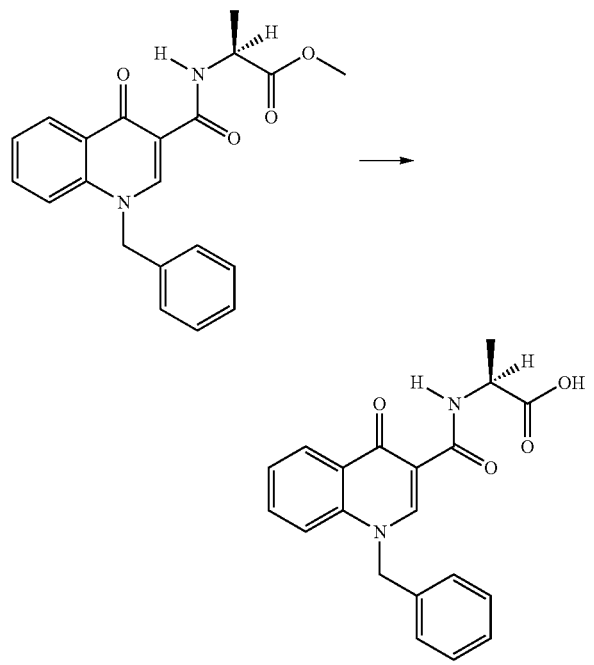

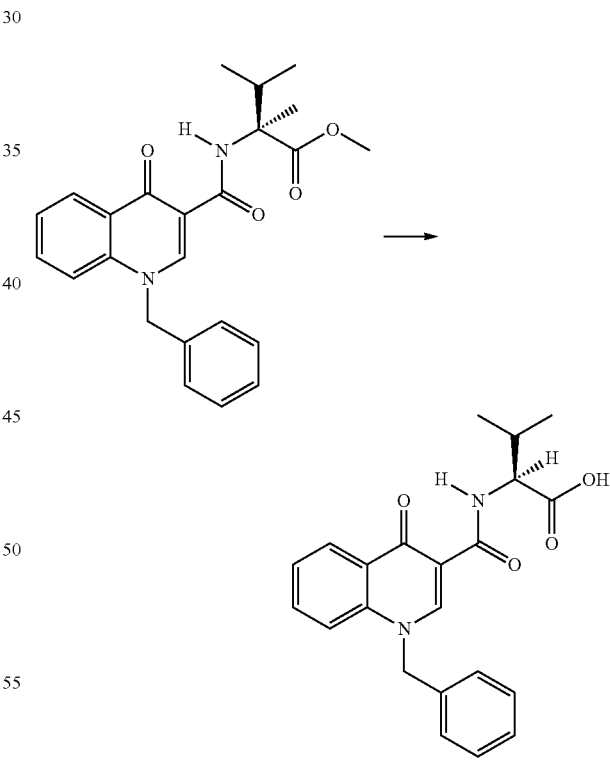

(S)-Methyl 2-(1-benzyl-4-oxo-1,4-dihydroquinoline-3-carboxamido)propanoate 21 (60 mg, 0.165 mmol) was stirred in acetone (2 mL) and an aqueous solution of sodium hydroxide (2 M, 5 mL) at room temperature for 24 hours. T.l.c. analysis (ethyl acetate) showed the presence of one UV-active product and complete consumption of the starting material. The reaction solution was acidified with an aque- (S)-Methyl 2-(1-benzyl-4-oxo-1,4-dihydroquinoline-3-carboxamido)-3-methylbutanoate 22 (55 mg, 0.140 mmol) was stirred in acetone (2 mL) and an aqueous solution of sodium hydroxide (2 M, 5 mL) at room temperature for 24 hours. T.l.c. analysis (ethyl acetate) showed the presence of one UV-active product and complete consumption of the starting material. The reaction solution was acidified with an aqueous solution of hydrochloric acid (2 M) until a white solid crushed out. The reaction mixture was filtered, the solid washed with water and dried under reduced pressure to yield (S)-2-(1-benzyl-4-oxo-1,4-dihydroquinoline-3-carboxamido)-3-methylbutanoic acid 28 (31 mg) as a white solid. HRMS (TOF MS ES+): found 401.1477 [M+Na]+ $C_{22}H_{22}N_2O_4Na$ requires 401.1477; $v_{max}$ (Ge): 3400 (m broad, COOH), 3251 (m, broad, sec. NH), 3065 (w, ArC—H), 2964, 2931, 2873 (m, alkyl C—H), 1655 (s broad with shoulder, C=ONH, I & C=OOH), 1603 (s, C=C conjugated with C=Os), 1546 (m, C=ONH, II) cm$^{-1}$; $\delta_H$ (methanol d$^4$, 500 MHz) 8.97 (1H, s, H$^E$), 8.45 (1H, d, $J_{HA,HB}$ 8.1 Hz, H$^A$), 7.69 (2H, m, H$^C$ & H$^D$), 7.48 (1H, dt, $J_{HB,HA}$ 8.1 Hz, J 3.9 Hz H$^B$), 7.37-7.21 (5H, m, 5×ArHs (Bn)), 5.68 (2H, s, CH$_2$ (Bn)), 4.50 (1H, d, J 4.5 Hz, C$_\alpha$H (Valine)), 2.40 (1H, d septet, $J_{CH,CH3}$ 6.8 Hz, $J_{CH,C\alpha H}$ 4.6 Hz, CH (Valine)), 1.07 (3Hs, d, $J_{CH3,CH}$ 6.9 Hz, CH$_3$ (Valine)), 1.05 (3Hs, d, $J_{CH3,CH}$ 6.9 Hz, CH$_3$ (Valine)). $\delta_C$ (methanol d$^4$, 150 MHz): 18.3, 20.6 (2×CH$_3$ (Valine)), 32.5 (1H, CH (Valine)), 58.4 (CH$_2$ (Bn)), 61.5 (C$_\alpha$H), 112.7 (O=C—C—C=O), 119.0 (C$^D$), 126.5 (C$^B$), 127.6, 129.4, 130.2 (5×ArCs (Bn)), 127.7 (C$^A$), 129.1 (C$^A$-Cq-C=O), 134.2 (C$^C$), 136.7 (Cq (Bn)), 140.8 (Cq-N-Bn), 150.3 (C$^E$), 166.5 (C=ONH), 178.2 (COOH), 178.8 (O=C—C=C).

Example 33

Compound 117. Synthesis of 2-(1-benzyl-4-oxo-1,4-dihydroquinoline-3-carboxamido)acetic acid 29

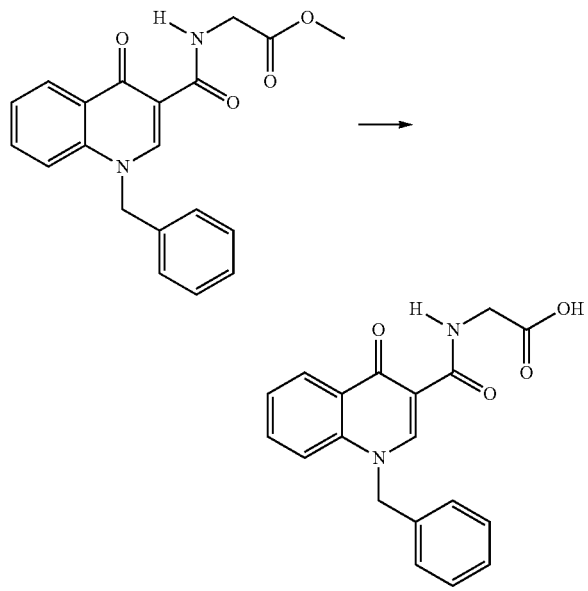

Methyl 2-(1-benzyl-4-oxo-1,4-dihydroquinoline-3-carboxamido)acetate 23 (60 mg, 0.171 mmol) was stirred in acetone (2 mL) and an aqueous solution of sodium hydroxide (2 M, 5 mL) at room temperature for 24 hours. T.l.c. analysis (ethyl acetate) showed the presence of one UV-active product and complete consumption of the starting material. The reaction solution was acidified with an aqueous solution of hydrochloric acid (2 M) until a white solid crushed out. The reaction mixture was filtered, the solid washed with water and dried under reduced pressure to yield 2-(1-benzyl-4-oxo-1,4-dihydroquinoline-3-carboxamido) acetic acid 29 as a pale yellow solid. M.p. At 182° C. decomposition occurred (turned brown); HRMS (TOF MS ES+): found 359.1018 [M+Na]+ $C_{19}H_{16}N_2O_4Na$ requires 359.1008; $v_{max}$ (Ge): 3487 (m broad, COOH), 3281 (m, broad, sec. NH), 3066 (w, ArC—H), 2920, 2851 (w, alkyl C—H), 1654 (s broad with shoulder, C=ONH, I & C=OOH), 1602 (s, C=C conjugated with C=Os), 1545 (m, C=ONH, II) cm$^{-1}$; $\delta_H$ (methanol d$^4$, 500 MHz) 8.99 (1H, s, H$^E$), 8.44 (1H, d, $J_{HA,HB}$ 7.9 Hz, H$^A$), 7.70-7.66 (2H, m, H$^C$ & H$^D$), 7.48 (1H, dt, $J_{HB,HA}$ 8.0 Hz, J 4.1 Hz H$^B$), 7.37-7.21 (5H, m, 5×ArHs (Bn)), 5.67 (2H, s, CH$_2$ (Bn)), 4.04 (1H, s, C$_\alpha$H$_2$ (Glycine)); $\delta_C$ (methanol d$^4$, 150 MHz): 44.7 (C$_\alpha$H$_2$), 58.3 (CH$_2$ (Bn)), 112.6 (O=C—C—C=O), 119.0 (C$^D$), 126.5 (C$^B$), 127.6, 129.4, 130.2 (5×ArCs (Bn)), 127.8 (C$^A$), 129.1 (C$^A$-Cq-C=O), 134.2 (C$^C$), 136.7 (Cq (Bn)), 140.9 (Cq-N-Bn), 150.3 (C$^E$), 166.6 (C=ONH), 176.3 (COOH), 178.1 (O=C—C=C).

Synthesis Example 1

Diethyl 2-((phenylamino)methylene)malonate

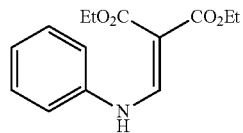 [SMILES: CCOC(=O)C(=CNc1ccccc1)C(=O)OCC]

A mixture of aniline (9.12 mL, 0.1 mol) and diethyl-ethoxymethylmalonate (20 mL, 0.1 mol) were stirred at 120° C. for 2 h. The ethanol formed was removed under reduced pressure to give a yellow solid which was used directly in the next step.

Example 34

Ethyl-4-oxo-1,4-dihydroquinoline-3-carboxylate

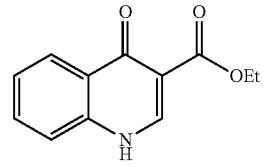 [SMILES: CCOC(=O)c1c[nH]c2ccccc2c1=O]

To diethyl 2-((phenylamino)methylene)malonate from the previous step (max 0.1 mol) was added Ph$_2$O (500 mL). In three batches the reaction mixture was heated to 260° C. for 4 h. Upon cooling to room temperature a white precipitate formed which was collected by filtration, washed with toluene and dried under vacuum to give the title product (12.4 g, 57% over two steps) as a white powder.

HRMS m/z (EI) 217.07352, calculated for $C_{12}H_{11}NO_3^+$ 217.07334; $^1$H NMR (500 MHz, DMSO) δ 12.32 (s, 1H, NH), 8.55 (s, 1H, aromatic), 8.19-8.13 (m, 1H, aromatic), 7.74-7.67 (m, 1H, aromatic), 7.62 (d, J=8.1, 1H, aromatic), 7.42 (t, J=7.1, 1H, aromatic), 4.22 (q, J=7.1, 2H, CH$_2$CH$_3$), 1.28 (t, J=7.1, 3H, CH$_2$CH$_3$); $^{13}$C NMR (126 MHz, DMSO) δ 173.40 (CO), 164.80 (CO), 144.87 (aromatic), 138.95 (aromatic), 132.37 (aromatic), 127.25 (aromatic), 125.60 (aromatic), 124.66 (aromatic), 118.77 (aromatic), 109.76 (aromatic), 59.54 (CH$_2$CH$_3$), 14.32 (CH$_2$CH$_3$).

Example 35

Compound 147. Ethyl 1-(2-fluorobenzyl)-4-oxo-1,4-dihydroquinoline-3-carboxylate

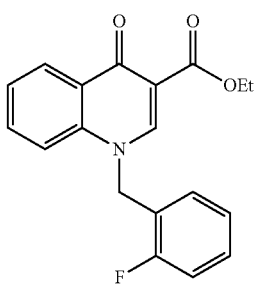

To a suspension of ethyl-4-oxo-1,4-dihydroquinoline-3-carboxylate (1 g, 4.60 mmol) and $K_2CO_3$ (1.20 g, 8.60 mmol) in DMF (7 mL) at 40° C. was added 2-fluorobenzyl bromide (2.02 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (1.106 g, 74%) as a white powder.

HRMS m/z (EI) 325.11090, calculated for $C_{19}H_{16}NO_3F^+$ 325.11087.

Example 36

Compound 148. Ethyl 4-oxo-1-(4-(trifluoromethoxy)benzyl)-1,4-dihydroquinoline-3-carboxylate

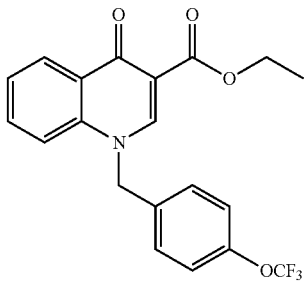 [SMILES: CCOC(=O)c1cn(Cc2ccc(OC(F)(F)F)cc2)c2ccccc2c1=O]

To a suspension of ethyl-4-oxo-1,4-dihydroquinoline-3-carboxylate (1 g, 4.60 mmol) and $K_2CO_3$ (1.20 g, 8.60 mmol) in DMF (7 mL) at 40° C. was added 4-trifluoromethoxybenzyl bromide (2.68 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (1.56 g, 87%) as a white powder.

HRMS m/z (EI) 391.10268, calculated for $C_{20}H_{16}NO_4F_3^+$ 391.10259.

Example 37

Compound 149. Ethyl 1-ethyl-4-oxo-1,4-dihydroquinoline-3-carboxylate

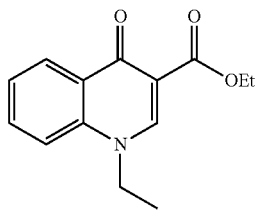 [SMILES: CCOC(=O)c1cn(CC)c2ccccc2c1=O]

To a suspension of ethyl-4-oxo-1,4-dihydroquinoline-3-carboxylate (1 g, 4.60 mmol) and $K_2CO_3$ (1.20 g, 8.60 mmol) in DMF (7 mL) at 40° C. was added bromoethane (1.25 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (921 mg, 82%) as a white powder.

HRMS m/z (EI) 245.10481, calculated for $C_{14}H_{15}NO_3^+$ 245.10464; $^1$H NMR (500 MHz, CDCl$_3$) δ 8.53 (s, 1H, aromatic), 8.51 (dd, J=8.1, 1.6, 1H, aromatic), 7.66 (ddd, J=8.6, 7.1, 1.6, 1H, aromatic), 7.45 (d, J=8.5, 1H, aromatic), 7.43-7.38 (m, 1H, aromatic), 4.37 (q, J=7.1, 2H, C$\underline{H}_2$CH$_3$), 4.26 (q, J=7.3, 2H, C$\underline{H}_2$CH$_3$), 1.52 (t, J=7.3, 3H, CH$_2$C$\underline{H}_3$), 1.38 (t, J=7.1, 3H, CH$_2$C$\underline{H}_3$); $^{13}$C NMR (126 MHz, CDCl$_3$) δ 174.40 (CO), 166.22 (CO), 148.85 (aromatic), 138.82 (aromatic), 132.88 (aromatic), 129.29 (aromatic), 128.28 (aromatic), 125.31 (aromatic), 115.76 (aromatic), 111.08 (aromatic), 61.15 ($\underline{C}H_2CH_3$), 49.11 ($\underline{C}H_2CH_3$), 14.71 (CH$_2$$\underline{C}H_3$), 14.62 (CH$_2$$\underline{C}H_3$).

Example 38

Compound 150. Ethyl 1-(3-chlorobenzyl)-4-oxo-1,4-dihydroquinoline-3-carboxylate

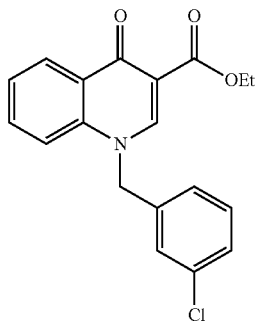 [SMILES: CCOC(=O)c1cn(Cc2cccc(Cl)c2)c2ccccc2c1=O]

To a suspension of ethyl-4-oxo-1,4-dihydroquinoline-3-carboxylate (1 g, 4.60 mmol) and $K_2CO_3$ (1.20 g, 8.60 mmol) in DMF (7 mL) at 40° C. was added 3-chlorobenzyl bromide (2.2 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (805 mg, 51%) as a white powder.

HRMS m/z (EI) 341.08162, calculated for C$_{19}$H$_{16}$NO$_3$$^{35}$Cl$^+$ 341.08132; $^1$H NMR (500 MHz, CDCl$_3$) δ 8.62 (s, 1H, aromatic), 8.52 (dd, J=8.1, 1.5, 1H, aromatic), 7.55 (ddd, J=8.6, 7.1, 1.6, 1H, aromatic), 7.43-7.37 (m, 1H, aromatic), 7.30-7.25 (m, 3H, aromatic), 7.15 (s, 1H, aromatic), 7.03-6.98 (m, 1H, aromatic), 5.38 (s, 2H, Bn-CH$_2$), 4.39 (q, J=7.1, 2H, C$\underline{H}$$_2$CH$_3$), 1.40 (t, J=7.1, 3H, CH$_2$C$\underline{H}$$_3$); $^{13}$C NMR (126 MHz, CDCl$_3$) δ 174.50 (CO), 165.99 (CO), 149.96 (aromatic), 139.18 (aromatic), 136.59 (aromatic), 135.63 (aromatic), 133.08 (aromatic), 130.91 (aromatic), 129.24 (aromatic), 129.08 (aromatic), 128.23 (aromatic), 126.40 (aromatic), 125.65 (aromatic), 124.29 (aromatic), 116.56 (aromatic), 111.57 (aromatic), 61.37 (Bn-CH$_2$), 57.02 ($\underline{C}$H$_2$CH$_3$), 14.63 (CH$_2$$\underline{C}$H$_3$).

Example 39

Compound 151. Ethyl 1-(4-methoxybenzyl)-4-oxo-1,4-dihydroquinoline-3-carboxylate

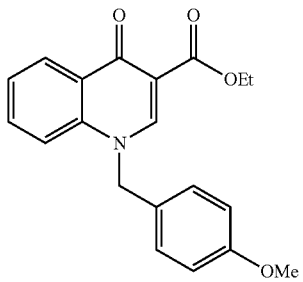 [SMILES: CCOC(=O)c1cn(Cc2ccc(OC)cc2)c2ccccc2c1=O]

To a suspension of ethyl-4-oxo-1,4-dihydroquinoline-3-carboxylate (1 g, 4.60 mmol) and K$_2$CO$_3$ (1.20 g, 8.60 mmol) in DMF (7 mL) at 40° C. was added 4-methoxybenzyl chloride (2.28 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (960 mg, 62%) as a white powder.

HRMS m/z (EI) 337.13145, calculated for C$_{20}$H$_{19}$NO$_4$$^+$ 337.13086; $^1$H NMR (500 MHz, CDCl$_3$) δ 8.68 (s, 1H, aromatic), 8.51 (dd, J=8.2, 1.6, 1H, aromatic), 7.56 (ddd, J=8.7, 7.2, 1.6, 1H, aromatic), 7.43-7.37 (m, 2H, aromatic), 7.28 (d, J=8.5, 1H, aromatic), 7.10 (d, J=8.7, 1H, aromatic), 6.85 (dd, J=8.7, 3.5, 2H, aromatic), 5.37 (s, 2H, Bn-CH$_2$), 4.39 (q, J=7.1, 2H, C$\underline{H}$$_2$CH$_3$), 3.75 (s, 3H, O—CH$_3$), 1.40 (t, J=7.1, 3H, CH$_2$C$\underline{H}$$_3$); $^{13}$C NMR (126 MHz, CDCl$_3$) δ 174.54 (CO), 166.20 (CO), 159.97 (aromatic), 149.87 (aromatic), 139.41 (aromatic), 132.97 (aromatic), 130.46 (aromatic), 129.11 (aromatic), 128.83 (aromatic), 128.04 (aromatic), 127.90 (aromatic), 126.13 (aromatic), 125.55 (aromatic), 116.84 (aromatic), 114.93 (aromatic), 114.12 (aromatic), 61.34 (Bn-CH$_2$), 57.31 ($\underline{C}$H$_2$CH$_3$), 55.52 (O—CH$_3$), 14.62 (CH$_2$$\underline{C}$H$_3$).

Example 40

Compound 152. Ethyl 1-(3.5-dimethylbenzyl)-4-oxo-1,4-dihydroquinoline-3-carboxylate

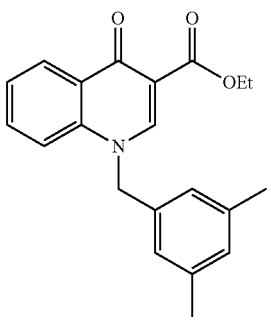

To a suspension of ethyl-4-oxo-1,4-dihydroquinoline-3-carboxylate (1 g, 4.60 mmol) and K$_2$CO$_3$ (1.20 g, 8.60 mmol) in DMF (7 mL) at 40° C. was added 3,5-dimethylbenzyl bromide (3.33 g, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (850 mg, 55%) as a white powder.

HRMS m/z (EI) 335.15192, calculated for C$_{21}$H$_{21}$NO$_3$$^+$ 335.15160; $^1$H NMR (500 MHz, CDCl$_3$) δ 8.61 (s, 1H, aromatic), 8.54 (d, J=8.0, 1H, aromatic), 7.55 (t, J=7.7, 1H, aromatic), 7.39 (t, J=7.5, 1H, aromatic), 7.34 (d, J=8.5, 1H, aromatic), 6.94 (s, 1H, aromatic), 6.75 (s, 2H, aromatic), 5.32 (s, 2H, Bn-CH$_2$), 4.41 (q, J=7.1, 2H, C$\underline{H}$$_2$CH$_3$), 2.26 (s, 6H 2×aromatic-CH$_3$), 1.42 (t, J=7.1, 3H, CH$_2$C$\underline{H}$$_3$); $^{13}$C NMR (126 MHz, CDCl$_3$) δ 174.56 (CO), 166.08 (CO), 149.96 (aromatic), 139.34 (aromatic), 139.20 (aromatic), 134.24 (aromatic), 132.73 (aromatic), 130.32 (aromatic), 129.26 (aromatic), 127.93 (aromatic), 125.27 (aromatic), 123.83 (aromatic), 116.70 (aromatic), 111.11 (aromatic), 61.10 (Bn-CH$_2$), 57.59 ($\underline{C}$H$_2$CH$_3$), 21.36 (aromatic-CH$_3$), 14.52 (CH$_2$$\underline{C}$H$_3$).

Example 41

Compound 153. Ethyl 1-(2-chlorobenzyl)-4-oxo-1,4-dihydroquinoline-3-carboxylate

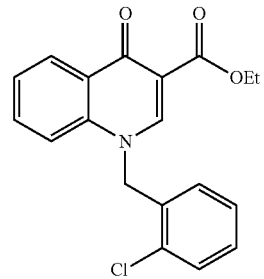 [SMILES: CCOC(=O)c1cn(Cc2ccccc2Cl)c2ccccc2c1=O]

To a suspension of ethyl-4-oxo-1,4-dihydroquinoline-3-carboxylate (1 g, 4.60 mmol) and K$_2$CO$_3$ (1.20 g, 8.60 mmol) in DMF (7 mL) at 40° C. was added 2-chlorobenzyl bromide (2.16 mL, 16.75 mmol) dropwise. The reaction mixture was stirred at 80° C. for 18 h. Solvent was removed under reduced pressure and the product purified by flash chromatography using a gradient of 0-20% MeOH in EtOAc to give the title product (452 mg, 29%) as a white powder.

HRMS m/z (EI) 341.08157, calculated for $C_{19}H_{16}NO_3{}^{35}Cl^+$ 341.08132; $^1$H NMR (500 MHz, CDCl$_3$) δ 8.61 (s, 1H, aromatic), 8.51 (dd, J=8.1, 1.5, 1H, aromatic), 7.57 (ddd, J=8.6, 7.1, 1.6, 1H, aromatic), 7.46 (dd, J=8.0, 0.9, 1H, aromatic), 7.41-7.36 (m, 1H, aromatic), 7.32-7.25 (m, 1H, aromatic), 7.22 (d, J=8.6, 1H, aromatic), 7.14 (td, J=7.7, 1.1, 1H, aromatic), 6.78 (d, J=7.1, 1H, aromatic), 5.49 (s, 2H, Bn-CH$_2$), 4.37 (q, J=7.1, 2H, CH$_2$CH$_3$), 1.38 (t, J=7.1, 3H, CH$_2$CH$_3$); $^{13}$C NMR (126 MHz, CDCl$_3$) δ 174.96 (CO), 165.88 (CO), 150.05 (aromatic), 139.29 (aromatic), 136.94 (aromatic), 133.23 (aromatic), 132.57 (aromatic), 131.89 (aromatic), 130.92 (aromatic), 130.32 (aromatic), 130.04 (aromatic), 128.13 (aromatic), 127.88 (aromatic), 127.49 (aromatic), 125.67 (aromatic), 116.59 (aromatic), 61.33 (Bn-CH$_2$), 55.11 (CH$_2$CH$_3$), 14.61 (CH$_2$CH$_3$).

Example 42

Compound 154. 1-Ethyl-4-oxo-1,4-dihydroquinoline-3-carboxylic acid

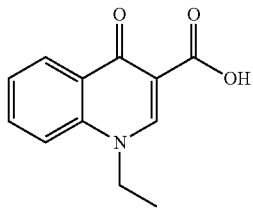 [SMILES: CCn1cc(C(=O)O)c(=O)c2ccccc21]

A suspension of ethyl 1-ethyl-4-oxo-1,4-dihydroquinoline-3-carboxylate (500 mg, 2.04 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (345 mg, 78%) as a white powder.

HRMS m/z (ES$^+$) 218.0806, calculated for $C_{12}H_{12}NO_3{}^+$ 218.0817; $^1$H NMR (500 MHz, DMSO) δ 15.25 (s, OH), 9.07 (s, 1H, aromatic), 8.40 (d, J=7.8, 1H, aromatic), 8.06 (d, J=8.6, 1H, aromatic), 7.98 (t, J=7.5, 1H, aromatic), 7.67 (t, J=7.4, 1H, aromatic), 4.61 (q, J=7.0, 2H, CH$_2$CH$_3$), 1.42 (t, J=7.1, 3H, CH$_2$CH$_3$); $^{13}$C NMR (126 MHz, DMSO) δ 177.70 (CO), 166.06 (CO), 149.19 (aromatic), 139.04 (aromatic), 134.30 (aromatic), 126.29 (aromatic), 125.96 (aromatic), 125.53 (aromatic), 118.08 (aromatic), 107.66 (aromatic), 48.98 (CH$_2$CH$_3$), 14.54 (CH$_2$CH$_3$).

Example 43

Compound 155. 1-(3-Chlorobenzyl)-4-oxo-1,4-dihydroquinoline-3-carboxylic acid

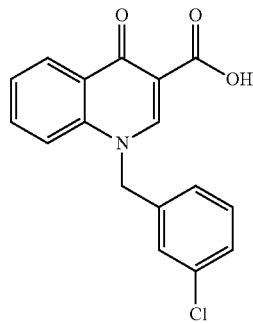 [SMILES: O=C(O)c1cn(Cc2cccc(Cl)c2)c2ccccc2c1=O]

A suspension of ethyl 1-(3-chlorobenzyl)-4-oxo-1,4-dihydroquinoline-3-carboxylate (500 mg, 1.46 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (410 mg, 90%) as a white powder.

HRMS m/z (ES$^+$) 314.0600, calculated for $C_{17}H_{13}NO_3{}^{35}Cl^+$ 314.0584; $^1$H NMR (500 MHz, DMSO) δ 15.13 (s, OH), 9.17 (s, 2H, aromatic), 8.37 (d, J=8.0, 1H, aromatic), 7.93-7.71 (m, 2H, aromatic), 7.56 (t, J=7.4, 1H, aromatic), 7.41 (s, 1H, aromatic), 7.37 (d, J=5.0, 2H, aromatic), 7.17 (t, J=3.6, 1H, aromatic), 5.82 (s, 2H Bn-CH$_2$); $^{13}$C NMR (126 MHz, DMSO) δ 177.49 (CO), 166.15 (CO), 149.96 (aromatic), 139.31 (aromatic), 138.33 (aromatic), 133.51 (aromatic), 130.82 (aromatic), 127.95 (aromatic), 126.54 (aromatic), 126.13 (aromatic), 125.67 (aromatic), 125.12 (aromatic), 118.09 (aromatic), 55.37 (Bn-CH$_2$).

Example 44

Compound 156. 1-tert-Butyl 3-ethyl 4-oxoquinoline-1,3(4H)-dicarboxylate

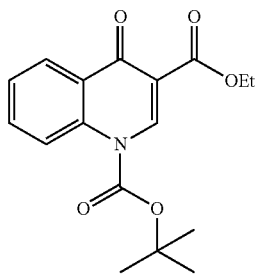 [SMILES: CCOC(=O)c1cn(C(=O)OC(C)(C)C)c2ccccc2c1=O]

To a suspension of ethyl-4-oxo-1,4-dihydroquinoline-3-carboxylate (500 mg, 2.30 mmol) in 1:1 H$_2$O/1,4-dioxane (4 mL) was added Et$_3$N, (700 μL, 5.02 mmol) followed by di-tert-butyl dicarbonate (750 mg, 3.44 mmol). The reaction mixture was stirred at room temperature for 18 h. Water (25 mL0 and EtOAc were added to the reaction mixture and the layers separated. The aqueous layer was extracted with EtOAc (2×50 mL) and the combined organic fractions were dried over MgSO$_4$, filtered and evaporated to give the title product (691 mg, 95%) as a white powder. HRMS m/z (EI) 317.12627, calculated for C$_{17}$H$_{19}$NO$_5$$^+$ 317.12577.

$^1$H NMR (500 MHz, CDCl$_3$) δ 9.12 (s, 1H, aromatic), 8.47 (d, J=8.8, 1H, aromatic), 8.43 (dd, J=8.0, 1.7, 1H, aromatic), 7.65 (ddd, J=8.8, 7.1, 1.8, 1H, aromatic), 7.44 (ddd, J=8.0, 7.1, 0.9, 1H, aromatic), 4.39 (q, J=7.1, 2H, CH$_2$CH$_3$), 1.68 (s, 9H, C(CH$_3$)$_3$), 1.39 (t, J=7.1, 3H, CH$_2$CH$_3$); $^{13}$C NMR (126 MHz, CDCl$_3$) δ 175.11 (CO), 165.04 (CO), 149.45 (CO), 145.22 (aromatic), 137.72 (aromatic), 133.07 (aromatic), 128.22 (aromatic), 127.59 (aromatic), 126.27 (aromatic), 119.96 (aromatic), 113.58 (aromatic), 88.12 (C(CH$_3$)$_3$), 61.54 (CH$_2$CH$_3$), 28.09 (C(CH$_3$)$_3$), 14.53 (CH$_2$CH$_3$).

Example 45

Compound 157. 1-(2-Fluorobenzyl)-4-oxo-1,4-dihydroquinoline-3-carboxylic acid

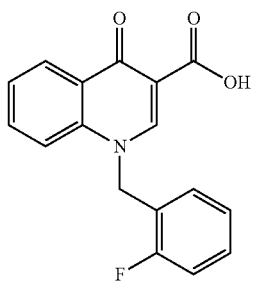 [SMILES: O=C(O)c1cn(Cc2ccccc2F)c2ccccc2c1=O]

A suspension of ethyl 1-(2-fluorobenzyl)-4-oxo-1,4-dihydroquinoline-3-carboxylate (500 mg, 1.54 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (379 mg, 83%) as a pale pink powder.

HRMS m/z (ES$^+$) 298.0871, calculated for C$_{17}$H$_{13}$NO$_3$F$^+$ 298.0879; $^1$H NMR (500 MHz, DMSO) δ 15.10 (s, 1H, OH), 9.27 (s, 1H, aromatic), 8.41 (d, J=7.8, 1H, aromatic), 7.87 (dd, J=17.7, 7.6, 2H, aromatic), 7.64 (t, J=7.3, 1H, aromatic), 7.39 (d, J=5.9, 1H, aromatic), 7.32-7.25 (m, 1H, aromatic), 7.18 (dd, J=19.1, 7.2, 2H, aromatic), 5.93 (s, 2H, Bn-CH$_2$); $^{13}$C NMR (126 MHz, DMSO) δ 178.02 (CO), 165.89 (CO), 150.53 (aromatic), 139.43 (aromatic), 134.33 (aromatic), 130.39 (aromatic), 128.99 (aromatic), 126.43 (aromatic), 126.03 (aromatic), 125.58 (aromatic), 124.98 (aromatic), 122.24 (aromatic), 118.16 (aromatic), 115.93 (aromatic), 115.76 (aromatic), 107.95 (aromatic), 51.38 (Bn-CH$_2$).

Example 46

Compound 158. 4-Oxo-1-(4-(trifluoromethoxy)benzyl)-1,4-dihydroquinoline-3-carboxylic acid

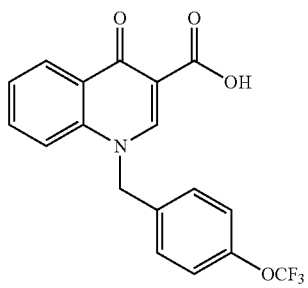 [SMILES: O=C(O)c1cn(Cc2ccc(OC(F)(F)F)cc2)c2ccccc2c1=O]

A suspension of ethyl 4-oxo-1-(4-(trifluoromethoxy)benzyl)-1,4-dihydroquinoline-3-carboxylate (500 mg, 1.28 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (282 mg, 61%) as a white powder.

HRMS m/z (ES$^+$) 364.0804, calculated for C$_{18}$H$_{13}$NO$_4$F$_3$$^+$ 364.0797.

Example 47

Compound 159. 1-(4-Methoxybenzyl)-4-oxo-1,4-dihydroquinoline-3-carboxylic acid

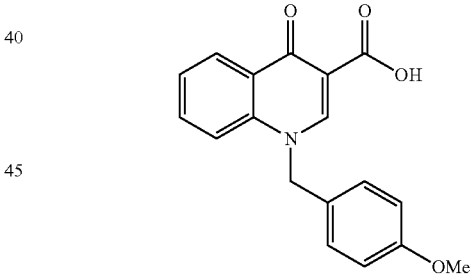

A suspension of ethyl 1-(4-methoxybenzyl)-4-oxo-1,4-dihydroquinoline-3-carboxylate (500 mg, 1.48 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (420 mg, 92%) as a pale pink powder.

HRMS m/z (ES$^+$) 332.0883, calculated for C$_{18}$H$_{15}$NO$_4$Na$^+$ 332.0899; $^1$H NMR (500 MHz, DMSO) δ 15.18 (s, 1H, OH), 9.26 (s, 1H, aromatic), 8.39 (d, J=7.9, 1H, aromatic), 7.95 (d, J=8.6, 1H, aromatic), 7.88 (dd, J=11.4, 4.2, 1H, aromatic), 7.63 (t, J=7.5, 1H, aromatic), 7.27 (d, J=8.5, 2H, aromatic), 6.91 (d, J=8.6, 2H, aromatic), 5.78 (s, 2H, Bn-CH$_2$), 3.71 (s, 3H, O—CH$_3$); $^{13}$C NMR (126 MHz, DMSO) δ 177.90 (CO), 166.02 (CO), 159.02 (aromatic), 149.84 (aromatic), 139.44 (aromatic), 134.12 (aromatic), 128.40 (aromatic), 127.88 (aromatic), 127.00 (aromatic), 126.36 (aromatic), 125.89 (aromatic), 125.70 (aromatic), 118.72 (aromatic), 114.31 (aromatic), 113.42 (aromatic), 107.77 (aromatic), 55.96 (Bn-CH$_2$), 55.08 (O—CH$_3$).

Example 48

Compound 160. 1-(3.5-Dimethylbenzyl)-4-oxo-1,4-dihydroquinoline-3-carboxylic acid

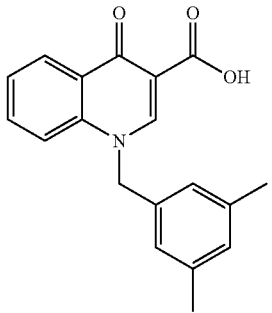 [SMILES: Cc1cc(C)cc(Cn2cc(C(=O)O)c(=O)c3ccccc32)c1]

A suspension of ethyl 1-(3.5-dimethylbenzyl)-4-oxo-1,4-dihydroquinoline-3-carboxylate (500 mg, 1.49 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (411 mg, 90%) as an off white powder.

HRMS m/z (EI) 307.12077, calculated for C$_{19}$H$_{17}$NO$_3$$^+$ 307.12029.

Example 49

Compound 161. 1-(2-Chlorobenzyl)-4-oxo-1,4-dihydroquinoline-3-carboxylic acid

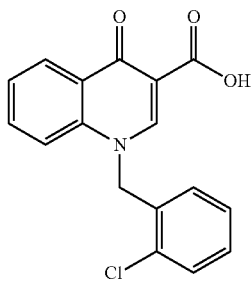 [SMILES: O=C(O)c1cn(Cc2ccccc2Cl)c2ccccc2c1=O]

A suspension of ethyl 1-(2-chlorobenzyl)-4-oxo-1,4-dihydroquinoline-3-carboxylate (350 mg, 1.02 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum to give the title product (198 mg, 62%) as a white powder.

HRMS m/z (ES$^+$) 314.0574, calculated for C$_{17}$H$_{13}$NO$_3$Cl$^+$ 314.0584; $^1$H NMR (500 MHz, DMSO) δ 15.06 (s, 1H, OH), 9.19 (s, 1H, aromatic), 8.42 (dd, J=8.0, 1.4, 1H, aromatic), 7.91-7.82 (m, 1H, aromatic), 7.61 (ddd, J=11.6, 9.0, 5.4, 3H, aromatic), 7.44-7.32 (m, 1H, aromatic), 7.24 (dd, J=10.9, 4.3, 1H, aromatic), 6.87 (d, J=7.7, 1H, aromatic), 5.91 (s, 2H, Bn-CH$_2$); $^{13}$C NMR (126 MHz, DMSO) δ 177.99 (CO), 165.89 (CO), 150.36 (aromatic), 139.52 (aromatic), 134.31 (aromatic), 132.62 (aromatic), 131.57 (aromatic), 129.85 (aromatic), 129.78 (aromatic), 127.86 (aromatic), 127.82 (aromatic), 126.31 (aromatic), 126.08 (aromatic), 125.77 (aromatic), 124.09 (aromatic), 118.06 (aromatic), 54.33 (Bn-CH$_2$).

Example 50

Compound 81. 1-tert-Butoxycarbonyl)-4-oxo-1,4-dihydroquinoline-3-carboxylic acid

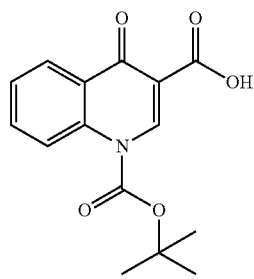 [SMILES: CC(C)(C)OC(=O)n1cc(C(=O)O)c(=O)c2ccccc21]

A suspension of 1-tert-butyl 3-ethyl 4-oxoquinoline-1,3 (4H)-dicarboxylate (500 mg, 1.58 mmol) in 2 M NaOH (aq) (10 mL, 20 mmol) was stirred at 100° C. for 2 h. After cooling to room temperature the reaction mixture was diluted with water (10 mL) and acidified by dropwise addition of conc. HCl. The resulting white precipitate was collected by filtration and dried under vacuum. LCMS showed that the product had lost the Boc group during the reaction work up. The amine (128 mg, 0.677 mmol) was taken up in H$_2$O/dioxane (1:1) (2 mL). Et$_3$N (180 μL, 1.29 mmol) and di-tert-butyl dicarbonate (155 mg, 0.70 mmol) were added. The reaction mixture was stirred at room temperature for 2 h. Water (5 mL) and EtOAc (10 mL) were added to the reaction mixture and the layers separated. The aqueous layer was extracted with EtOAc (2×10 mL) and the combined organic fractions were dried over MgSO$_4$, filtered and evaporated to give the title product (180 mg, 40% over two steps) as a white powder.

HRMS m/z (ES+) 190.0495, calculated for C$_{10}$H$_8$NO$_3$$^+$ (M-Boc$^+$) 190.0504; $^1$H NMR (500 MHz, CDCl$_3$) δ 14.25 (s, 1H, OH), 9.36 (s, 1H, aromatic), 8.56 (d, J=8.9, 1H, aromatic), 8.50 (dd, J=8.1, 1.6, 1H, aromatic), 7.83 (ddd, J=8.8, 7.1, 1.7, 1H, aromatic), 7.59 (dd, J=11.2, 4.0, 1H, aromatic), 1.73 (s, 9H, C(CH$_3$)$_3$); $^{13}$C NMR (126 MHz, CDCl$_3$) δ 180.16 (CO), 165.79 (CO), 148.81 (CO), 146.95 (aromatic), 146.15 (aromatic), 138.42 (aromatic), 134.73 (aromatic), 127.13 (aromatic), 127.05 (aromatic), 125.89 (aromatic), 120.31 (aromatic), 110.01 (aromatic), 89.81 (C(CH$_3$)$_3$), 28.02 (C(CH$_3$)$_3$).

Example 51

Compound 163. Methyl 2-(1-ethyl-4-oxo-1,4-dihydroquinoline-3-carboxamido)acetate

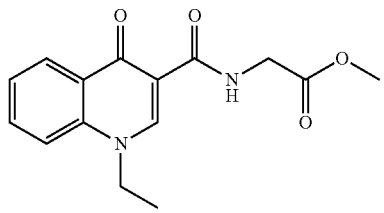 [SMILES: CCn1cc(C(=O)NCC(=O)OC)c(=O)c2ccccc21]

To a suspension of 1-ethyl-4-oxo-1,4-dihydroquinoline-3-carboxylic acid (173 mg, 0.797 mmol) in anhydrous DMF (5 mL) was added DIEA (555 µL, 3.188 mmol) and O-(7-azabenzotriazol-1-yl)-N,N,N',N'-tetramethyluronium hexafluorophosphate (288 mg, 0.757 mmol). After stirring for 2 min, Glycine methylester hydrochloride (200 mg, 1.594 mmol) was added and the reaction mixture was stirred at room temperature for 18 h. Solvent was removed under reduced pressure and the product purified by flash chromatography using a gradient of 0-100% EtOAc in cyclohexane, some product precipitated on the top of the column and was also collected to afford the title product (165 mg, 72%) as a white powder.

HRMS m/z (EI) 288.11017, calculated for $C_{15}H_{16}O_4N_2^+$ 288.11045; $^1$H NMR (500 MHz, CDCl$_3$) δ 10.39 (s, 1H, NH), 8.79 (s, 1H, aromatic), 8.53 (dd, J=8.1, 1.5, 1H, aromatic), 7.82-7.68 (m, 1H, aromatic), 7.56 (d, J=8.6, 1H, aromatic), 7.49 (t, J=7.5, 1H, aromatic), 4.35 (q, J=7.2, 2H, C$\underline{H}_2$CH$_3$), 4.23 (d, J=5.6, 2H, Gly-CH$_2$), 3.75 (s, 3H, O—CH$_3$), 1.54 (t, J=7.3, 3H, CH$_2$C$\underline{H}_3$); $^{13}$C NMR (126 MHz, CDCl$_3$) δ 176.65 (CO), 170.39 (CO), 165.93 (CO), 162.91 (aromatic), 147.50 (aromatic), 139.01 (aromatic), 133.37 (aromatic), 127.77 (aromatic), 125.56 (aromatic), 116.11 (aromatic), 55.83 (O—CH$_3$), 49.50 (CH$_2$CH$_3$), 41.54 (Gly-CH$_2$), 14.79 (CH$_2$C$\underline{H}_3$).

Example 52

Compound 164. Methyl 2-(1-(3-chlorobenzyl)-4-oxo-1,4-dihydroquinoline-3-carboxamido)acetate

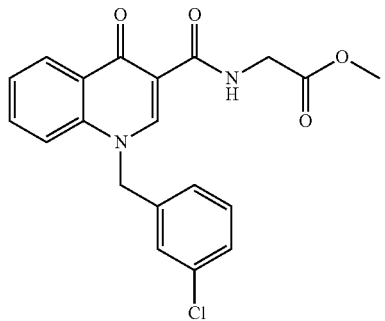 [SMILES: COC(=O)CNC(=O)c1cn(Cc2cccc(Cl)c2)c2ccccc2c1=O]

To a suspension of 1-(3-chlorobenzyl)-4-oxo-1,4-dihydroquinoline-3-carboxylic acid (250 mg, 0.797 mmol) in anhydrous DMF (5 mL) was added DIEA (555 µL, 3.188 mmol) and O-(7-azabenzotriazol-1-yl)-N,N,N',N'-tetramethyluronium hexafluorophosphate (288 mg, 0.757 mmol). After stirring for 2 min, Glycine methylester hydrochloride (200 mg, 1.594 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (211 mg, 69%) as a white powder.

HRMS m/z (EI) 384.08751, calculated for $C_{20}H_{17}O_4N_2Cl^+$ 384.08713; $^1$H NMR (500 MHz, CDCl$_3$) δ 10.45 (s, 1H, NH), 8.96 (s, 1H, aromatic), 8.52 (dd, J=8.1, 1.5, 1H, aromatic), 7.65-7.56 (m, 1H, aromatic), 7.46 (t, J=7.5, 1H, aromatic), 7.36 (d, J=8.6, 1H, aromatic), 7.32-7.19 (m, 2H, aromatic), 7.15 (s, 1H, aromatic), 7.00 (d, J=6.9, 1H, aromatic), 5.46 (s, 2H, Bn-CH$_2$), 4.25 (d, J=5.4, 2H, Gly-CH$_2$), 3.76 (s, 3H, O—CH$_3$); $^{13}$C NMR (126 MHz, CDCl$_3$) δ 176.86 (CO), 170.32 (CO), 165.74 (CO), 148.79 (aromatic), 139.33 (aromatic), 136.40 (aromatic), 135.61 (aromatic), 133.59 (aromatic), 130.89 (aromatic), 129.15 (aromatic), 127.71 (aromatic), 126.48 (aromatic), 125.87 (aromatic), 124.40 (aromatic), 116.90 (aromatic), 57.38 (Bn-CH$_2$), 52.50 (O—CH$_3$), 41.56 (Gly-CH$_2$).

Example 53

Compound 165. Methyl-2-(1-(2-fluorobenzyl)-4-oxo-1,4-dihydroquinoline-3-carboxamido)acetate

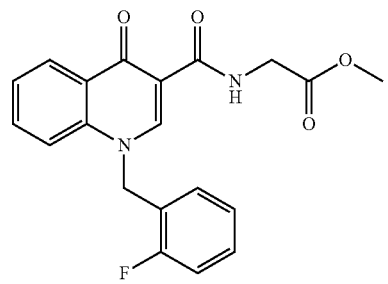 [SMILES: COC(=O)CNC(=O)c1cn(Cc2ccccc2F)c2ccccc2c1=O]

To a suspension of 1-(2-fluorobenzyl)-4-oxo-1,4-dihydroquinoline-3-carboxylic acid (237 mg, 0.797 mmol) in anhydrous DMF (5 mL) was added DIEA (555 µL, 3.188 mmol) and O-(7-azabenzotriazol-1-yl)-N,N,N',N'-tetramethyluronium hexafluorophosphate (288 mg, 0.757 mmol). After stirring for 2 min, Glycine methylester hydrochloride (200 mg, 1.594 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (250 mg, 85%) as a white powder.

HRMS m/z (EI) 368.11711, calculated for $C_{20}H_{17}O_4N_2F^+$ 368.11668; $^1$H NMR (500 MHz, CDCl$_3$) δ 10.48 (s, 1H, NH), 8.95 (s, 1H, aromatic), 8.55 (d, J=7.9, 1H, aromatic), 7.66 (t, J=7.4, 1H, aromatic), 7.46 (dd, J=16.3, 8.3, 2H, aromatic), 7.32 (d, J=6.8, 1H, aromatic), 7.15 (t, J=9.2, 1H, aromatic), 7.06 (t, J=7.5, 1H, aromatic), 6.95 (t, J=7.2, 1H, aromatic), 5.51 (s, 2H, Bn-CH$_2$), 4.27 (d, J=5.4, 2H, Gly-CH$_2$), 3.78 (s, 3H, O—CH$_3$); $^{13}$C NMR (126 MHz, CDCl$_3$) δ 176.84 (CO), 170.30 (CO), 165.46 (CO), 160.97 (aromatic), 159.00 (aromatic), 148.65 (aromatic), 139.25 (aromatic), 133.26 (aromatic), 130.66 (aromatic), 128.00 (aromatic), 127.63 (aromatic), 125.51 (aromatic), 125.05 (aromatic), 121.41 (aromatic), 116.33 (aromatic), 116.17 (aromatic), 116.01 (aromatic), 54.22 (O—CH$_3$), 51.43 (Bn-CH$_2$), 41.41 (Gly-CH$_2$).

Example 54

Compound 166. Methyl 2-(1-(4-methoxybenzyl)-4-oxo-1,4-dihydroquinoline-3-carboxamido)acetate

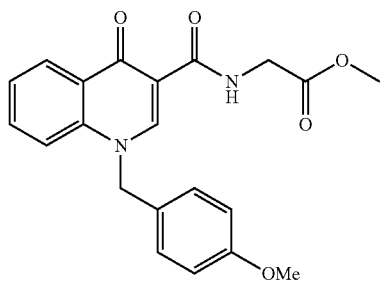 [SMILES: COC(=O)CNC(=O)c1cn(Cc2ccc(OC)cc2)c2ccccc2c1=O]

To a suspension of 1-(4-methoxybenzyl)-4-oxo-1,4-dihydroquinoline-3-carboxylic acid (246 mg, 0.797 mmol) in anhydrous DMF (5 mL) was added DIEA (555 µL, 3.188 mmol) and O-(7-azabenzotriazol-1-yl)-N,N,N',N'-tetramethyluronium hexafluorophosphate (288 mg, 0.757 mmol). After stirring for 2 min, Glycine methylester hydrochloride (200 mg, 1.594 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (231 mg, 76%) as a white powder.

HRMS m/z (EI) 380.13589, calculated for C$_{21}$H$_{20}$O$_5$N$_2$$^+$ 380.13667; $^1$H NMR (500 MHz, CDCl$_3$) δ 10.46 (s, 1H, NH), 8.93 (s, 1H, aromatic), 8.51 (d, J=8.1, 1H, aromatic), 7.61 (t, J=7.8, 1H, aromatic), 7.52-7.39 (m, 2H, aromatic), 7.09 (d, J=8.6, 2H, aromatic), 6.83 (d, J=8.7, 2H, aromatic), 5.40 (s, 2H, Bn-CH$_2$), 4.24 (d, J=5.2, 2H, Gly-CH$_2$), 3.75 (s, 3H, O—CH$_3$), 3.74 (s, 3H, O—CH$_3$); $^{13}$C NMR (126 MHz, CDCl$_3$) δ 176.85 (CO), 170.40 (CO), 165.83 (CO), 159.98 (aromatic), 148.55 (aromatic), 139.51 (aromatic), 133.26 (aromatic), 127.98 (aromatic), 127.54 (aromatic), 126.03 (aromatic), 125.59 (aromatic), 117.08 (aromatic), 114.90 (aromatic), 111.33 (aromatic), 57.59 (Bn-CH$_2$), 55.51 (O—CH$_3$), 52.45 (O—CH$_3$), 41.52 (Gly-CH$_2$).

Example 55

Compound 167. Methyl 2-(1-(3.5-dimethylbenzyl)-4-oxo-1,4-dihydroquinoline-3-carboxamido)acetate

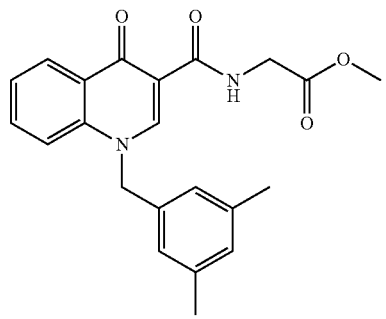 [SMILES: COC(=O)CNC(=O)c1cn(Cc2cc(C)cc(C)c2)c2ccccc2c1=O]

To a suspension of 1-(3.5-dimethylbenzyl)-4-oxo-1,4-dihydroquinoline-3-carboxylic acid (245 mg, 0.797 mmol) in anhydrous DMF (5 mL) was added DIEA (555 µL, 3.188 mmol) and O-(7-Azabenzotriazol-1-yl)-N,N,N',N'-tetramethyluronium hexafluorophosphate (288 mg, 0.757 mmol). After stirring for 2 min, Glycine methylester hydrochloride (200 mg, 1.594 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (246 mg, 81%) as a white powder.

HRMS m/z (EI) 378.15705, calculated for C$_{22}$H$_{22}$O$_4$N$_2$$^+$ 378.15740; $^1$H NMR (500 MHz, CDCl$_3$) δ 10.46 (s, 1H, NH), 9.03 (s, 1H, aromatic), 8.53 (dd, J=8.1, 1.4, 1H, aromatic), 7.68-7.60 (m, 1H, aromatic), 7.52-7.42 (m, 2H, aromatic), 6.91 (s, 1H, aromatic), 6.74 (s, 2H, aromatic), 5.43 (s, 2H, Bn-CH$_2$), 4.26 (d, J=4.1, 2H, Gly-CH$_2$), 3.77 (s, 3H, O—CH$_3$), 2.23 (s, 6H, 2×aromatic-CH$_3$); $^{13}$C NMR (126 MHz, CDCl$_3$) δ 176.77 (CO), 170.24 (CO), 166.18 (CO), 148.88 (aromatic), 139.63 (aromatic), 139.36 (aromatic), 134.04 (aromatic), 133.68 (aromatic), 130.89 (aromatic), 130.61 (aromatic), 127.44 (aromatic), 125.94 (aromatic), 124.12 (aromatic), 117.38 (aromatic), 58.41 (Bn-CH$_2$), 52.51 (O—CH$_3$), 41.59 (Gly-CH$_2$), 21.46 (aromatic-CH$_3$s).

Example 56

Compound 168. Methyl 2-(4-oxo-1-(4-(trifluoromethoxy)benzyl)-1,4-dihydroquinoline-3-carboxamido)acetate

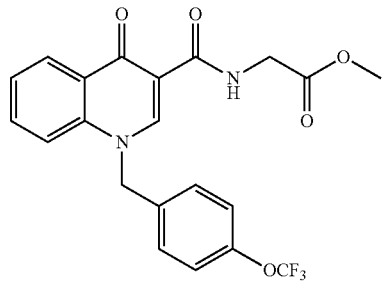 [SMILES: COC(=O)CNC(=O)c1cn(Cc2ccc(OC(F)(F)F)cc2)c2ccccc2c1=O]

To a suspension of 4-oxo-1-(4-(trifluoromethoxy)benzyl)-1,4-dihydroquinoline-3-carboxylic acid (127 mg, 0.325 mmol) in anhydrous DMF (2.5 mL) was added DIEA (230 µL, 1.30 mmol) and O-(7-Azabenzotriazol-1-yl)-N,N,N',N'-tetramethyluronium hexafluorophosphate (117 mg, 0.308 mmol). After stirring for 2 min, Glycine methylester hydrochloride (82 mg, 0.65 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (101 mg, 72%) as a white powder.

HRMS m/z (EI) 434.10909, calculated for $C_{21}H_{17}O_5N_2F_3^+$ 434.10840; $^1$H NMR (500 MHz, CDCl$_3$) δ 10.40 (s, 1H, NH), 8.91 (s, 1H, aromatic), 8.59-8.41 (m, 1H, aromatic), 7.69-7.56 (m, 1H, aromatic), 7.46 (td, J=7.8, 4.3, 1H, aromatic), 7.36 (dd, J=8.5, 4.0, 1H, aromatic), 7.18 (d, J=3.8, 4H, aromatic), 5.47 (s, 2H, Bn-CH$_2$), 4.25 (s, 2H, Gly-CH$_2$), 3.76 (s, 3H, O—CH$_3$); $^{13}$C NMR (126 MHz, CDCl$_3$) δ 176.89 (CO), 170.41 (CO), 165.56 (CO), 149.48 (aromatic), 148.67 (aromatic), 139.35 (aromatic), 133.46 (aromatic), 133.01 (aromatic), 128.14 (aromatic), 127.87 (aromatic), 127.78 (aromatic), 125.75 (aromatic), 121.99 (aromatic), 116.79 (aromatic), 111.82 (aromatic), 57.12 (Bn-CH$_2$), 52.47 (O—CH$_3$), 41.53 (Gly-CH$_2$).

Example 57

Compound 169. Methyl 2-(1-(2-chlorobenzyl)-4-oxo-1,4-dihydroquinoline-3-carboxyamido)acetate

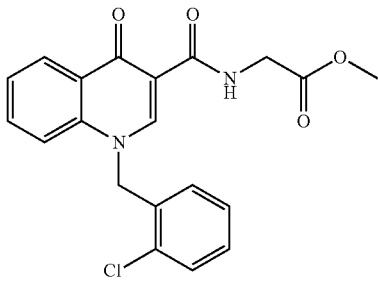 [SMILES: COC(=O)CNC(=O)c1cn(Cc2ccccc2Cl)c2ccccc2c1=O]

To a suspension of 1-(2-chlorobenzyl)-4-oxo-1,4-dihydroquinoline-3-carboxylic acid (150 mg, 0.478 mmol) in anhydrous DMF (3.5 mL) was added DIEA (335 µL, 1.912 mmol) and O-(7-Azabenzotriazol-1-yl)-N,N,N',N'-tetramethyluronium hexafluorophosphate (173 mg, 0.454 mmol). After stirring for 2 min, Glycine methylester hydrochloride (120 mg, 0.956 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (142 mg, 77%) as a white powder.

HRMS m/z (EI) 384.08671, calculated for $C_{20}H_{17}O_4N_2Cl^+$ 384.08713; $^1$H NMR (500 MHz, CDCl$_3$) δ 10.44 (s, 1H, NH), 8.86 (s, 1H, aromatic), 8.54 (dd, J=8.1, 1.5, 1H, aromatic), 7.61 (ddd, J=8.6, 7.2, 1.5, 1H, aromatic), 7.45 (t, J=7.3, 2H, aromatic), 7.27 (d, J=9.2, 2H, aromatic), 7.12 (td, J=7.7, 1.0, 1H, aromatic), 6.75-6.67 (m, 1H, aromatic), 5.52 (s, 2H, Bn-CH$_2$), 4.24 (d, J=5.5, 2H, Gly-CH$_2$), 3.75 (s, 3H, O—CH$_3$); $^{13}$C NMR (126 MHz, CDCl$_3$) δ 176.97 (CO), 170.43 (CO), 165.45 (CO), 148.77 (aromatic), 139.43 (aromatic), 133.43 (aromatic), 132.42 (aromatic), 131.83 (aromatic), 130.29 (aromatic), 130.04 (aromatic), 128.18 (aromatic), 127.85 (aromatic), 127.73 (aromatic), 127.35 (aromatic), 125.65 (aromatic), 116.67 (aromatic), 112.03 (aromatic), 55.14 (Bn-CH$_2$), 52.44 (O—CH$_3$), 41.50 (Gly-CH$_2$).

Example 58

Compound 170. tert-Butyl 3-(2-tert-butoxy-2-oxoethylcarbamoyl)-4-oxoquinoline-

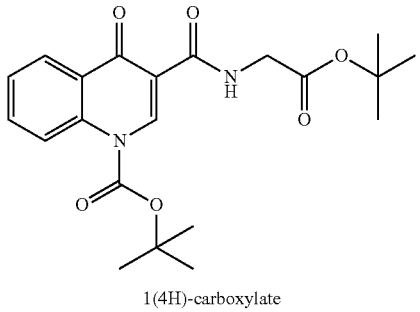 [SMILES: CC(C)(C)OC(=O)CNC(=O)c1cn(C(=O)OC(C)(C)C)c2ccccc2c1=O]

1(4H)-carboxylate

To a suspension of 1-tert-butoxycarbonyl-4-oxo-1,4-dihydroquinoline-3-carboxylic acid (138 mg, 0.478 mmol) in anhydrous DMF (3.5 mL) was added DIEA (335 µL, 1.912 mmol) and O-(7-Azabenzotriazol-1-yl)-N,N,N',N'-tetramethyluronium hexafluorophosphate (173 mg, 0.454 mmol). After stirring for 2 min, Glycine tert-butylester hydrochloride (160 mg, 0.956 mmol) was added and the reaction mixture was stirred at room temperature for 18 h. Solvent was removed under reduced pressure and the product purified by flash chromatography using a gradient of 50-100% EtOAc in cyclohexane, some product precipitated on the top of the column and was also collected to afford the title product (63 mg, 33%) as a pale yellow oil.

HRMS m/z (ES−) 301.1192, calculated for $C_{16}H_{17}N_2O_4$ (M-Boc$^-$) 301.1188; $^1$H NMR (500 MHz, CDCl$_3$) δ 10.56 (t, J=5.3, 1H, NH), 8.60 (s, 1H, aromatic), 8.13 (dd, J=8.2, 1.1, 1H, aromatic), 7.54 (ddd, J=8.4, 7.1, 1.4, 1H, aromatic), 7.43 (d, J=8.2, 1H, aromatic), 7.29-7.26 (m, 1H, aromatic), 4.10 (d, J=5.4, 2H, Gly-CH$_2$), 1.45 (s, 9H C(CH$_3$)$_3$), 1.42 (s, 9H, C(CH$_3$)$_3$); $^{13}$C NMR (126 MHz, CDCl$_3$) δ 177.28 (CO), 170.28 (CO), 166.60 (CO), 166.31 (CO), 144.08 (aromatic), 138.86 (aromatic), 133.11 (aromatic), 126.30 (aromatic), 125.98 (aromatic), 125.60 (aromatic), 118.92 (aromatic), 110.46 (aromatic), 84.98 ($\underline{C}$(CH$_3$)$_3$), 82.96 ($\underline{C}$(CH$_3$)$_3$), 41.73 (Gly-CH$_2$), 28.19 (C($\underline{CH}_3$)$_3$), 27.99 (C($\underline{CH}_3$)$_3$).

Example 59

Compound 171. 2-(1-Ethyl-4-oxo-1,4-dihydroquinoline-3-carboxamido)acetic acid

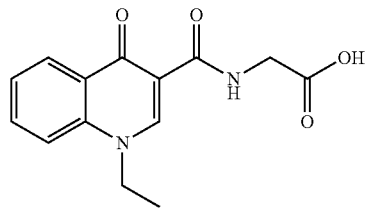 [SMILES: CCn1cc(C(=O)NCC(=O)O)c(=O)c2ccccc21]

To a solution of methyl 2-(1-ethyl-4-oxo-1,4-dihydroquinoline-3-carboxamido)acetate (50 mg, 0.173 mmol) in THF (2 mL) was added 1 M NaOH (aq) (1 mL, 1 mmol), the reaction mixture was stirred at room temperature for 18 h. The pH of the mixture was then adjusted to 2 by addition of 1 M HCl(aq). Water (10 mL) was added and the product was extracted with EtOAc (3×25 mL). The combined organic fractions were dried over $MgSO_4$, filtered and evaporated. NMR showed some impurities so the product was purified by flash chromatography using a gradient of 0-50% MeOH in EtOAc to give the title product (21.5 mg, 45%) as a white powder.

HRMS m/z (ES+) 297.0864, calculated for $C_{14}H_{14}N_2O_4Na^+$ 297.0851;

Example 60

Compound 172. 2-(1-(3-Chlorobenzyl)-4-oxo-1,4-dihydroquinoline-3-carboxamido)acetic acid

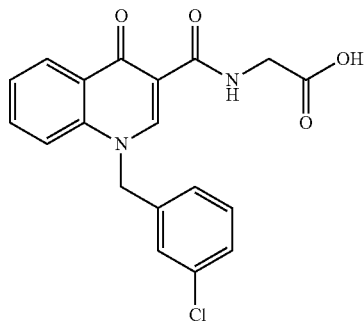 [SMILES: O=C(O)CNC(=O)c1cn(Cc2cccc(Cl)c2)c2ccccc2c1=O]

To a solution of methyl 2-(1-(3-chlorobenzyl)-4-oxo-1,4-dihydroquinoline-3-carboxamido)acetate (40 mg, 0.104 mmol) in THF (2 mL) was added 1 M NaOH (aq) (1 mL, 1 mmol), the reaction mixture was stirred at room temperature for 18 h. LCMS showed starting material remaining so a further 1 mL 1M NaOH (aq) was added and the reaction mixture stirred at room temperature for 72 h. The pH of the mixture was then adjusted to 2 by addition of 1 M HCl (aq). Water (10 mL) was added and the product was extracted with EtOAc (3×25 mL). The combined organic fractions were dried over $MgSO_4$, filtered and evaporated to give the title product (15 mg, 39%) as a white powder.

HRMS m/z (ES+) 371.0781, calculated for $C_{19}H_{16}N_2O_4Cl^+$ 371.0799;

Example 61

Compound 173. 2-(1-(2-Fluorobenzyl)-4-oxo-1,4-dihydroquinoline-3-carboxamido)acetic acid

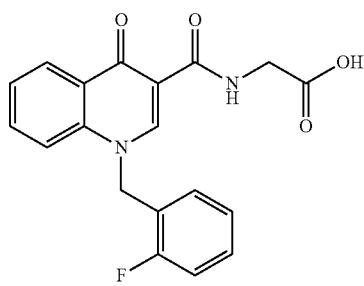 [SMILES: O=C(O)CNC(=O)c1cn(Cc2ccccc2F)c2ccccc2c1=O]

To a solution of methyl-2-(1-(2-fluorobenzyl)-4-oxo-1,4-dihydroquinoline-3-carboxamido)acetate (50 mg, 0.136 mmol) in THF (2 mL) was added 1 M NaOH (aq) (1 mL, 1 mmol), the reaction mixture was stirred at room temperature for 18 h. The pH of the mixture was then adjusted to 2 by addition of 1 M HCl (aq). Water (10 mL) was added and the product was extracted with EtOAc (3×25 mL). The combined organic fractions were dried over $MgSO_4$, filtered and evaporated. NMR showed some impurities so the product was purified by flash chromatography using a gradient of 0-50% MeOH in EtOAc to give the title product (27 mg, 56%) as a white powder. HRMS m/z (ES+) 377.0908, calculated for $C_{19}H_{15}N_2O_4FNa^+$ 377.0914; $^1$H NMR (500 MHz, MeOH) δ 9.00 (s, 1H, aromatic), 8.48-8.42 (m, 1H, aromatic), 7.70 (t, J=9.1, 2H, aromatic), 7.49 (t, J=6.9, 1H, aromatic), 7.39-7.31 (m, 1H, aromatic), 7.22-7.02 (m, 3H, aromatic), 5.72 (s, 2H, Bn-$CH_2$), 4.03 (s, 2H Gly-$CH_2$);

Example 62

Compound 174 (RW94). 2-(1-(4-Methoxybenzyl)-4-oxo-1,4-dihydroquinoline-3-carboxamido)acetic acid

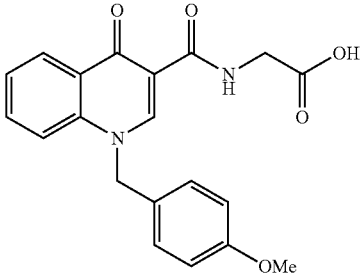 [SMILES: COc1ccc(Cn2cc(C(=O)NCC(=O)O)c(=O)c3ccccc32)cc1]

To a solution of methyl 2-(1-(4-methoxybenzyl)-4-oxo-1,4-dihydroquinoline-3-carboxamido)acetate (40 mg, 0.105 mmol) in THF (2 mL) was added 1 M NaOH (aq) (1 mL, 1 mmol), the reaction mixture was stirred at room temperature for 18 h. The pH of the mixture was then adjusted to 2 by addition of 1 M HCl (aq). Water (10 mL) was added and the product was extracted with EtOAc (3×25 mL). The combined organic fractions were dried over $MgSO_4$, filtered and evaporated to give the title product (22 mg, 57%) as a white powder.

HRMS m/z (ES+) 389.1115, calculated for $C_{20}H_{18}N_2O_5Na^+$ 389.1113;

Example 63

Compound 175. 2-(1-(3,5-Dimethylbenzyl)-4-oxo-1,4-dihydroquinoline-3-carboxamido)acetic acid

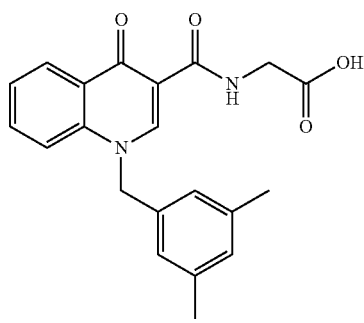 [SMILES: Cc1cc(C)cc(Cn2cc(C(=O)NCC(=O)O)c(=O)c3ccccc32)c1]

To a solution of methyl 2-(1-(3,5-dimethylbenzyl)-4-oxo-1,4-dihydroquinoline-3-carboxamido)acetate (30 mg, 0.0793 mmol) in THF (2 mL) was added 1 M NaOH (aq) (1 mL, 1 mmol), the reaction mixture was stirred at room temperature for 18 h. The pH of the mixture was then adjusted to 2 by addition of 1 M HCl (aq). Water (10 mL) was added and the product was extracted with EtOAc (3×25 mL). The combined organic fractions were dried over MgSO$_4$, filtered and evaporated. NMR showed some impurities so the product was purified by flash chromatography using a gradient of 0-50% MeOH in EtOAc to give the title product (16 mg, 55%) as a white powder. HRMS m/z (ES+) 387.1310, calculated for $C_{21}H_{20}N_2O_4Na^+$ 387.1321;

Example 64

Compound 176. 2-(4-Oxo-1-(4-(trifluoromethoxy)benzyl)-1,4-dihydroquinoline-3-carboxamido)acetic acid

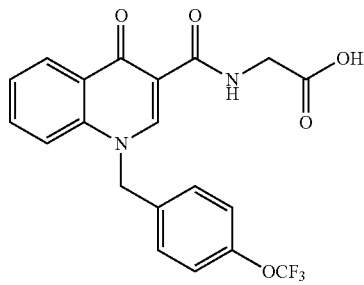 [SMILES: O=C(O)CNC(=O)c1cn(Cc2ccc(OC(F)(F)F)cc2)c2ccccc2c1=O]

To a solution of methyl 2-(4-oxo-1-(4-(trifluoromethoxy)benzyl)-1,4-dihydroquinoline-3-carboxamido)acetate (50 mg, 0.115 mmol) in THF (2 mL) was added 1 M NaOH (aq) (1 mL, 1 mmol), the reaction mixture was stirred at room temperature for 18 h. The pH of the mixture was then adjusted to 2 by addition of 1 M HCl(aq). Water (10 mL) was added and the product was extracted with EtOAc (3×25 mL). The combined organic fractions were dried over MgSO$_4$, filtered and evaporated to give the title product (38 mg, 79%) as a white powder.

HRMS m/z (ES+) 443.0817, calculated for $C_{20}H_{15}N_2O_5F_3Na^+$ 443.0831; $^1$H NMR (500 MHz, MeOH) δ 9.02 (s, 1H), 8.45 (dd, J=8.1, 1.2, 1H), 7.71 (ddt, J=18.1, 14.8, 4.9, 2H), 7.51 (ddd, J=8.0, 6.9, 1.1, 1H), 7.35 (d, J=8.8, 2H), 7.26 (d, J=8.1, 2H), 5.73 (s, 2H), 4.22 (s, 2H); $^{13}$C NMR (126 MHz, MeOH) δ 178.33, 173.10, 167.42, 150.59, 140.95, 136.07, 134.65, 133.76, 132.55, 130.02, 129.60, 129.24, 127.98, 126.87, 122.88, 119.00, 112.36, 111.16, 57.63, 42.14.

Example 65

Compound 177. 2-(1-(2-Chlorobenzyl)-4-oxo-1,4-dihydroquinoline-3-carboxyamido)acetic acid

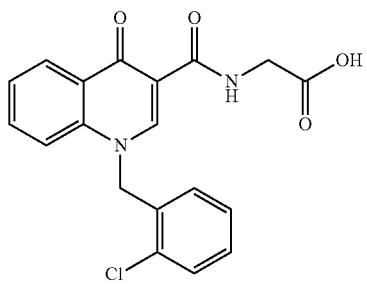 [SMILES: O=C(O)CNC(=O)c1cn(Cc2ccccc2Cl)c2ccccc2c1=O]

To a solution of methyl 2-(1-(2-chlorobenzyl)-4-oxo-1,4-dihydroquinoline-3-carboxyamido)acetate (30 mg, 0.0780 mmol) in THF (2 mL) was added 1 M NaOH (aq) (1 mL, 1 mmol), the reaction mixture was stirred at room temperature for 18 h. LCMS showed starting material remaining so a further 1 mL 1M NaOH (aq) was added and the reaction mixture stirred at room temperature for 72 h. The pH of the mixture was then adjusted to 2 by addition of 1 M HCl (aq). Water (10 mL) was added and the product was extracted with EtOAc (3×25 mL). The combined organic fractions were dried over MgSO$_4$, filtered and evaporated to give the title product (21 mg, 73%) as a white powder.

HRMS m/z (ES+) 393.0628, calculated for $C_{19}H_{15}N_2O_4NaCl^+$ 393.0618;

Example 66

Compound 178. 2-(4-Oxo-1,4-dihydroquinoline-3-carboxamido)acetic acid

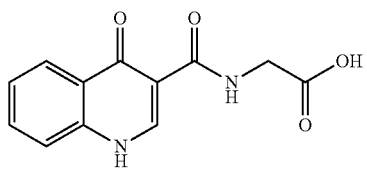 [SMILES: O=C(O)CNC(=O)c1c[nH]c2ccccc2c1=O]

To a solution of tert-butyl 3-(2-tert-butoxy-2-oxoethylcarbamoyl)-4-oxoquinoline-1(4H)-carboxylate (30 mg, 0.0745 mmol) in DCM (2 mL) was added TFA/m-cresol (95:5), (1 mL). The reaction mixture was stirred at room temperature for 3 h. Solvent was removed under educed pressure and the product was purified by precipitation from Et$_2$O then dried under vacuum to give the title product (12 mg, 65%) as a white powder.

HRMS m/z (ES+) 269.0526, calculated for $C_{12}H_{10}N_2O_4Na^+$ 269.0538; $^1$H NMR (500 MHz, MeOH) δ 8.76 (s, 1H, aromatic), 8.35 (dd, J=8.2, 1.0, 1H, aromatic), 7.77 (ddd, J=8.4, 7.1, 1.4, 1H, aromatic), 7.63 (d, J=8.3, 1H, aromatic), 7.55-7.44 (m, 1H, aromatic), 4.20 (s, 2H, Gly-CH$_2$).

Example 67

Compound 304. 1-benzyl-4-oxo-6-(thiophen-3-yl)-1,4-dihydroquinoline-3-carbonyl)glycine

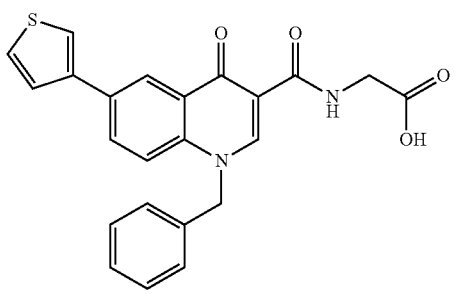 [SMILES: O=C(O)CNC(=O)c1cn(Cc2ccccc2)c2ccc(-c3ccsc3)cc2c1=O]

To 118 (165.6 mg, 0.4 mmol) and thiophene boronic acid or ester (0.4 mmol) in isopropanol (2.6 mL) was added K$_2$CO$_3$ (300 mg, 2 mmol) in water (1.2 mL) followed by Pd.CH$_2$Cl$_2$.dppf (8 mg, 0.04 mmol). The reaction mixture was stirred and purged with nitrogen by bubbling with a needle inserted below the level of the solvents for 5 min. The reaction vessel was sealed and transferred to a microwave reactor. The reaction mixture was heated at 120° for 10 min. On cooling the reaction mixture was poured onto 20% aq. NaHSO$_4$ (20 mL) and stirred for 30 mins. Clumps of solid were broken up by placing in an ultrasonic bath for 5 min. The resulting suspension was filtered and washed extensively with water. The resultant solid was dried in vacuo to give the title product.

$^1$H NMR (500 MHz, DMSO) δ 12.68 (s, 1H), 10.26 (t, J=5.5 Hz, 1H), 9.06 (s, 1H), 8.58 (d, J=2.2 Hz, 1H), 8.09 (dd, J=8.9, 2.2 Hz, 1H), 8.01 (dd, J=2.8, 1.3 Hz, 1H), 7.77 (d, J=9.0 Hz, 2H), 7.67 (dd, J=5.0, 2.9 Hz, 1H), 7.62 (dd, J=5.0, 1.2 Hz, 1H), 7.41-7.17 (m, 5H), 5.80 (s, 2H), 4.11 (d, J=5.5 Hz, 2H).

$^{13}$C NMR (126 MHz, DMSO) δ 175.49, 171.32, 164.26, 148.66, 139.85, 138.11, 135.96, 132.02, 131.03, 128.96, 127.90, 127.77, 127.66, 126.50, 126.08, 122.51, 122.23, 118.77, 110.85, 55.86, 40.98.

HRMS (TOF MS ES$^+$) Calc. for $C_{23}H_{19}N_2O_4$ 419.1064 found 419.1066.

Example 68

Compound 305. 3-(1-benzyl-3-((carboxymethyl)carbamoyl)-4-oxo-1,4-dihydroquinolin-6-yl)benzoic acid

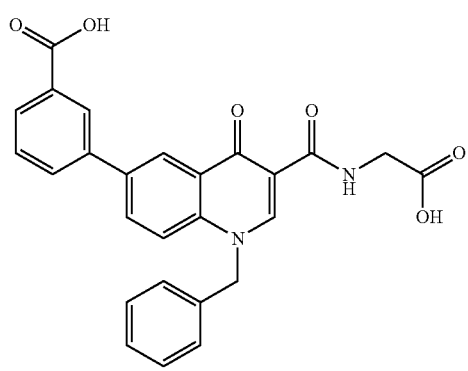

Molecular Weight = 456.46

Example 67 was repeated, except that a boronic acid or ester of benzoic acid was used in place of thiophene boronic acid or ester.

$^1$H NMR (500 MHz, DMSO) δ 10.21 (t, J=5.4 Hz, 1H), 9.09 (s, 1H), 8.58 (d, J=1.9 Hz, 1H), 8.24 (s, 1H), 8.10 (dd, J=8.9, 1.9 Hz, 1H), 7.98 (dd, J=14.4, 7.7 Hz, 2H), 7.86 (d, J=9.0 Hz, 1H), 7.62 (t, J=7.7 Hz, 1H), 7.40-7.21 (m, 5H), 5.82 (s, 2H), 4.11 (d, J=5.5 Hz, 2H).

$^{13}$C NMR (151 MHz, DMSO) δ 175.54, 171.37, 167.13, 164.24, 149.05, 138.89, 138.79, 135.95, 135.92, 131.70, 131.52, 131.28, 129.64, 129.03, 128.79, 127.96, 127.78, 127.42, 126.52, 123.69, 119.07, 111.07, 55.90, 41.01.

HRMS (TOF MS ES$^+$) Calc. for $C_{26}H_{21}N_2O_6$ 457.1400 found 457.1359.

Example 69

Compound 306. 1-benzyl-6-(3-(hydroxymethyl)phenyl)-4-oxo-1,4-dihydroquinoline-3-carbonyl)glycine

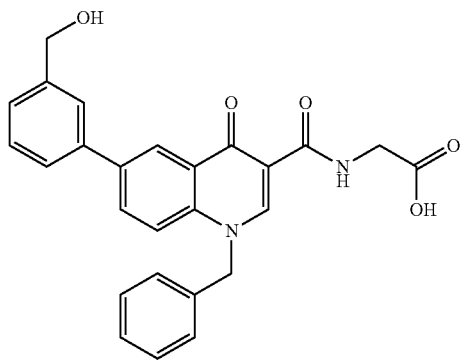

Molecular Weight = 442.48

Example 67 was repeated, except that a boronic acid or ester of hydroxymethyl benzene was used in place of thiophene boronic acid or ester.

Example 70

Compound 307. 2-(6-(3-(acetamidomethyl)phenyl)-1-benzyl-4-oxo-1,4-dihydroquinoline-3-carbonyl)glycine

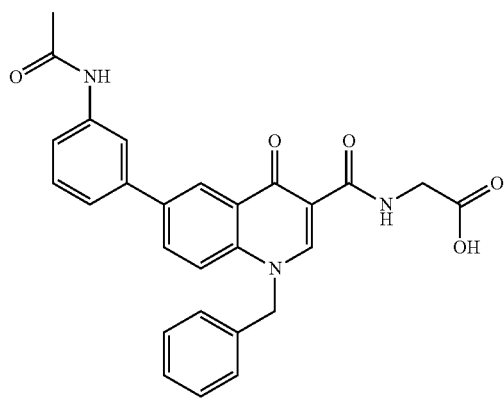 [SMILES: CC(=O)Nc1cccc(-c2ccc3c(c2)c(=O)c(C(=O)NCC(=O)O)cn3Cc2ccccc2)c1]

Example 67 was repeated, except that a boronic acid or ester of acetamidomethyl benzene was used in place of thiophene boronic acid or ester.

$^1$H NMR (500 MHz, DMSO) δ 12.68 (s, 1H), 10.24 (t, J=5.1 Hz, 1H), 10.07 (s, 1H), 9.08 (s, 1H), 8.55 (s, 1H), 8.00 (d, J=5.0 Hz, 2H), 7.84 (d, J=8.8 Hz, 1H), 7.61 (d, J=3.4 Hz, 1H), 7.32 (ddd, J=25.6, 19.6, 10.0 Hz, 7H), 5.79 (d, J=17.9 Hz, 2H), 4.11 (d, J=5.2 Hz, 2H), 3.16 (s, 2H), 2.06 (s, 3H).

$^{13}$C NMR (126 MHz, DMSO) δ 175.54, 171.32, 168.51, 164.23, 148.86, 140.11, 138.90, 138.57, 136.71, 135.91, 131.24, 129.58, 128.97, 127.91, 127.71, 126.51, 123.33, 121.39, 118.88, 118.48, 117.16, 110.98, 55.85, 40.99, 24.08.

HRMS (TOF MS ES$^+$) Calc. for $C_{27}H_{23}N_3O_5$ 470.1716 found 470.1741.

Example 71

Compound 310. 2-(1-benzyl-4-oxo-6-(pyridin-3-yl)-1,4-dihydroquinoline-3-carboxamido)acetic acid

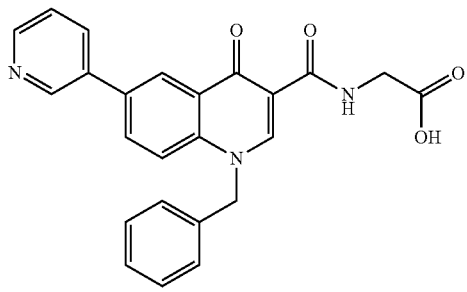 [SMILES: O=C(O)CNC(=O)c1cn(Cc2ccccc2)c2ccc(-c3cccnc3)cc2c1=O]

Example 67 was repeated, except that a boronic acid or ester of pyridine was used in place of thiophene boronic acid or ester. The title compound was obtained as a beige solid.

$^1$H NMR (500 MHz, DMSO) δ 10.19 (t, J=5.3 Hz, 1H), 9.15 (s, 1H), 9.11 (s, 1H), 8.76 (d, J=4.9 Hz, 1H), 8.68 (d, J=2.1 Hz, 1H), 8.56 (d, J=7.6 Hz, 1H), 8.21-8.10 (m, 1H), 7.90 (d, J=8.9 Hz, 1H), 7.87-7.77 (m, 1H), 7.42-7.16 (m, 5H), 5.84 (s, 2H), 4.11 (d, J=5.5 Hz, 2H).

$^{13}$C NMR (151 MHz, DMSO) δ 175.44, 171.36, 164.10, 149.31, 144.96, 144.21, 139.37, 139.09, 135.91, 135.83, 132.16, 131.67, 129.03, 127.98, 127.80, 126.51, 125.70, 124.66, 119.26, 111.32, 55.92, 48.64.

HRMS (TOF MS ES$^+$) Calc. for $C_{24}H_{20}N_3O_4$ 414,1454 found 414.1447.

Example 72

Compound 311. Methyl (6-bromo-1-(4-(methylsulfonyl)benzyl)-4-oxo-1,4-dihydroquinoline-3-carbonyl)glycinate

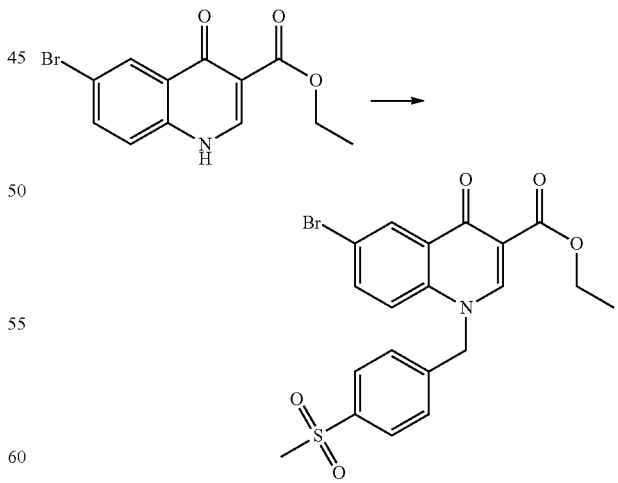

To the quinoline compound shown above (2.94 g, 10 mmol) in DMF (60 mL) was added K$_2$CO$_3$ (5.5 g, 40 mmol) followed by 4-chloromethylmethlsulfone (Fluorochem) (2.04 g, 10 mmol) and the reaction mixture heated to 90° for 4 h. The DMF was removed on a rotary evaporator (1 mm Hg) and water (200 mL) and ethyl acetate (100 mL) added. The mixture was stirred for 30 mins and the light grey solid product filtered off and washed with ethyl acetate (100 mL). 3.58 g, 82%.

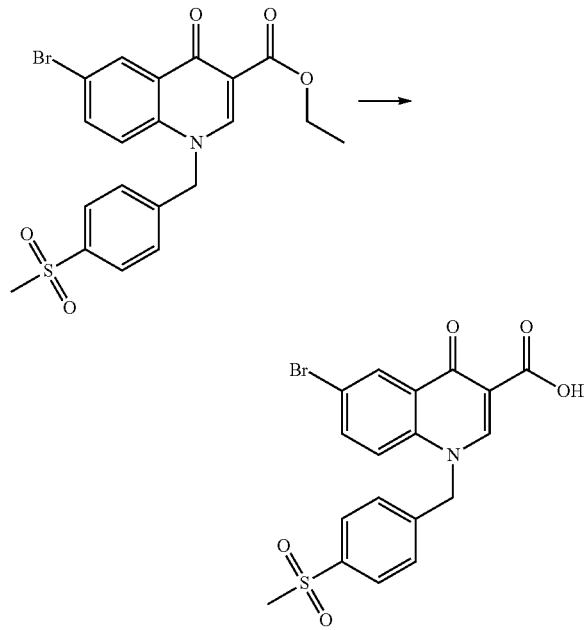

To the ester obtained in the previous step and shown above (2.32 g, 5 mmol) was added sodium hydroxide (1.6 g, 40 mmol) in water (25 mL) and the reaction mixture heated under reflux for 8 h. The grey solid product was filtered off and the product used directly for the next step.

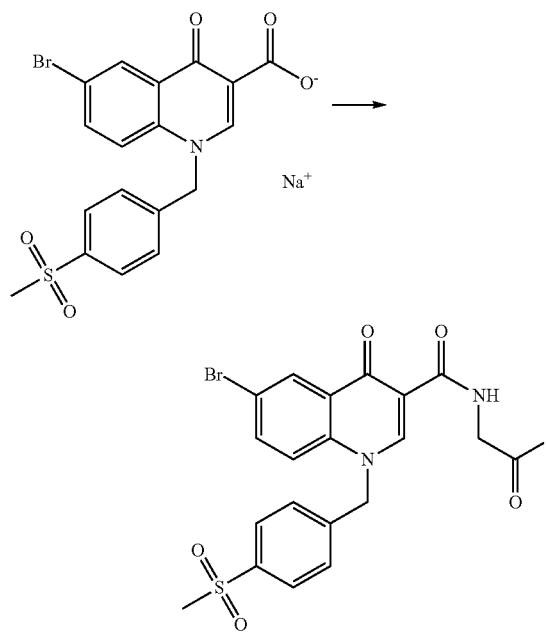

To the quinoline carboxylic acid sodium salt obtained in the previous step and shown above (91 mg, 0.2 mmol) in DMF was added PyBOP (104 mg, 0.2 mmol) followed by DIPEA (90 µL) and the reaction stirred for 16 h. The volatiles were removed under a stream of nitrogen and the residue stirred in DCM (20 mL) and 1 M HCl (20 mL) for 2 h. The mixture was filtered through Whatman filter paper (no. 3)10025-33. The DCM was separated off and Silica gel (1 g) added. The DCM was removed on a rotary evaporator and the dry silica gel loaded onto a silica column (Pur1flash, $SiO_2$, 50 µm) and eluted with methanol/DCM to obtain the title product (58 mg, 0.114 mM, 57%).

$^1$H NMR (600 MHz, DMSO) δ 10.10 (t, J=5.8 Hz, 1H), 9.14 (s, 1H), 8.43 (d, J=2.4 Hz, 1H), 7.92 (dd, J=9.1, 2.4 Hz, 1H), 7.89 (d, J=8.5 Hz, 2H), 7.65 (d, J=9.2 Hz, 1H), 7.46 (d, J=8.5 Hz, 2H), 5.94 (s, 2H), 4.19 (d, J=5.7 Hz, 2H), 3.67 (s, 3H), 3.19 (s, 3H).

$^{13}$C NMR (151 MHz, DMSO) δ 174.45, 170.44, 164.10, 149.68, 141.72, 140.29, 138.19, 135.83, 128.95, 128.43, 127.70, 127.28, 120.52, 118.46, 111.50, 55.46, 51.86, 45.90, 45.87, 43.44.

HMRS (TOF MS ES$^+$), Calculated for $C_{21}H_{20}BrN_2O_6S$ 507.0225, found 507.0231.

Example 73

Compound 302. 6-Bromo-1-(4-(methylsulfonyl) benzyl)-4-oxo-1,4-dihydroquinoline-3-carbonyl) glycine

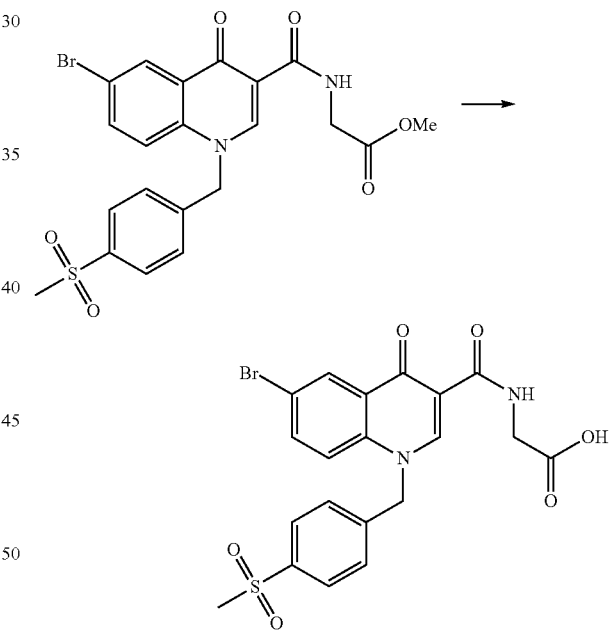

To the methyl ester 311 (102 mg, 200 µmol) in methanol (2 mL) was added sodium hydroxide (400 µL, of a 1 M solution in water) and the reaction stirred for 48 h. The volatiles were removed on a rotary evaporator and the residue partitioned between water (10 mL) and DCM. The aqueous layer was acidified to pH 2-3 with 1M HCl. The DCM was separated and the aqueous phase extracted with DCM (2×20 mL). The combined DCM extracts were dried (MgSO$_4$), 38 mg crude as a white solid. The crude product was purified using a SiO$_2$ Puriflash column (6 g) with DCM and a gradient elution of methanol containing 1% acetic acid. The title product was obtained as a white solid, yield 31 mg, 63 mol, 32%.

$^1$H NMR (500 MHz, DMSO) δ 10.04 (t, J=5.6 Hz, 1H), 9.12 (s, 1H), 8.42 (d, J=2.4 Hz, 1H), 7.91-7.86 (m, 3H), 7.64 (d, J=9.2 Hz, 1H), 7.44 (d, J=8.5 Hz, 2H), 5.92 (s, 2H), 4.09 (d, J=5.7 Hz, 3H), 3.16 (d, J=6.5 Hz, 3H).

$^{13}$C NMR (126 MHz, DMSO) δ 174.40, 171.20, 163.81, 149.54, 141.67, 140.31, 138.18, 135.74, 128.94, 128.43, 127.64, 127.26, 120.44, 118.35, 111.67, 55.41, 43.43, 41.00.

HMRS (TOF MS ES$^+$), Calculated for $C_{20}H_{18}N_2O_6SBr$, 493.0069 found 493.0080.

Example 74

Compound 312. Methyl 3-(1-benzyl-6-bromo-4-oxo-1,4-dihydroquinoline-3-carboxamido)propanoate

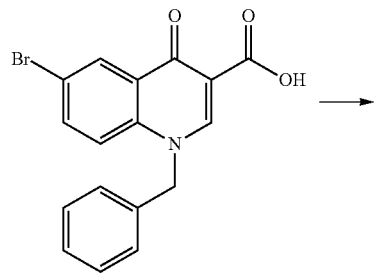

To the quinoline carboxylic acid shown above (374 mg, 1.0 mmol) in DMF (10 mL) was added PyBOP (520 mg, 1.0 mmol) followed by DIPEA (260 mg, 351 μL, 2 mmol) and beta-alanine, methyl ester (139.6 mg, 1.0 mmol). The reaction mixture was stirred at 30° for 3 hours. The volatiles were removed under a stream of nitrogen at room temperature. The resulting solid was partitioned between DCM (10 mL) and water (20 mL). The DCM was separated and the water extracted with DCM (2×10 mL). The combined DCM extracts were dried over MgSO$_4$. The crude product was purified using a silica column eluting with 0-15% acetone in DCM, to give the title compound as a cream coloured solid. Yield (290 mg, 0.52 mmol, 52%).

Example 75

Compound 308. 3-(1-Benzyl-6-bromo-4-oxo-1,4-dihydroquinoline-3-carboxamido)propanoic acid

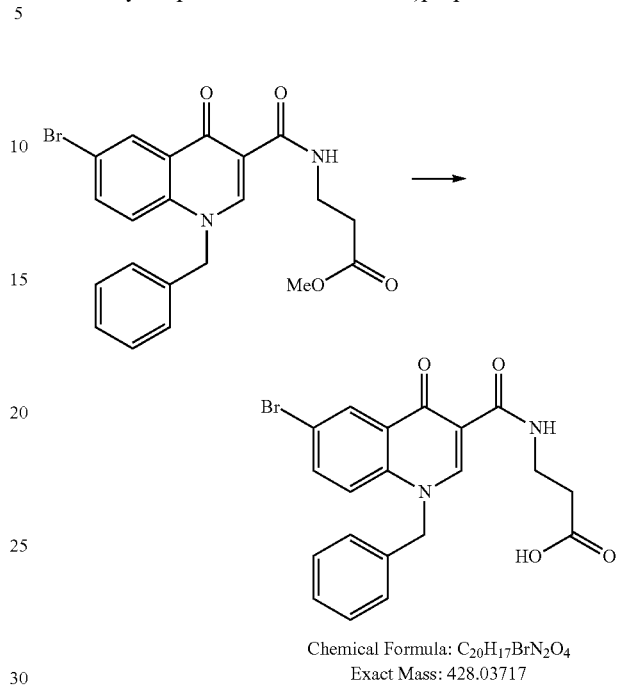

Chemical Formula: $C_{20}H_{17}BrN_2O_4$
Exact Mass: 428.03717

To the methyl ester 312 (55 mg, 125 μmol) in THF (1 mL) was added sodium hydroxide (1 mL, of a 1 mM solution in water) and the reaction stirred for 48 h. Aqueous 1 M HCl (2 mL) was added and the reaction mixture stirred for 1 h. The precipitated solid was filtered off and dried in vacuo to give the title compound. Yield 33.5 mg, 78.3 μmol, 63%.

Example 76

Ca$^{2+}$ Flux in Isolated Rat Mesenteric Artery Smooth Muscle Cells

Mesenteric artery smooth muscle cells were isolated from male Sprague-Dawley rats (200-250 g). Mesenteric arteries were dissected, cleared of extraneous tissue and incubated in an enzyme solution containing collagenase type I (1 mg/ml), soybean trypsin inhibitor (0.25 mg/ml), bovine albumin (1 mg/ml), CaCl$_2$ (0.2 mM), 100 U/ml penicillin (100 U/ml) and streptomycin (100 μg/ml) in a humidified incubator with 5% CO$_2$ in air. The enzyme solution was replenished at 30 min intervals and cells were pelleted by centrifugation (200 g, 5 min) and differentially plated (×2) for 15 min in Dulbecco's Modified Eagle's Medium (DMEM) supplemented with penicillin (100 U/ml), streptomycin (100 μg/ml), L-Glutamine (2 mM) and 10% heat inactivated New Zealand foetal calf serum. Cells were passaged by trypsinisation and viability determined by trypan blue exclusion.

Measurements of Ca$^{2+}$ flux in response to Angiotensin II were conducted using a Fluorescent Imaging Plate Reader (FLIPR; Molecular Devices). Cells were plated at a density of 10,000 cells/well into black, clear-bottomed 96-well plates in DMEM supplemented with penicillin (100 U/ml), streptomycin (100 μg/ml), L-Glutamine (2 mM) and 10% heat inactivated New Zealand foetal calf serum. 24 hrs later the cells were incubated with Fluo-3-AM (4 μM) for 60 min at 37° C. Once dye-loaded, the cells were washed thoroughly with the proprietary assay buffer to remove any unincorporated dye. The cells were then incubated with varying concentrations of a number of representative NPR-C agonist molecules of the invention, C-type natriuretic peptide or vehicle (DMSO) and placed into the FLIPR. After 15 mins, Angiotensin II (100 nM) was automatically dispensed into each well and the fluorescence signal followed for 5 mins. Potency was determined by comparison of the peak fluorescence in each test well (run in triplicate) with that of the control (Angiotensin II alone). Background fluorescence (assay buffer only) was subtracted from all values.

The results for a number of compounds of the invention are shown in the Table below.

| Compound | % inhibition 1 µM | % inhibition 10 µM |
|---|---|---|
| CNP | 100 | 100 |
| 27 | 0 | 50 |
| 28 | 100 | 100 |
| 57 | 0 | 35 |
| 59 | 20 | 90 |
| 60 | 0 | 80 |
| 61 | 27 | 100 |
| 62 | 0 | 50 |
| 63 | 58 | 100 |
| 84 | 40 | 45 |
| 85 | 0 | 97 |
| 86 | 0 | 45 |
| 87 | 0 | 67 |
| 88 | 12 | 55 |
| 103 | 0 | 65 |
| 104 | 0 | 69 |
| 105 | 80 | 100 |
| 106 | 90 | 90 |
| 107 | 15 | 100 |
| 108 | 0 | 90 |
| 109 | 18 | 100 |
| 110 | 70 | 100 |
| 111 | 100 | 100 |
| 112 | 100 | 100 |
| 113 | 12 | 100 |
| 114 | 100 | 100 |
| 116 | 80 | 100 |
| 117 | 87 | 100 |
| 118 | 95 | 100 |
| 119 | 80 | 100 |
| 134 | 55 | 80 |
| 136 | 15 | 20 |
| 138 | 11 | 40 |
| 139 | 5 | 50 |
| 141 | 0 | 28 |
| 142 | 18 | 75 |
| 143 | 0 | 37 |
| 144 | 23 | 40 |

It can be seen from the above results that the NPR-C agonist compounds of the invention inhibit the $Ca^{2+}$ flux in rat smooth muscle cells, indicating that they will be effective in reducing the associated contractile response.

The Table above shows the structure-activity relationship (SAR) for a selection of compounds of the present invention using an identical cell based assay using AngII-mediated increases in $Ca^{2+}$ as readout.

Example 77

Vasoreactivity in Rat Mesenteric Arteries In Vitro

Male rats (Sprague-Dawley; 200-250 g) were stunned and killed by cervical dislocation. The mesentery was removed and third-order arteries mounted in an automated tension myograph (Danish Myotechnology). After an equilibration period of 45 min, vessels were normalized and diameter determined. Following normalization, each vessel was contracted repeatedly with the thromboxane $A_2$-mimetic 9,11-dideoxy-11α,9α-epoxymethano-prostaglandin $F_{2\alpha}$ (U46619; 1 µM) until the response was reproducible. The vessels were then washed to restore basal tone before contracting to approximately 50% of the maximum U46619-induced response. Once a stable response to U46619 was achieved, cumulative concentration-response curves were constructed with a variety of NPR-C agonists of the invention at varying concentrations (0.001-30 µM), or vehicle (DMSO). In some studies, concentration-response curves to NPR-C agonists were conducted in the presence of the NPR-C antagonist M372049 (10 µM). Only one curve to any one agonist was constructed in any single tissue.

The results for a number of compounds of the invention are shown in the Table below.

| Compound | % relaxation 1 µM | % relaxation 3 µM | % relaxation 10 µM | % relaxation 30 µM |
|---|---|---|---|---|
| 28 | 22 | 55 | 97 | 100 |
| 187 | 31 | 57 | 93 | 100 |
| 172 | 5 | 20 | 43 | 91 |
| 200 | 4 | 10 | 67 | 89 |
| 189 | 4 | 12 | 64 | 84 |
| 204 | 9 | 18 | 30 | 92 |
| 119 | 2 | 5 | 26 | 94 |
| 176 | 8 | 9 | 17 | 91 |
| 175 | 8 | 8 | 12 | 88 |
| 188 | 4 | 3 | 2 | 87 |
| 201 | 0 | 0 | 0 | 82 |
| 173 | 4 | 13 | 15 | 79 |
| 137 | 0 | 1 | 9 | 69 |
| 203 | 7 | 6 | 28 | 50 |
| 177 | 1 | 3 | 6 | 52 |
| 117 | 0 | 0 | 2 | 42 |
| 202 | 2 | 3 | 20 | 36 |
| 155 | 4 | 6 | 10 | 25 |
| 81 | 1 | 1 | 7 | 25 |
| 174 | 4 | 4 | 8 | 20 |
| 171 | 2 | 2 | 8 | 20 |
| 120 | 0 | 3 | 3 | 20 |
| 121 | 5 | 2 | 3 | 17 |
| 178 | 5 | 6 | 11 | 16 |
| 205 | −9 | 13 | 13 | 14 |
| 116 | 4 | 0 | 0 | 9 |

$EC_{50}$ values were also calculated for a number of compounds, as detailed in the Table below.

| Compound | $EC_{50}$ (µM) |
|---|---|
| CNP | 0.0138 |
| 28 | 1.6 |
| 117 | >50 |
| 118 | 2.8 |
| 119 | >50 |
| 171 | >50 |
| 172 | >50 |
| 173 | >50 |
| 174 | >50 |
| 175 | >50 |
| 176 | >50 |
| 177 | >50 |
| 178 | 17.4 |
| 187 | 1.6 |
| 188 | >50 |
| 200 | >50 |
| 201 | >50 |
| 202 | 20.3 |

The results above demonstrate the potent vasorelaxant properties of the compounds of the invention.

Example 78

Human Platelet Aggregation

Blood samples (35 ml) were taken from healthy volunteers who had abstained from aspirin, non-steroidal anti-inflammatory drugs or paracetamol for 14 days. Blood was collected by venepuncture into tri-sodium citrate (3.2% w/v) and centrifuged at 175 g for 15 min to obtain platelet rich plasma (PRP). Platelet poor plasma (PPP) was obtained by centrifugation of PRP at 15000 g for 5 min. The PRP (100 μl) was then added to the wells of 96-well plates and incubated for 15 mins with representative NPR-C agonists of the invention or vehicle (DMSO). Subsequently, platelet agonists (10 μl each) were added to wells in triplicate: adenosine diphosphate (ADP, 0.1-30 μM), arachidonic acid (AA, 0.03-1.3 mM), collagen (type I equine tendon 0.1-30 μg/ml), adrenaline (0.001-100 μM), ristocetin (0.2-3 mg/ml), TRAP6 (thrombin receptor activating peptide) amide (SFLLRN; 0.1-30 μM), U46619 (0.1-30 μM) or vehicle. Plates were then immediately placed in a 96-well plate reader and absorbance determined at 595 nm every 15 s for 16 min between vigorous shaking at 37° C. Changes in absorbance were converted to % aggregation by reference to the absorbances of PRP and PPP.

The results for a number of compounds of the invention are shown in the Table below.

| Compound | % inhibition of human platelet aggregation (at 1 microM) |
|---|---|
| CNP | 71.8 |
| 28 | 14.3 |
| 118 | 16.7 |

These results show that the compounds of the present invention have strong antiaggregatory properties in human platelets.

Example 79

Vascular Reactivity Studies

Male mice (C57BL6, 8 to 12 weeks old) were killed by neck dislocation and the mesentery was removed and placed in physiological salt solution (PSS) composed of (in mmol/L) NaCl 119, KCl 4.7, $CaCl_2.2H_2O$ 2.5, $MgSO_4.7H_2O$ 1.2, $NaHCO_3$ 25, $KH_2PO_4$ 1.2, and glucose 5.5. Second or third order arteries were mounted in an automated tension myograph (Danish Myotechnology) and bathed in PSS (37° C. gassed with 5% $CO_2$ in $O_2$). After equilibration of 45 min, vessels were normalized according to published protocols and vessel diameter determined (Mulvany M. J., Halpern W (1977). Contractile properties of small arterial resistance vessels in spontaneously hypertensive and normotensive rats. Circ Res 41:19-26.).

Following normalization, each vessel was contracted repeatedly with the thromboxane $A_2$-mimetic 9,11-dideoxy-$11\alpha,9\alpha$-epoxymethano-prostaglandin $F_{2\alpha}$ (U46619; 1 μM) until the response was reproducible. The vessels were then washed to restore basal tone before contracting to approximately 50% of the maximum U46619-induced response. Once a stable response to U46619 was achieved, cumulative concentration-response curves were constructed to the following representative compounds of of the present invention: 118, 304(Szk1r), 305(Szk2r), 306(Szk4r), 307(Szk5r) and 310(Szk6r).

Figure 8:
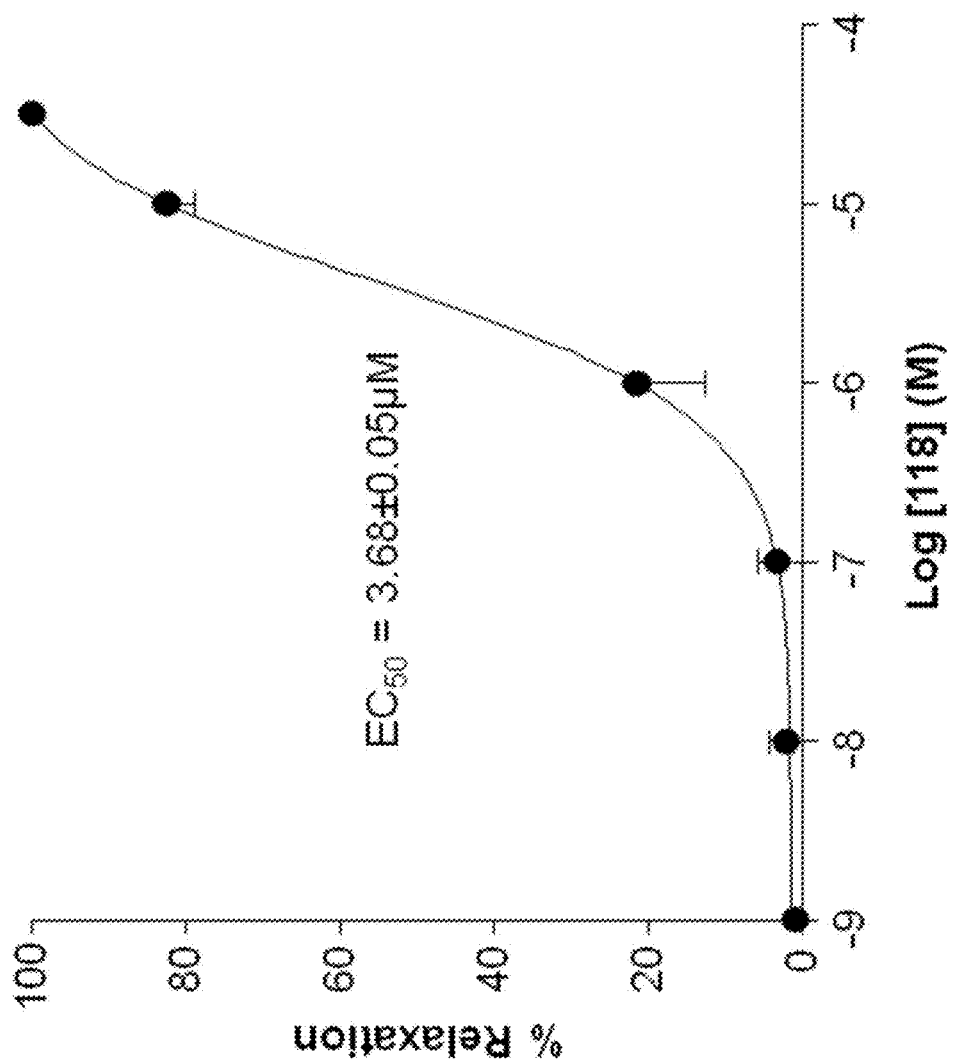
FIG. 8 shows in vitro bioactivity in rat mesenteric artery for two representative compounds of the present invention, compounds 28 and 118.
Figure 9:
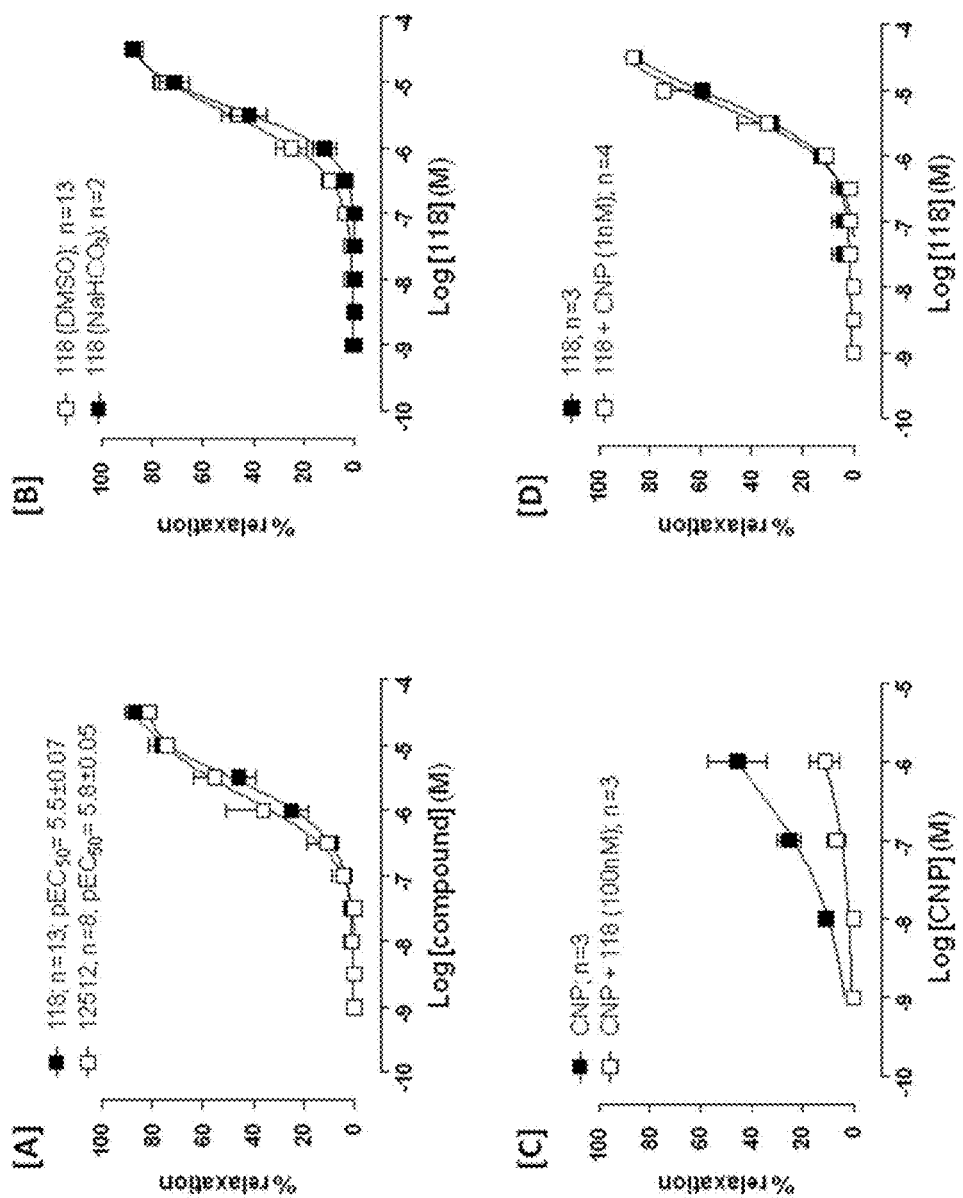
FIG. 9 shows in vitro bioactivity in rat mesenteric artery for representative compound 118 of the invention, CNP and combinations thereof.

The results obtained are shown as FIG. 1. Further dose response curves for representative compounds 28 and 118 are shown as FIG. 8. FIG. 9 shows further dose response curves for representative compound 118, CNP and combinations thereof.

Example 80

Mean Arterial Pressure Measurements

Mice were maintained under anesthesia (isoflurane, 1-1.5%, in 100% $O_2$ at 0.4 L·min) throughout the experiment and body temperature was kept constant at 37.5° C. A Millar pressure transducer catheter (Millar Instruments, Houston, Tex., USA) was placed in the carotid artery for arterial blood pressure (BP) measurements and a tube catheter (polyvinyl tubing, 0.61 mm outside diameter) in the jugular vein for intravenous bolus doses of 118 (0.001 g-3 mg/kg) and vehicle (10% DMSO in PBS) using a 0.5 mL insulin syringe. A pump (flow 0.5 ml/h) was used for infusion of 118 (1 mg/kg/min) or vehicle (10% dimethylsulfoxide; DMSO in PBS) during 10 min. BP was evaluated throughout.

Figure 2:
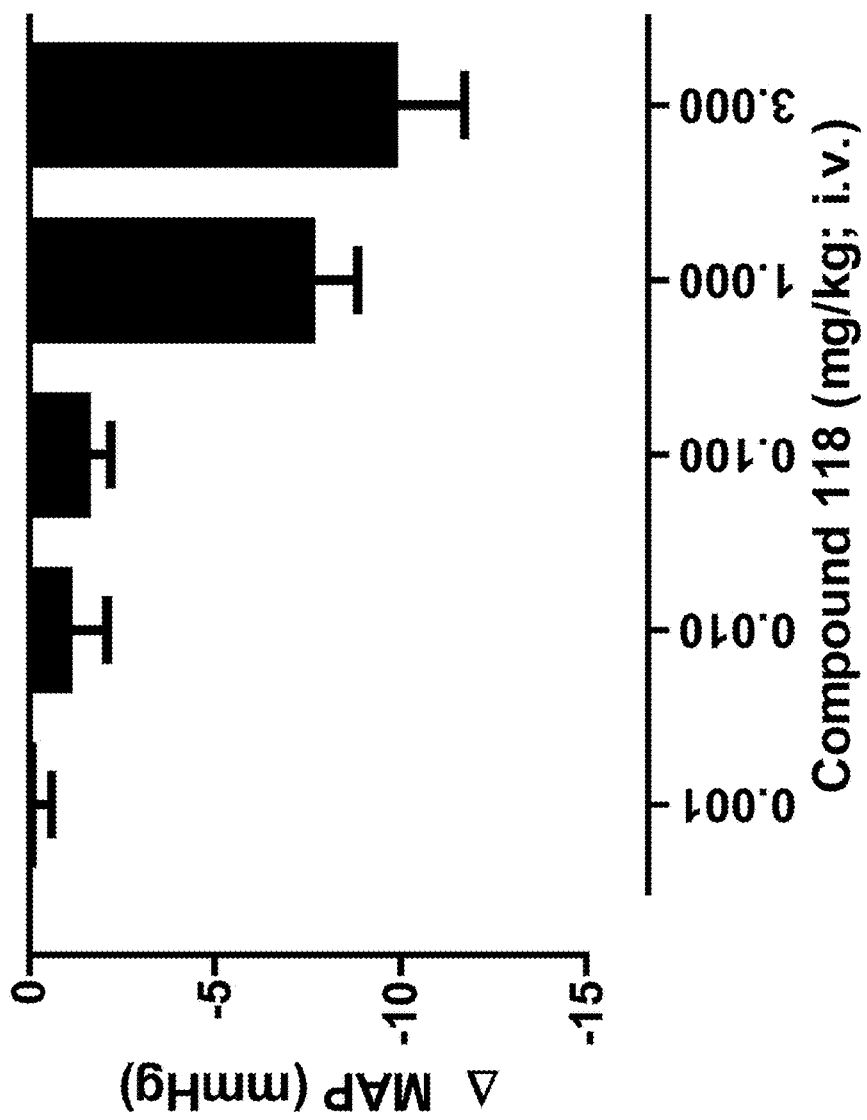
FIG. 2 shows mean dose-dependent decrease in blood pressure induced by a compound of the present invention in anesthetized mice.
Figure 3:
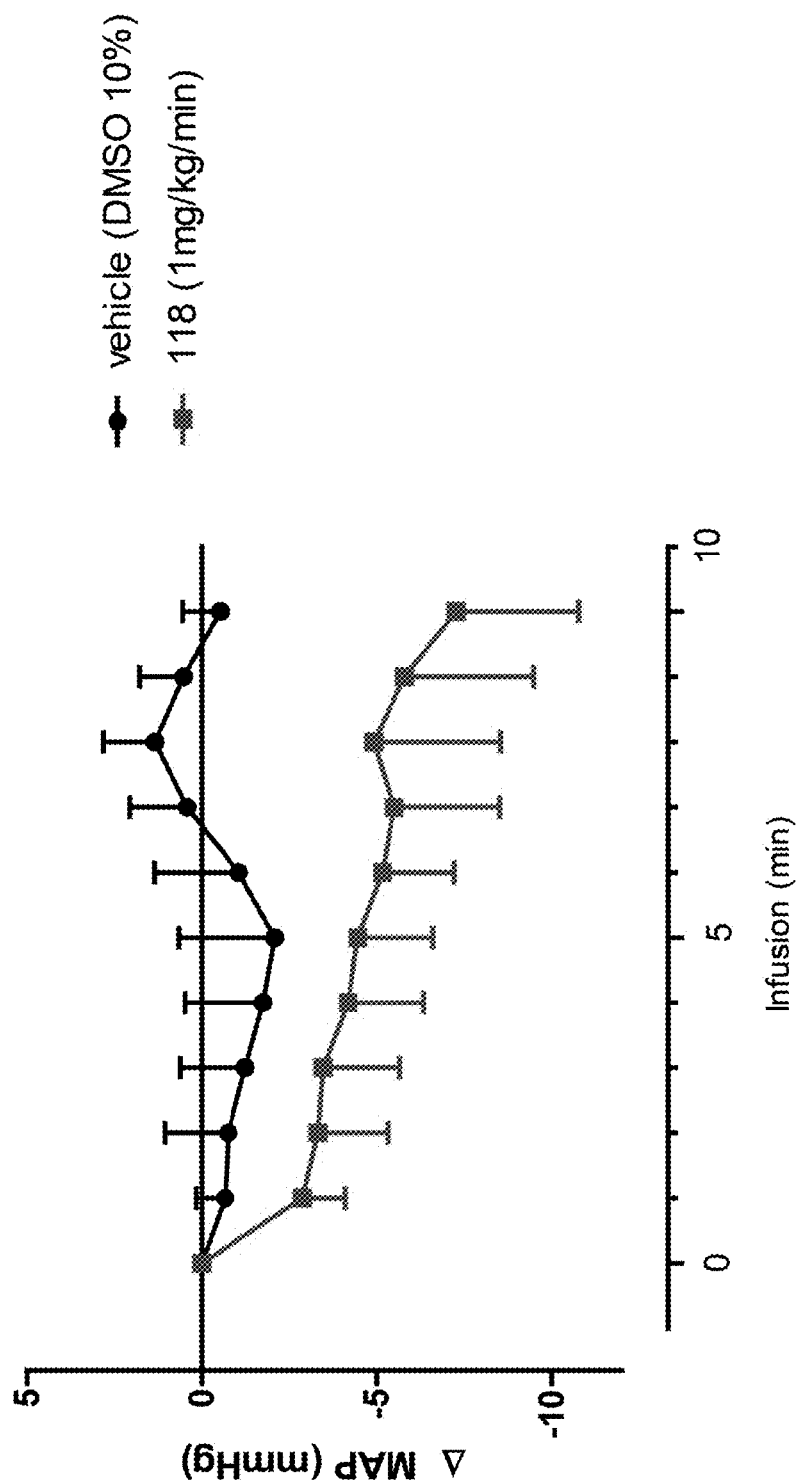
FIG. 3 shows reduction in blood pressure during the infusion of a compound of the present invention or vehicle in anesthetized mice.
Figure 4:
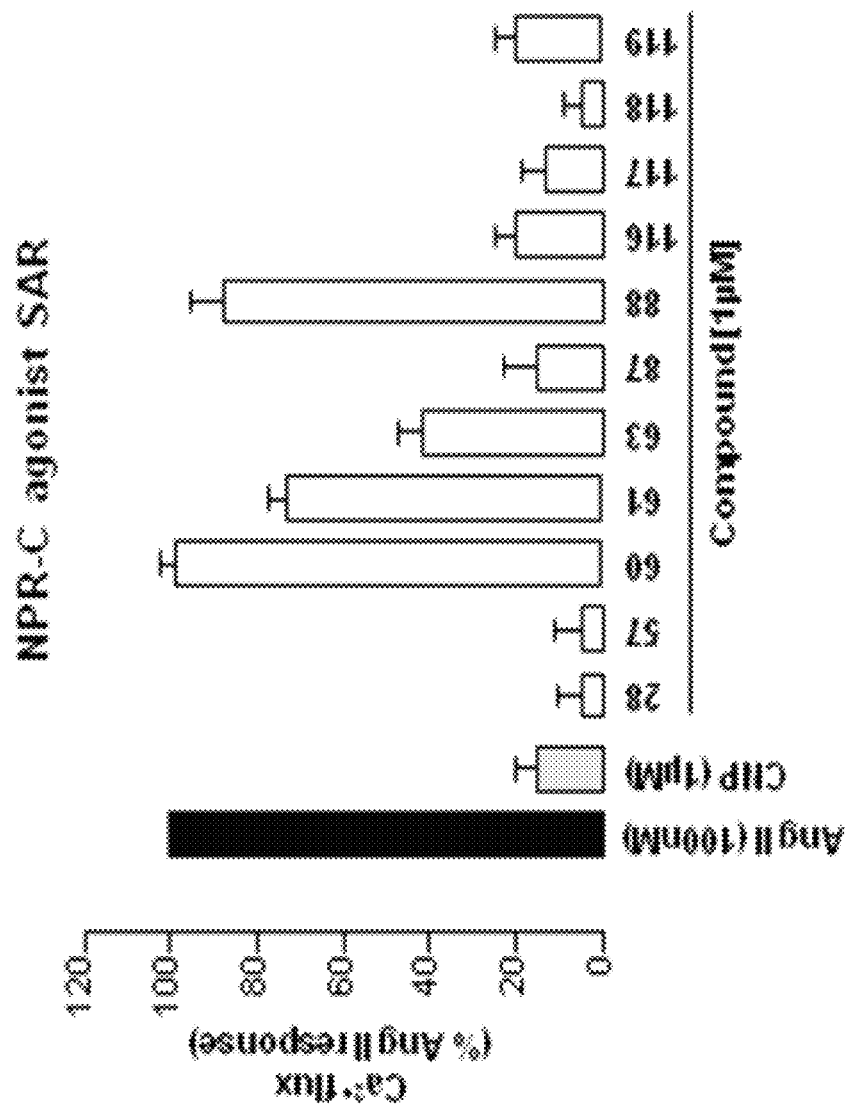
FIG. 4 shows the structure-activity relationship (SAR) for a selection of compounds of the present invention using AngII-mediated increases in $Ca^{2+}$ as readout.

It can be seen from the results depicted in FIG. 2 that 118 caused a dose-dependent decrease in BP in anesthetized mice. It can be seen from the results in FIG. 3 that infusion of 118 (1 mg/kg/min) caused a reduction in BP that was sustained during 10 minutes. The vehicle (10% of DMSO in PBS) did not cause any change in BP.

Example 81

Surface Plasmon Resonance (SPR) Spectroscopy

All SPR analysis was performed on a BIAcore T200 system using series S CM5 sensor chips. Data processing and analysis were performed using BIAevaluation software and Scrubber2. All sensorgrams were double referenced by subtracting the response on a reference flowcell and a blank sample.

Human NPR-C (OriGene, Rockville, USA), was covalently attached to a CM5 chip via amine coupling. A surface density of 2700 RU was used for measurements with natriuretic peptides and the NPR-C antagonist M372049, and a density of 5200 RU for measurements with compound 118. Sequential injections of CNP (0.25, 0.50, 1, 2 & 4 nM) were performed at a flow rate of 30 μL/min for (240 s for each), followed by a dissociation time of 3600 s. Binding site saturation was observed and the surface was regenerated by two injections of 1M NaCl (200 s each). Binding of M372049 (0.94, 1.88, 3.75, 7.5, 15, 30 & 60 nM) and Compound 118 (1.17, 2.34, 4.70, 9.38, 18.75, 37.50, 75 & 150 μM) was analysed by sequential injections (120 s for M372049, 30 s for compound 118) followed by undisturbed dissociation (600 s for M372049, 30 s for compound 118), during which curves returned to baseline. Kinetic parameters were calculated assuming a simple 1:1 (Langmuir) binding.

Figure 5:
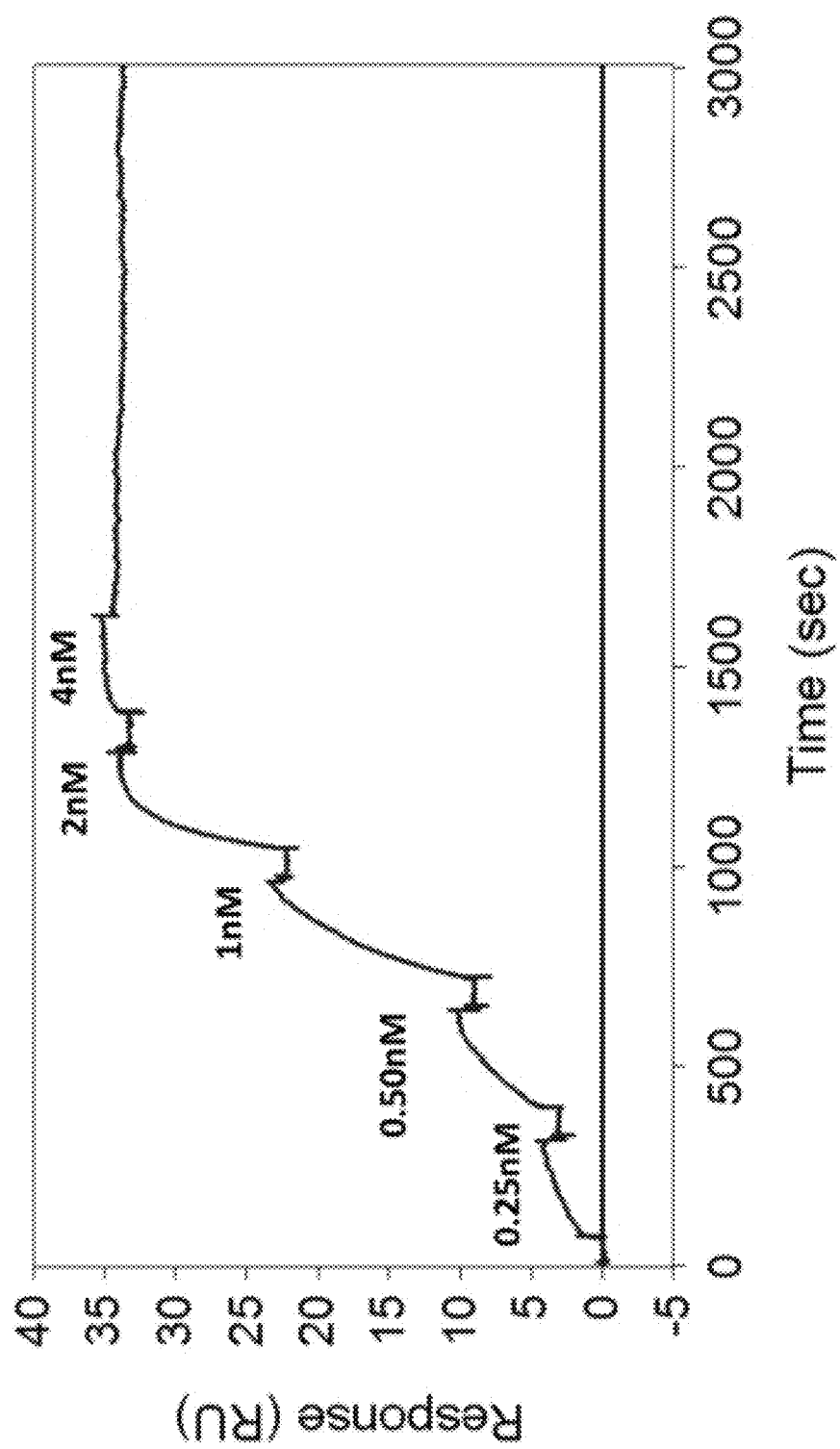
FIG. 5 shows surface plasmon resonance (SPR) spectroscopic analysis of the dynamics of the interaction of CNP (0.25 to 4 nM) with human NPR-C.
Figure 6:
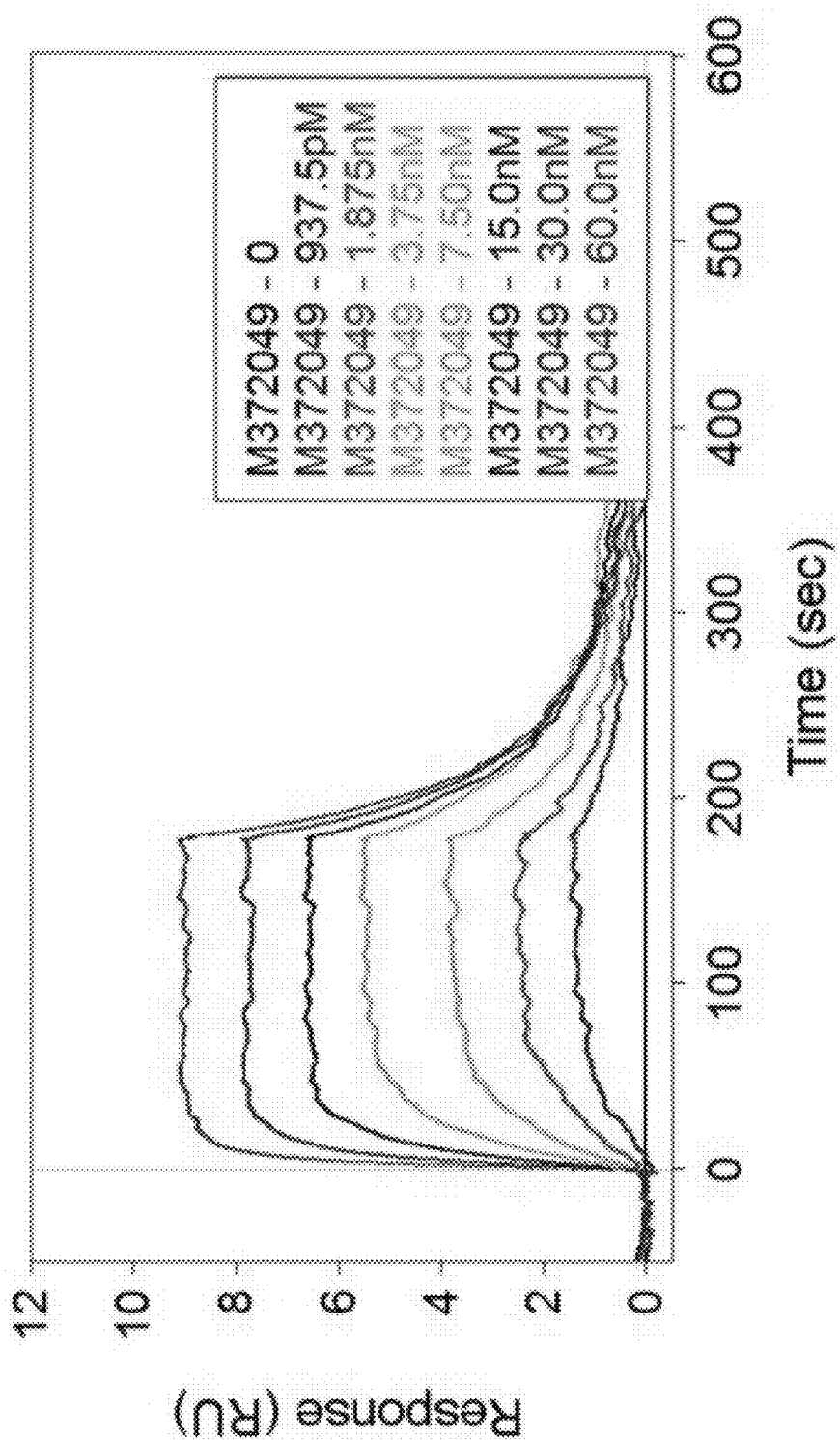
FIG. 6 shows surface plasmon resonance (SPR) spectroscopic analysis of the dynamics of the interaction of M372049 (1 to 60 nM) with human NPR-C.
Figure 7:
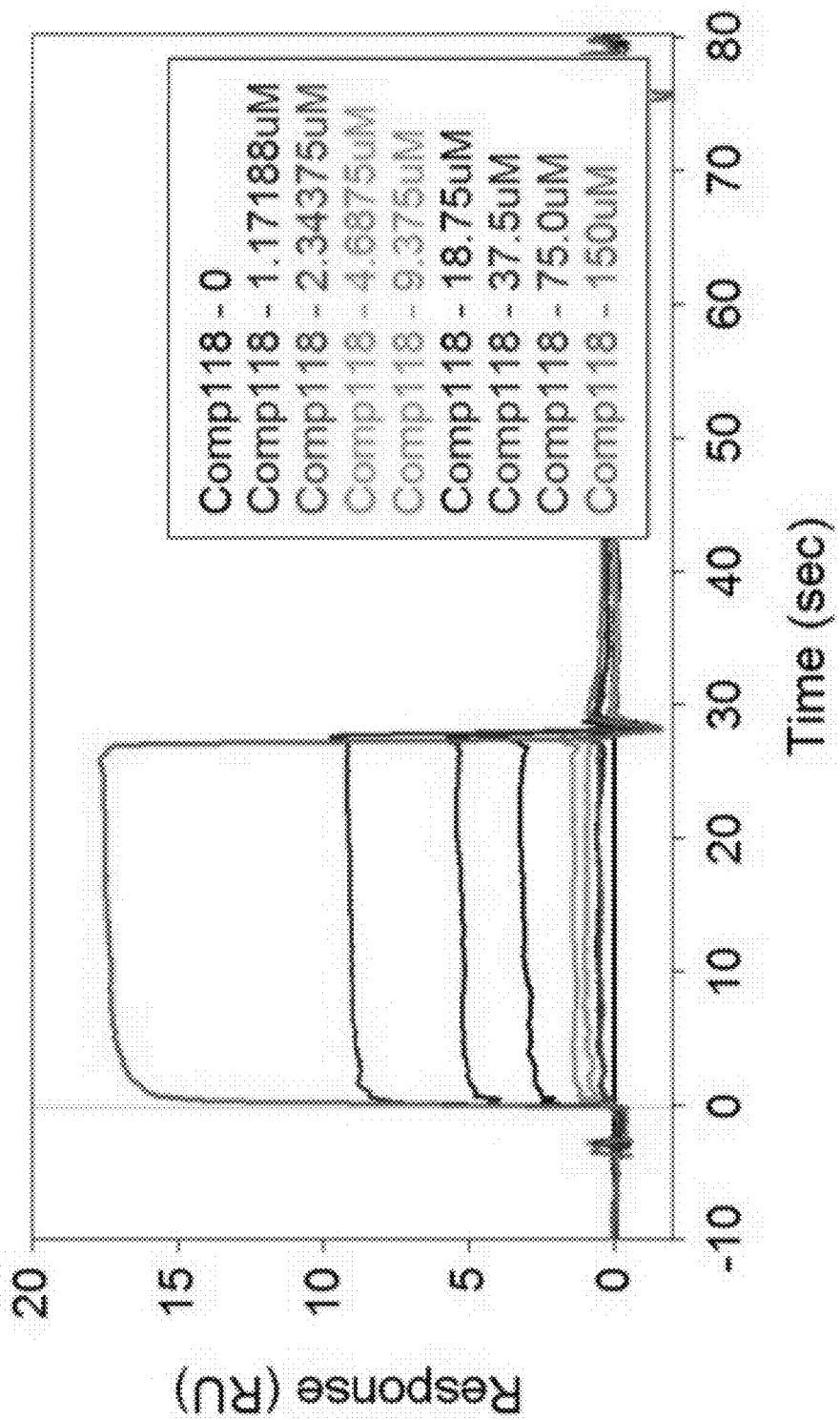
FIG. 7 shows surface plasmon resonance (SPR) spectroscopic analysis of the dynamics of the interaction of representative compound 118 of the present invention with human NPR-C.

FIGS. 5, 6 and 7 confirm binding of endogenous ligand CNP, the selective receptor antagonist M372049, and compound 118 to human NPR-C.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound of formula (1), a tautomer thereof, or a pharmaceutically acceptable salt or N-oxide thereof:

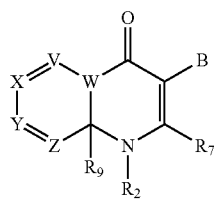

(I)

wherein
V is N or $CR_3$;
X is N or $CR_4$;
Y is N or $CR_5$;
Z is N or $CR_6$;
B is —(C=O)$R_1$;
$R_1$ is a proteinogenic α amino acid, which is linked to the carbonyl moiety in the compound of formula (I) via the α amino group, which amino acid is optionally esterified at the α carboxylic acid group with a $C_1$-$C_6$ alkyl group or a $C_6$-$C_{10}$ aryl group;
W is $CR_8$;
$R_8$ and $R_9$ together form a bond;
$R_2$ is -L'-$A_2$ group;
$R_3$ is a hydrogen atom, a halogen atom, or a hydroxy, $C_1$-$C_6$ alkyl, $C_1$-$C_6$ alkoxy, $C_1$-$C_6$ haloalkyl, $C_1$-$C_6$ haloalkoxy, nitro, or —NR'R" group, wherein R' and R" are the same or different and each represent a hydrogen atom or $C_1$-$C_6$ alkyl group;
$R_4$ and $R_5$ are the same or different and each represent a hydrogen atom, a halogen atom, or a hydroxyl, $C_1$-$C_8$ alkyl, $C_1$-$C_8$ haloalkyl, $C_1$-$C_6$ alkoxy, $C_1$-$C_6$ haloalkoxy, nitro, —NR'R", —$CO_2$R'", $C_6$-$C_{10}$ aryl, 5- to 10-membered heteroaryl, 5 to 10-membered heterocyclyl, or —CO—($C_1$-$C_6$ alkyl) group, wherein R', R" and R'" are the same or different and each represent a hydrogen atom or $C_1$-$C_6$ alkyl group, or $R_4$ and $R_5$ and the carbon atoms bonded to $R_4$ and $R_5$ together form a 5- to 6-membered heterocyclic ring;
$R_6$ is a hydrogen atom, a halogen atom, or a $C_1$-$C_6$ alkyl, $C_1$-$C_6$ haloalkyl, $C_1$-$C_6$ alkoxy, $C_1$-$C_6$ haloalkoxy or —$CO_2$R' group, wherein R' is hydrogen or $C_1$-$C_6$ alkyl;
$R_7$ is a hydrogen atom, a halogen atom, or a $C_1$-$C_6$ alkyl, or $C_1$-$C_6$ haloalkyl group;
$A_2$ is a $C_6$-$C_{10}$ aryl or 5- to 10-membered heteroaryl group; and
L' is a $C_1$-$C_6$ alkylene, $C_2$-$C_6$ alkenylene, or $C_2$-$C_6$ alkynylene group;
wherein each aryl, heteroaryl, cycloalkyl and heterocyclyl independently is unsubstituted or substituted with one or more substituents selected from halogen, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, —SOR, —$SO_2$R, —NR'R", —NR'(C=O)R", —COOR, nitro or cyano substituents, wherein R, R' and R" are the same or different and each represents a hydrogen atom or $C_1$-$C_4$ alkyl group.

2. A product, comprising (i) the compound of claim 1, and (ii) a at least one additional therapeutic agent selected from a statin, an anti-platelet agent, or an antihypertensive.

3. The compound of claim 1, wherein $R_1$ is a group of formula —NH—CHR—$CO_2$R', wherein R' is hydrogen or $C_1$-$C_4$ alkyl, and R is hydrogen, methyl, —$CH_2CH(CH_3)_2$, —$CH_2$-Ph, or —$CH(CH_3)_2$.

4. The compound of claim 1, wherein L' is $C_1$-$C_4$ alkylene.

5. The compound of claim 1, wherein $A_2$ is an unsubstituted phenyl or a phenyl substituted with one, two or three substituents selected from halogen, $C_1$-$C_4$ alkyl, $C_1$-$C_4$ alkoxy, $C_1$-$C_4$ haloalkyl, $C_1$-$C_4$ haloalkoxy, —$SO_2$R, or —NR'(C=O)R", wherein R, R' and R" are the same or different and each represents hydrogen or $C_1$-$C_4$ alkyl.

6. The compound of claim 1, wherein $R_1$ is NH—CHR$^{IV}$—$CO_2$R$^V$, wherein R$^V$ is a hydrogen atom or $C_1$-$C_6$ alkyl group, and R$^{IV}$ is hydrogen, methyl, —$(CH_2)_3$—NH—(C=NH)—$NH_2$, —$CH_2CONH_2$, —$CH_2CO_2H$, —$CH_2SH$, —$(CH_2)_2CO_2H$, —$(CH_2)_2CONH_2$, —$CH(CH_3)CH_2CH_3$, $CH_2CH(CH_3)_2$, —$(CH_2)_4NH_2$, —$(CH_2)_2SCH_3$, —$CH_2Ph$, —$CH_2OH$, —$CH(CH_3)OH$, —$CH_2$-p-hydroxy-Ph, —$CH(CH_3)_2$, —$CH_2SeH$,

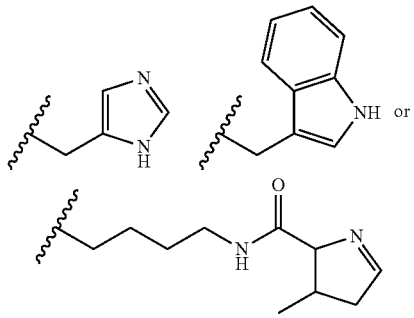

7. The compound of claim 1, wherein $R_3$ is hydrogen, or —NR'R", wherein R' and R" are the same or different and each represent hydrogen or $C_1$-$C_4$ alkyl.

8. The compound of claim 1, wherein $R_4$ is hydrogen, halogen, or hydroxyl, $C_1$-$C_8$ alkyl, $C_1$-$C_8$ haloalkyl, $C_1$-$C_6$ alkoxy, $C_1$-$C_6$ haloalkoxy, nitro, 5- to 6-membered heteroaryl, $C_6$-$C_{10}$ aryl, —NR'R", —$CO_2$R'", or —CO—($C_1$-$C_6$ alkyl), wherein R', R" and R'" are the same or different and each represent hydrogen or $C_1$-$C_6$ alkyl; or
when Y is a moiety $CR_5$, then $R_4$ may form, together with $R_5$ and the carbon atoms bonded to $R_4$ and $R_5$, a 5- to 6-membered heterocyclic ring.

9. The compound of claim 1, wherein $R_5$ is hydrogen, halogen, $C_1$-$C_6$ alkyl, $C_1$-$C_6$ haloalkyl, 5 to 10-membered heterocyclyl, or —$CO_2$R', wherein R' is hydrogen or $C_1$-$C_6$ alkyl; or
when X is a moiety $CR_4$, then $R_5$ may form, together with $R_4$ and the carbon atoms bonded to $R_4$ and $R_5$, a 5- to 6-membered heterocyclic ring.

10. The compound of claim 1, wherein $R_6$ is hydrogen, halogen, $C_1$-$C_6$ alkyl, $C_1$-$C_6$ alkoxy, or —$CO_2$R', wherein R' is hydrogen or $C_1$-$C_4$ alkyl.

11. The compound of claim 1, wherein $R_7$ is hydrogen.

12. The compound of claim 1, wherein not more than two of V, W, X, Y and Z are N.

13. The compound of claim 1, wherein the compound has a formula (If), (Ig), or (Ih)

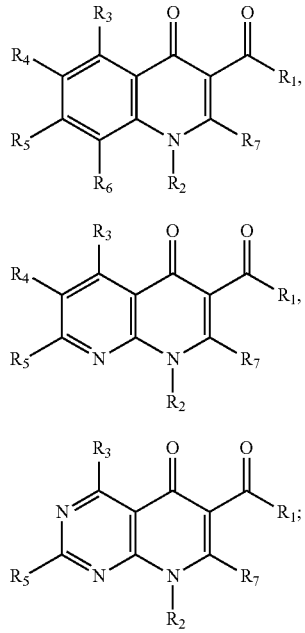

and
R₁ to R₇ are as defined in claim 1.

14. The compound of claim 1, wherein:
B is —(C═O)R₁;
R₁ is a group of formula —NH—CHR—CO₂R", wherein R" is a hydrogen atom or C₁-C₄ alkyl group, and R is a hydrogen atom, or a methyl, —CH₂CH(CH₃)₂, —CH₂-Ph or —CH(CH₃)₂ group;
L' is a —CH₂— group;
A₂ is a phenyl group which is unsubstituted or substituted by one or two substituents selected from chlorine, fluorine, C₁-C₂ alkyl, C₁-C₂ alkoxy, CF₃O—, —NHAc or —SO₂Me substituents;
V is CR₃;
R₃ is hydrogen or —NH₂;
R₄ is a hydrogen, bromine, fluorine, C₁-C₆ alkyl, methoxy, trifluoromethoxy, nitro, —NMe₂, —CO₂H, —COMe, unsubstituted thiophene, unsubstituted pyridine, or phenyl, the phenyl being unsubstituted or substituted by a substituent selected from —COOH, —CH₂OH or —NHAc, or when Y is a moiety CR₅, then R₄ may form, together with R₅ and the carbon atoms bonded to R₄ and R₅, an unsubstituted 1,3-dioxolane group;
R₅ is hydrogen, methyl, trifluoromethyl, unsubstituted octahydro-1H-pyrrolo[3,4-b]pyridine, unsubstituted piperazine, N-methyl-piperazine, dimethylpiperazine, hydroxypiperidine, or —CO₂H group, or when X is a moiety CR₄, then R₅ may form, together with R₅ and the carbon atoms bonded to R₄ and R₅, an unsubstituted 1,3-dioxolane group;
R₆ is hydrogen, C₁-C₃ alkyl, methoxy, or —CO₂H group; and
R₇ is a hydrogen atom.

15. The compound of claim 1, having a structure

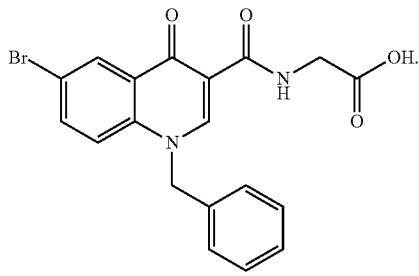 [SMILES: O=C(O)CNC(=O)c1cn(Cc2ccccc2)c2ccc(Br)cc2c1=O]

16. The compound of claim 1, wherein the compound has a formula (If)

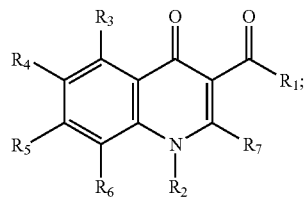

and
R₁ to R₇ are as defined in claim 1.

* * * * *

UNITED STATES PATENT AND TRADEMARK OFFICE
CERTIFICATE OF CORRECTION

| | |
|---|---|
| PATENT NO. | : 10,087,144 B2 |
| APPLICATION NO. | : 15/356311 |
| DATED | : October 2, 2018 |
| INVENTOR(S) | : David Selwood et al. |

It is certified that error appears in the above-identified patent and that said Letters Patent is hereby corrected as shown below:

On the Title Page

Column 1 Under "Foreign Applications", please add:
--GREAT BRITAIN 1409044.3 05/21/2014--.

Signed and Sealed this
Fourth Day of December, 2018

Andrei Iancu
*Director of the United States Patent and Trademark Office*